US011534428B1

(12) United States Patent
Gotteland et al.

(10) Patent No.: US 11,534,428 B1
(45) Date of Patent: Dec. 27, 2022

(54) COMPOSITIONS AND METHODS FOR DELAYING THE INCIDENCE OF LABOR

(71) Applicant: ObsEva S.A., Plan-les-Ouates (CH)

(72) Inventors: Jean-Pierre Gotteland, Geneva (CH); Oliver Pohl, Plan-les-Ouates (CH)

(73) Assignee: XOMA (US) LLC, Emeryville, CA (US)

( * ) Notice: Subject to any disclaimer, the term of this patent is extended or adjusted under 35 U.S.C. 154(b) by 0 days.

(21) Appl. No.: 16/411,974

(22) Filed: May 14, 2019

Related U.S. Application Data

(60) Provisional application No. 62/672,278, filed on May 16, 2018.

(51) Int. Cl.
| | |
|---|---|
| *A61K 31/426* | (2006.01) |
| *A61P 15/06* | (2006.01) |
| *A61K 31/573* | (2006.01) |
| *A61K 31/4422* | (2006.01) |

(52) U.S. Cl.
CPC ........ *A61K 31/426* (2013.01); *A61K 31/4422* (2013.01); *A61K 31/573* (2013.01); *A61P 15/06* (2018.01)

(58) Field of Classification Search
CPC .................................................... A61K 31/426
See application file for complete search history.

(56) References Cited

U.S. PATENT DOCUMENTS

| | | | |
|---|---|---|---|
| 5,508,045 A | 4/1996 | Harrison et al. | |
| 5,872,126 A | 2/1999 | Cukierski et al. | |
| 8,415,480 B2 | 4/2013 | Page et al. | |
| 9,447,055 B1 * | 9/2016 | Page | C07D 277/06 |
| 9,834,528 B2 * | 12/2017 | Page | C07D 277/06 |
| 10,259,795 B2 * | 4/2019 | Page | C07D 277/06 |
| 10,555,934 B2 * | 2/2020 | Page | A61K 9/0053 |
| 2006/0211626 A1 | 9/2006 | Peri et al. | |
| 2017/0050099 A1 | 2/2017 | Roelle et al. | |
| 2018/0201591 A1 | 7/2018 | Page et al. | |
| 2019/0000812 A1 | 1/2019 | Page et al. | |
| 2019/0194151 A1 | 6/2019 | Page et al. | |

FOREIGN PATENT DOCUMENTS

| | | |
|---|---|---|
| EP | 1487442 B1 | 12/2010 |
| JP | H09-504108 A | 4/1997 |
| JP | 2005-537225 A | 12/2005 |
| WO | WO-03/082278 A1 | 10/2003 |
| WO | WO-2015/192878 A1 | 12/2015 |

OTHER PUBLICATIONS

Read et al., Br J Obstet Gynaecol., 1986, 93(9): 933-7.*
Vig et al., "Amino acids as promoieties in prodrug design and development," Adv Drug Deliv Rev. 65(10):1370-85 (2013).
Arrowsmith et al., "Oxytocin: Its Mechanism of Action and Receptor Signalling in the Myometrium," J Neuroendocrinol. 26(6):356-69 (2014).
Ahmad et al., "Selective modulation of the prostaglandin F2alpha pathway markedly impacts on endometriosis progression in a xenograft mouse model," Mol Hum Reprod. 21(12):905-16 (2015).
Huttunen et al., "Prodrugs—from serendipity to rational design," Pharmacol Rev. 63(3):750-71 (2011).
MacDougall et al., "Pharmacokinetics of valaciclovir," J Antimicrob Chemother. 53(6):899-901 (2004).
Flenady et al., "Calcium channel blockers for inhibiting preterm labour and birth," Cochrane Database Syst Rev. (6):CD002255 (2014) (179 pages).
Gyetvai et al., "Tocolytics for preterm labor: a systematic review," Obstet Gynecol. 94(5 Pt 2):869-77 (1999).
Miracle et al., "Guideline for the use of antenatal corticosteroids for fetal maturation," J Perinat Med. 36(3):191-6 (2008).
Jobe et al., "Choice and dose of corticosteroid for antenatal treatments," Am J Obstet Gynecol. 190(4):878-81 (2004).
Haas et al., "Short-term tocolytics for preterm delivery—current perspectives," Int J Womens Health. 6:343-9 (2014).
NICE guideline, "Preterm labour and birth," <https://www.nice.org.uk/guidance/ng25>, published Nov. 20, 2015 (24 pages).
International Search Report for International Application No. PCT/EP2017/050099, dated Mar. 29, 2017 (5 pages).
Written Opinion for International Application No. PCT/EP2017/050099, dated Mar. 29, 2017 (8 pages).
International Search Report for International Application No. PCT/EP2017/050101, dated Apr. 5, 2017 (5 pages).
Written Opinion for International Application No. PCT/EP2017/050101, dated Apr. 5, 2017 (8 pages).

(Continued)

*Primary Examiner* — Rei Tsang Shiao
(74) *Attorney, Agent, or Firm* — Clark & Elbing LLP

(57) ABSTRACT

The invention provides compositions and methods for delaying the onset of delivery in a pregnant subject, such as a pregnant human subject, that is undergoing or at risk of undergoing preterm labor at a gestational age of from about 24 weeks to about 34 weeks. Using the compositions and methods described herein, such subjects may be administered nifedipine in combination with a prostaglandin F2α (PGF2α) antagonist. Exemplary PGF2α receptor antagonists that may be used for the treatment or prevention of preterm labor as described herein include 1,3-thiazolidine-2-carboxamide compounds, such as (3S)-3-({[(2S)-3-(biphenyl-4-ylsulfonyl)-1,3-thiazolidin-2-yl]carbonyl}-amino)-3-(4-fluorophenyl)propyl L-valinate or a pharmaceutically acceptable salt thereof (e.g., (3S)-3-({[(2S)-3-(biphenyl-4-ylsulfonyl)-1,3-thiazolidin-2-yl]carbonyl}-amino)-3-(4-fluorophenyl)propyl L-valinate hydrochloride. Using the compositions and methods described herein, a subject may be dosed with a PGF2α receptor antagonist and a reduced amount or frequency of nifedipine relative to the amount or frequency of nifedipine that would otherwise be used if the nifedipine were given in the absence of the PGF2α receptor antagonist.

11 Claims, 6 Drawing Sheets

(56) References Cited

OTHER PUBLICATIONS

Page et al., "Alpha-Amino Esters of Hydroxypropylthiazolidine Carboxamide Derivative and Salt Form, Crystal Polymorph Thereof," U.S. Appl. No. 16/289,235, filed Feb. 28, 2019 (122 pages).

First Office Action for Eurasian Patent Application No. 201891095/28, dated Feb. 22, 2019 (6 pages).

Search Report and Written Opinion for Singaporean Patent Application No. 11201804594Y, dated Sep. 6, 2019 (10 pages).

Singhal et al., "Drug polymorphism and dosage form design: a practical perspective," Adv Drug Deliv Rev. 56(3):335-47 (2004).

Caira, M.R., Crystalline Polymorphism of Organic Compound, *Design of Organic Solids*. Springer Verlag Berlin Heidelberg 163-208 (2003).

Pohl et al., "OBE022, an Oral and Selective Prostaglandin $F_{2alpha}$ Receptor Antagonist as an Effective and Safe Modality for the Treatment of Preterm Labor," J Pharmacol Exp Ther. 366(2):349-364 (2018).

Pohl et al., "Coadministration of the prostaglandin F2alpha receptor antagonist preterm labour drug candidate OBE022 with magnesium sulfate, atosiban, nifedipine and betamethasone," Br J Clin Pharmacol. 85(7):1516-1527 (2019).

"ObsEva SA Reports Initial Good Safety of OBE022 in Pregnant Women with Preterm Labour and Announces Start of Part B of the Prolong Trial," <https://ml-eu.globenewswire.com/Resource/Download/3e5183ef-cbfb-4010-86ee-99a0e4ef0a71>, dated Jan. 23, 2018 (4 pages).

\* cited by examiner

US 11,534,428 B1

COMPOSITIONS AND METHODS FOR DELAYING THE INCIDENCE OF LABOR

FIELD OF THE INVENTION

The invention relates to the field of therapeutic treatment of pregnant subjects, such as pregnant human subjects, undergoing or at risk of undergoing preterm labor at the early gestational stage.

BACKGROUND OF THE INVENTION

Preterm delivery represents a prevalent cause of perinatal mortality in the developed world and occurs in approximately 7% to 10% of all deliveries (Berkowitz et al. Epidemiol. Rev. 15:414-443 (1993)).

Severe morbidity, especially respiratory distress syndrome, intraventricular hemorrhage, bronchopulmonary dysplasia, and necrotizing enterocolitis, are far more common in preterm than in term infants. Long-term impairments, such as cerebral palsy, visual impairment, and hearing loss, are also more common in preterm infants. At present, preterm birth remains a leading cause of infant mortality and morbidity in the United States, where, despite the significant improvements in obstetrical medicine, the infant mortality rate is higher than in many other industrialized nations, causing costs exceeding $5 billion per year for neonatal intensive care of low birth-weight babies. The actual costs associated with this care are even higher when taking into consideration the healthcare provision of preterm childbirth-related ailments, such as respiratory distress syndrome, heart conditions, cerebral palsy, epilepsy, and severe learning disabilities.

Fundamentally, term and preterm labor are similar processes in that they share a common physiological endpoint characterized by uterine contractions, cervical dilatation, and activation of the fetal membranes. The differences lie in the gestational age at which these processes occur and the mechanisms by which they are activated. Term labor is thought to result from physiological activation of the terminal pathway, whereas preterm labor is a pathological condition characterized by multiple etiologies in which one or more components of this pathway are aberrantly activated.

There remains a need for combinations of agents that can be used to treat or prevent preterm labor, as well as dosing regimens for the use of such agents at levels that are therapeutically effective and physiologically safe.

SUMMARY OF THE INVENTION

The present disclosure relates to compositions and methods for treating or preventing preterm labor in a patient, such as a mammalian patient, and particularly a human female patient. Using the compositions and methods described herein, a patient undergoing or at risk of undergoing premature parturition, such as a subject being prepared for cesarean delivery, may be administered a prostaglandin F2α (PGF2α) receptor antagonist in combination with nifedipine so as to slow the onset of delivery, for instance, by a matter of hours, days, or weeks. The compositions and methods described herein can additionally be used to ameliorate one or more symptoms of preterm labor, such as to diminish the frequency of uterine contractions, slow or halt vaginal bleeding, and/or to suppress the rupture of uterine membranes. The PGF2α receptor antagonist may be, for example, a 1,3-thiazolidine-2-carboxamide compound described herein, such as (3S)-3-({[(2S)-3-(biphenyl-4-ylsulfonyl)-1,3-thiazolidin-2-yl]carbonyl}-amino)-3-(4-fluorophenyl)propyl L-valinate or a pharmaceutically acceptable salt thereof, such as (3S)-3-({[(2S)-3-(biphenyl-4-ylsulfonyl)-1,3-thiazolidin-2-yl]carbonyl}-amino)-3-(4-fluorophenyl)propyl L-valinate hydrochloride, or another 1,3-thiazolidine-2-carboxamide that gives rise to 3-([1,1'-biphenyl]-4-ylsulfonyl)-N-[1-(4-fluorophenyl)-3-hydroxypropyl]-1,3-thiazolidine-2-carboxamide in vivo.

The compositions and methods described herein provide a variety of clinical and pharmacological benefits. Using the compositions and methods described herein, a patient undergoing or at risk of undergoing preterm labor may be administered a PGF2α receptor antagonist, such as a 1,3-thiazolidine-2-carboxamide compound described herein, in combination with a reduced dosage of a calcium channel inhibitor, such as nifedipine, relative to an amount of the calcium channel inhibitor that would ordinarily be administered to the patient if given in the absence of the PGF2α receptor antagonist. Additionally or alternatively, the patient may be administered a PGF2α receptor antagonist, such as a 1,3-thiazolidine-2-carboxamide compound described herein, in combination with a calcium channel inhibitor, such as nifedipine, that is administered with a reduced frequency relative to the frequency of calcium channel inhibitor administration that would otherwise be used if the nifedipine were given in the absence of the PGF2α receptor antagonist. Using the compositions and methods described herein, despite the reduced dosage and/or frequency of administration of the calcium channel inhibitor when given in combination with a PGF2α receptor antagonist, the patient is still able to experience the beneficial therapeutic effects, for example, of a prolonged pregnancy and a delayed onset of labor.

The present disclosure is based, in part, on the unexpected discovery that administration of nifedipine to a patient in combination with a PGF2α receptor antagonist described herein, such as (3S)-3-({[(2S)-3-(biphenyl-4-ylsulfonyl)-1,3-thiazolidin-2-yl]carbonyl}-amino)-3-(4-fluorophenyl)propyl L-valinate or a pharmaceutically acceptable salt thereof (e.g., (3S)-3-({[(2S)-3-(biphenyl-4-ylsulfonyl)-1,3-thiazolidin-2-yl]carbonyl}-amino)-3-(4-fluorophenyl)propyl L-valinate hydrochloride) and other 1,3-thiazolidine-2-carboxamides that give rise to 3-([1,1'-biphenyl]-4-ylsulfonyl)-N-[1-(4-fluorophenyl)-3-hydroxypropyl]-1,3-thiazolidine-2-carboxamide in vivo, results in an elevated plasma concentration of nifedipine relative to that observed when nifedipine is administered alone. As described herein, this finding is particularly advantageous, as it enables a patient undergoing or at risk of undergoing preterm labor to be administered lower quantities or reduced frequencies of nifedipine, thereby reducing the likelihood of any potential side effects associated with nifedipine treatment, while, surprisingly, still experiencing beneficial treatment outcomes.

To obtain these advantageous pharmacological benefits, the subject may be administered therapeutically effective amounts of the PGF2α receptor antagonist and nifedipine, for example, either concurrently or at different times. The patient may receive multiple, continuous doses of the PGF2α antagonist and/or the nifedipine. The patient may receive the PGF2α antagonist and the nifedipine on the same or different dosing schedules. For instance, each time the patient receives a dose of one of these agents, the patient may or may not receive a dose of the second agent. The patient may receive the PGF2α antagonist, for example, one or more times per day, such as once or twice daily, and the nifedipine may be administered to the subject, for example, one or more times every 4 hours, every 6 hours, every 8 hours, every 10 hours, every 12 hours, every 48 hours, or more. The combined administration of nifedipine and the PGF2α receptor antagonist may occur one or more times per day, week, or month, as described herein, and may continue, for example, up until the patient undergoes delivery or until a full gestational term has been reached.

In a first aspect, the invention features a method of delaying the onset of delivery (i.e., delaying the incidence of delivery) in a pregnant subject (e.g., a pregnant human female) by administering to the subject therapeutically effective amounts of nifedipine and a PGF2α receptor antagonist, such as a compound represented by formula (I)

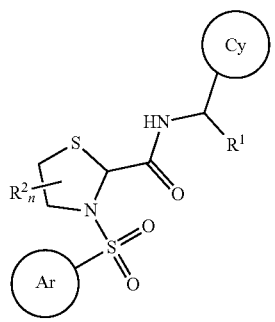

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine may be administered to the subject in an amount, for example, of about 40 mg or less per dose. For instance, the nifedipine may be administered to the subject in an amount of from about 1 mg to about 40 mg per dose, about 2 mg to about 39 mg per dose, about 3 mg to about 38 mg per dose, about 4 mg to about 37 mg per dose, about 5 mg to about 36 mg per dose, about 6 mg to about 35 mg per dose, about 7 mg to about 34 mg per dose, about 8 mg to about 33 mg per dose, about 9 mg to about 32 mg per dose, about 10 mg to about 30 mg per dose, about 11 mg to about 29 mg per dose, about 12 mg to about 28 mg per dose, about 13 mg to about 27 mg per dose, about 14 mg to about 26 mg per dose, about 15 mg to about 25 mg per dose, about 16 mg to about 24 mg per dose, about 17 mg to about 23 mg per dose, about 18 mg to about 22 mg per dose, or about 19 mg to about 21 mg per dose, among others. Exemplary doses of nifedipine that may be administered to the subject include doses of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as a dose of about 20 mg, among others.

In another aspect, the invention features a method of delaying the onset of delivery (i.e., delaying the incidence of delivery) in a pregnant subject (e.g., a pregnant human female) by administering to the subject a therapeutically effective amount of a PGF2α receptor antagonist, such as a compound represented by formula (I)

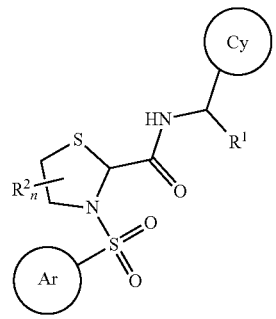

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 40 mg or less per dose. For instance, the subject may be one that is concurrently being administered nifedipine (or that has previously been administered nifedipine) in an amount of from about 1 mg to about 40 mg per dose, about 2 mg to about 39 mg per dose, about 3 mg to about 38 mg per dose, about 4 mg to about 37 mg per dose, about 5 mg to about 36 mg per dose, about 6 mg to about 35 mg per dose, about 7 mg to about 34 mg per dose, about 8 mg to about 33 mg per dose, about 9 mg to about 32 mg per dose, about 10 mg to about 30 mg per dose, about 11 mg to about 29 mg per dose, about 12 mg to about 28 mg per dose, about 13 mg to about 27 mg per dose, about 14 mg to about 26 mg per dose, about 15 mg to about 25 mg per dose, about 16 mg to about 24 mg per dose, about 17 mg to about 23 mg per dose, about 18 mg to about 22 mg per dose, or about 19 mg to about 21 mg per dose, among others. Exemplary doses of nifedipine that may be (or may have been) administered to the subject include doses of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as a dose of about 20 mg, among others.

In another aspect, the invention features a method of delaying the onset of delivery (i.e., delaying the incidence of delivery) in a pregnant subject (e.g., a pregnant human female) by administering to the subject therapeutically effective amounts of nifedipine and a PGF2α receptor antagonist, such as a compound represented by formula (I)

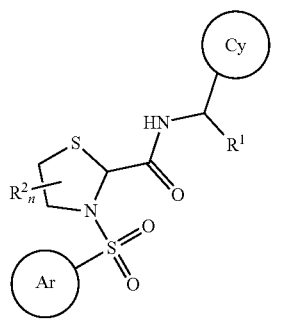

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine may be administered to the subject in an amount of about 40 mg or less in the first hour of treatment. For instance, the nifedipine may be administered to the subject in an amount of from about 1 mg to about 40 mg in the first hour of treatment, about 2 mg to about 39 mg in the first hour of treatment, about 3 mg to about 38 mg in the first hour of treatment, about 4 mg to about 37 mg in the first hour of treatment, about 5 mg to about 36 mg in the first hour of treatment, about 6 mg to about 35 mg in the first hour of treatment, about 7 mg to about 34 mg in the first hour of treatment, about 8 mg to about 33 mg in the first hour of treatment, about 9 mg to about 32 mg in the first hour of treatment, about 10 mg to about 30 mg in the first hour of treatment, about 11 mg to about 29 mg in the first hour of treatment, about 12 mg to about 28 mg in the first hour of treatment, about 13 mg to about 27 mg in the first hour of treatment, about 14 mg to about 26 mg in the first hour of treatment, about 15 mg to about 25 mg in the first hour of treatment, about 16 mg to about 24 mg in the first hour of treatment, about 17 mg to about 23 mg in the first hour of treatment, about 18 mg to about 22 mg in the first hour of treatment, or about 19 mg to about 21 mg in the first hour of treatment, among others. Exemplary amounts of nifedipine that may be administered to the subject in the first hour of treatment include amounts of nifedipine of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as an amount of about 20 mg, among others.

In another aspect, the invention features a method of delaying the onset of delivery (i.e., delaying the incidence of delivery) in a pregnant subject (e.g., a pregnant human female) by administering to the subject a therapeutically effective amount of a PGF2α receptor antagonist, such as a compound represented by formula (I)

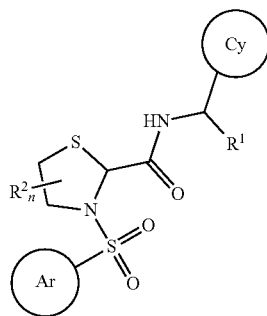

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 40 mg or less in the first hour of treatment. For instance, the subject may be one that is concurrently being administered nifedipine (or that has previously been administered nifedipine) in an amount of from about 1 mg to about 40 mg in the first hour of treatment, about 2 mg to about 39 mg in the first hour of treatment, about 3 mg to about 38 mg in the first hour of treatment, about 4 mg to about 37 mg in the first hour of treatment, about 5 mg to about 36 mg in the first hour of treatment, about 6 mg to about 35 mg in the first hour of treatment, about 7 mg to about 34 mg in the first hour of treatment, about 8 mg to about 33 mg in the first hour of treatment, about 9 mg to about 32 mg in the first hour of treatment, about 10 mg to about 30 mg in the first hour of treatment, about 11 mg to about 29 mg in the first hour of treatment, about 12 mg to about 28 mg in the first hour of treatment, about 13 mg to about 27 mg in the first hour of treatment, about 14 mg to about 26 mg in the first hour of treatment, about 15 mg to about 25 mg in the first hour of treatment, about 16 mg to about 24 mg in the first hour of treatment, about 17 mg to about 23 mg in the first hour of treatment, about 18 mg to about 22 mg in the first hour of treatment, or about 19 mg to about 21 mg in the first hour of treatment, among others. Exemplary amounts of nifedipine that may be (or may have been) administered to the subject in the first hour of treatment include amounts of nifedipine of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as an amount of about 20 mg, among others.

In another aspect, the invention features a method of delaying the onset of delivery (i.e., delaying the incidence of delivery) in a pregnant subject (e.g., a pregnant human female) by administering to the subject therapeutically effective amounts of nifedipine and a PGF2α receptor antagonist, such as a compound represented by formula (I)

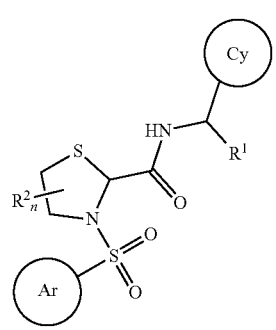

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine is administered to the subject in an amount of about 200 mg or less per day. For example, the nifedipine may be administered to the subject in an amount of from about 1 mg to about 200 mg per day, about 2 mg to about 199 mg per day, about 3 mg to about 198 mg per day, about 4 mg to about 197 mg per day, about 5 mg to about 196 mg per day, about 6 mg to about 195 mg per day, about 7 mg to about 194 mg per day, about 8 mg to about 193 per day, about 9 mg to about 192 per day, about 10 mg to about 191 per day, about 11 mg to about 190 per day, about 12 mg to about 189 per day, about 13 mg to about 188 per day, about 14 mg to about 187 per day, about 15 mg to about 186 per day, about 16 mg to about 185 mg per day, about 17 mg to about 184 per day, about 18 mg to about 183 per day, about 19 mg to about 182 per day, about 20 mg to about 181 per day, about 21 mg to about 180 per day, about 22 mg to about 179 mg per day, about 23 mg to about 178 mg per day, about 24 mg to about 177 mg per day, about 25 mg to about 176 mg per day, about 26 mg to about 175 mg per day, about 27 mg to about 174 mg per day, about 28 mg to about 173 mg per day, about 29 mg to about 172 mg per day, about 30 mg to about 171 mg per day, about 31 mg to about 170 mg per day, about 32 mg to about 169 mg per day, about 33 mg to about 168 mg per day, about 34 mg to about 167 mg per day, about 35 mg to about 166 mg per day, about 36 mg to about 165 mg per day, about 37 mg to about 164 mg per day, about 38 mg to about 163 mg per day, about 39 mg to about 162 per day, about 40 mg to about 161 mg per day, about 41 to about 160 mg per day, about 42 to about 159 mg per day, about 43 mg to about 158 mg per day, about 44 mg to about 157 mg per day, about 45 mg to about 156 mg per day, about 46 mg to about 155 mg per day, about 47 mg to about 154 mg per day, about 48 mg to about 153 mg per day, about 49 mg to about 152 mg per day, about 50 mg to about 151 mg per day, about 51 mg to about 150 mg per day, about 52 mg to about 149 mg per day, about 53 mg to about 148 mg per day, about 54 mg to about 147 mg per day, about 55 mg to about 146 mg per day, about 56 mg to about 145 mg per day, about 57 mg to about 144 mg per day, about 58 mg to about 143 mg per day, about 59 mg to about 142 mg per day, about 60 mg to about 141 mg per day, about 61 mg to about 140 mg per day, about 62 mg to about 139 mg per day, about 63 mg to about 138 mg per day, about 64 mg to about 137 mg per day, about 65 mg to about 136 mg per day, about 66 mg to about 135 mg per day, about 67 mg to about 134 mg per day, about 68 mg to about 133 mg per day, about 69 mg to about 132 mg per day, about 70 mg to about 131 mg per day, about 71 mg to about 130 mg per day, about 72 mg to about 129 per day, about 73 mg to about 128 mg per day, about 74 mg to about 127 mg per day, about 75 mg to about 126 mg per day, about 76 mg to about 125 mg per day, about 77 mg to about 124 mg per day, about 78 mg to about 123 mg per day, about 79 mg to about 122 mg per day, about 80 mg to about 121 mg per day, about 81 mg to about 120 mg per day, about 82 mg to about 119 mg per day, about 83 mg to about 118 mg per day, about 84 mg to about 117 mg per day, about 85 mg to about 116 mg per day, about 86 mg to about 115 mg per day, about 87 mg to about 114 mg per day, about 88 mg to about 113 mg per day, about 89 mg to about 112 mg per day, about 90 mg to about 111 mg per day, about 91 mg to about 110 mg per day, about 92 mg to about 109 mg per day, about 93 mg to about 108 mg per day, about 94 mg to about 107 mg per day, about 95 mg to about 106 mg per day, about 96 mg to about 105 mg per day, about 97 mg to about 104 mg per day, about 98 mg to about 103 mg per day, about 99 mg to about 102 mg per day, or about 100 to about 101 mg per day, among others. Exemplary total daily quantities of nifedipine that may be administered to the subject include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, and 200 mg, among others.

In another aspect, the invention features a method of delaying the onset of delivery (i.e., delaying the incidence of delivery) in a pregnant subject (e.g., a pregnant human female) by administering to the subject a therapeutically effective amount of a PGF2α receptor antagonist, such as a compound represented by formula (I)

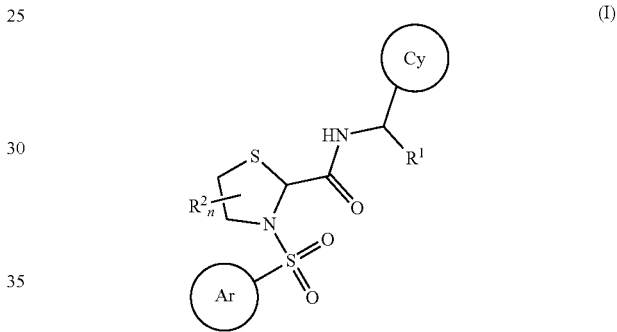

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 200 mg or less per day. For example, the subject may be one that is concurrently being administered nifedipine (or that has previously been administered nifedipine) in an amount of from about 1 mg to about 200 mg per day, about 2 mg to about 199 mg per day, about 3 mg to about 198 mg per day, about 4 mg to about 197 mg per day, about 5 mg to about 196 mg per day, about 6 mg to about 195 mg per day, about 7 mg to about 194 mg per day, about 8 mg to about 193 per day, about 9 mg to about 192 per day, about 10 mg to about 191 per day, about 11 mg to about 190 per day, about 12 mg to about 189 per day, about 13 mg to about 188 per day, about 14 mg to about 187 per day, about 15 mg to about 186 per day, about 16 mg to about 185 mg per day, about 17 mg to about 184 per day, about 18 mg to about 183 per day, about 19 mg to about 182 per day, about 20 mg to about 181 mg per day, about 21 mg to about 180 per day, about 22 mg to about 179 mg per day, about 23 mg to about 178 mg per day, about 24 mg to about 177 mg per day, about 25 mg to about 176 mg per day, about 26 mg to about 175 mg per day, about 27 mg to about 174 mg per day, about 28 mg to about 173 mg per day, about 29 mg to about 172 mg per day, about 30 mg to about 171 mg per day, about 31 mg to about 170 mg per day, about 32 mg to about 169 mg per day, about 33 mg to about 168 mg per day, about 34 mg to about 167 mg per day, about 35 mg to about 166 mg per day, about 36 mg to about 165 mg per day, about 37 mg to about 164 mg per day, about 38 mg to about 163 mg per day, about 39 mg to about 162 per day, about 40 mg to about 161 mg per day, about 41 to about 160 mg per day, about 42 to about 159 mg per day, about 43 mg to about 158 mg per day, about 44 mg to about 157 mg per day, about 45 mg to about 156 mg per day, about 46 mg to about 155 mg per day, about 47 mg to about 154 mg per day, about 48 mg to about 153 mg per day, about 49 mg to about 152 mg per day, about 50 mg to about 151 mg per day, about 51 mg to about 150 mg per day, about 52 mg to about 149 mg per day, about 53 mg to about 148 mg per day, about 54 mg to about 147 mg per day, about 55 mg to about 146 mg per day, about 56 mg to about 145 mg per day, about 57 mg to about 144 mg per day, about 58 mg to about 143 mg per day, about 59 mg to about 142 mg per day, about 60 mg to about 141 mg per day, about 61 mg to about 140 mg per day, about 62 mg to about 139 mg per day, about 63 mg to about 138 mg per day, about 64 mg to about 137 mg per day, about 65 mg to about 136 mg per day, about 66 mg to about 135 mg per day, about 67 mg to about 134 mg per day, about 68 mg to about 133 mg per day, about 69 mg to about 132 mg per day, about 70 mg to about 131 mg per day, about 71 mg to about 130 mg per day, about 72 mg to about 129 per day, about 73 mg to about 128 mg per day, about 74 mg to about 127 mg per day, about 75 mg to about 126 mg per day, about 76 mg to about 125 mg per day, about 77 mg to about 124 mg per day, about 78 mg to about 123 mg per day, about 79 mg to about 122 mg per day, about 80 mg to about 121 mg per day, about 81 mg to about 120 mg per day, about 82 mg to about 119 mg per day, about 83 mg to about 118 mg per day, about 84 mg to about 117 mg per day, about 85 mg to about 116 mg per day, about 86 mg to about 115 mg per day, about 87 mg to about 114 mg per day, about 88 mg to about 113 mg per day, about 89 mg to about 112 mg per day, about 90 mg to about 111 mg per day, about 91 mg to about 110 mg per day, about 92 mg to about 109 mg per day, about 93 mg to about 108 mg per day, about 94 mg to about 107 mg per day, about 95 mg to about 106 mg per day, about 96 mg to about 105 mg per day, about 97 mg to about 104 mg per day, about 98 mg to about 103 mg per day, about 99 mg to about 102 mg per day, or about 100 to about 101 mg per day, among others. Exemplary total daily quantities of nifedipine that may be (or may have been) administered to the subject include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, and 200 mg, among others.

In yet another aspect, the invention provides a method of delaying the onset of delivery (i.e., delaying the incidence of delivery) in a pregnant subject (e.g., a pregnant human female) by administering to the subject therapeutically effective amounts of nifedipine and a PGF2α receptor antagonist, such as a compound represented by formula (I)

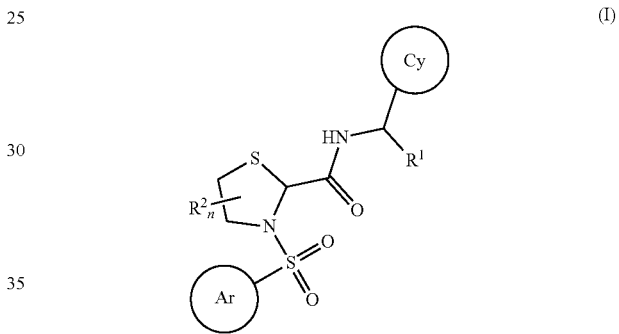

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine is administered to the subject in an amount of about 1,500 mg or less per week. For example, the subject may be administered from about 1 mg to about 1,500 mg of nifedipine per week, such as from about 10 mg to about 1,490 mg per week, about 20 mg to about 1,480 mg per week, about 30 mg to about 1,470 mg per week, about 40 mg to about 1,460 mg per week, about 50 mg to about 1,450 mg per week, about 60 mg to about 1,440 mg per week, about 70 mg to about 1,430 mg per week, about 80 mg to about 1,420 mg per week, about 90 mg to about 1,410 mg per week, about 100 mg to about 1,400 mg per week, about 110 mg to about 1,390 mg per week, about 120 mg to about 1,380 mg per week, about 130 mg to about 1,370 mg per week, about 140 mg to about 1,360 mg per week, about 150 mg to about 1,350 mg per week, about 160 mg to about 1,340 mg per week, about 170 mg to about 1,330 mg per week, about 180 mg to about 1,320 mg per week, about 190 mg to about 1,310 mg per week, about 200 mg to about 1,300 mg per week, about 210 mg to about 1,290 mg per week, about 220 mg to about 1,280 mg per week, about 230 mg to about 1,270 mg per week, about 240 mg to about 1,260 mg per week, about 250 mg to about 1,250 mg per week, about 260 mg to about 1,240 mg per week, about 270 mg to about 1,230 mg per week, about 280 mg to about 1,220 mg per week, about 290 mg to about 1,210 mg per week, about 300 mg to about 1,200 mg per week, about 310 mg to about 1,190 mg per week, about 320 mg to about 1,180 mg per week, about 330 mg to about 1,170 mg per week, about 340 mg to about 1,160 mg per week, about 350 mg to about 1,150 mg per week, about 360 mg to about 1,140 mg per week, about 370 mg to about 1,130 mg per week, about 380 mg to about 1,120 mg per week, about 390 mg to about 1,110 mg per week, about 400 mg to about 1,100 mg per week, about 410 mg to about 1,090 mg per week, about 420 mg to about 1,080 mg per week, about 430 mg to about 1,070 mg per week, about 440 mg to about 1,060 mg per week, about 450 mg to about 1,050 mg per week, about 460 mg to about 1,040 mg per week, about 470 mg to about 1,030 mg per week, about 480 mg to about 1,020 mg per week, about 490 mg to about 1,010 mg per week, about 500 mg to about 1,000 mg per week, about 510 mg to about 990 mg per week, about 520 mg to about 980 mg per week, about 530 mg to about 970 mg per week, about 540 mg to about 960 mg per week, about 550 mg to about 950 mg per week, about 560 mg to about 940 mg per week, about 570 mg to about 930 mg per week, about 580 mg to about 920 mg per week, about 590 mg to about 910 mg per week, about 600 mg to about 900 mg per week, about 610 mg to about 890 mg per week, about 620 mg to about 880 mg per week, about 630 mg to about 870 mg per week, about 640 mg to about 860 mg per week, about 650 mg to about 850 mg per week, about 660 mg to about 840 mg per week, about 670 mg to about 830 mg per week, about 680 mg to about 820 mg per week, about 690 mg to about 810 mg per week, about 700 mg to about 800 mg per week, about 710 mg to about 790 mg per week, about 720 mg to about 780 mg per week, about 730 mg to about 770 mg per week, or about 740 mg to about 760 mg per week, among others.

Exemplary total weekly quantities of nifedipine that may be administered to the subject in accordance with the preceding aspect include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, 1,000 mg, 1,005 mg, 1,010 mg, 1,015 mg, 1,020 mg, 1,025 mg, 1,030 mg, 1,035 mg, 1,040 mg, 1,045 mg, 1,050 mg, 1,055 mg, 1,060 mg, 1,065 mg, 1,070 mg, 1,075 mg, 1,080 mg, 1,085 mg, 1,090 mg, 1,095 mg, 1,100 mg, 1,105 mg, 1,110 mg, 1,115 mg, 1,120 mg, 1,125 mg, 1,130 mg, 1,135 mg, 1,140 mg, 1,145 mg, 1,150 mg, 1,155 mg, 1,160 mg, 1,165 mg, 1,170 mg, 1,175 mg, 1,180 mg, 1,185 mg, 1,190 mg, 1,195 mg, 1,200 mg, 1,205 mg, 1,210 mg, 1,215 mg, 1,220 mg, 1,225 mg, 1,230 mg, 1,235 mg, 1,240 mg, 1,245 mg, 1,250 mg, 1,255 mg, 1,260 mg, 1,265 mg, 1,270 mg, 1,275 mg, 1,280 mg, 1,285 mg, 1,290 mg, 1,295 mg, 1,300 mg, 1,305 mg, 1,310 mg, 1,315 mg, 1,320 mg, 1,325 mg, 1,330 mg, 1,335 mg, 1,340 mg, 1,345 mg, 1,350 mg, 1,355 mg, 1,360 mg, 1,365 mg, 1,370 mg, 1,375 mg, 1,380 mg, 1,385 mg, 1,390 mg, 1,395 mg, 900 mg, 1,405 mg, 1,410 mg, 1,415 mg, 1,420 mg, 1,425 mg, 1,430 mg, 1,435 mg, 1,440 mg, 1,445 mg, 1,450 mg, 1,455 mg, 1,460 mg, 1,465 mg, 1,470 mg, 1,475 mg, 1,480 mg, 1,485 mg, 1,490 mg, 1,495 mg, and 1,500 mg, among others.

In yet another aspect, the invention provides a method of delaying the onset of delivery (i.e., delaying the incidence of delivery) in a pregnant subject (e.g., a pregnant human female) by administering to the subject a therapeutically effective amount of a PGF2α receptor antagonist, such as a compound represented by formula (I)

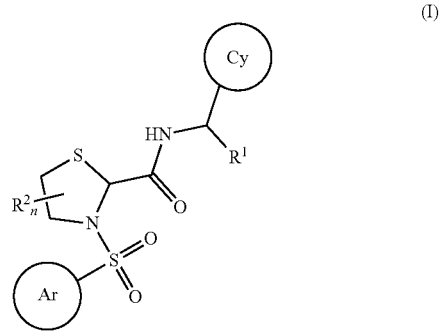

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 1,500 mg or less per week. For example, the subject may be one that is concurrently being administered nifedipine (or that has previously been administered nifedipine) in an amount of from about 1 mg to about 1,500 mg of nifedipine per week, such as from about 10 mg to about 1,490 mg per week, about 20 mg to about 1,480 mg per week, about 30 mg to about 1,470 mg per week, about 40 mg to about 1,460 mg per week, about 50 mg to about 1,450 mg per week, about 60 mg to about 1,440 mg per week, about 70 mg to about 1,430 mg per week, about 80 mg to about 1,420 mg per week, about 90 mg to about 1,410 mg per week, about 100 mg to about 1,400 mg per week, about 110 mg to about 1,390 mg per week, about 120 mg to about 1,380 mg per week, about 130 mg to about 1,370 mg per week, about 140 mg to about 1,360 mg per week, about 150 mg to about 1,350 mg per week, about 160 mg to about 1,340 mg per week, about 170 mg to about 1,330 mg per week, about 180 mg to about 1,320 mg per week, about 190 mg to about 1,310 mg per week, about 200 mg to about 1,300 mg per week, about 210 mg to about 1,290 mg per week, about 220 mg to about 1,280 mg per week, about 230 mg to about 1,270 mg per week, about 240 mg to about 1,260 mg per week, about 250 mg to about 1,250 mg per week, about 260 mg to about 1,240 mg per week, about 270 mg to about 1,230 mg per week, about 280 mg to about 1,220 mg per week, about 290 mg to about 1,210 mg per week, about 300 mg to about 1,200 mg per week, about 310 mg to about 1,190 mg per week, about 320 mg to about 1,180 mg per week, about 330 mg to about 1,170 mg per week, about 340 mg to about 1,160 mg per week, about 350 mg to about 1,150 mg per week, about 360 mg to about 1,140 mg per week, about 370 mg to about 1,130 mg per week, about 380 mg to about 1,120 mg per week, about 390 mg to about 1,110 mg per week, about 400 mg to about 1,100 mg per week, about 410 mg to about 1,090 mg per week, about 420 mg to about 1,080 mg per week, about 430 mg to about 1,070 mg per week, about 440 mg to about 1,060 mg per week, about 450 mg to about 1,050 mg per week, about 460 mg to about 1,040 mg per week, about 470 mg to about 1,030 mg per week, about 480 mg to about 1,020 mg per week, about 490 mg to about 1,010 mg per week, about 500 mg to about 1,000 mg per week, about 510 mg to about 990 mg per week, about 520 mg to about 980 mg per week, about 530 mg to about 970 mg per week, about 540 mg to about 960 mg per week, about 550 mg to about 950 mg per week, about 560 mg to about 940 mg per week, about 570 mg to about 930 mg per week, about 580 mg to about 920 mg per week, about 590 mg to about 910 mg per week, about 600 mg to about 900 mg per week, about 610 mg to about 890 mg per week, about 620 mg to about 880 mg per week, about 630 mg to about 870 mg per week, about 640 mg to about 860 mg per week, about 650 mg to about 850 mg per week, about 660 mg to about 840 mg per week, about 670 mg to about 830 mg per week, about 680 mg to about 820 mg per week, about 690 mg to about 810 mg per week, about 700 mg to about 800 mg per week, about 710 mg to about 790 mg per week, about 720 mg to about 780 mg per week, about 730 mg to about 770 mg per week, or about 740 mg to about 760 mg per week, among others.

Exemplary total weekly quantities of nifedipine that may be (or may have been) administered to the subject in accordance with the preceding aspect include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, 1,000 mg, 1,005 mg, 1,010 mg, 1,015 mg, 1,020 mg, 1,025 mg, 1,030 mg, 1,035 mg, 1,040 mg, 1,045 mg, 1,050 mg, 1,055 mg, 1,060 mg, 1,065 mg, 1,070 mg, 1,075 mg, 1,080 mg, 1,085 mg, 1,090 mg, 1,095 mg, 1,100 mg, 1,105 mg, 1,110 mg, 1,115 mg, 1,120 mg, 1,125 mg, 1,130 mg, 1,135 mg, 1,140 mg, 1,145 mg, 1,150 mg, 1,155 mg, 1,160 mg, 1,165 mg, 1,170 mg, 1,175 mg, 1,180 mg, 1,185 mg, 1,190 mg, 1,195 mg, 1,200 mg, 1,205 mg, 1,210 mg, 1,215 mg, 1,220 mg, 1,225 mg, 1,230 mg, 1,235 mg, 1,240 mg, 1,245 mg, 1,250 mg, 1,255 mg, 1,260 mg, 1,265 mg, 1,270 mg, 1,275 mg, 1,280 mg, 1,285 mg, 1,290 mg, 1,295 mg, 1,300 mg, 1,305 mg, 1,310 mg, 1,315 mg, 1,320 mg, 1,325 mg, 1,330 mg, 1,335 mg, 1,340 mg, 1,345 mg, 1,350 mg, 1,355 mg, 1,360 mg, 1,365 mg, 1,370 mg, 1,375 mg, 1,380 mg, 1,385 mg, 1,390 mg, 1,395 mg, 900 mg, 1,405 mg, 1,410 mg, 1,415 mg, 1,420 mg, 1,425 mg, 1,430 mg, 1,435 mg, 1,440 mg, 1,445 mg, 1,450 mg, 1,455 mg, 1,460 mg, 1,465 mg, 1,470 mg, 1,475 mg, 1,480 mg, 1,485 mg, 1,490 mg, 1,495 mg, and 1,500 mg, among others.

In an additional aspect, the invention features a method of reducing the frequency of, peak amplitude of, duration of, and/or work done by, uterine contractions in a pregnant subject (e.g., a pregnant human female) by administering to the subject therapeutically effective amounts of nifedipine and a PGF2α receptor antagonist, such as a compound represented by formula (I)

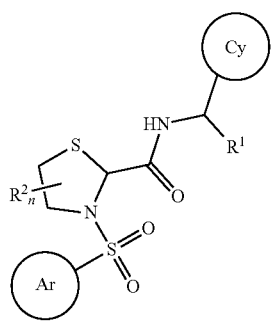

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group; $R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine may be administered to the subject in an amount, for example, of about 40 mg or less per dose. For instance, the nifedipine may be administered to the subject in an amount of from about 1 mg to about 40 mg per dose, about 2 mg to about 39 mg per dose, about 3 mg to about 38 mg per dose, about 4 mg to about 37 mg per dose, about 5 mg to about 36 mg per dose, about 6 mg to about 35 mg per dose, about 7 mg to about 34 mg per dose, about 8 mg to about 33 mg per dose, about 9 mg to about 32 mg per dose, about 10 mg to about 30 mg per dose, about 11 mg to about 29 mg per dose, about 12 mg to about 28 mg per dose, about 13 mg to about 27 mg per dose, about 14 mg to about 26 mg per dose, about 15 mg to about 25 mg per dose, about 16 mg to about 24 mg per dose, about 17 mg to about 23 mg per dose, about 18 mg to about 22 mg per dose, or about 19 mg to about 21 mg per dose, among others. Exemplary doses of nifedipine that may be administered to the subject include doses of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as a dose of about 20 mg, among others.

In an additional aspect, the invention features a method of reducing the frequency of, peak amplitude of, duration of, and/or work done by, uterine contractions in a pregnant subject (e.g., a pregnant human female) by administering to the subject a therapeutically effective amount of a PGF2α receptor antagonist, such as a compound represented by formula (I)

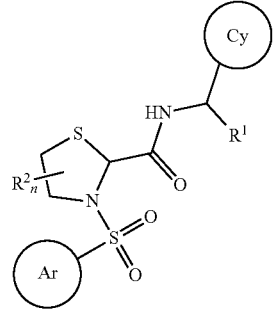

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount, for example, of about 40 mg or less per dose. For instance, the subject may be one that is concurrently being administered nifedipine (or that has previously been administered nifedipine) in an amount of from about 1 mg to about 40 mg per dose, about 2 mg to about 39 mg per dose, about 3 mg to about 38 mg per dose, about 4 mg to about 37 mg per dose, about 5 mg to about 36 mg per dose, about 6 mg to about 35 mg per dose, about 7 mg to about 34 mg per dose, about 8 mg to about 33 mg per dose, about 9 mg to about 32 mg per dose, about 10 mg to about 30 mg per dose, about 11 mg to about 29 mg per dose, about 12 mg to about 28 mg per dose, about 13 mg to about 27 mg per dose, about 14 mg to about 26 mg per dose, about 15 mg to about 25 mg per dose, about 16 mg to about 24 mg per dose, about 17 mg to about 23 mg per dose, about 18 mg to about 22 mg per dose, or about 19 mg to about 21 mg per dose, among others. Exemplary doses of nifedipine that may be (or may have been) administered to the subject include doses of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as a dose of about 20 mg, among others.

In another aspect, the invention features a method of reducing the frequency of, peak amplitude of, duration of, and/or work done by, uterine contractions in a pregnant subject (e.g., a pregnant human female) by administering to the subject therapeutically effective amounts of nifedipine and a PGF2α receptor antagonist, such as a compound represented by formula (I)

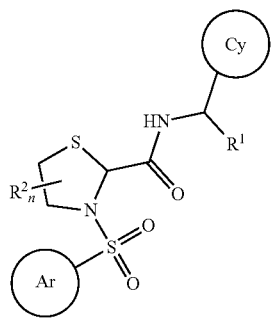

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine may be administered to the subject in an amount of about 40 mg or less in the first hour of treatment. For instance, the nifedipine may be administered to the subject in an amount of from about 1 mg to about 40 mg in the first hour of treatment, about 2 mg to about 39 mg in the first hour of treatment, about 3 mg to about 38 mg in the first hour of treatment, about 4 mg to about 37 mg in the first hour of treatment, about 5 mg to about 36 mg in the first hour of treatment, about 6 mg to about 35 mg in the first hour of treatment, about 7 mg to about 34 mg in the first hour of treatment, about 8 mg to about 33 mg in the first hour of treatment, about 9 mg to about 32 mg in the first hour of treatment, about 10 mg to about 30 mg in the first hour of treatment, about 11 mg to about 29 mg in the first hour of treatment, about 12 mg to about 28 mg in the first hour of treatment, about 13 mg to about 27 mg in the first hour of treatment, about 14 mg to about 26 mg in the first hour of treatment, about 15 mg to about 25 mg in the first hour of treatment, about 16 mg to about 24 mg in the first hour of treatment, about 17 mg to about 23 mg in the first hour of treatment, about 18 mg to about 22 mg in the first hour of treatment, or about 19 mg to about 21 mg in the first hour of treatment, among others. Exemplary amounts of nifedipine that may be administered to the subject in the first hour of treatment include amounts of nifedipine of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as an amount of about 20 mg, among others.

In another aspect, the invention features a method of reducing the frequency of, peak amplitude of, duration of, and/or work done by, uterine contractions in a pregnant subject (e.g., a pregnant human female) by administering to the subject a therapeutically effective amount of a PGF2α receptor antagonist, such as a compound represented by formula (I)

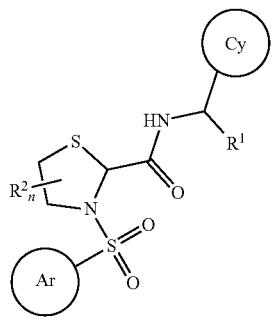

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 40 mg or less in the first hour of treatment. For instance, the subject may be one that is concurrently being administered nifedipine (or that has previously been administered nifedipine) in an amount of from about 1 mg to about 40 mg in the first hour of treatment, about 2 mg to about 39 mg in the first hour of treatment, about 3 mg to about 38 mg in the first hour of treatment, about 4 mg to about 37 mg in the first hour of treatment, about 5 mg to about 36 mg in the first hour of treatment, about 6 mg to about 35 mg in the first hour of treatment, about 7 mg to about 34 mg in the first hour of treatment, about 8 mg to about 33 mg in the first hour of treatment, about 9 mg to about 32 mg in the first hour of treatment, about 10 mg to about 30 mg in the first hour of treatment, about 11 mg to about 29 mg in the first hour of treatment, about 12 mg to about 28 mg in the first hour of treatment, about 13 mg to about 27 mg in the first hour of treatment, about 14 mg to about 26 mg in the first hour of treatment, about 15 mg to about 25 mg in the first hour of treatment, about 16 mg to about 24 mg in the first hour of treatment, about 17 mg to about 23 mg in the first hour of treatment, about 18 mg to about 22 mg in the first hour of treatment, or about 19 mg to about 21 mg in the first hour of treatment, among others. Exemplary amounts of nifedipine that may be (or may have been) administered to the subject in the first hour of treatment include amounts of nifedipine of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as an amount of about 20 mg, among others.

In another aspect, the invention features a method of reducing the frequency of, peak amplitude of, duration of, and/or work done by, uterine contractions in a pregnant subject (e.g., a pregnant human female) by administering to the subject therapeutically effective amounts of nifedipine and a PGF2α receptor antagonist, such as a compound represented by formula (I)

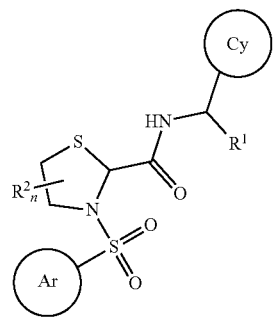

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine is administered to the subject in an amount of about 200 mg or less per day. For example, the nifedipine may be administered to the subject in an amount of from about 1 mg to about 200 mg per day, about 2 mg to about 199 mg per day, about 3 mg to about 198 mg per day, about 4 mg to about 197 mg per day, about 5 mg to about 196 mg per day, about 6 mg to about 195 mg per day, about 7 mg to about 194 mg per day, about 8 mg to about 193 per day, about 9 mg to about 192 per day, about 10 mg to about 191 per day, about 11 mg to about 190 per day, about 12 mg to about 189 per day, about 13 mg to about 188 per day, about 14 mg to about 187 per day, about 15 mg to about 186 per day, about 16 mg to about 185 mg per day, about 17 mg to about 184 per day, about 18 mg to about 183 per day, about 19 mg to about 182 per day, about 20 mg to about 181 mg per day, about 21 mg to about 180 per day, about 22 mg to about 179 mg per day, about 23 mg to about 178 mg per day, about 24 mg to about 177 mg per day, about 25 mg to about 176 mg per day, about 26 mg to about 175 mg per day, about 27 mg to about 174 mg per day, about 28 mg to about 173 mg per day, about 29 mg to about 172 mg per day, about 30 mg to about 171 mg per day, about 31 mg to about 170 mg per day, about 32 mg to about 169 mg per day, about 33 mg to about 168 mg per day, about 34 mg to about 167 mg per day, about 35 mg to about 166 mg per day, about 36 mg to about 165 mg per day, about 37 mg to about 164 mg per day, about 38 mg to about 163 mg per day, about 39 mg to about 162 per day, about 40 mg to about 161 mg per day, about 41 to about 160 mg per day, about 42 to about 159 mg per day, about 43 mg to about 158 mg per day, about 44 mg to about 157 mg per day, about 45 mg to about 156 mg per day, about 46 mg to about 155 mg per day, about 47 mg to about 154 mg per day, about 48 mg to about 153 mg per day, about 49 mg to about 152 mg per day, about 50 mg to about 151 mg per day, about 51 mg to about 150 mg per day, about 52 mg to about 149 mg per day, about 53 mg to about 148 mg per day, about 54 mg to about 147 mg per day, about 55 mg to about 146 mg per day, about 56 mg to about 145 mg per day, about 57 mg to about 144 mg per day, about 58 mg to about 143 mg per day, about 59 mg to about 142 mg per day, about 60 mg to about 141 mg per day, about 61 mg to about 140 mg per day, about 62 mg to about 139 mg per day, about 63 mg to about 138 mg per day, about 64 mg to about 137 mg per day, about 65 mg to about 136 mg per day, about 66 mg to about 135 mg per day, about 67 mg to about 134 mg per day, about 68 mg to about 133 mg per day, about 69 mg to about 132 mg per day, about 70 mg to about 131 mg per day, about 71 mg to about 130 mg per day, about 72 mg to about 129 mg per day, about 73 mg to about 128 mg per day, about 74 mg to about 127 mg per day, about 75 mg to about 126 mg per day, about 76 mg to about 125 mg per day, about 77 mg to about 124 mg per day, about 78 mg to about 123 mg per day, about 79 mg to about 122 mg per day, about 80 mg to about 121 mg per day, about 81 mg to about 120 mg per day, about 82 mg to about 119 mg per day, about 83 mg to about 118 mg per day, about 84 mg to about 117 mg per day, about 85 mg to about 116 mg per day, about 86 mg to about 115 mg per day, about 87 mg to about 114 mg per day, about 88 mg to about 113 mg per day, about 89 mg to about 112 mg per day, about 90 mg to about 111 mg per day, about 91 mg to about 110 mg per day, about 92 mg to about 109 mg per day, about 93 mg to about 108 mg per day, about 94 mg to about 107 mg per day, about 95 mg to about 106 mg per day, about 96 mg to about 105 mg per day, about 97 mg to about 104 mg per day, about 98 mg to about 103 mg per day, about 99 mg to about 102 mg per day, or about 100 to about 101 mg per day, among others. Exemplary total daily quantities of nifedipine that may be administered to the subject include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, and 200 mg, among others.

In another aspect, the invention features a method of reducing the frequency of, peak amplitude of, duration of, and/or work done by, uterine contractions in a pregnant subject (e.g., a pregnant human female) by administering to the subject a therapeutically effective amount of a PGF2α receptor antagonist, such as a compound represented by formula (I)

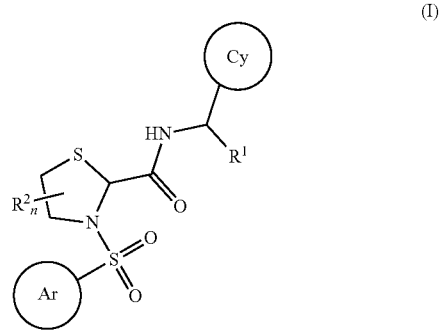

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 200 mg or less per day. For example, the subject may be one that is concurrently being administered nifedipine (or that has previously been administered nifedipine) in an amount of from about 1 mg to about 200 mg per day, about 2 mg to about 199 mg per day, about 3 mg to about 198 mg per day, about 4 mg to about 197 mg per day, about 5 mg to about 196 mg per day, about 6 mg to about 195 mg per day, about 7 mg to about 194 mg per day, about 8 mg to about 193 per day, about 9 mg to about 192 per day, about 10 mg to about 191 per day, about 11 mg to about 190 per day, about 12 mg to about 189 per day, about 13 mg to about 188 per day, about 14 mg to about 187 per day, about 15 mg to about 186 per day, about 16 mg to about 185 mg per day, about 17 mg to about 184 per day, about 18 mg to about 183 per day, about 19 mg to about 182 per day, about 20 mg to about 181 mg per day, about 21 mg to about 180 per day, about 22 mg to about 179 mg per day, about 23 mg to about 178 mg per day, about 24 mg to about 177 mg per day, about 25 mg to about 176 mg per day, about 26 mg to about 175 mg per day, about 27 mg to about 174 mg per day, about 28 mg to about 173 mg per day, about 29 mg to about 172 mg per day, about 30 mg to about 171 mg per day, about 31 mg to about 170 mg per day, about 32 mg to about 169 mg per day, about 33 mg to about 168 mg per day, about 34 mg to about 167 mg per day, about 35 mg to about 166 mg per day, about 36 mg to about 165 mg per day, about 37 mg to about 164 mg per day, about 38 mg to about 163 mg per day, about 39 mg to about 162 per day, about 40 mg to about 161 mg per day, about 41 to about 160 mg per day, about 42 to about 159 mg per day, about 43 mg to about 158 mg per day, about 44 mg to about 157 mg per day, about 45 mg to about 156 mg per day, about 46 mg to about 155 mg per day, about 47 mg to about 154 mg per day, about 48 mg to about 153 mg per day, about 49 mg to about 152 mg per day, about 50 mg to about 151 mg per day, about 51 mg to about 150 mg per day, about 52 mg to about 149 mg per day, about 53 mg to about 148 mg per day, about 54 mg to about 147 mg per day, about 55 mg to about 146 mg per day, about 56 mg to about 145 mg per day, about 57 mg to about 144 mg per day, about 58 mg to about 143 mg per day, about 59 mg to about 142 mg per day, about 60 mg to about 141 mg per day, about 61 mg to about 140 mg per day, about 62 mg to about 139 mg per day, about 63 mg to about 138 mg per day, about 64 mg to about 137 mg per day, about 65 mg to about 136 mg per day, about 66 mg to about 135 mg per day, about 67 mg to about 134 mg per day, about 68 mg to about 133 mg per day, about 69 mg to about 132 mg per day, about 70 mg to about 131 mg per day, about 71 mg to about 130 mg per day, about 72 mg to about 129 mg per day, about 73 mg to about 128 mg per day, about 74 mg to about 127 mg per day, about 75 mg to about 126 mg per day, about 76 mg to about 125 mg per day, about 77 mg to about 124 mg per day, about 78 mg to about 123 mg per day, about 79 mg to about 122 mg per day, about 80 mg to about 121 mg per day, about 81 mg to about 120 mg per day, about 82 mg to about 119 mg per day, about 83 mg to about 118 mg per day, about 84 mg to about 117 mg per day, about 85 mg to about 116 mg per day, about 86 mg to about 115 mg per day, about 87 mg to about 114 mg per day, about 88 mg to about 113 mg per day, about 89 mg to about 112 mg per day, about 90 mg to about 111 mg per day, about 91 mg to about 110 mg per day, about 92 mg to about 109 mg per day, about 93 mg to about 108 mg per day, about 94 mg to about 107 mg per day, about 95 mg to about 106 mg per day, about 96 mg to about 105 mg per day, about 97 mg to about 104 mg per day, about 98 mg to about 103 mg per day, about 99 mg to about 102 mg per day, or about 100 to about 101 mg per day, among others. Exemplary total daily quantities of nifedipine that may be (or may have been) administered to the subject include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, and 200 mg, among others.

In yet another aspect, the invention provides a method of reducing the frequency of, peak amplitude of, duration of, and/or work done by, uterine contractions in a pregnant subject (e.g., a pregnant human female) by administering to the subject therapeutically effective amounts of nifedipine and a PGF2α receptor antagonist, such as a compound represented by formula (I)

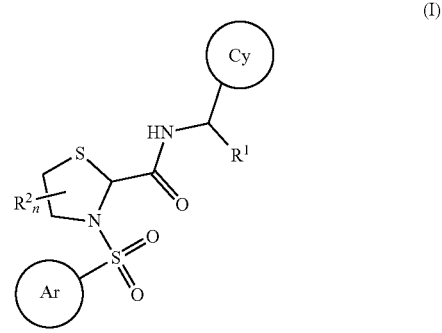

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine is administered to the subject in an amount of about 1,500 mg or less per week. For example, the subject may be administered from about 1 mg to about 1,500 mg of nifedipine per week, such as from about 10 mg to about 1,490 mg per week, about 20 mg to about 1,480 mg per week, about 30 mg to about 1,470 mg per week, about 40 mg to about 1,460 mg per week, about 50 mg to about 1,450 mg per week, about 60 mg to about 1,440 mg per week, about 70 mg to about 1,430 mg per week, about 80 mg to about 1,420 mg per week, about 90 mg to about 1,410 mg per week, about 100 mg to about 1,400 mg per week, about 110 mg to about 1,390 mg per week, about 120 mg to about 1,380 mg per week, about 130 mg to about 1,370 mg per week, about 140 mg to about 1,360 mg per week, about 150 mg to about 1,350 mg per week, about 160 mg to about 1,340 mg per week, about 170 mg to about 1,330 mg per week, about 180 mg to about 1,320 mg per week, about 190 mg to about 1,310 mg per week, about 200 mg to about 1,300 mg per week, about 210 mg to about 1,290 mg per week, about 220 mg to about 1,280 mg per week, about 230 mg to about 1,270 mg per week, about 240 mg to about 1,260 mg per week, about 250 mg to about 1,250 mg per week, about 260 mg to about 1,240 mg per week, about 270 mg to about 1,230 mg per week, about 280 mg to about 1,220 mg per week, about 290 mg to about 1,210 mg per week, about 300 mg to about 1,200 mg per week, about 310 mg to about 1,190 mg per week, about 320 mg to about 1,180 mg per week, about 330 mg to about 1,170 mg per week, about 340 mg to about 1,160 mg per week, about 350 mg to about 1,150 mg per week, about 360 mg to about 1,140 mg per week, about 370 mg to about 1,130 mg per week, about 380 mg to about 1,120 mg per week, about 390 mg to about 1,110 mg per week, about 400 mg to about 1,100 mg per week, about 410 mg to about 1,090 mg per week, about 420 mg to about 1,080 mg per week, about 430 mg to about 1,070 mg per week, about 440 mg to about 1,060 mg per week, about 450 mg to about 1,050 mg per week, about 460 mg to about 1,040 mg per week, about 470 mg to about 1,030 mg per week, about 480 mg to about 1,020 mg per week, about 490 mg to about 1,010 mg per week, about 500 mg to about 1,000 mg per week, about 510 mg to about 990 mg per week, about 520 mg to about 980 mg per week, about 530 mg to about 970 mg per week, about 540 mg to about 960 mg per week, about 550 mg to about 950 mg per week, about 560 mg to about 940 mg per week, about 570 mg to about 930 mg per week, about 580 mg to about 920 mg per week, about 590 mg to about 910 mg per week, about 600 mg to about 900 mg per week, about 610 mg to about 890 mg per week, about 620 mg to about 880 mg per week, about 630 mg to about 870 mg per week, about 640 mg to about 860 mg per week, about 650 mg to about 850 mg per week, about 660 mg to about 840 mg per week, about 670 mg to about 830 mg per week, about 680 mg to about 820 mg per week, about 690 mg to about 810 mg per week, about 700 mg to about 800 mg per week, about 710 mg to about 790 mg per week, about 720 mg to about 780 mg per week, about 730 mg to about 770 mg per week, or about 740 mg to about 760 mg per week, among others.

Exemplary total weekly quantities of nifedipine that may be administered to the subject in accordance with the preceding aspect include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, 1,000 mg, 1,005 mg, 1,010 mg, 1,015 mg, 1,020 mg, 1,025 mg, 1,030 mg, 1,035 mg, 1,040 mg, 1,045 mg, 1,050 mg, 1,055 mg, 1,060 mg, 1,065 mg, 1,070 mg, 1,075 mg, 1,080 mg, 1,085 mg, 1,090 mg, 1,095 mg, 1,100 mg, 1,105 mg, 1,110 mg, 1,115 mg, 1,120 mg, 1,125 mg, 1,130 mg, 1,135 mg, 1,140 mg, 1,145 mg, 1,150 mg, 1,155 mg, 1,160 mg, 1,165 mg, 1,170 mg, 1,175 mg, 1,180 mg, 1,185 mg, 1,190 mg, 1,195 mg, 1,200 mg, 1,205 mg, 1,210 mg, 1,215 mg, 1,220 mg, 1,225 mg, 1,230 mg, 1,235 mg, 1,240 mg, 1,245 mg, 1,250 mg, 1,255 mg, 1,260 mg, 1,265 mg, 1,270 mg, 1,275 mg, 1,280 mg, 1,285 mg, 1,290 mg, 1,295 mg, 1,300 mg, 1,305 mg, 1,310 mg, 1,315 mg, 1,320 mg, 1,325 mg, 1,330 mg, 1,335 mg, 1,340 mg, 1,345 mg, 1,350 mg, 1,355 mg, 1,360 mg, 1,365 mg, 1,370 mg, 1,375 mg, 1,380 mg, 1,385 mg, 1,390 mg, 1,395 mg, 900 mg, 1,405 mg, 1,410 mg, 1,415 mg, 1,420 mg, 1,425 mg, 1,430 mg, 1,435 mg, 1,440 mg, 1,445 mg, 1,450 mg, 1,455 mg, 1,460 mg, 1,465 mg, 1,470 mg, 1,475 mg, 1,480 mg, 1,485 mg, 1,490 mg, 1,495 mg, and 1,500 mg, among others.

In yet another aspect, the invention provides a method of reducing the frequency of, peak amplitude of, duration of, and/or work done by, uterine contractions in a pregnant subject (e.g., a pregnant human female) by administering to the subject a therapeutically effective amount of a PGF2α receptor antagonist, such as a compound represented by formula (I)

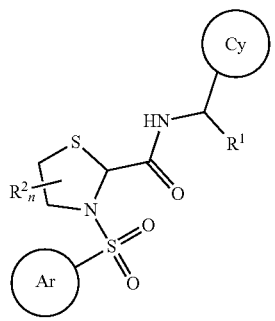

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 1,500 mg or less per week. For example, the subject may be one that is concurrently being administered nifedipine (or that has previously been administered nifedipine) in an amount of from about 1 mg to about 1,500 mg of nifedipine per week, such as from about 10 mg to about 1,490 mg per week, about 20 mg to about 1,480 mg per week, about 30 mg to about 1,470 mg per week, about 40 mg to about 1,460 mg per week, about 50 mg to about 1,450 mg per week, about 60 mg to about 1,440 mg per week, about 70 mg to about 1,430 mg per week, about 80 mg to about 1,420 mg per week, about 90 mg to about 1,410 mg per week, about 100 mg to about 1,400 mg per week, about 110 mg to about 1,390 mg per week, about 120 mg to about 1,380 mg per week, about 130 mg to about 1,370 mg per week, about 140 mg to about 1,360 mg per week, about 150 mg to about 1,350 mg per week, about 160 mg to about 1,340 mg per week, about 170 mg to about 1,330 mg per week, about 180 mg to about 1,320 mg per week, about 190 mg to about 1,310 mg per week, about 200 mg to about 1,300 mg per week, about 210 mg to about 1,290 mg per week, about 220 mg to about 1,280 mg per week, about 230 mg to about 1,270 mg per week, about 240 mg to about 1,260 mg per week, about 250 mg to about 1,250 mg per week, about 260 mg to about 1,240 mg per week, about 270 mg to about 1,230 mg per week, about 280 mg to about 1,220 mg per week, about 290 mg to about 1,210 mg per week, about 300 mg to about 1,200 mg per week, about 310 mg to about 1,190 mg per week, about 320 mg to about 1,180 mg per week, about 330 mg to about 1,170 mg per week, about 340 mg to about 1,160 mg per week, about 350 mg to about 1,150 mg per week, about 360 mg to about 1,140 mg per week, about 370 mg to about 1,130 mg per week, about 380 mg to about 1,120 mg per week, about 390 mg to about 1,110 mg per week, about 400 mg to about 1,100 mg per week, about 410 mg to about 1,090 mg per week, about 420 mg to about 1,080 mg per week, about 430 mg to about 1,070 mg per week, about 440 mg to about 1,060 mg per week, about 450 mg to about 1,050 mg per week, about 460 mg to about 1,040 mg per week, about 470 mg to about 1,030 mg per week, about 480 mg to about 1,020 mg per week, about 490 mg to about 1,010 mg per week, about 500 mg to about 1,000 mg per week, about 510 mg to about 990 mg per week, about 520 mg to about 980 mg per week, about 530 mg to about 970 mg per week, about 540 mg to about 960 mg per week, about 550 mg to about 950 mg per week, about 560 mg to about 940 mg per week, about 570 mg to about 930 mg per week, about 580 mg to about 920 mg per week, about 590 mg to about 910 mg per week, about 600 mg to about 900 mg per week, about 610 mg to about 890 mg per week, about 620 mg to about 880 mg per week, about 630 mg to about 870 mg per week, about 640 mg to about 860 mg per week, about 650 mg to about 850 mg per week, about 660 mg to about 840 mg per week, about 670 mg to about 830 mg per week, about 680 mg to about 820 mg per week, about 690 mg to about 810 mg per week, about 700 mg to about 800 mg per week, about 710 mg to about 790 mg per week, about 720 mg to about 780 mg per week, about 730 mg to about 770 mg per week, or about 740 mg to about 760 mg per week, among others.

Exemplary total weekly quantities of nifedipine that may be (or may have been) administered to the subject in accordance with the preceding aspect include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, 1,000 mg, 1,005 mg, 1,010 mg, 1,015 mg, 1,020 mg, 1,025 mg, 1,030 mg, 1,035 mg, 1,040 mg, 1,045 mg, 1,050 mg, 1,055 mg, 1,060 mg, 1,065 mg, 1,070 mg, 1,075 mg, 1,080 mg, 1,085 mg, 1,090 mg, 1,095 mg, 1,100 mg, 1,105 mg, 1,110 mg, 1,115 mg, 1,120 mg, 1,125 mg, 1,130 mg, 1,135 mg, 1,140 mg, 1,145 mg, 1,150 mg, 1,155 mg, 1,160 mg, 1,165 mg, 1,170 mg, 1,175 mg, 1,180 mg, 1,185 mg, 1,190 mg, 1,195 mg, 1,200 mg, 1,205 mg, 1,210 mg, 1,215 mg, 1,220 mg, 1,225 mg, 1,230 mg, 1,235 mg, 1,240 mg, 1,245 mg, 1,250 mg, 1,255 mg, 1,260 mg, 1,265 mg, 1,270 mg, 1,275 mg, 1,280 mg, 1,285 mg, 1,290 mg, 1,295 mg, 1,300 mg, 1,305 mg, 1,310 mg, 1,315 mg, 1,320 mg, 1,325 mg, 1,330 mg, 1,335 mg, 1,340 mg, 1,345 mg, 1,350 mg, 1,355 mg, 1,360 mg, 1,365 mg, 1,370 mg, 1,375 mg, 1,380 mg, 1,385 mg, 1,390 mg, 1,395 mg, 900 mg, 1,405 mg, 1,410 mg, 1,415 mg, 1,420 mg, 1,425 mg, 1,430 mg, 1,435 mg, 1,440 mg, 1,445 mg, 1,450 mg, 1,455 mg, 1,460 mg, 1,465 mg, 1,470 mg, 1,475 mg, 1,480 mg, 1,485 mg, 1,490 mg, 1,495 mg, and 1,500 mg, among others.

In yet another aspect, the invention features a method of reducing the expression of a proinflammatory and/or contractile gene, such as cyclooxygenase-2 (Cox2), in a pregnant subject (e.g., a pregnant human female), such as in the myometrium of a pregnant human subject, by administering to the subject therapeutically effective amounts of nifedipine and a PGF2α receptor antagonist, such as a compound represented by formula (I)

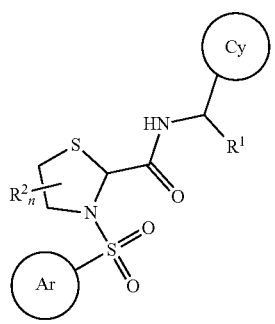

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine may be administered to the subject in an amount, for example, of about 40 mg or less per dose. For instance, the nifedipine may be administered to the subject in an amount of from about 1 mg to about 40 mg per dose, about 2 mg to about 39 mg per dose, about 3 mg to about 38 mg per dose, about 4 mg to about 37 mg per dose, about 5 mg to about 36 mg per dose, about 6 mg to about 35 mg per dose, about 7 mg to about 34 mg per dose, about 8 mg to about 33 mg per dose, about 9 mg to about 32 mg per dose, about 10 mg to about 30 mg per dose, about 11 mg to about 29 mg per dose, about 12 mg to about 28 mg per dose, about 13 mg to about 27 mg per dose, about 14 mg to about 26 mg per dose, about 15 mg to about 25 mg per dose, about 16 mg to about 24 mg per dose, about 17 mg to about 23 mg per dose, about 18 mg to about 22 mg per dose, or about 19 mg to about 21 mg per dose, among others. Exemplary doses of nifedipine that may be administered to the subject include doses of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as a dose of about 20 mg, among others.

In yet another aspect, the invention features a method of reducing the expression of a proinflammatory and/or contractile gene, such as cyclooxygenase-2 (Cox2), in a pregnant subject (e.g., a pregnant human female), such as in the myometrium of a pregnant human subject, by administering to the subject a therapeutically effective amount of a PGF2α receptor antagonist, such as a compound represented by formula (I)

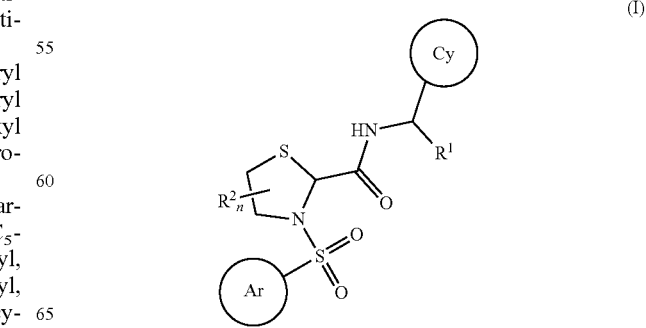

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 40 mg or less per dose. For instance, the subject may be one that is concurrently being administered nifedipine (or that has previously been administered nifedipine) in an amount of from about 1 mg to about 40 mg per dose, about 2 mg to about 39 mg per dose, about 3 mg to about 38 mg per dose, about 4 mg to about 37 mg per dose, about 5 mg to about 36 mg per dose, about 6 mg to about 35 mg per dose, about 7 mg to about 34 mg per dose, about 8 mg to about 33 mg per dose, about 9 mg to about 32 mg per dose, about 10 mg to about 30 mg per dose, about 11 mg to about 29 mg per dose, about 12 mg to about 28 mg per dose, about 13 mg to about 27 mg per dose, about 14 mg to about 26 mg per dose, about 15 mg to about 25 mg per dose, about 16 mg to about 24 mg per dose, about 17 mg to about 23 mg per dose, about 18 mg to about 22 mg per dose, or about 19 mg to about 21 mg per dose, among others. Exemplary doses of nifedipine that may be (or may have been) administered to the subject include doses of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as a dose of about 20 mg, among others.

In another aspect, the invention features a method of reducing the expression of a proinflammatory and/or contractile gene, such as Cox2, in a pregnant subject (e.g., a pregnant human female), such as in the myometrium of a pregnant human subject, by administering to the subject therapeutically effective amounts of nifedipine and a PGF2α receptor antagonist, such as a compound represented by formula (I)

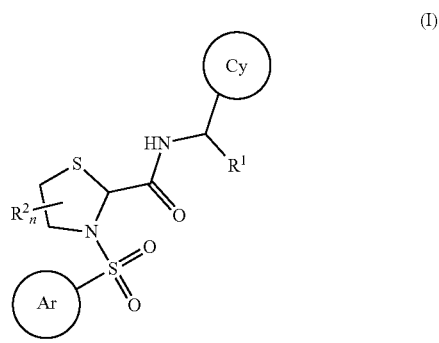

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine may be administered to the subject in an amount of about 40 mg or less in the first hour of treatment. For instance, the nifedipine may be administered to the subject in an amount of from about 1 mg to about 40 mg in the first hour of treatment, about 2 mg to about 39 mg in the first hour of treatment, about 3 mg to about 38 mg in the first hour of treatment, about 4 mg to about 37 mg in the first hour of treatment, about 5 mg to about 36 mg in the first hour of treatment, about 6 mg to about 35 mg in the first hour of treatment, about 7 mg to about 34 mg in the first hour of treatment, about 8 mg to about 33 mg in the first hour of treatment, about 9 mg to about 32 mg in the first hour of treatment, about 10 mg to about 30 mg in the first hour of treatment, about 11 mg to about 29 mg in the first hour of treatment, about 12 mg to about 28 mg in the first hour of treatment, about 13 mg to about 27 mg in the first hour of treatment, about 14 mg to about 26 mg in the first hour of treatment, about 15 mg to about 25 mg in the first hour of treatment, about 16 mg to about 24 mg in the first hour of treatment, about 17 mg to about 23 mg in the first hour of treatment, about 18 mg to about 22 mg in the first hour of treatment, or about 19 mg to about 21 mg in the first hour of treatment, among others.

Exemplary amounts of nifedipine that may be administered to the subject in the first hour of treatment include amounts of nifedipine of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as an amount of about 20 mg, among others.

In another aspect, the invention features a method of reducing the expression of a proinflammatory and/or contractile gene, such as Cox2, in a pregnant subject (e.g., a pregnant human female), such as in the myometrium of a pregnant human subject, by administering to the subject a therapeutically effective amount of a PGF2α receptor antagonist, such as a compound represented by formula (I)

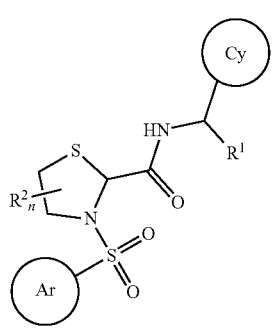

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 40 mg or less in the first hour of treatment. For instance, the subject may be one that is concurrently being administered nifedipine (or that has previously been administered nifedipine) in an amount of from about 1 mg to about 40 mg in the first hour of treatment, about 2 mg to about 39 mg in the first hour of treatment, about 3 mg to about 38 mg in the first hour of treatment, about 4 mg to about 37 mg in the first hour of treatment, about 5 mg to about 36 mg in the first hour of treatment, about 6 mg to about 35 mg in the first hour of treatment, about 7 mg to about 34 mg in the first hour of treatment, about 8 mg to about 33 mg in the first hour of treatment, about 9 mg to about 32 mg in the first hour of treatment, about 10 mg to about 30 mg in the first hour of treatment, about 11 mg to about 29 mg in the first hour of treatment, about 12 mg to about 28 mg in the first hour of treatment, about 13 mg to about 27 mg in the first hour of treatment, about 14 mg to about 26 mg in the first hour of treatment, about 15 mg to about 25 mg in the first hour of treatment, about 16 mg to about 24 mg in the first hour of treatment, about 17 mg to about 23 mg in the first hour of treatment, about 18 mg to about 22 mg in the first hour of treatment, or about 19 mg to about 21 mg in the first hour of treatment, among others. Exemplary amounts of nifedipine that may be (or may have been) administered to the subject in the first hour of treatment include amounts of nifedipine of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as an amount of about 20 mg, among others.

In another aspect, the invention features a method of reducing the expression of a proinflammatory and/or contractile gene, such as Cox2, in a pregnant subject (e.g., a pregnant human female), such as in the myometrium of a pregnant human subject) by administering to the subject therapeutically effective amounts of nifedipine and a PGF2α receptor antagonist, such as a compound represented by formula (I)

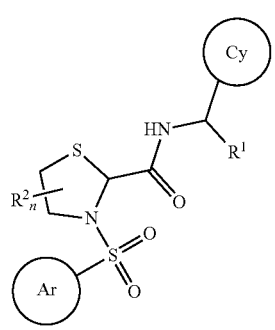

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine is administered to the subject in an amount of about 200 mg or less per day. For example, the nifedipine may be administered to the subject in an amount of from about 1 mg to about 200 mg per day, about 2 mg to about 199 mg per day, about 3 mg to about 198 mg per day, about 4 mg to about 197 mg per day, about 5 mg to about 196 mg per day, about 6 mg to about 195 mg per day, about 7 mg to about 194 mg per day, about 8 mg to about 193 per day, about 9 mg to about 192 per day, about 10 mg to about 191 per day, about 11 mg to about 190 per day, about 12 mg to about 189 per day, about 13 mg to about 188 per day, about 14 mg to about 187 per day, about 15 mg to about 186 per day, about 16 mg to about 185 mg per day, about 17 mg to about 184 per day, about 18 mg to about 183 per day, about 19 mg to about 182 per day, about 20 mg to about 181 per day, about 21 mg to about 180 per day, about 22 mg to about 179 per day, about 23 mg to about 178 per day, about 24 mg to about 177 mg per day, about 25 mg to about 176 mg per day, about 26 mg to about 175 mg per day, about 27 mg to about 174 mg per day, about 28 mg to about 173 mg per day, about 29 mg to about 172 mg per day, about 30 mg to about 171 mg per day, about 31 mg to about 170 mg per day, about 32 mg to about 169 mg per day, about 33 mg to about 168 mg per day, about 34 mg to about 167 mg per day, about 35 mg to about 166 mg per day, about 36 mg to about 165 mg per day, about 37 mg to about 164 mg per day, about 38 mg to about 163 mg per day, about 39 mg to about 162 per day, about 40 mg to about 161 mg per day, about 41 to about 160 mg per day, about 42 to about 159 mg per day, about 43 mg to about 158 mg per day, about 44 mg to about 157 mg per day, about 45 mg to about 156 mg per day, about 46 mg to about 155 mg per day, about 47 mg to about 154 mg per day, about 48 mg to about 153 mg per day, about 49 mg to about 152 mg per day, about 50 mg to about 151 mg per day, about 51 mg to about 150 mg per day, about 52 mg to about 149 mg per day, about 53 mg to about 148 mg per day, about 54 mg to about 147 mg per day, about 55 mg to about 146 mg per day, about 56 mg to about 145 mg per day, about 57 mg to about 144 mg per day, about 58 mg to about 143 mg per day, about 59 mg to about 142 mg per day, about 60 mg to about 141 mg per day, about 61 mg to about 140 mg per day, about 62 mg to about 139 mg per day, about 63 mg to about 138 mg per day, about 64 mg to about 137 mg per day, about 65 mg to about 136 mg per day, about 66 mg to about 135 mg per day, about 67 mg to about 134 mg per day, about 68 mg to about 133 mg per day, about 69 mg to about 132 mg per day, about 70 mg to about 131 mg per day, about 71 mg to about 130 mg per day, about 72 mg to about 129 per day, about 73 mg to about 128 mg per day, about 74 mg to about 127 mg per day, about 75 mg to about 126 mg per day, about 76 mg to about 125 mg per day, about 77 mg to about 124 mg per day, about 78 mg to about 123 mg per day, about 79 mg to about 122 mg per day, about 80 mg to about 121 mg per day, about 81 mg to about 120 mg per day, about 82 mg to about 119 mg per day, about 83 mg to about 118 mg per day, about 84 mg to about 117 mg per day, about 85 mg to about 116 mg per day, about 86 mg to about 115 mg per day, about 87 mg to about 114 mg per day, about 88 mg to about 113 mg per day, about 89 mg to about 112 mg per day, about 90 mg to about 111 mg per day, about 91 mg to about 110 mg per day, about 92 mg to about 109 mg per day, about 93 mg to about 108 mg per day, about 94 mg to about 107 mg per day, about 95 mg to about 106 mg per day, about 96 mg to about 105 mg per day, about 97 mg to about 104 mg per day, about 98 mg to about 103 mg per day, about 99 mg to about 102 mg per day, or about 100 to about 101 mg per day, among others. Exemplary total daily quantities of nifedipine that may be administered to the subject include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, and 200 mg, among others.

In another aspect, the invention features a method of reducing the expression of a proinflammatory and/or contractile gene, such as Cox2, in a pregnant subject (e.g., a pregnant human female), such as in the myometrium of a pregnant human subject) by administering to the subject a therapeutically effective amount of a PGF2α receptor antagonist, such as a compound represented by formula (I)

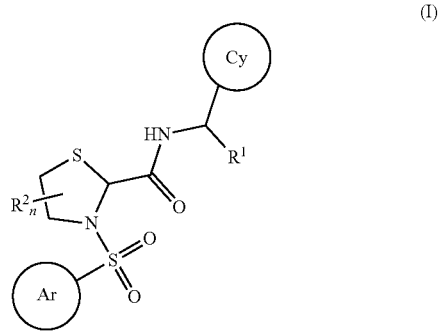

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 200 mg or less per day. For example, the subject may be one that is concurrently being administered nifedipine (or that has previously been administered nifedipine) in an amount of from about 1 mg to about 200 mg per day, about 2 mg to about 199 mg per day, about 3 mg to about 198 mg per day, about 4 mg to about 197 mg per day, about 5 mg to about 196 mg per day, about 6 mg to about 195 mg per day, about 7 mg to about 194 mg per day, about 8 mg to about 193 per day, about 9 mg to about 192 per day, about 10 mg to about 191 per day, about 11 mg to about 190 per day, about 12 mg to about 189 per day, about 13 mg to about 188 per day, about 14 mg to about 187 per day, about 15 mg to about 186 per day, about 16 mg to about 185 mg per day, about 17 mg to about 184 per day, about 18 mg to about 183 per day, about 19 mg to about 182 per day, about 20 mg to about 181 mg per day, about 21 mg to about 180 per day, about 22 mg to about 179 mg per day, about 23 mg to about 178 mg per day, about 24 mg to about 177 mg per day, about 25 mg to about 176 mg per day, about 26 mg to about 175 mg per day, about 27 mg to about 174 mg per day, about 28 mg to about 173 mg per day, about 29 mg to about 172 mg per day, about 30 mg to about 171 mg per day, about 31 mg to about 170 mg per day, about 32 mg to about 169 mg per day, about 33 mg to about 168 mg per day, about 34 mg to about 167 mg per day, about 35 mg to about 166 mg per day, about 36 mg to about 165 mg per day, about 37 mg to about 164 mg per day, about 38 mg to about 163 mg per day, about 39 mg to about 162 mg per day, about 40 mg to about 161 mg per day, about 41 to about 160 mg per day, about 42 to about 159 mg per day, about 43 mg to about 158 mg per day, about 44 mg to about 157 mg per day, about 45 mg to about 156 mg per day, about 46 mg to about 155 mg per day, about 47 mg to about 154 mg per day, about 48 mg to about 153 mg per day, about 49 mg to about 152 mg per day, about 50 mg to about 151 mg per day, about 51 mg to about 150 mg per day, about 52 mg to about 149 mg per day, about 53 mg to about 148 mg per day, about 54 mg to about 147 mg per day, about 55 mg to about 146 mg per day, about 56 mg to about 145 mg per day, about 57 mg to about 144 mg per day, about 58 mg to about 143 mg per day, about 59 mg to about 142 mg per day, about 60 mg to about 141 mg per day, about 61 mg to about 140 mg per day, about 62 mg to about 139 mg per day, about 63 mg to about 138 mg per day, about 64 mg to about 137 mg per day, about 65 mg to about 136 mg per day, about 66 mg to about 135 mg per day, about 67 mg to about 134 mg per day, about 68 mg to about 133 mg per day, about 69 mg to about 132 mg per day, about 70 mg to about 131 mg per day, about 71 mg to about 130 mg per day, about 72 mg to about 129 per day, about 73 mg to about 128 mg per day, about 74 mg to about 127 mg per day, about 75 mg to about 126 mg per day, about 76 mg to about 125 mg per day, about 77 mg to about 124 mg per day, about 78 mg to about 123 mg per day, about 79 mg to about 122 mg per day, about 80 mg to about 121 mg per day, about 81 mg to about 120 mg per day, about 82 mg to about 119 mg per day, about 83 mg to about 118 mg per day, about 84 mg to about 117 mg per day, about 85 mg to about 116 mg per day, about 86 mg to about 115 mg per day, about 87 mg to about 114 mg per day, about 88 mg to about 113 mg per day, about 89 mg to about 112 mg per day, about 90 mg to about 111 mg per day, about 91 mg to about 110 mg per day, about 92 mg to about 109 mg per day, about 93 mg to about 108 mg per day, about 94 mg to about 107 mg per day, about 95 mg to about 106 mg per day, about 96 mg to about 105 mg per day, about 97 mg to about 104 mg per day, about 98 mg to about 103 mg per day, about 99 mg to about 102 mg per day, or about 100 to about 101 mg per day, among others. Exemplary total daily quantities of nifedipine that may be (or may have been) administered to the subject include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, and 200 mg, among others.

In yet another aspect, the invention provides a method of reducing the expression of a proinflammatory and/or contractile gene, such as Cox2, in a pregnant subject (e.g., a pregnant human female), such as in the myometrium of a pregnant human subject) by administering to the subject therapeutically effective amounts of nifedipine and a PGF2α receptor antagonist, such as a compound represented by formula (I)

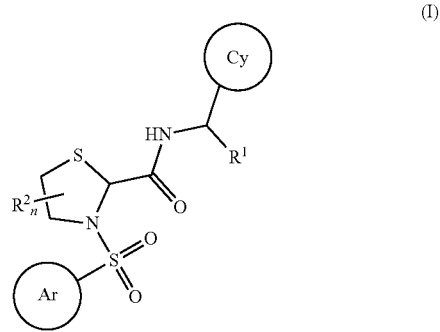

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine is administered to the subject in an amount of about 1,500 mg or less per week. For example, the subject may be administered from about 1 mg to about 1,500 mg of nifedipine per week, such as from about 10 mg to about 1,490 mg per week, about 20 mg to about 1,480 mg per week, about 30 mg to about 1,470 mg per week, about 40 mg to about 1,460 mg per week, about 50 mg to about 1,450 mg per week, about 60 mg to about 1,440 mg per week, about 70 mg to about 1,430 mg per week, about 80 mg to about 1,420 mg per week, about 90 mg to about 1,410 mg per week, about 100 mg to about 1,400 mg per week, about 110 mg to about 1,390 mg per week, about 120 mg to about 1,380 mg per week, about 130 mg to about 1,370 mg per week, about 140 mg to about 1,360 mg per week, about 150 mg to about 1,350 mg per week, about 160 mg to about 1,340 mg per week, about 170 mg to about 1,330 mg per week, about 180 mg to about 1,320 mg per week, about 190 mg to about 1,310 mg per week, about 200 mg to about 1,300 mg per week, about 210 mg to about 1,290 mg per week, about 220 mg to about 1,280 mg per week, about 230 mg to about 1,270 mg per week, about 240 mg to about 1,260 mg per week, about 250 mg to about 1,250 mg per week, about 260 mg to about 1,240 mg per week, about 270 mg to about 1,230 mg per week, about 280 mg to about 1,220 mg per week, about 290 mg to about 1,210 mg per week, about 300 mg to about 1,200 mg per week, about 310 mg to about 1,190 mg per week, about 320 mg to about 1,180 mg per week, about 330 mg to about 1,170 mg per week, about 340 mg to about 1,160 mg per week, about 350 mg to about 1,150 mg per week, about 360 mg to about 1,140 mg per week, about 370 mg to about 1,130 mg per week, about 380 mg to about 1,120 mg per week, about 390 mg to about 1,110 mg per week, about 400 mg to about 1,100 mg per week, about 410 mg to about 1,090 mg per week, about 420 mg to about 1,080 mg per week, about 430 mg to about 1,070 mg per week, about 440 mg to about 1,060 mg per week, about 450 mg to about 1,050 mg per week, about 460 mg to about 1,040 mg per week, about 470 mg to about 1,030 mg per week, about 480 mg to about 1,020 mg per week, about 490 mg to about 1,010 mg per week, about 500 mg to about 1,000 mg per week, about 510 mg to about 990 mg per week, about 520 mg to about 980 mg per week, about 530 mg to about 970 mg per week, about 540 mg to about 960 mg per week, about 550 mg to about 950 mg per week, about 560 mg to about 940 mg per week, about 570 mg to about 930 mg per week, about 580 mg to about 920 mg per week, about 590 mg to about 910 mg per week, about 600 mg to about 900 mg per week, about 610 mg to about 890 mg per week, about 620 mg to about 880 mg per week, about 630 mg to about 870 mg per week, about 640 mg to about 860 mg per week, about 650 mg to about 850 mg per week, about 660 mg to about 840 mg per week, about 670 mg to about 830 mg per week, about 680 mg to about 820 mg per week, about 690 mg to about 810 mg per week, about 700 mg to about 800 mg per week, about 710 mg to about 790 mg per week, about 720 mg to about 780 mg per week, about 730 mg to about 770 mg per week, or about 740 mg to about 760 mg per week, among others.

Exemplary total weekly quantities of nifedipine that may be administered to the subject in accordance with the preceding aspect include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, 1,000 mg, 1,005 mg, 1,010 mg, 1,015 mg, 1,020 mg, 1,025 mg, 1,030 mg, 1,035 mg, 1,040 mg, 1,045 mg, 1,050 mg, 1,055 mg, 1,060 mg, 1,065 mg, 1,070 mg, 1,075 mg, 1,080 mg, 1,085 mg, 1,090 mg, 1,095 mg, 1,100 mg, 1,105 mg, 1,110 mg, 1,115 mg, 1,120 mg, 1,125 mg, 1,130 mg, 1,135 mg, 1,140 mg, 1,145 mg, 1,150 mg, 1,155 mg, 1,160 mg, 1,165 mg, 1,170 mg, 1,175 mg, 1,180 mg, 1,185 mg, 1,190 mg, 1,195 mg, 1,200 mg, 1,205 mg, 1,210 mg, 1,215 mg, 1,220 mg, 1,225 mg, 1,230 mg, 1,235 mg, 1,240 mg, 1,245 mg, 1,250 mg, 1,255 mg, 1,260 mg, 1,265 mg, 1,270 mg, 1,275 mg, 1,280 mg, 1,285 mg, 1,290 mg, 1,295 mg, 1,300 mg, 1,305 mg, 1,310 mg, 1,315 mg, 1,320 mg, 1,325 mg, 1,330 mg, 1,335 mg, 1,340 mg, 1,345 mg, 1,350 mg, 1,355 mg, 1,360 mg, 1,365 mg, 1,370 mg, 1,375 mg, 1,380 mg, 1,385 mg, 1,390 mg, 1,395 mg, 900 mg, 1,405 mg, 1,410 mg, 1,415 mg, 1,420 mg, 1,425 mg, 1,430 mg, 1,435 mg, 1,440 mg, 1,445 mg, 1,450 mg, 1,455 mg, 1,460 mg, 1,465 mg, 1,470 mg, 1,475 mg, 1,480 mg, 1,485 mg, 1,490 mg, 1,495 mg, and 1,500 mg, among others.

In yet another aspect, the invention provides a method of reducing the expression of a proinflammatory and/or contractile gene, such as Cox2, in a pregnant subject (e.g., a pregnant human female), such as in the myometrium of a pregnant human subject) by administering to the subject a therapeutically effective amount of a PGF2α receptor antagonist, such as a compound represented by formula (I)

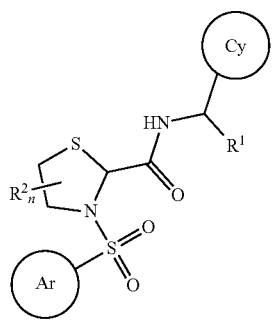

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 1,500 mg or less per week. For example, the subject may be one that is concurrently being administered nifedipine (or that has previously been administered nifedipine) in an amount of from about 1 mg to about 1,500 mg of nifedipine per week, such as from about 10 mg to about 1,490 mg per week, about 20 mg to about 1,480 mg per week, about 30 mg to about 1,470 mg per week, about 40 mg to about 1,460 mg per week, about 50 mg to about 1,450 mg per week, about 60 mg to about 1,440 mg per week, about 70 mg to about 1,430 mg per week, about 80 mg to about 1,420 mg per week, about 90 mg to about 1,410 mg per week, about 100 mg to about 1,400 mg per week, about 110 mg to about 1,390 mg per week, about 120 mg to about 1,380 mg per week, about 130 mg to about 1,370 mg per week, about 140 mg to about 1,360 mg per week, about 150 mg to about 1,350 mg per week, about 160 mg to about 1,340 mg per week, about 170 mg to about 1,330 mg per week, about 180 mg to about 1,320 mg per week, about 190 mg to about 1,310 mg per week, about 200 mg to about 1,300 mg per week, about 210 mg to about 1,290 mg per week, about 220 mg to about 1,280 mg per week, about 230 mg to about 1,270 mg per week, about 240 mg to about 1,260 mg per week, about 250 mg to about 1,250 mg per week, about 260 mg to about 1,240 mg per week, about 270 mg to about 1,230 mg per week, about 280 mg to about 1,220 mg per week, about 290 mg to about 1,210 mg per week, about 300 mg to about 1,200 mg per week, about 310 mg to about 1,190 mg per week, about 320 mg to about 1,180 mg per week, about 330 mg to about 1,170 mg per week, about 340 mg to about 1,160 mg per week, about 350 mg to about 1,150 mg per week, about 360 mg to about 1,140 mg per week, about 370 mg to about 1,130 mg per week, about 380 mg to about 1,120 mg per week, about 390 mg to about 1,110 mg per week, about 400 mg to about 1,100 mg per week, about 410 mg to about 1,090 mg per week, about 420 mg to about 1,080 mg per week, about 430 mg to about 1,070 mg per week, about 440 mg to about 1,060 mg per week, about 450 mg to about 1,050 mg per week, about 460 mg to about 1,040 mg per week, about 470 mg to about 1,030 mg per week, about 480 mg to about 1,020 mg per week, about 490 mg to about 1,010 mg per week, about 500 mg to about 1,000 mg per week, about 510 mg to about 990 mg per week, about 520 mg to about 980 mg per week, about 530 mg to about 970 mg per week, about 540 mg to about 960 mg per week, about 550 mg to about 950 mg per week, about 560 mg to about 940 mg per week, about 570 mg to about 930 mg per week, about 580 mg to about 920 mg per week, about 590 mg to about 910 mg per week, about 600 mg to about 900 mg per week, about 610 mg to about 890 mg per week, about 620 mg to about 880 mg per week, about 630 mg to about 870 mg per week, about 640 mg to about 860 mg per week, about 650 mg to about 850 mg per week, about 660 mg to about 840 mg per week, about 670 mg to about 830 mg per week, about 680 mg to about 820 mg per week, about 690 mg to about 810 mg per week, about 700 mg to about 800 mg per week, about 710 mg to about 790 mg per week, about 720 mg to about 780 mg per week, about 730 mg to about 770 mg per week, or about 740 mg to about 760 mg per week, among others.

Exemplary total weekly quantities of nifedipine that may be (or may have been) administered to the subject in accordance with the preceding aspect include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, 1,000 mg, 1,005 mg, 1,010 mg, 1,015 mg, 1,020 mg, 1,025 mg, 1,030 mg, 1,035 mg, 1,040 mg, 1,045 mg, 1,050 mg, 1,055 mg, 1,060 mg, 1,065 mg, 1,070 mg, 1,075 mg, 1,080 mg, 1,085 mg, 1,090 mg, 1,095 mg, 1,100 mg, 1,105 mg, 1,110 mg, 1,115 mg, 1,120 mg, 1,125 mg, 1,130 mg, 1,135 mg, 1,140 mg, 1,145 mg, 1,150 mg, 1,155 mg, 1,160 mg, 1,165 mg, 1,170 mg, 1,175 mg, 1,180 mg, 1,185 mg, 1,190 mg, 1,195 mg, 1,200 mg, 1,205 mg, 1,210 mg, 1,215 mg, 1,220 mg, 1,225 mg, 1,230 mg, 1,235 mg, 1,240 mg, 1,245 mg, 1,250 mg, 1,255 mg, 1,260 mg, 1,265 mg, 1,270 mg, 1,275 mg, 1,280 mg, 1,285 mg, 1,290 mg, 1,295 mg, 1,300 mg, 1,305 mg, 1,310 mg, 1,315 mg, 1,320 mg, 1,325 mg, 1,330 mg, 1,335 mg, 1,340 mg, 1,345 mg, 1,350 mg, 1,355 mg, 1,360 mg, 1,365 mg, 1,370 mg, 1,375 mg, 1,380 mg, 1,385 mg, 1,390 mg, 1,395 mg, 900 mg, 1,405 mg, 1,410 mg, 1,415 mg, 1,420 mg, 1,425 mg, 1,430 mg, 1,435 mg, 1,440 mg, 1,445 mg, 1,450 mg, 1,455 mg, 1,460 mg, 1,465 mg, 1,470 mg, 1,475 mg, 1,480 mg, 1,485 mg, 1,490 mg, 1,495 mg, and 1,500 mg, among others.

In yet another aspect, the invention features a method of treating or preventing preterm labor in a pregnant subject (e.g., a pregnant human female) by administering to the subject therapeutically effective amounts of nifedipine and a PGF2α receptor antagonist, such as a compound represented by formula (I)

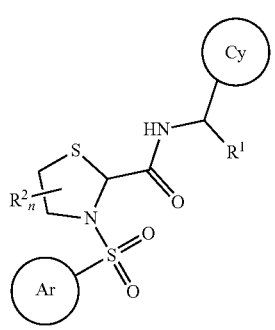

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine may be administered to the subject in an amount, for example, of about 40 mg or less per dose. For instance, the nifedipine may be administered to the subject in an amount of from about 1 mg to about 40 mg per dose, about 2 mg to about 39 mg per dose, about 3 mg to about 38 mg per dose, about 4 mg to about 37 mg per dose, about 5 mg to about 36 mg per dose, about 6 mg to about 35 mg per dose, about 7 mg to about 34 mg per dose, about 8 mg to about 33 mg per dose, about 9 mg to about 32 mg per dose, about 10 mg to about 30 mg per dose, about 11 mg to about 29 mg per dose, about 12 mg to about 28 mg per dose, about 13 mg to about 27 mg per dose, about 14 mg to about 26 mg per dose, about 15 mg to about 25 mg per dose, about 16 mg to about 24 mg per dose, about 17 mg to about 23 mg per dose, about 18 mg to about 22 mg per dose, or about 19 mg to about 21 mg per dose, among others. Exemplary doses of nifedipine that may be administered to the subject include doses of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as a dose of about 20 mg, among others.

In yet another aspect, the invention features a method of treating or preventing preterm labor in a pregnant subject (e.g., a pregnant human female) by administering to the subject a therapeutically effective amount of a PGF2α receptor antagonist, such as a compound represented by formula (I)

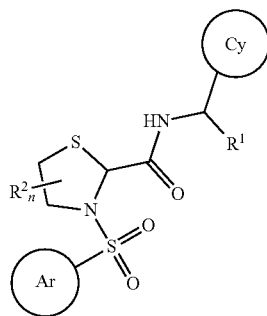

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 40 mg or less per dose. For instance, the subject may be one that is concurrently being administered nifedipine (or that has previously been administered nifedipine) in an amount of from about 1 mg to about 40 mg per dose, about 2 mg to about 39 mg per dose, about 3 mg to about 38 mg per dose, about 4 mg to about 37 mg per dose, about 5 mg to about 36 mg per dose, about 6 mg to about 35 mg per dose, about 7 mg to about 34 mg per dose, about 8 mg to about 33 mg per dose, about 9 mg to about 32 mg per dose, about 10 mg to about 30 mg per dose, about 11 mg to about 29 mg per dose, about 12 mg to about 28 mg per dose, about 13 mg to about 27 mg per dose, about 14 mg to about 26 mg per dose, about 15 mg to about 25 mg per dose, about 16 mg to about 24 mg per dose, about 17 mg to about 23 mg per dose, about 18 mg to about 22 mg per dose, or about 19 mg to about 21 mg per dose, among others. Exemplary doses of nifedipine that may be (or may have been) administered to the subject include doses of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as a dose of about 20 mg, among others.

In another aspect, the invention features a method of treating or preventing preterm labor in a pregnant subject (e.g., a pregnant human female) by administering to the subject therapeutically effective amounts of nifedipine and a PGF2α receptor antagonist, such as a compound represented by formula (I)

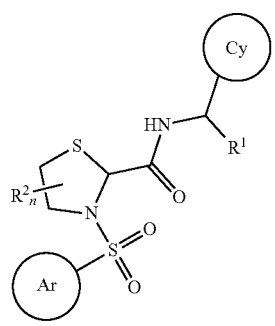

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine may be administered to the subject in an amount of about 40 mg or less in the first hour of treatment. For instance, the nifedipine may be administered to the subject in an amount of from about 1 mg to about 40 mg in the first hour of treatment, about 2 mg to about 39 mg in the first hour of treatment, about 3 mg to about 38 mg in the first hour of treatment, about 4 mg to about 37 mg in the first hour of treatment, about 5 mg to about 36 mg in the first hour of treatment, about 6 mg to about 35 mg in the first hour of treatment, about 7 mg to about 34 mg in the first hour of treatment, about 8 mg to about 33 mg in the first hour of treatment, about 9 mg to about 32 mg in the first hour of treatment, about 10 mg to about 30 mg in the first hour of treatment, about 11 mg to about 29 mg in the first hour of treatment, about 12 mg to about 28 mg in the first hour of treatment, about 13 mg to about 27 mg in the first hour of treatment, about 14 mg to about 26 mg in the first hour of treatment, about 15 mg to about 25 mg in the first hour of treatment, about 16 mg to about 24 mg in the first hour of treatment, about 17 mg to about 23 mg in the first hour of treatment, about 18 mg to about 22 mg in the first hour of treatment, or about 19 mg to about 21 mg in the first hour of treatment, among others. Exemplary amounts of nifedipine that may be administered to the subject in the first hour of treatment include amounts of nifedipine of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as an amount of about 20 mg, among others.

In another aspect, the invention features a method of treating or preventing preterm labor in a pregnant subject (e.g., a pregnant human female) by administering to the subject a therapeutically effective amount of a PGF2α receptor antagonist, such as a compound represented by formula (I)

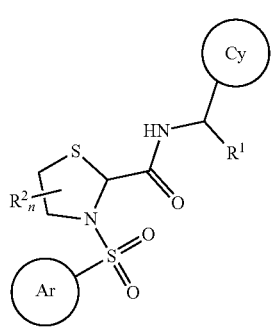

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 40 mg or less in the first hour of treatment. For instance, the subject may be one that is concurrently being administered nifedipine (or that has previously been administered nifedipine) in an amount of from about 1 mg to about 40 mg in the first hour of treatment, about 2 mg to about 39 mg in the first hour of treatment, about 3 mg to about 38 mg in the first hour of treatment, about 4 mg to about 37 mg in the first hour of treatment, about 5 mg to about 36 mg in the first hour of treatment, about 6 mg to about 35 mg in the first hour of treatment, about 7 mg to about 34 mg in the first hour of treatment, about 8 mg to about 33 mg in the first hour of treatment, about 9 mg to about 32 mg in the first hour of treatment, about 10 mg to about 30 mg in the first hour of treatment, about 11 mg to about 29 mg in the first hour of treatment, about 12 mg to about 28 mg in the first hour of treatment, about 13 mg to about 27 mg in the first hour of treatment, about 14 mg to about 26 mg in the first hour of treatment, about 15 mg to about 25 mg in the first hour of treatment, about 16 mg to about 24 mg in the first hour of treatment, about 17 mg to about 23 mg in the first hour of treatment, about 18 mg to about 22 mg in the first hour of treatment, or about 19 mg to about 21 mg in the first hour of treatment, among others. Exemplary amounts of nifedipine that may be (or may have been) administered to the subject in the first hour of treatment include amounts of nifedipine of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as an amount of about 20 mg, among others.

In another aspect, the invention features a method of treating or preventing preterm labor in a pregnant subject (e.g., a pregnant human female) by administering to the subject therapeutically effective amounts of nifedipine and a PGF2α receptor antagonist, such as a compound represented by formula (I)

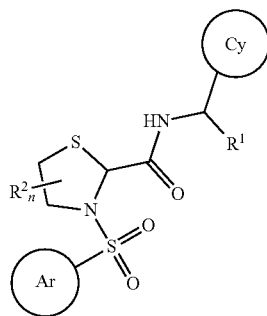

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine is administered to the subject in an amount of about 200 mg or less per day. For example, the nifedipine may be administered to the subject in an amount of from about 1 mg to about 200 mg per day, about 2 mg to about 199 mg per day, about 3 mg to about 198 mg per day, about 4 mg to about 197 mg per day, about 5 mg to about 196 mg per day, about 6 mg to about 195 mg per day, about 7 mg to about 194 mg per day, about 8 mg to about 193 per day, about 9 mg to about 192 per day, about 10 mg to about 191 per day, about 11 mg to about 190 per day, about 12 mg to about 189 per day, about 13 mg to about 188 per day, about 14 mg to about 187 per day, about 15 mg to about 186 per day, about 16 mg to about 185 mg per day, about 17 mg to about 184 per day, about 18 mg to about 183 mg per day, about 19 mg to about 182 per day, about 20 mg to about 181 per day, about 21 mg to about 180 per day, about 22 mg to about 179 per day, about 23 mg to about 178 mg per day, about 24 mg to about 177 mg per day, about 25 mg to about 176 mg per day, about 26 mg to about 175 mg per day, about 27 mg to about 174 mg per day, about 28 mg to about 173 mg per day, about 29 mg to about 172 mg per day, about 30 mg to about 171 mg per day, about 31 mg to about 170 mg per day, about 32 mg to about 169 mg per day, about 33 mg to about 168 mg per day, about 34 mg to about 167 mg per day, about 35 mg to about 166 mg per day, about 36 mg to about 165 mg per day, about 37 mg to about 164 mg per day, about 38 mg to about 163 mg per day, about 39 mg to about 162 per day, about 40 mg to about 161 mg per day, about 41 to about 160 mg per day, about 42 to about 159 mg per day, about 43 mg to about 158 mg per day, about 44 mg to about 157 mg per day, about 45 mg to about 156 mg per day, about 46 mg to about 155 mg per day, about 47 mg to about 154 mg per day, about 48 mg to about 153 mg per day, about 49 mg to about 152 mg per day, about 50 mg to about 151 mg per day, about 51 mg to about 150 mg per day, about 52 mg to about 149 mg per day, about 53 mg to about 148 mg per day, about 54 mg to about 147 mg per day, about 55 mg to about 146 mg per day, about 56 mg to about 145 mg per day, about 57 mg to about 144 mg per day, about 58 mg to about 143 mg per day, about 59 mg to about 142 mg per day, about 60 mg to about 141 mg per day, about 61 mg to about 140 mg per day, about 62 mg to about 139 mg per day, about 63 mg to about 138 mg per day, about 64 mg to about 137 mg per day, about 65 mg to about 136 mg per day, about 66 mg to about 135 mg per day, about 67 mg to about 134 mg per day, about 68 mg to about 133 mg per day, about 69 mg to about 132 mg per day, about 70 mg to about 131 mg per day, about 71 mg to about 130 mg per day, about 72 mg to about 129 per day, about 73 mg to about 128 mg per day, about 74 mg to about 127 mg per day, about 75 mg to about 126 mg per day, about 76 mg to about 125 mg per day, about 77 mg to about 124 mg per day, about 78 mg to about 123 mg per day, about 79 mg to about 122 mg per day, about 80 mg to about 121 mg per day, about 81 mg to about 120 mg per day, about 82 mg to about 119 mg per day, about 83 mg to about 118 mg per day, about 84 mg to about 117 mg per day, about 85 mg to about 116 mg per day, about 86 mg to about 115 mg per day, about 87 mg to about 114 mg per day, about 88 mg to about 113 mg per day, about 89 mg to about 112 mg per day, about 90 mg to about 111 mg per day, about 91 mg to about 110 mg per day, about 92 mg to about 109 mg per day, about 93 mg to about 108 mg per day, about 94 mg to about 107 mg per day, about 95 mg to about 106 mg per day, about 96 mg to about 105 mg per day, about 97 mg to about 104 mg per day, about 98 mg to about 103 mg per day, about 99 mg to about 102 mg per day, or about 100 to about 101 mg per day, among others. Exemplary total daily quantities of nifedipine that may be administered to the subject include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, and 200 mg, among others.

In another aspect, the invention features a method of treating or preventing preterm labor in a pregnant subject (e.g., a pregnant human female) by administering to the subject a therapeutically effective amount of a PGF2α receptor antagonist, such as a compound represented by formula (I)

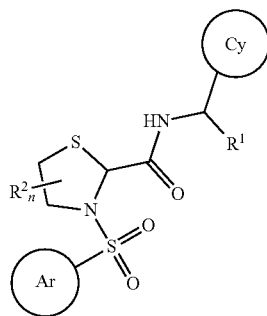

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 200 mg or less per day. For example, the subject may be one that is concurrently being administered nifedipine (or that has previously been administered nifedipine) in an amount of from about 1 mg to about 200 mg per day, about 2 mg to about 199 mg per day, about 3 mg to about 198 mg per day, about 4 mg to about 197 mg per day, about 5 mg to about 196 mg per day, about 6 mg to about 195 mg per day, about 7 mg to about 194 mg per day, about 8 mg to about 193 per day, about 9 mg to about 192 mg per day, about 10 mg to about 191 per day, about 11 mg to about 190 per day, about 12 mg to about 189 per day, about 13 mg to about 188 per day, about 14 mg to about 187 per day, about 15 mg to about 186 per day, about 16 mg to about 185 mg per day, about 17 mg to about 184 per day, about 18 mg to about 183 per day, about 19 mg to about 182 per day, about 20 mg to about 181 mg per day, about 21 mg to about 180 per day, about 22 mg to about 179 mg per day, about 23 mg to about 178 mg per day, about 24 mg to about 177 mg per day, about 25 mg to about 176 mg per day, about 26 mg to about 175 mg per day, about 27 mg to about 174 mg per day, about 28 mg to about 173 mg per day, about 29 mg to about 172 mg per day, about 30 mg to about 171 mg per day, about 31 mg to about 170 mg per day, about 32 mg to about 169 mg per day, about 33 mg to about 168 mg per day, about 34 mg to about 167 mg per day, about 35 mg to about 166 mg per day, about 36 mg to about 165 mg per day, about 37 mg to about 164 mg per day, about 38 mg to about 163 mg per day, about 39 mg to about 162 per day, about 40 mg to about 161 mg per day, about 41 to about 160 mg per day, about 42 to about 159 mg per day, about 43 mg to about 158 mg per day, about 44 mg to about 157 mg per day, about 45 mg to about 156 mg per day, about 46 mg to about 155 mg per day, about 47 mg to about 154 mg per day, about 48 mg to about 153 mg per day, about 49 mg to about 152 mg per day, about 50 mg to about 151 mg per day, about 51 mg to about 150 mg per day, about 52 mg to about 149 mg per day, about 53 mg to about 148 mg per day, about 54 mg to about 147 mg per day, about 55 mg to about 146 mg per day, about 56 mg to about 145 mg per day, about 57 mg to about 144 mg per day, about 58 mg to about 143 mg per day, about 59 mg to about 142 mg per day, about 60 mg to about 141 mg per day, about 61 mg to about 140 mg per day, about 62 mg to about 139 mg per day, about 63 mg to about 138 mg per day, about 64 mg to about 137 mg per day, about 65 mg to about 136 mg per day, about 66 mg to about 135 mg per day, about 67 mg to about 134 mg per day, about 68 mg to about 133 mg per day, about 69 mg to about 132 mg per day, about 70 mg to about 131 mg per day, about 71 mg to about 130 mg per day, about 72 mg to about 129 per day, about 73 mg to about 128 mg per day, about 74 mg to about 127 mg per day, about 75 mg to about 126 mg per day, about 76 mg to about 125 mg per day, about 77 mg to about 124 mg per day, about 78 mg to about 123 mg per day, about 79 mg to about 122 mg per day, about 80 mg to about 121 mg per day, about 81 mg to about 120 mg per day, about 82 mg to about 119 mg per day, about 83 mg to about 118 mg per day, about 84 mg to about 117 mg per day, about 85 mg to about 116 mg per day, about 86 mg to about 115 mg per day, about 87 mg to about 114 mg per day, about 88 mg to about 113 mg per day, about 89 mg to about 112 mg per day, about 90 mg to about 111 mg per day, about 91 mg to about 110 mg per day, about 92 mg to about 109 mg per day, about 93 mg to about 108 mg per day, about 94 mg to about 107 mg per day, about 95 mg to about 106 mg per day, about 96 mg to about 105 mg per day, about 97 mg to about 104 mg per day, about 98 mg to about 103 mg per day, about 99 mg to about 102 mg per day, or about 100 to about 101 mg per day, among others. Exemplary total daily quantities of nifedipine that may be (or may have been) administered to the subject include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, and 200 mg, among others.

In yet another aspect, the invention provides a method of treating or preventing preterm labor in a pregnant subject (e.g., a pregnant human female) by administering to the subject therapeutically effective amounts of nifedipine and a PGF2α receptor antagonist, such as a compound represented by formula (I)

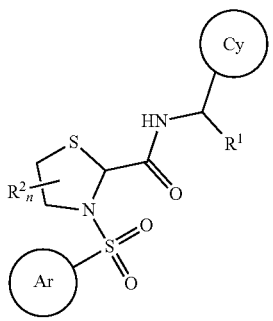

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine is administered to the subject in an amount of about 1,500 mg or less per week. For example, the subject may be administered from about 1 mg to about 1,500 mg of nifedipine per week, such as from about 10 mg to about 1,490 mg per week, about 20 mg to about 1,480 mg per week, about 30 mg to about 1,470 mg per week, about 40 mg to about 1,460 mg per week, about 50 mg to about 1,450 mg per week, about 60 mg to about 1,440 mg per week, about 70 mg to about 1,430 mg per week, about 80 mg to about 1,420 mg per week, about 90 mg to about 1,410 mg per week, about 100 mg to about 1,400 mg per week, about 110 mg to about 1,390 mg per week, about 120 mg to about 1,380 mg per week, about 130 mg to about 1,370 mg per week, about 140 mg to about 1,360 mg per week, about 150 mg to about 1,350 mg per week, about 160 mg to about 1,340 mg per week, about 170 mg to about 1,330 mg per week, about 180 mg to about 1,320 mg per week, about 190 mg to about 1,310 mg per week, about 200 mg to about 1,300 mg per week, about 210 mg to about 1,290 mg per week, about 220 mg to about 1,280 mg per week, about 230 mg to about 1,270 mg per week, about 240 mg to about 1,260 mg per week, about 250 mg to about 1,250 mg per week, about 260 mg to about 1,240 mg per week, about 270 mg to about 1,230 mg per week, about 280 mg to about 1,220 mg per week, about 290 mg to about 1,210 mg per week, about 300 mg to about 1,200 mg per week, about 310 mg to about 1,190 mg per week, about 320 mg to about 1,180 mg per week, about 330 mg to about 1,170 mg per week, about 340 mg to about 1,160 mg per week, about 350 mg to about 1,150 mg per week, about 360 mg to about 1,140 mg per week, about 370 mg to about 1,130 mg per week, about 380 mg to about 1,120 mg per week, about 390 mg to about 1,110 mg per week, about 400 mg to about 1,100 mg per week, about 410 mg to about 1,090 mg per week, about 420 mg to about 1,080 mg per week, about 430 mg to about 1,070 mg per week, about 440 mg to about 1,060 mg per week, about 450 mg to about 1,050 mg per week, about 460 mg to about 1,040 mg per week, about 470 mg to about 1,030 mg per week, about 480 mg to about 1,020 mg per week, about 490 mg to about 1,010 mg per week, about 500 mg to about 1,000 mg per week, about 510 mg to about 990 mg per week, about 520 mg to about 980 mg per week, about 530 mg to about 970 mg per week, about 540 mg to about 960 mg per week, about 550 mg to about 950 mg per week, about 560 mg to about 940 mg per week, about 570 mg to about 930 mg per week, about 580 mg to about 920 mg per week, about 590 mg to about 910 mg per week, about 600 mg to about 900 mg per week, about 610 mg to about 890 mg per week, about 620 mg to about 880 mg per week, about 630 mg to about 870 mg per week, about 640 mg to about 860 mg per week, about 650 mg to about 850 mg per week, about 660 mg to about 840 mg per week, about 670 mg to about 830 mg per week, about 680 mg to about 820 mg per week, about 690 mg to about 810 mg per week, about 700 mg to about 800 mg per week, about 710 mg to about 790 mg per week, about 720 mg to about 780 mg per week, about 730 mg to about 770 mg per week, or about 740 mg to about 760 mg per week, among others.

Exemplary total weekly quantities of nifedipine that may be administered to the subject in accordance with the preceding aspect include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, 1,000 mg, 1,005 mg, 1,010 mg, 1,015 mg, 1,020 mg, 1,025 mg, 1,030 mg, 1,035 mg, 1,040 mg, 1,045 mg, 1,050 mg, 1,055 mg, 1,060 mg, 1,065 mg, 1,070 mg, 1,075 mg, 1,080 mg, 1,085 mg, 1,090 mg, 1,095 mg, 1,100 mg, 1,105 mg, 1,110 mg, 1,115 mg, 1,120 mg, 1,125 mg, 1,130 mg, 1,135 mg, 1,140 mg, 1,145 mg, 1,150 mg, 1,155 mg, 1,160 mg, 1,165 mg, 1,170 mg, 1,175 mg, 1,180 mg, 1,185 mg, 1,190 mg, 1,195 mg, 1,200 mg, 1,205 mg, 1,210 mg, 1,215 mg, 1,220 mg, 1,225 mg, 1,230 mg, 1,235 mg, 1,240 mg, 1,245 mg, 1,250 mg, 1,255 mg, 1,260 mg, 1,265 mg, 1,270 mg, 1,275 mg, 1,280 mg, 1,285 mg, 1,290 mg, 1,295 mg, 1,300 mg, 1,305 mg, 1,310 mg, 1,315 mg, 1,320 mg, 1,325 mg, 1,330 mg, 1,335 mg, 1,340 mg, 1,345 mg, 1,350 mg, 1,355 mg, 1,360 mg, 1,365 mg, 1,370 mg, 1,375 mg, 1,380 mg, 1,385 mg, 1,390 mg, 1,395 mg, 900 mg, 1,405 mg, 1,410 mg, 1,415 mg, 1,420 mg, 1,425 mg, 1,430 mg, 1,435 mg, 1,440 mg, 1,445 mg, 1,450 mg, 1,455 mg, 1,460 mg, 1,465 mg, 1,470 mg, 1,475 mg, 1,480 mg, 1,485 mg, 1,490 mg, 1,495 mg, and 1,500 mg, among others.

In yet another aspect, the invention provides a method of treating or preventing preterm labor in a pregnant subject (e.g., a pregnant human female) by administering to the subject a therapeutically effective amount of a PGF2α receptor antagonist, such as a compound represented by formula (I)

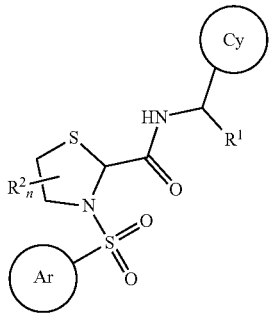

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 1,500 mg or less per week. For example, the subject may be one that is concurrently being administered nifedipine (or that has previously been administered nifedipine) in an amount of from about 1 mg to about 1,500 mg of nifedipine per week, such as from about 10 mg to about 1,490 mg per week, about 20 mg to about 1,480 mg per week, about 30 mg to about 1,470 mg per week, about 40 mg to about 1,460 mg per week, about 50 mg to about 1,450 mg per week, about 60 mg to about 1,440 mg per week, about 70 mg to about 1,430 mg per week, about 80 mg to about 1,420 mg per week, about 90 mg to about 1,410 mg per week, about 100 mg to about 1,400 mg per week, about 110 mg to about 1,390 mg per week, about 120 mg to about 1,380 mg per week, about 130 mg to about 1,370 mg per week, about 140 mg to about 1,360 mg per week, about 150 mg to about 1,350 mg per week, about 160 mg to about 1,340 mg per week, about 170 mg to about 1,330 mg per week, about 180 mg to about 1,320 mg per week, about 190 mg to about 1,310 mg per week, about 200 mg to about 1,300 mg per week, about 210 mg to about 1,290 mg per week, about 220 mg to about 1,280 mg per week, about 230 mg to about 1,270 mg per week, about 240 mg to about 1,260 mg per week, about 250 mg to about 1,250 mg per week, about 260 mg to about 1,240 mg per week, about 270 mg to about 1,230 mg per week, about 280 mg to about 1,220 mg per week, about 290 mg to about 1,210 mg per week, about 300 mg to about 1,200 mg per week, about 310 mg to about 1,190 mg per week, about 320 mg to about 1,180 mg per week, about 330 mg to about 1,170 mg per week, about 340 mg to about 1,160 mg per week, about 350 mg to about 1,150 mg per week, about 360 mg to about 1,140 mg per week, about 370 mg to about 1,130 mg per week, about 380 mg to about 1,120 mg per week, about 390 mg to about 1,110 mg per week, about 400 mg to about 1,100 mg per week, about 410 mg to about 1,090 mg per week, about 420 mg to about 1,080 mg per week, about 430 mg to about 1,070 mg per week, about 440 mg to about 1,060 mg per week, about 450 mg to about 1,050 mg per week, about 460 mg to about 1,040 mg per week, about 470 mg to about 1,030 mg per week, about 480 mg to about 1,020 mg per week, about 490 mg to about 1,010 mg per week, about 500 mg to about 1,000 mg per week, about 510 mg to about 990 mg per week, about 520 mg to about 980 mg per week, about 530 mg to about 970 mg per week, about 540 mg to about 960 mg per week, about 550 mg to about 950 mg per week, about 560 mg to about 940 mg per week, about 570 mg to about 930 mg per week, about 580 mg to about 920 mg per week, about 590 mg to about 910 mg per week, about 600 mg to about 900 mg per week, about 610 mg to about 890 mg per week, about 620 mg to about 880 mg per week, about 630 mg to about 870 mg per week, about 640 mg to about 860 mg per week, about 650 mg to about 850 mg per week, about 660 mg to about 840 mg per week, about 670 mg to about 830 mg per week, about 680 mg to about 820 mg per week, about 690 mg to about 810 mg per week, about 700 mg to about 800 mg per week, about 710 mg to about 790 mg per week, about 720 mg to about 780 mg per week, about 730 mg to about 770 mg per week, or about 740 mg to about 760 mg per week, among others.

Exemplary total weekly quantities of nifedipine that may be (or may have been) administered to the subject in accordance with the preceding aspect include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, 1,000 mg, 1,005 mg, 1,010 mg, 1,015 mg, 1,020 mg, 1,025 mg, 1,030 mg, 1,035 mg, 1,040 mg, 1,045 mg, 1,050 mg, 1,055 mg, 1,060 mg, 1,065 mg, 1,070 mg, 1,075 mg, 1,080 mg, 1,085 mg, 1,090 mg, 1,095 mg, 1,100 mg, 1,105 mg, 1,110 mg, 1,115 mg, 1,120 mg, 1,125 mg, 1,130 mg, 1,135 mg, 1,140 mg, 1,145 mg, 1,150 mg, 1,155 mg, 1,160 mg, 1,165 mg, 1,170 mg, 1,175 mg, 1,180 mg, 1,185 mg, 1,190 mg, 1,195 mg, 1,200 mg, 1,205 mg, 1,210 mg, 1,215 mg, 1,220 mg, 1,225 mg, 1,230 mg, 1,235 mg, 1,240 mg, 1,245 mg, 1,250 mg, 1,255 mg, 1,260 mg, 1,265 mg, 1,270 mg, 1,275 mg, 1,280 mg, 1,285 mg, 1,290 mg, 1,295 mg, 1,300 mg, 1,305 mg, 1,310 mg, 1,315 mg, 1,320 mg, 1,325 mg, 1,330 mg, 1,335 mg, 1,340 mg, 1,345 mg, 1,350 mg, 1,355 mg, 1,360 mg, 1,365 mg, 1,370 mg, 1,375 mg, 1,380 mg, 1,385 mg, 1,390 mg, 1,395 mg, 900 mg, 1,405 mg, 1,410 mg, 1,415 mg, 1,420 mg, 1,425 mg, 1,430 mg, 1,435 mg, 1,440 mg, 1,445 mg, 1,450 mg, 1,455 mg, 1,460 mg, 1,465 mg, 1,470 mg, 1,475 mg, 1,480 mg, 1,485 mg, 1,490 mg, 1,495 mg, and 1,500 mg, among others.

In yet another aspect, the invention features a method of preventing or delaying labor prior to cesarean delivery in a pregnant subject (e.g., a pregnant human female) by administering to the subject therapeutically effective amounts of nifedipine and a PGF2α receptor antagonist, such as a compound represented by formula (I)

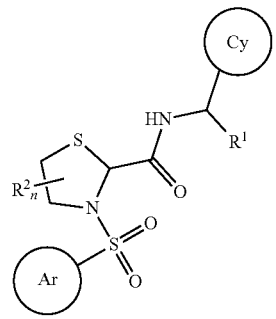

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine may be administered to the subject in an amount, for example, of about 40 mg or less per dose. For instance, the nifedipine may be administered to the subject in an amount of from about 1 mg to about 40 mg per dose, about 2 mg to about 39 mg per dose, about 3 mg to about 38 mg per dose, about 4 mg to about 37 mg per dose, about 5 mg to about 36 mg per dose, about 6 mg to about 35 mg per dose, about 7 mg to about 34 mg per dose, about 8 mg to about 33 mg per dose, about 9 mg to about 32 mg per dose, about 10 mg to about 30 mg per dose, about 11 mg to about 29 mg per dose, about 12 mg to about 28 mg per dose, about 13 mg to about 27 mg per dose, about 14 mg to about 26 mg per dose, about 15 mg to about 25 mg per dose, about 16 mg to about 24 mg per dose, about 17 mg to about 23 mg per dose, about 18 mg to about 22 mg per dose, or about 19 mg to about 21 mg per dose, among others. Exemplary doses of nifedipine that may be administered to the subject include doses of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as a dose of about 20 mg, among others.

In yet another aspect, the invention features a method of preventing or delaying labor prior to cesarean delivery in a pregnant subject (e.g., a pregnant human female) by administering to the subject a therapeutically effective amount of a PGF2α receptor antagonist, such as a compound represented by formula (I)

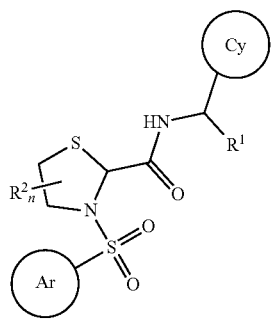

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 40 mg or less per dose. For instance, the subject may be one that is concurrently being administered nifedipine (or that has previously been administered nifedipine) in an amount of from about 1 mg to about 40 mg per dose, about 2 mg to about 39 mg per dose, about 3 mg to about 38 mg per dose, about 4 mg to about 37 mg per dose, about 5 mg to about 36 mg per dose, about 6 mg to about 35 mg per dose, about 7 mg to about 34 mg per dose, about 8 mg to about 33 mg per dose, about 9 mg to about 32 mg per dose, about 10 mg to about 30 mg per dose, about 11 mg to about 29 mg per dose, about 12 mg to about 28 mg per dose, about 13 mg to about 27 mg per dose, about 14 mg to about 26 mg per dose, about 15 mg to about 25 mg per dose, about 16 mg to about 24 mg per dose, about 17 mg to about 23 mg per dose, about 18 mg to about 22 mg per dose, or about 19 mg to about 21 mg per dose, among others. Exemplary doses of nifedipine that may be (or may have been) administered to the subject include doses of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as a dose of about 20 mg, among others.

In another aspect, the invention features a method of preventing or delaying labor prior to cesarean delivery in a pregnant subject (e.g., a pregnant human female) by administering to the subject therapeutically effective amounts of nifedipine and a PGF2α receptor antagonist, such as a compound represented by formula (I)

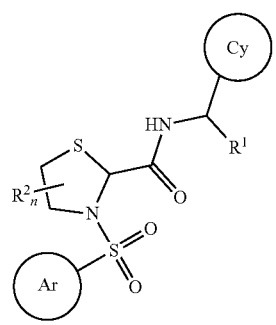

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine may be administered to the subject in an amount of about 40 mg or less in the first hour of treatment. For instance, the nifedipine may be administered to the subject in an amount of from about 1 mg to about 40 mg in the first hour of treatment, about 2 mg to about 39 mg in the first hour of treatment, about 3 mg to about 38 mg in the first hour of treatment, about 4 mg to about 37 mg in the first hour of treatment, about 5 mg to about 36 mg in the first hour of treatment, about 6 mg to about 35 mg in the first hour of treatment, about 7 mg to about 34 mg in the first hour of treatment, about 8 mg to about 33 mg in the first hour of treatment, about 9 mg to about 32 mg in the first hour of treatment, about 10 mg to about 30 mg in the first hour of treatment, about 11 mg to about 29 mg in the first hour of treatment, about 12 mg to about 28 mg in the first hour of treatment, about 13 mg to about 27 mg in the first hour of treatment, about 14 mg to about 26 mg in the first hour of treatment, about 15 mg to about 25 mg in the first hour of treatment, about 16 mg to about 24 mg in the first hour of treatment, about 17 mg to about 23 mg in the first hour of treatment, about 18 mg to about 22 mg in the first hour of treatment, or about 19 mg to about 21 mg in the first hour of treatment, among others.

Exemplary amounts of nifedipine that may be administered to the subject in the first hour of treatment include amounts of nifedipine of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as an amount of about 20 mg, among others.

In another aspect, the invention features a method of preventing or delaying labor prior to cesarean delivery in a pregnant subject (e.g., a pregnant human female) by administering to the subject a therapeutically effective amount of a PGF2α receptor antagonist, such as a compound represented by formula (I)

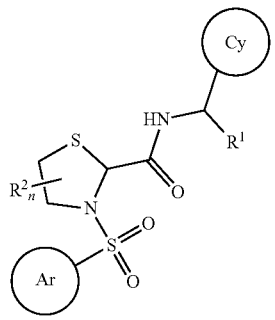

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 40 mg or less in the first hour of treatment. For instance, the subject may be one that is concurrently being administered nifedipine (or that has previously been administered nifedipine) in an amount of from about 1 mg to about 40 mg in the first hour of treatment, about 2 mg to about 39 mg in the first hour of treatment, about 3 mg to about 38 mg in the first hour of treatment, about 4 mg to about 37 mg in the first hour of treatment, about 5 mg to about 36 mg in the first hour of treatment, about 6 mg to about 35 mg in the first hour of treatment, about 7 mg to about 34 mg in the first hour of treatment, about 8 mg to about 33 mg in the first hour of treatment, about 9 mg to about 32 mg in the first hour of treatment, about 10 mg to about 30 mg in the first hour of treatment, about 11 mg to about 29 mg in the first hour of treatment, about 12 mg to about 28 mg in the first hour of treatment, about 13 mg to about 27 mg in the first hour of treatment, about 14 mg to about 26 mg in the first hour of treatment, about 15 mg to about 25 mg in the first hour of treatment, about 16 mg to about 24 mg in the first hour of treatment, about 17 mg to about 23 mg in the first hour of treatment, about 18 mg to about 22 mg in the first hour of treatment, or about 19 mg to about 21 mg in the first hour of treatment, among others. Exemplary amounts of nifedipine that may be (or may have been) administered to the subject in the first hour of treatment include amounts of nifedipine of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as an amount of about 20 mg, among others.

In another aspect, the invention features a method of preventing or delaying labor prior to cesarean delivery in a pregnant subject (e.g., a pregnant human female) by administering to the subject therapeutically effective amounts of nifedipine and a PGF2α receptor antagonist, such as a compound represented by formula (I)

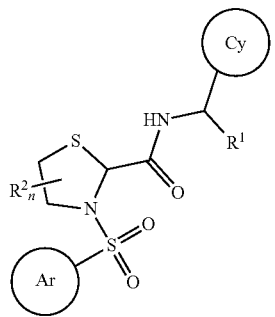

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine is administered to the subject in an amount of about 200 mg or less per day. For example, the nifedipine may be administered to the subject in an amount of from about 1 mg to about 200 mg per day, about 2 mg to about 199 mg per day, about 3 mg to about 198 mg per day, about 4 mg to about 197 mg per day, about 5 mg to about 196 mg per day, about 6 mg to about 195 mg per day, about 7 mg to about 194 mg per day, about 8 mg to about 193 per day, about 9 mg to about 192 per day, about 10 mg to about 191 per day, about 11 mg to about 190 per day, about 12 mg to about 189 per day, about 13 mg to about 188 per day, about 14 mg to about 187 per day, about 15 mg to about 186 per day, about 16 mg to about 185 mg per day, about 17 mg to about 184 per day, about 18 mg to about 183 per day, about 19 mg to about 182 per day, about 20 mg to about 181 mg per day, about 21 mg to about 180 per day, about 22 mg to about 179 mg per day, about 23 mg to about 178 mg per day, about 24 mg to about 177 mg per day, about 25 mg to about 176 mg per day, about 26 mg to about 175 mg per day, about 27 mg to about 174 mg per day, about 28 mg to about 173 mg per day, about 29 mg to about 172 mg per day, about 30 mg to about 171 mg per day, about 31 mg to about 170 mg per day, about 32 mg to about 169 mg per day, about 33 mg to about 168 mg per day, about 34 mg to about 167 mg per day, about 35 mg to about 166 mg per day, about 36 mg to about 165 mg per day, about 37 mg to about 164 mg per day, about 38 mg to about 163 mg per day, about 39 mg to about 162 per day, about 40 mg to about 161 mg per day, about 41 to about 160 mg per day, about 42 to about 159 mg per day, about 43 mg to about 158 mg per day, about 44 mg to about 157 mg per day, about 45 mg to about 156 mg per day, about 46 mg to about 155 mg per day, about 47 mg to about 154 mg per day, about 48 mg to about 153 mg per day, about 49 mg to about 152 mg per day, about 50 mg to about 151 mg per day, about 51 mg to about 150 mg per day, about 52 mg to about 149 mg per day, about 53 mg to about 148 mg per day, about 54 mg to about 147 mg per day, about 55 mg to about 146 mg per day, about 56 mg to about 145 mg per day, about 57 mg to about 144 mg per day, about 58 mg to about 143 mg per day, about 59 mg to about 142 mg per day, about 60 mg to about 141 mg per day, about 61 mg to about 140 mg per day, about 62 mg to about 139 mg per day, about 63 mg to about 138 mg per day, about 64 mg to about 137 mg per day, about 65 mg to about 136 mg per day, about 66 mg to about 135 mg per day, about 67 mg to about 134 mg per day, about 68 mg to about 133 mg per day, about 69 mg to about 132 mg per day, about 70 mg to about 131 mg per day, about 71 mg to about 130 mg per day, about 72 mg to about 129 per day, about 73 mg to about 128 mg per day, about 74 mg to about 127 mg per day, about 75 mg to about 126 mg per day, about 76 mg to about 125 mg per day, about 77 mg to about 124 mg per day, about 78 mg to about 123 mg per day, about 79 mg to about 122 mg per day, about 80 mg to about 121 mg per day, about 81 mg to about 120 mg per day, about 82 mg to about 119 mg per day, about 83 mg to about 118 mg per day, about 84 mg to about 117 mg per day, about 85 mg to about 116 mg per day, about 86 mg to about 115 mg per day, about 87 mg to about 114 mg per day, about 88 mg to about 113 mg per day, about 89 mg to about 112 mg per day, about 90 mg to about 111 mg per day, about 91 mg to about 110 mg per day, about 92 mg to about 109 mg per day, about 93 mg to about 108 mg per day, about 94 mg to about 107 mg per day, about 95 mg to about 106 mg per day, about 96 mg to about 105 mg per day, about 97 mg to about 104 mg per day, about 98 mg to about 103 mg per day, about 99 mg to about 102 mg per day, or about 100 to about 101 mg per day, among others. Exemplary total daily quantities of nifedipine that may be administered to the subject include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, and 200 mg, among others.

In another aspect, the invention features a method of preventing or delaying labor prior to cesarean delivery in a pregnant subject (e.g., a pregnant human female) by administering to the subject a therapeutically effective amount of a PGF2α receptor antagonist, such as a compound represented by formula (I)

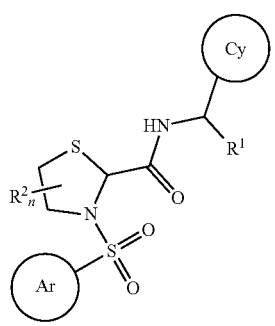

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 200 mg or less per day. For example, the subject may be one that is concurrently being administered nifedipine (or that has previously been administered nifedipine) in an amount of from about 1 mg to about 200 mg per day, about 2 mg to about 199 mg per day, about 3 mg to about 198 mg per day, about 4 mg to about 197 mg per day, about 5 mg to about 196 mg per day, about 6 mg to about 195 mg per day, about 7 mg to about 194 mg per day, about 8 mg to about 193 per day, about 9 mg to about 192 per day, about 10 mg to about 191 per day, about 11 mg to about 190 per day, about 12 mg to about 189 per day, about 13 mg to about 188 per day, about 14 mg to about 187 per day, about 15 mg to about 186 per day, about 16 mg to about 185 mg per day, about 17 mg to about 184 per day, about 18 mg to about 183 per day, about 19 mg to about 182 per day, about 20 mg to about 181 mg per day, about 21 mg to about 180 per day, about 22 mg to about 179 mg per day, about 23 mg to about 178 mg per day, about 24 mg to about 177 mg per day, about 25 mg to about 176 mg per day, about 26 mg to about 175 mg per day, about 27 mg to about 174 mg per day, about 28 mg to about 173 mg per day, about 29 mg to about 172 mg per day, about 30 mg to about 171 mg per day, about 31 mg to about 170 mg per day, about 32 mg to about 169 mg per day, about 33 mg to about 168 mg per day, about 34 mg to about 167 mg per day, about 35 mg to about 166 mg per day, about 36 mg to about 165 mg per day, about 37 mg to about 164 mg per day, about 38 mg to about 163 mg per day, about 39 mg to about 162 per day, about 40 mg to about 161 mg per day, about 41 to about 160 mg per day, about 42 to about 159 mg per day, about 43 mg to about 158 mg per day, about 44 mg to about 157 mg per day, about 45 mg to about 156 mg per day, about 46 mg to about 155 mg per day, about 47 mg to about 154 mg per day, about 48 mg to about 153 mg per day, about 49 mg to about 152 mg per day, about 50 mg to about 151 mg per day, about 51 mg to about 150 mg per day, about 52 mg to about 149 mg per day, about 53 mg to about 148 mg per day, about 54 mg to about 147 mg per day, about 55 mg to about 146 mg per day, about 56 mg to about 145 mg per day, about 57 mg to about 144 mg per day, about 58 mg to about 143 mg per day, about 59 mg to about 142 mg per day, about 60 mg to about 141 mg per day, about 61 mg to about 140 mg per day, about 62 mg to about 139 mg per day, about 63 mg to about 138 mg per day, about 64 mg to about 137 mg per day, about 65 mg to about 136 mg per day, about 66 mg to about 135 mg per day, about 67 mg to about 134 mg per day, about 68 mg to about 133 mg per day, about 69 mg to about 132 mg per day, about 70 mg to about 131 mg per day, about 71 mg to about 130 mg per day, about 72 mg to about 129 per day, about 73 mg to about 128 mg per day, about 74 mg to about 127 mg per day, about 75 mg to about 126 mg per day, about 76 mg to about 125 mg per day, about 77 mg to about 124 mg per day, about 78 mg to about 123 mg per day, about 79 mg to about 122 mg per day, about 80 mg to about 121 mg per day, about 81 mg to about 120 mg per day, about 82 mg to about 119 mg per day, about 83 mg to about 118 mg per day, about 84 mg to about 117 mg per day, about 85 mg to about 116 mg per day, about 86 mg to about 115 mg per day, about 87 mg to about 114 mg per day, about 88 mg to about 113 mg per day, about 89 mg to about 112 mg per day, about 90 mg to about 111 mg per day, about 91 mg to about 110 mg per day, about 92 mg to about 109 mg per day, about 93 mg to about 108 mg per day, about 94 mg to about 107 mg per day, about 95 mg to about 106 mg per day, about 96 mg to about 105 mg per day, about 97 mg to about 104 mg per day, about 98 mg to about 103 mg per day, about 99 mg to about 102 mg per day, or about 100 to about 101 mg per day, among others. Exemplary total daily quantities of nifedipine that may be (or may have been) administered to the subject include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, and 200 mg, among others.

In yet another aspect, the invention provides a method of preventing or delaying labor prior to cesarean delivery in a pregnant subject (e.g., a pregnant human female) by administering to the subject therapeutically effective amounts of nifedipine and a PGF2α receptor antagonist, such as a compound represented by formula (I)

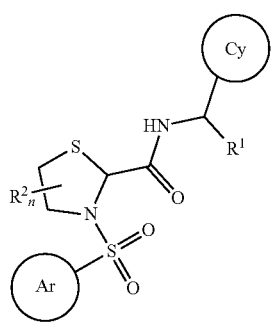

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine is administered to the subject in an amount of about 1,500 mg or less per week. For example, the subject may be administered from about 1 mg to about 1,500 mg of nifedipine per week, such as from about 10 mg to about 1,490 mg per week, about 20 mg to about 1,480 mg per week, about 30 mg to about 1,470 mg per week, about 40 mg to about 1,460 mg per week, about 50 mg to about 1,450 mg per week, about 60 mg to about 1,440 mg per week, about 70 mg to about 1,430 mg per week, about 80 mg to about 1,420 mg per week, about 90 mg to about 1,410 mg per week, about 100 mg to about 1,400 mg per week, about 110 mg to about 1,390 mg per week, about 120 mg to about 1,380 mg per week, about 130 mg to about 1,370 mg per week, about 140 mg to about 1,360 mg per week, about 150 mg to about 1,350 mg per week, about 160 mg to about 1,340 mg per week, about 170 mg to about 1,330 mg per week, about 180 mg to about 1,320 mg per week, about 190 mg to about 1,310 mg per week, about 200 mg to about 1,300 mg per week, about 210 mg to about 1,290 mg per week, about 220 mg to about 1,280 mg per week, about 230 mg to about 1,270 mg per week, about 240 mg to about 1,260 mg per week, about 250 mg to about 1,250 mg per week, about 260 mg to about 1,240 mg per week, about 270 mg to about 1,230 mg per week, about 280 mg to about 1,220 mg per week, about 290 mg to about 1,210 mg per week, about 300 mg to about 1,200 mg per week, about 310 mg to about 1,190 mg per week, about 320 mg to about 1,180 mg per week, about 330 mg to about 1,170 mg per week, about 340 mg to about 1,160 mg per week, about 350 mg to about 1,150 mg per week, about 360 mg to about 1,140 mg per week, about 370 mg to about 1,130 mg per week, about 380 mg to about 1,120 mg per week, about 390 mg to about 1,110 mg per week, about 400 mg to about 1,100 mg per week, about 410 mg to about 1,090 mg per week, about 420 mg to about 1,080 mg per week, about 430 mg to about 1,070 mg per week, about 440 mg to about 1,060 mg per week, about 450 mg to about 1,050 mg per week, about 460 mg to about 1,040 mg per week, about 470 mg to about 1,030 mg per week, about 480 mg to about 1,020 mg per week, about 490 mg to about 1,010 mg per week, about 500 mg to about 1,000 mg per week, about 510 mg to about 990 mg per week, about 520 mg to about 980 mg per week, about 530 mg to about 970 mg per week, about 540 mg to about 960 mg per week, about 550 mg to about 950 mg per week, about 560 mg to about 940 mg per week, about 570 mg to about 930 mg per week, about 580 mg to about 920 mg per week, about 590 mg to about 910 mg per week, about 600 mg to about 900 mg per week, about 610 mg to about 890 mg per week, about 620 mg to about 880 mg per week, about 630 mg to about 870 mg per week, about 640 mg to about 860 mg per week, about 650 mg to about 850 mg per week, about 660 mg to about 840 mg per week, about 670 mg to about 830 mg per week, about 680 mg to about 820 mg per week, about 690 mg to about 810 mg per week, about 700 mg to about 800 mg per week, about 710 mg to about 790 mg per week, about 720 mg to about 780 mg per week, about 730 mg to about 770 mg per week, or 740 mg to about 760 mg per week, among others.

Exemplary total weekly quantities of nifedipine that may be administered to the subject in accordance with the preceding aspect include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, 1,000 mg, 1,005 mg, 1,010 mg, 1,015 mg, 1,020 mg, 1,025 mg, 1,030 mg, 1,035 mg, 1,040 mg, 1,045 mg, 1,050 mg, 1,055 mg, 1,060 mg, 1,065 mg, 1,070 mg, 1,075 mg, 1,080 mg, 1,085 mg, 1,090 mg, 1,095 mg, 1,100 mg, 1,105 mg, 1,110 mg, 1,115 mg, 1,120 mg, 1,125 mg, 1,130 mg, 1,135 mg, 1,140 mg, 1,145 mg, 1,150 mg, 1,155 mg, 1,160 mg, 1,165 mg, 1,170 mg, 1,175 mg, 1,180 mg, 1,185 mg, 1,190 mg, 1,195 mg, 1,200 mg, 1,205 mg, 1,210 mg, 1,215 mg, 1,220 mg, 1,225 mg, 1,230 mg, 1,235 mg, 1,240 mg, 1,245 mg, 1,250 mg, 1,255 mg, 1,260 mg, 1,265 mg, 1,270 mg, 1,275 mg, 1,280 mg, 1,285 mg, 1,290 mg, 1,295 mg, 1,300 mg, 1,305 mg, 1,310 mg, 1,315 mg, 1,320 mg, 1,325 mg, 1,330 mg, 1,335 mg, 1,340 mg, 1,345 mg, 1,350 mg, 1,355 mg, 1,360 mg, 1,365 mg, 1,370 mg, 1,375 mg, 1,380 mg, 1,385 mg, 1,390 mg, 1,395 mg, 900 mg, 1,405 mg, 1,410 mg, 1,415 mg, 1,420 mg, 1,425 mg, 1,430 mg, 1,435 mg, 1,440 mg, 1,445 mg, 1,450 mg, 1,455 mg, 1,460 mg, 1,465 mg, 1,470 mg, 1,475 mg, 1,480 mg, 1,485 mg, 1,490 mg, 1,495 mg, and 1,500 mg, among others.

In yet another aspect, the invention provides a method of preventing or delaying labor prior to cesarean delivery in a pregnant subject (e.g., a pregnant human female) by administering to the subject a therapeutically effective amount of a PGF2α receptor antagonist, such as a compound represented by formula (I)

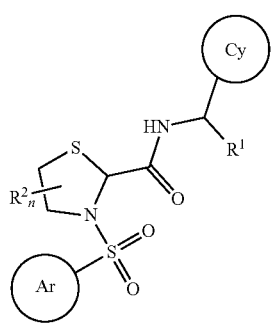

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 1,500 mg or less per week. For example, the subject may be one that is concurrently being administered nifedipine (or that has previously been administered nifedipine) in an amount of from about 1 mg to about 1,500 mg of nifedipine per week, such as from about 10 mg to about 1,490 mg per week, about 20 mg to about 1,480 mg per week, about 30 mg to about 1,470 mg per week, about 40 mg to about 1,460 mg per week, about 50 mg to about 1,450 mg per week, about 60 mg to about 1,440 mg per week, about 70 mg to about 1,430 mg per week, about 80 mg to about 1,420 mg per week, about 90 mg to about 1,410 mg per week, about 100 mg to about 1,400 mg per week, about 110 mg to about 1,390 mg per week, about 120 mg to about 1,380 mg per week, about 130 mg to about 1,370 mg per week, about 140 mg to about 1,360 mg per week, about 150 mg to about 1,350 mg per week, about 160 mg to about 1,340 mg per week, about 170 mg to about 1,330 mg per week, about 180 mg to about 1,320 mg per week, about 190 mg to about 1,310 mg per week, about 200 mg to about 1,300 mg per week, about 210 mg to about 1,290 mg per week, about 220 mg to about 1,280 mg per week, about 230 mg to about 1,270 mg per week, about 240 mg to about 1,260 mg per week, about 250 mg to about 1,250 mg per week, about 260 mg to about 1,240 mg per week, about 270 mg to about 1,230 mg per week, about 280 mg to about 1,220 mg per week, about 290 mg to about 1,210 mg per week, about 300 mg to about 1,200 mg per week, about 310 mg to about 1,190 mg per week, about 320 mg to about 1,180 mg per week, about 330 mg to about 1,170 mg per week, about 340 mg to about 1,160 mg per week, about 350 mg to about 1,150 mg per week, about 360 mg to about 1,140 mg per week, about 370 mg to about 1,130 mg per week, about 380 mg to about 1,120 mg per week, about 390 mg to about 1,110 mg per week, about 400 mg to about 1,100 mg per week, about 410 mg to about 1,090 mg per week, about 420 mg to about 1,080 mg per week, about 430 mg to about 1,070 mg per week, about 440 mg to about 1,060 mg per week, about 450 mg to about 1,050 mg per week, about 460 mg to about 1,040 mg per week, about 470 mg to about 1,030 mg per week, about 480 mg to about 1,020 mg per week, about 490 mg to about 1,010 mg per week, about 500 mg to about 1,000 mg per week, about 510 mg to about 990 mg per week, about 520 mg to about 980 mg per week, about 530 mg to about 970 mg per week, about 540 mg to about 960 mg per week, about 550 mg to about 950 mg per week, about 560 mg to about 940 mg per week, about 570 mg to about 930 mg per week, about 580 mg to about 920 mg per week, about 590 mg to about 910 mg per week, about 600 mg to about 900 mg per week, about 610 mg to about 890 mg per week, about 620 mg to about 880 mg per week, about 630 mg to about 870 mg per week, about 640 mg to about 860 mg per week, about 650 mg to about 850 mg per week, about 660 mg to about 840 mg per week, about 670 mg to about 830 mg per week, about 680 mg to about 820 mg per week, about 690 mg to about 810 mg per week, about 700 mg to about 800 mg per week, about 710 mg to about 790 mg per week, about 720 mg to about 780 mg per week, about 730 mg to about 770 mg per week, or about 740 mg to about 760 mg per week, among others.

Exemplary total weekly quantities of nifedipine that may be (or may have been) administered to the subject in accordance with the preceding aspect include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, 1,000 mg, 1,005 mg, 1,010 mg, 1,015 mg, 1,020 mg, 1,025 mg, 1,030 mg, 1,035 mg, 1,040 mg, 1,045 mg, 1,050 mg, 1,055 mg, 1,060 mg, 1,065 mg, 1,070 mg, 1,075 mg, 1,080 mg, 1,085 mg, 1,090 mg, 1,095 mg, 1,100 mg, 1,105 mg, 1,110 mg, 1,115 mg, 1,120 mg, 1,125 mg, 1,130 mg, 1,135 mg, 1,140 mg, 1,145 mg, 1,150 mg, 1,155 mg, 1,160 mg, 1,165 mg, 1,170 mg, 1,175 mg, 1,180 mg, 1,185 mg, 1,190 mg, 1,195 mg, 1,200 mg, 1,205 mg, 1,210 mg, 1,215 mg, 1,220 mg, 1,225 mg, 1,230 mg, 1,235 mg, 1,240 mg, 1,245 mg, 1,250 mg, 1,255 mg, 1,260 mg, 1,265 mg, 1,270 mg, 1,275 mg, 1,280 mg, 1,285 mg, 1,290 mg, 1,295 mg, 1,300 mg, 1,305 mg, 1,310 mg, 1,315 mg, 1,320 mg, 1,325 mg, 1,330 mg, 1,335 mg, 1,340 mg, 1,345 mg, 1,350 mg, 1,355 mg, 1,360 mg, 1,365 mg, 1,370 mg, 1,375 mg, 1,380 mg, 1,385 mg, 1,390 mg, 1,395 mg, 900 mg, 1,405 mg, 1,410 mg, 1,415 mg, 1,420 mg, 1,425 mg, 1,430 mg, 1,435 mg, 1,440 mg, 1,445 mg, 1,450 mg, 1,455 mg, 1,460 mg, 1,465 mg, 1,470 mg, 1,475 mg, 1,480 mg, 1,485 mg, 1,490 mg, 1,495 mg, and 1,500 mg, among others.

In yet another aspect, the invention features a method of prolonging gestation in a pregnant subject (e.g., a pregnant human female) for a time sufficient for the subject to be administered one or more antenatal corticosteroids (e.g., betamethasone, dexamethasone, and/or hydrocortisone), such as to promote fetal lung maturation. The method includes administering to the subject therapeutically effective amounts of nifedipine and a PGF2α receptor antagonist, such as a compound represented by formula (I)

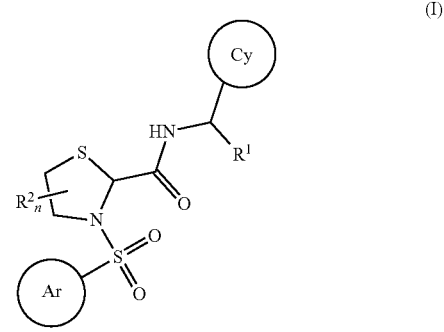

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine may be administered to the subject in an amount, for example, of about 40 mg or less per dose. For instance, the nifedipine may be administered to the subject in an amount of from about 1 mg to about 40 mg per dose, about 2 mg to about 39 mg per dose, about 3 mg to about 38 mg per dose, about 4 mg to about 37 mg per dose, about 5 mg to about 36 mg per dose, about 6 mg to about 35 mg per dose, about 7 mg to about 34 mg per dose, about 8 mg to about 33 mg per dose, about 9 mg to about 32 mg per dose, about 10 mg to about 30 mg per dose, about 11 mg to about 29 mg per dose, about 12 mg to about 28 mg per dose, about 13 mg to about 27 mg per dose, about 14 mg to about 26 mg per dose, about 15 mg to about 25 mg per dose, about 16 mg to about 24 mg per dose, about 17 mg to about 23 mg per dose, about 18 mg to about 22 mg per dose, or about 19 mg to about 21 mg per dose, among others. Exemplary doses of nifedipine that may be administered to the subject include doses of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as a dose of about 20 mg, among others.

In yet another aspect, the invention features a method of prolonging gestation in a pregnant subject (e.g., a pregnant human female) for a time sufficient for the subject to be administered one or more antenatal corticosteroids (e.g., betamethasone, dexamethasone, and/or hydrocortisone), such as to promote fetal lung maturation. The method includes administering to the subject a therapeutically effective amount of a PGF2α receptor antagonist, such as a compound represented by formula (I)

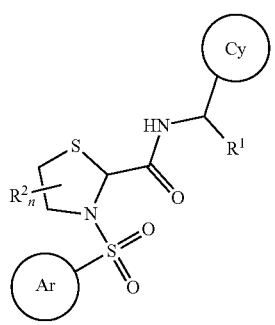

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 40 mg or less per dose. For instance, the subject may be one that is concurrently being administered nifedipine (or that has previously been administered nifedipine) in an amount of from about 1 mg to about 40 mg per dose, about 2 mg to about 39 mg per dose, about 3 mg to about 38 mg per dose, about 4 mg to about 37 mg per dose, about 5 mg to about 36 mg per dose, about 6 mg to about 35 mg per dose, about 7 mg to about 34 mg per dose, about 8 mg to about 33 mg per dose, about 9 mg to about 32 mg per dose, about 10 mg to about 30 mg per dose, about 11 mg to about 29 mg per dose, about 12 mg to about 28 mg per dose, about 13 mg to about 27 mg per dose, about 14 mg to about 26 mg per dose, about 15 mg to about 25 mg per dose, about 16 mg to about 24 mg per dose, about 17 mg to about 23 mg per dose, about 18 mg to about 22 mg per dose, or about 19 mg to about 21 mg per dose, among others. Exemplary doses of nifedipine that may be (or may have been) administered to the subject include doses of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as a dose of about 20 mg, among others.

In another aspect, the invention features a method of prolonging gestation in a pregnant subject (e.g., a pregnant human female) for a time sufficient for the subject to be administered one or more antenatal corticosteroids (e.g., betamethasone, dexamethasone, and/or hydrocortisone), such as to promote fetal lung maturation. The method includes administering to the subject therapeutically effective amounts of nifedipine and a PGF2α receptor antagonist, such as a compound represented by formula (I)

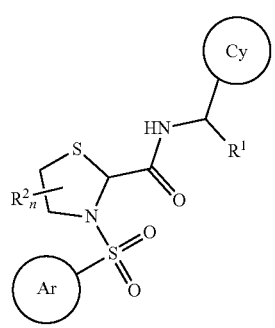

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine may be administered to the subject in an amount of about 40 mg or less in the first hour of treatment. For instance, the nifedipine may be administered to the subject in an amount of from about 1 mg to about 40 mg in the first hour of treatment, about 2 mg to about 39 mg in the first hour of treatment, about 3 mg to about 38 mg in the first hour of treatment, about 4 mg to about 37 mg in the first hour of treatment, about 5 mg to about 36 mg in the first hour of treatment, about 6 mg to about 35 mg in the first hour of treatment, about 7 mg to about 34 mg in the first hour of treatment, about 8 mg to about 33 mg in the first hour of treatment, about 9 mg to about 32 mg in the first hour of treatment, about 10 mg to about 30 mg in the first hour of treatment, about 11 mg to about 29 mg in the first hour of treatment, about 12 mg to about 28 mg in the first hour of treatment, about 13 mg to about 27 mg in the first hour of treatment, about 14 mg to about 26 mg in the first hour of treatment, about 15 mg to about 25 mg in the first hour of treatment, about 16 mg to about 24 mg in the first hour of treatment, about 17 mg to about 23 mg in the first hour of treatment, about 18 mg to about 22 mg in the first hour of treatment, or about 19 mg to about 21 mg in the first hour of treatment, among others. Exemplary amounts of nifedipine that may be administered to the subject in the first hour of treatment include amounts of nifedipine of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as an amount of about 20 mg, among others.

In another aspect, the invention features a method of prolonging gestation in a pregnant subject (e.g., a pregnant human female) for a time sufficient for the subject to be administered one or more antenatal corticosteroids (e.g., betamethasone, dexamethasone, and/or hydrocortisone), such as to promote fetal lung maturation. The method includes administering to the subject a therapeutically effective amount of a PGF2α receptor antagonist, such as a compound represented by formula (I)

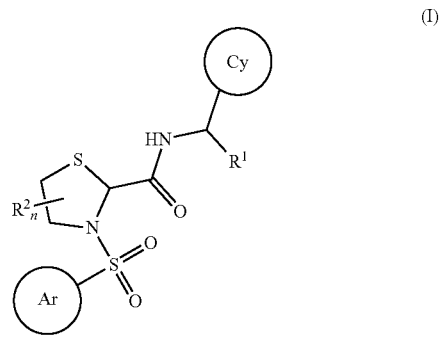

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 40 mg or less in the first hour of treatment. For instance, the subject may be one that is concurrently being administered nifedipine (or that has previously been administered nifedipine) in an amount of from about 1 mg to about 40 mg in the first hour of treatment, about 2 mg to about 39 mg in the first hour of treatment, about 3 mg to about 38 mg in the first hour of treatment, about 4 mg to about 37 mg in the first hour of treatment, about 5 mg to about 36 mg in the first hour of treatment, about 6 mg to about 35 mg in the first hour of treatment, about 7 mg to about 34 mg in the first hour of treatment, about 8 mg to about 33 mg in the first hour of treatment, about 9 mg to about 32 mg in the first hour of treatment, about 10 mg to about 30 mg in the first hour of treatment, about 11 mg to about 29 mg in the first hour of treatment, about 12 mg to about 28 mg in the first hour of treatment, about 13 mg to about 27 mg in the first hour of treatment, about 14 mg to about 26 mg in the first hour of treatment, about 15 mg to about 25 mg in the first hour of treatment, about 16 mg to about 24 mg in the first hour of treatment, about 17 mg to about 23 mg in the first hour of treatment, about 18 mg to about 22 mg in the first hour of treatment, or about 19 mg to about 21 mg in the first hour of treatment, among others. Exemplary amounts of nifedipine that may be (or may have been) administered to the subject in the first hour of treatment include amounts of nifedipine of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as an amount of about 20 mg, among others.

In another aspect, the invention features a method of prolonging gestation in a pregnant subject (e.g., a pregnant human female) for a time sufficient for the subject to be administered one or more antenatal corticosteroids (e.g., betamethasone, dexamethasone, and/or hydrocortisone), such as to promote fetal lung maturation. The method includes administering to the subject therapeutically effective amounts of nifedipine and a PGF2α receptor antagonist, such as a compound represented by formula (I)

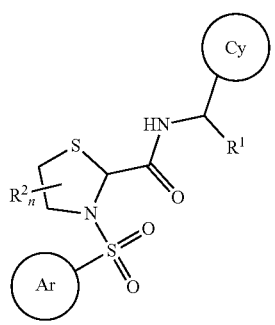

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine is administered to the subject in an amount of about 200 mg or less per day. For example, the nifedipine may be administered to the subject in an amount of from about 1 mg to about 200 mg per day, about 2 mg to about 199 mg per day, about 3 mg to about 198 mg per day, about 4 mg to about 197 mg per day, about 5 mg to about 196 mg per day, about 6 mg to about 195 mg per day, about 7 mg to about 194 mg per day, about 8 mg to about 193 per day, about 9 mg to about 192 per day, about 10 mg to about 191 per day, about 11 mg to about 190 per day, about 12 mg to about 189 per day, about 13 mg to about 188 per day, about 14 mg to about 187 per day, about 15 mg to about 186 per day, about 16 mg to about 185 mg per day, about 17 mg to about 184 per day, about 18 mg to about 183 per day, about 19 mg to about 182 per day, about 20 mg to about 181 mg per day, about 21 mg to about 180 per day, about 22 mg to about 179 per day, about 23 mg to about 178 mg per day, about 24 mg to about 177 mg per day, about 25 mg to about 176 mg per day, about 26 mg to about 175 mg per day, about 27 mg to about 174 mg per day, about 28 mg to about 173 mg per day, about 29 mg to about 172 mg per day, about 30 mg to about 171 mg per day, about 31 mg to about 170 mg per day, about 32 mg to about 169 mg per day, about 33 mg to about 168 mg per day, about 34 mg to about 167 mg per day, about 35 mg to about 166 mg per day, about 36 mg to about 165 mg per day, about 37 mg to about 164 mg per day, about 38 mg to about 163 mg per day, about 39 mg to about 162 per day, about 40 mg to about 161 mg per day, about 41 to about 160 mg per day, about 42 to about 159 mg per day, about 43 mg to about 158 mg per day, about 44 mg to about 157 mg per day, about 45 mg to about 156 mg per day, about 46 mg to about 155 mg per day, about 47 mg to about 154 mg per day, about 48 mg to about 153 mg per day, about 49 mg to about 152 mg per day, about 50 mg to about 151 mg per day, about 51 mg to about 150 mg per day, about 52 mg to about 149 mg per day, about 53 mg to about 148 mg per day, about 54 mg to about 147 mg per day, about 55 mg to about 146 mg per day, about 56 mg to about 145 mg per day, about 57 mg to about 144 mg per day, about 58 mg to about 143 mg per day, about 59 mg to about 142 mg per day, about 60 mg to about 141 mg per day, about 61 mg to about 140 mg per day, about 62 mg to about 139 mg per day, about 63 mg to about 138 mg per day, about 64 mg to about 137 mg per day, about 65 mg to about 136 mg per day, about 66 mg to about 135 mg per day, about 67 mg to about 134 mg per day, about 68 mg to about 133 mg per day, about 69 mg to about 132 mg per day, about 70 mg to about 131 mg per day, about 71 mg to about 130 mg per day, about 72 mg to about 129 per day, about 73 mg to about 128 mg per day, about 74 mg to about 127 mg per day, about 75 mg to about 126 mg per day, about 76 mg to about 125 mg per day, about 77 mg to about 124 mg per day, about 78 mg to about 123 mg per day, about 79 mg to about 122 mg per day, about 80 mg to about 121 mg per day, about 81 mg to about 120 mg per day, about 82 mg to about 119 mg per day, about 83 mg to about 118 mg per day, about 84 mg to about 117 mg per day, about 85 mg to about 116 mg per day, about 86 mg to about 115 mg per day, about 87 mg to about 114 mg per day, about 88 mg to about 113 mg per day, about 89 mg to about 112 mg per day, about 90 mg to about 111 mg per day, about 91 mg to about 110 mg per day, about 92 mg to about 109 mg per day, about 93 mg to about 108 mg per day, about 94 mg to about 107 mg per day, about 95 mg to about 106 mg per day, about 96 mg to about 105 mg per day, about 97 mg to about 104 mg per day, about 98 mg to about 103 mg per day, about 99 mg to about 102 mg per day, or about 100 to about 101 mg per day, among others. Exemplary total daily quantities of nifedipine that may be administered to the subject include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, and 200 mg, among others.

In another aspect, the invention features a method of prolonging gestation in a pregnant subject (e.g., a pregnant human female) for a time sufficient for the subject to be administered one or more antenatal corticosteroids (e.g., betamethasone, dexamethasone, and/or hydrocortisone), such as to promote fetal lung maturation. The method includes administering to the subject a therapeutically effective amount of a PGF2α receptor antagonist, such as a compound represented by formula (I)

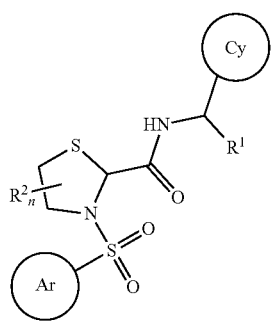

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 200 mg or less per day. For example, the subject may be one that is concurrently being administered nifedipine (or that has previously been administered nifedipine) in an amount of from about 1 mg to about 200 mg per day, about 2 mg to about 199 mg per day, about 3 mg to about 198 mg per day, about 4 mg to about 197 mg per day, about 5 mg to about 196 mg per day, about 6 mg to about 195 mg per day, about 7 mg to about 194 mg per day, about 8 mg to about 193 mg per day, about 9 mg to about 192 mg per day, about 10 mg to about 191 mg per day, about 11 mg to about 190 mg per day, about 12 mg to about 189 per day, about 13 mg to about 188 per day, about 14 mg to about 187 per day, about 15 mg to about 186 per day, about 16 mg to about 185 mg per day, about 17 mg to about 184 per day, about 18 mg to about 183 per day, about 19 mg to about 182 per day, about 20 mg to about 181 mg per day, about 21 mg to about 180 per day, about 22 mg to about 179 mg per day, about 23 mg to about 178 mg per day, about 24 mg to about 177 mg per day, about 25 mg to about 176 mg per day, about 26 mg to about 175 mg per day, about 27 mg to about 174 mg per day, about 28 mg to about 173 mg per day, about 29 mg to about 172 mg per day, about 30 mg to about 171 mg per day, about 31 mg to about 170 mg per day, about 32 mg to about 169 mg per day, about 33 mg to about 168 mg per day, about 34 mg to about 167 mg per day, about 35 mg to about 166 mg per day, about 36 mg to about 165 mg per day, about 37 mg to about 164 mg per day, about 38 mg to about 163 mg per day, about 39 mg to about 162 per day, about 40 mg to about 161 mg per day, about 41 to about 160 mg per day, about 42 to about 159 mg per day, about 43 mg to about 158 mg per day, about 44 mg to about 157 mg per day, about 45 mg to about 156 mg per day, about 46 mg to about 155 mg per day, about 47 mg to about 154 mg per day, about 48 mg to about 153 mg per day, about 49 mg to about 152 mg per day, about 50 mg to about 151 mg per day, about 51 mg to about 150 mg per day, about 52 mg to about 149 mg per day, about 53 mg to about 148 mg per day, about 54 mg to about 147 mg per day, about 55 mg to about 146 mg per day, about 56 mg to about 145 mg per day, about 57 mg to about 144 mg per day, about 58 mg to about 143 mg per day, about 59 mg to about 142 mg per day, about 60 mg to about 141 mg per day, about 61 mg to about 140 mg per day, about 62 mg to about 139 mg per day, about 63 mg to about 138 mg per day, about 64 mg to about 137 mg per day, about 65 mg to about 136 mg per day, about 66 mg to about 135 mg per day, about 67 mg to about 134 mg per day, about 68 mg to about 133 mg per day, about 69 mg to about 132 mg per day, about 70 mg to about 131 mg per day, about 71 mg to about 130 mg per day, about 72 mg to about 129 mg per day, about 73 mg to about 128 mg per day, about 74 mg to about 127 mg per day, about 75 mg to about 126 mg per day, about 76 mg to about 125 mg per day, about 77 mg to about 124 mg per day, about 78 mg to about 123 mg per day, about 79 mg to about 122 mg per day, about 80 mg to about 121 mg per day, about 81 mg to about 120 mg per day, about 82 mg to about 119 mg per day, about 83 mg to about 118 mg per day, about 84 mg to about 117 mg per day, about 85 mg to about 116 mg per day, about 86 mg to about 115 mg per day, about 87 mg to about 114 mg per day, about 88 mg to about 113 mg per day, about 89 mg to about 112 mg per day, about 90 mg to about 111 mg per day, about 91 mg to about 110 mg per day, about 92 mg to about 109 mg per day, about 93 mg to about 108 mg per day, about 94 mg to about 107 mg per day, about 95 mg to about 106 mg per day, about 96 mg to about 105 mg per day, about 97 mg to about 104 mg per day, about 98 mg to about 103 mg per day, about 99 mg to about 102 mg per day, or about 100 to about 101 mg per day, among others. Exemplary total daily quantities of nifedipine that may be (or may have been) administered to the subject include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, and 200 mg, among others.

In yet another aspect, the invention provides a method of prolonging gestation in a pregnant subject (e.g., a pregnant human female) for a time sufficient for the subject to be administered one or more antenatal corticosteroids (e.g., betamethasone, dexamethasone, and/or hydrocortisone), such as to promote fetal lung maturation. The method includes administering to the subject therapeutically effective amounts of nifedipine and a PGF2α receptor antagonist, such as a compound represented by formula (I)

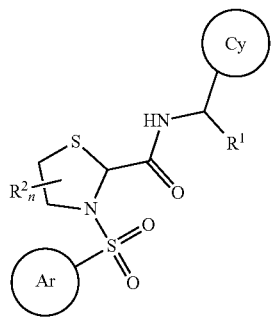

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the nifedipine is administered to the subject in an amount of about 1,500 mg or less per week. For example, the subject may be administered from about 1 mg to about 1,500 mg of nifedipine per week, such as from about 10 mg to about 1,490 mg per week, about 20 mg to about 1,480 mg per week, about 30 mg to about 1,470 mg per week, about 40 mg to about 1,460 mg per week, about 50 mg to about 1,450 mg per week, about 60 mg to about 1,440 mg per week, about 70 mg to about 1,430 mg per week, about 80 mg to about 1,420 mg per week, about 90 mg to about 1,410 mg per week, about 100 mg to about 1,400 mg per week, about 110 mg to about 1,390 mg per week, about 120 mg to about 1,380 mg per week, about 130 mg to about 1,370 mg per week, about 140 mg to about 1,360 mg per week, about 150 mg to about 1,350 mg per week, about 160 mg to about 1,340 mg per week, about 170 mg to about 1,330 mg per week, about 180 mg to about 1,320 mg per week, about 190 mg to about 1,310 mg per week, about 200 mg to about 1,300 mg per week, about 210 mg to about 1,290 mg per week, about 220 mg to about 1,280 mg per week, about 230 mg to about 1,270 mg per week, about 240 mg to about 1,260 mg per week, about 250 mg to about 1,250 mg per week, about 260 mg to about 1,240 mg per week, about 270 mg to about 1,230 mg per week, about 280 mg to about 1,220 mg per week, about 290 mg to about 1,210 mg per week, about 300 mg to about 1,200 mg per week, about 310 mg to about 1,190 mg per week, about 320 mg to about 1,180 mg per week, about 330 mg to about 1,170 mg per week, about 340 mg to about 1,160 mg per week, about 350 mg to about 1,150 mg per week, about 360 mg to about 1,140 mg per week, about 370 mg to about 1,130 mg per week, about 380 mg to about 1,120 mg per week, about 390 mg to about 1,110 mg per week, about 400 mg to about 1,100 mg per week, about 410 mg to about 1,090 mg per week, about 420 mg to about 1,080 mg per week, about 430 mg to about 1,070 mg per week, about 440 mg to about 1,060 mg per week, about 450 mg to about 1,050 mg per week, about 460 mg to about 1,040 mg per week, about 470 mg to about 1,030 mg per week, about 480 mg to about 1,020 mg per week, about 490 mg to about 1,010 mg per week, about 500 mg to about 1,000 mg per week, about 510 mg to about 990 mg per week, about 520 mg to about 980 mg per week, about 530 mg to about 970 mg per week, about 540 mg to about 960 mg per week, about 550 mg to about 950 mg per week, about 560 mg to about 940 mg per week, about 570 mg to about 930 mg per week, about 580 mg to about 920 mg per week, about 590 mg to about 910 mg per week, about 600 mg to about 900 mg per week, about 610 mg to about 890 mg per week, about 620 mg to about 880 mg per week, about 630 mg to about 870 mg per week, about 640 mg to about 860 mg per week, about 650 mg to about 850 mg per week, about 660 mg to about 840 mg per week, about 670 mg to about 830 mg per week, about 680 mg to about 820 mg per week, about 690 mg to about 810 mg per week, about 700 mg to about 800 mg per week, about 710 mg to about 790 mg per week, about 720 mg to about 780 mg per week, about 730 mg to about 770 mg per week, or about 740 mg to about 760 mg per week, among others.

Exemplary total weekly quantities of nifedipine that may be administered to the subject in accordance with the preceding aspect include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, 1,000 mg, 1,005 mg, 1,010 mg, 1,015 mg, 1,020 mg, 1,025 mg, 1,030 mg, 1,035 mg, 1,040 mg, 1,045 mg, 1,050 mg, 1,055 mg, 1,060 mg, 1,065 mg, 1,070 mg, 1,075 mg, 1,080 mg, 1,085 mg, 1,090 mg, 1,095 mg, 1,100 mg, 1,105 mg, 1,110 mg, 1,115 mg, 1,120 mg, 1,125 mg, 1,130 mg, 1,135 mg, 1,140 mg, 1,145 mg, 1,150 mg, 1,155 mg, 1,160 mg, 1,165 mg, 1,170 mg, 1,175 mg, 1,180 mg, 1,185 mg, 1,190 mg, 1,195 mg, 1,200 mg, 1,205 mg, 1,210 mg, 1,215 mg, 1,220 mg, 1,225 mg, 1,230 mg, 1,235 mg, 1,240 mg, 1,245 mg, 1,250 mg, 1,255 mg, 1,260 mg, 1,265 mg, 1,270 mg, 1,275 mg, 1,280 mg, 1,285 mg, 1,290 mg, 1,295 mg, 1,300 mg, 1,305 mg, 1,310 mg, 1,315 mg, 1,320 mg, 1,325 mg, 1,330 mg, 1,335 mg, 1,340 mg, 1,345 mg, 1,350 mg, 1,355 mg, 1,360 mg, 1,365 mg, 1,370 mg, 1,375 mg, 1,380 mg, 1,385 mg, 1,390 mg, 1,395 mg, 900 mg, 1,405 mg, 1,410 mg, 1,415 mg, 1,420 mg, 1,425 mg, 1,430 mg, 1,435 mg, 1,440 mg, 1,445 mg, 1,450 mg, 1,455 mg, 1,460 mg, 1,465 mg, 1,470 mg, 1,475 mg, 1,480 mg, 1,485 mg, 1,490 mg, 1,495 mg, and 1,500 mg, among others.

In yet another aspect, the invention provides a method of prolonging gestation in a pregnant subject (e.g., a pregnant human female) for a time sufficient for the subject to be administered one or more antenatal corticosteroids (e.g., betamethasone, dexamethasone, and/or hydrocortisone), such as to promote fetal lung maturation. The method includes administering to the subject a therapeutically effective amount of a PGF2α receptor antagonist, such as a compound represented by formula (I)

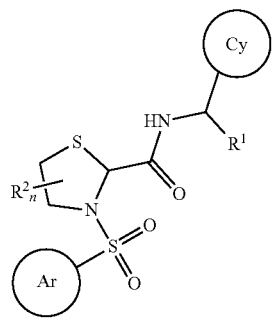

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In accordance with this aspect, the subject is concurrently undergoing treatment with nifedipine, or has previously been administered nifedipine, for example, in an amount of about 1,500 mg or less per week. For example, the subject may be one that is concurrently being administered nifedipine (or that has previously been administered nifedipine) in an amount of from about 1 mg to about 1,500 mg of nifedipine per week, such as from about 10 mg to about 1,490 mg per week, about 20 mg to about 1,480 mg per week, about 30 mg to about 1,470 mg per week, about 40 mg to about 1,460 mg per week, about 50 mg to about 1,450 mg per week, about 60 mg to about 1,440 mg per week, about 70 mg to about 1,430 mg per week, about 80 mg to about 1,420 mg per week, about 90 mg to about 1,410 mg per week, about 100 mg to about 1,400 mg per week, about 110 mg to about 1,390 mg per week, about 120 mg to about 1,380 mg per week, about 130 mg to about 1,370 mg per week, about 140 mg to about 1,360 mg per week, about 150 mg to about 1,350 mg per week, about 160 mg to about 1,340 mg per week, about 170 mg to about 1,330 mg per week, about 180 mg to about 1,320 mg per week, about 190 mg to about 1,310 mg per week, about 200 mg to about 1,300 mg per week, about 210 mg to about 1,290 mg per week, about 220 mg to about 1,280 mg per week, about 230 mg to about 1,270 mg per week, about 240 mg to about 1,260 mg per week, about 250 mg to about 1,250 mg per week, about 260 mg to about 1,240 mg per week, about 270 mg to about 1,230 mg per week, about 280 mg to about 1,220 mg per week, about 290 mg to about 1,210 mg per week, about 300 mg to about 1,200 mg per week, about 310 mg to about 1,190 mg per week, about 320 mg to about 1,180 mg per week, about 330 mg to about 1,170 mg per week, about 340 mg to about 1,160 mg per week, about 350 mg to about 1,150 mg per week, about 360 mg to about 1,140 mg per week, about 370 mg to about 1,130 mg per week, about 380 mg to about 1,120 mg per week, about 390 mg to about 1,110 mg per week, about 400 mg to about 1,100 mg per week, about 410 mg to about 1,090 mg per week, about 420 mg to about 1,080 mg per week, about 430 mg to about 1,070 mg per week, about 440 mg to about 1,060 mg per week, about 450 mg to about 1,050 mg per week, about 460 mg to about 1,040 mg per week, about 470 mg to about 1,030 mg per week, about 480 mg to about 1,020 mg per week, about 490 mg to about 1,010 mg per week, about 500 mg to about 1,000 mg per week, about 510 mg to about 990 mg per week, about 520 mg to about 980 mg per week, about 530 mg to about 970 mg per week, about 540 mg to about 960 mg per week, about 550 mg to about 950 mg per week, about 560 mg to about 940 mg per week, about 570 mg to about 930 mg per week, about 580 mg to about 920 mg per week, about 590 mg to about 910 mg per week, about 600 mg to about 900 mg per week, about 610 mg to about 890 mg per week, about 620 mg to about 880 mg per week, about 630 mg to about 870 mg per week, about 640 mg to about 860 mg per week, about 650 mg to about 850 mg per week, about 660 mg to about 840 mg per week, about 670 mg to about 830 mg per week, about 680 mg to about 820 mg per week, about 690 mg to about 810 mg per week, about 700 mg to about 800 mg per week, about 710 mg to about 790 mg per week, about 720 mg to about 780 mg per week, about 730 mg to about 770 mg per week, or about 740 mg to about 760 mg per week, among others.

Exemplary total weekly quantities of nifedipine that may be (or may have been) administered to the subject in accordance with the preceding aspect include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, 1,000 mg, 1,005 mg, 1,010 mg, 1,015 mg, 1,020 mg, 1,025 mg, 1,030 mg, 1,035 mg, 1,040 mg, 1,045 mg, 1,050 mg, 1,055 mg, 1,060 mg, 1,065 mg, 1,070 mg, 1,075 mg, 1,080 mg, 1,085 mg, 1,090 mg, 1,095 mg, 1,100 mg, 1,105 mg, 1,110 mg, 1,115 mg, 1,120 mg, 1,125 mg, 1,130 mg, 1,135 mg, 1,140 mg, 1,145 mg, 1,150 mg, 1,155 mg, 1,160 mg, 1,165 mg, 1,170 mg, 1,175 mg, 1,180 mg, 1,185 mg, 1,190 mg, 1,195 mg, 1,200 mg, 1,205 mg, 1,210 mg, 1,215 mg, 1,220 mg, 1,225 mg, 1,230 mg, 1,235 mg, 1,240 mg, 1,245 mg, 1,250 mg, 1,255 mg, 1,260 mg, 1,265 mg, 1,270 mg, 1,275 mg, 1,280 mg, 1,285 mg, 1,290 mg, 1,295 mg, 1,300 mg, 1,305 mg, 1,310 mg, 1,315 mg, 1,320 mg, 1,325 mg, 1,330 mg, 1,335 mg, 1,340 mg, 1,345 mg, 1,350 mg, 1,355 mg, 1,360 mg, 1,365 mg, 1,370 mg, 1,375 mg, 1,380 mg, 1,385 mg, 1,390 mg, 1,395 mg, 900 mg, 1,405 mg, 1,410 mg, 1,415 mg, 1,420 mg, 1,425 mg, 1,430 mg, 1,435 mg, 1,440 mg, 1,445 mg, 1,450 mg, 1,455 mg, 1,460 mg, 1,465 mg, 1,470 mg, 1,475 mg, 1,480 mg, 1,485 mg, 1,490 mg, 1,495 mg, and 1,500 mg, among others.

In some embodiments of any of the above aspects, the ring Ar is selected from substituents (Ia) to (Iy):

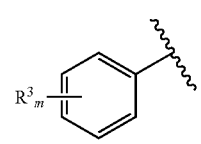

(Ia)

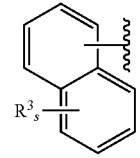

(Ib)

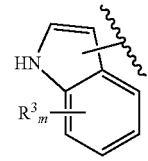

(Ic)

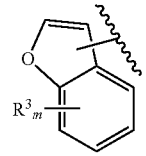

(Id)

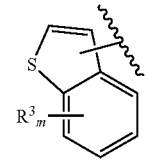

(Ie)

-continued (If) 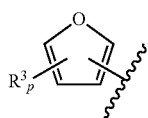

(Ig) 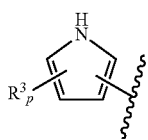

(Ih) 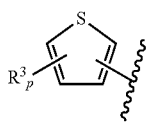

(Ii) 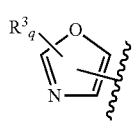

(Ij) 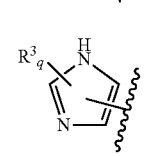

(Ik) 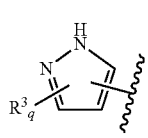

(Il) 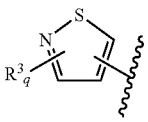

(Im) 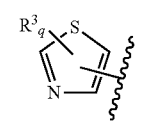

(In) 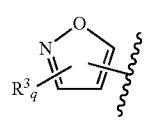

(Io) 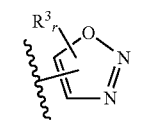

(Ip) 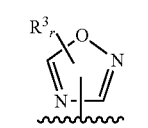

(Iq) 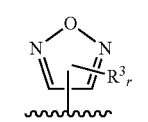

(Ir)

-continued (Is) 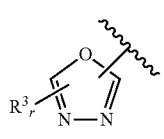

(It) 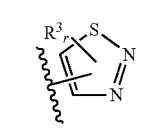

(Iu) 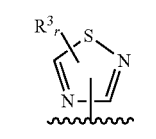

(Iv) 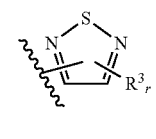

(Iw) 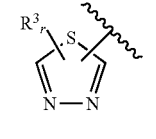

(Ix) 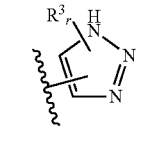

(Iy) 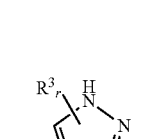

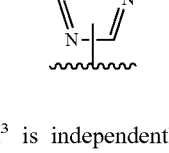

wherein each $R^3$ is independently halogen, haloalkyl, cyano, optionally substituted amino, hydroxyl, thiol, optionally substituted alkoxy, optionally substituted acyloxy, optionally substituted alkoxycarbonyl, carboxy, ureido, alkyl sulfonyl, aryl sulfonyl, heteroaryl sulfonyl, cycloalkyl sulfonyl, heterocycloalkyl sulfonyl, alkyl sulfanyl, aryl sulfanyl, heteroaryl sulfanyl, cycloalkyl sulfanyl, heterocycloalkyl sulfanyl, alkyl sulfinyl, aryl sulfinyl, heteroaryl sulfinyl, cycloalkyl sulfinyl, heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

each m is independently an integer from 0-5;

each p is independently an integer from 0-3;

each q is independently an integer from 0-2;

each r is independently an integer from 0-1; and each s is independently an integer from 0-7.

In some embodiments, each $R^3$ is independently selected from substituents (IIa) to (IIy).
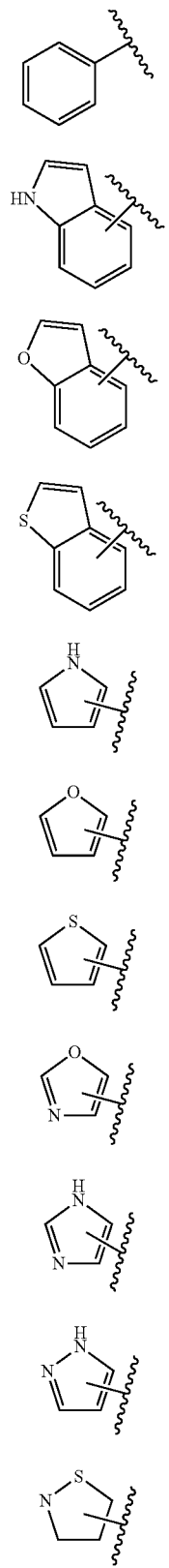
(IIa)
(IIb)
(IIc)
(IId)
(IIe)
(IIf)
(IIg)
(IIh)
(IIi)
(IIj)
(IIk)
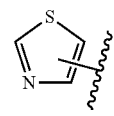 (IIm)
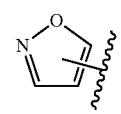 (IIn)
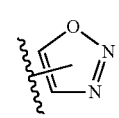 (IIp)
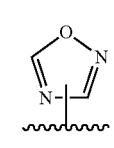 (IIq)
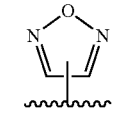 (IIr)
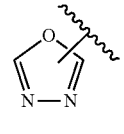 (IIs)
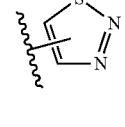 (IIt)
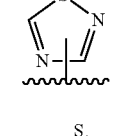 (IIu)
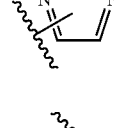 (IIv)
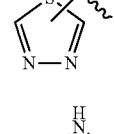 (IIw)
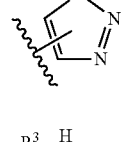 (IIx)
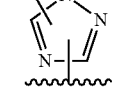 (IIy)

In some embodiments, the ring Ar is a substituent represented by formula (Ia)

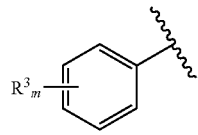

(Ia)

and each R³ is, independently, optionally substituted and optionally fused aryl, optionally substituted and optionally fused heteroaryl, optionally substituted and optionally fused cycloalkyl, or optionally substituted and optionally fused heterocycloalkyl.

In some embodiments, the ring Cy is selected from substituents (IIIa) to (IIIaa):

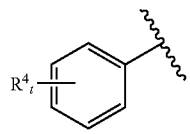

(IIIa)

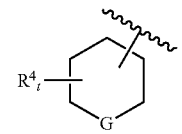

(IIIb)

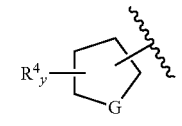

(IIIc)

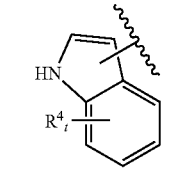

(IIId)

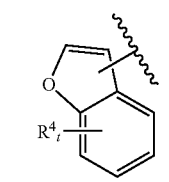

(IIIe)

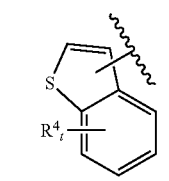

(IIIf)

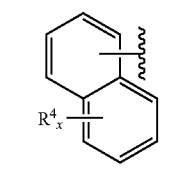

(IIIg)

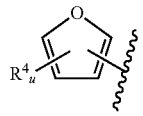

(IIIh)

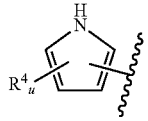

(IIIi)

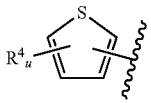

(IIIj)

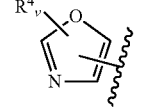

(IIIk)

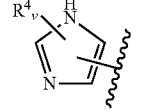

(IIIm)

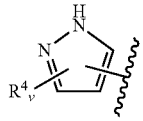

(IIIn)

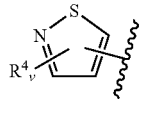

(IIIo)

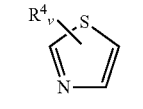

(IIIp)

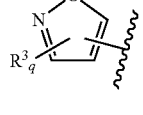

(IIIq)

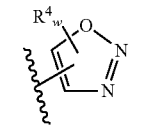

(IIIr)

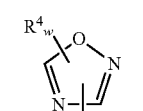

(IIIs)

(IIIt)

-continued

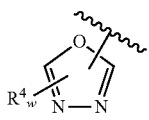 (IIIu)

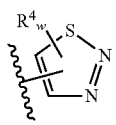 (IIIv)

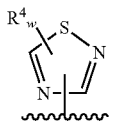 (IIIw)

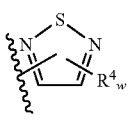 (IIIx)

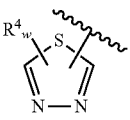 (IIIy)

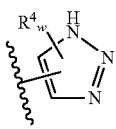 (IIIz)

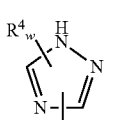 (IIIaa)

wherein each $R^4$ is independently halogen, haloalkyl, cyano, optionally substituted amino, hydroxyl, thiol, optionally substituted alkoxy, optionally substituted acyloxy, optionally substituted alkoxycarbonyl, carboxy, ureido, alkyl sulfonyl, aryl sulfonyl, heteroaryl sulfonyl, cycloalkyl sulfonyl, heterocycloalkyl sulfonyl, alkyl sulfanyl, aryl sulfanyl, heteroaryl sulfanyl, cycloalkyl sulfanyl, heterocycloalkyl sulfanyl, alkyl sulfinyl, aryl sulfinyl, heteroaryl sulfinyl, cycloalkyl sulfinyl, heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

each G is independently —CH$_2$—, —CR$^4$H—, —NH—, —NR$^4$—, —O—, or —S—;

each t is independently an integer from 0-5;

each u is independently an integer from 0-3;

each v is independently an integer from 0-2;

each w is independently an integer from 0-1;

each x is independently an integer from 0-7; and each y is independently an integer from 0-4.

In some embodiments, the ring Cy is an optionally substituted aryl group represented by formula (IVa).

(IVa)

In some embodiments, the ring Cy is a substituted aryl group represented by formula (IVb).

(IVb)

In some embodiments, $R^1$ is $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, substituted $C_1$-$C_5$-alkyl carboxy, substituted $C_1$-$C_5$-alkyl acyl, substituted $C_1$-$C_5$-alkyl alkoxycarbonyl, or substituted $C_1$-$C_5$-alkyl acyloxy. In some embodiments, $R^1$ is optionally substituted $C_1$-$C_5$-alkyl acyloxy.

In some embodiments, the compound is represented by formula (V)

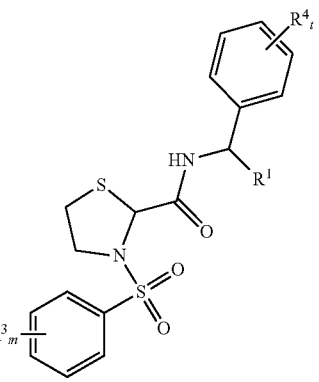 (V)

wherein $R^1$ is $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, substituted $C_1$-$C_5$-alkyl carboxy, substituted $C_1$-$C_5$-alkyl acyl, substituted $C_1$-$C_5$-alkyl alkoxycarbonyl, or substituted $C_1$-$C_5$-alkyl acyloxy;

each $R^3$ is independently halogen, haloalkyl, cyano, optionally substituted amino, hydroxyl, thiol, optionally substituted alkoxy, optionally substituted acyloxy, optionally substituted alkoxycarbonyl, carboxy, ureido, alkyl sulfonyl, aryl sulfonyl, heteroaryl sulfonyl, cycloalkyl sulfonyl, heterocycloalkyl sulfonyl, alkyl sulfanyl, aryl sulfanyl, heteroaryl sulfanyl, cycloalkyl sulfanyl, heterocycloalkyl sulfanyl, alkyl sulfinyl, aryl sulfinyl, heteroaryl sulfinyl, cycloalkyl sulfinyl, heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

each $R^4$ is independently halogen, haloalkyl, cyano, optionally substituted amino, hydroxyl, thiol, optionally substituted alkoxy, optionally substituted acyloxy, optionally substituted alkoxycarbonyl, carboxy, ureido, alkyl sulfonyl, aryl sulfonyl, heteroaryl sulfonyl, cycloalkyl sulfonyl, heterocycloalkyl sulfonyl, alkyl sulfanyl, aryl sulfanyl, heteroaryl sulfanyl, cycloalkyl sulfanyl, heterocycloalkyl sulfanyl, alkyl sulfinyl, aryl sulfinyl, heteroaryl sulfinyl, cycloalkyl sulfinyl, heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

m is an integer from 0-5; and t is an integer from 0-5, or a pharmaceutically acceptable salt thereof.

In some embodiments, the compound is represented by formula (Va)

(Va)

or a pharmaceutically acceptable salt thereof.

In some embodiments, the compound is represented by formula (VI)

(VI)

wherein $R^6$ is hydroxyl, acyl, alkoxycarbonyl, or acyloxy;

each $R^5$ is independently halogen, haloalkyl, cyano, optionally substituted amino, hydroxyl, thiol, optionally substituted alkoxy, optionally substituted acyloxy, optionally substituted alkoxycarbonyl, carboxy, ureido, alkyl sulfonyl, aryl sulfonyl, heteroaryl sulfonyl, cycloalkyl sulfonyl, heterocycloalkyl sulfonyl, alkyl sulfanyl, aryl sulfanyl, heteroaryl sulfanyl, cycloalkyl sulfanyl, heterocycloalkyl sulfanyl, alkyl sulfinyl, aryl sulfinyl, heteroaryl sulfinyl, cycloalkyl sulfinyl, heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl; $R^4$ is halogen, haloalkyl, cyano, optionally substituted amino, hydroxyl, thiol, optionally substituted alkoxy, optionally substituted acyloxy, optionally substituted alkoxycarbonyl, carboxy, ureido, alkyl sulfonyl, aryl sulfonyl, heteroaryl sulfonyl, cycloalkyl sulfonyl, heterocycloalkyl sulfonyl, alkyl sulfanyl, aryl sulfanyl, heteroaryl sulfanyl, cycloalkyl sulfanyl, heterocycloalkyl sulfanyl, alkyl sulfinyl, aryl sulfinyl, heteroaryl sulfinyl, cycloalkyl sulfinyl, heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

i is an integer from 0-3; and x is an integer from 0-5, or a pharmaceutically acceptable salt thereof.

In some embodiments, the compound is represented by formula (VII)

(VII)

wherein $R^7$ is H or optionally substituted aminoacyl;

each $R^5$ is independently halogen, haloalkyl, cyano, optionally substituted amino, hydroxyl, thiol, optionally substituted alkoxy, optionally substituted acyloxy, optionally substituted alkoxycarbonyl, carboxy, ureido, alkyl sulfonyl, aryl sulfonyl, heteroaryl sulfonyl, cycloalkyl sulfonyl, heterocycloalkyl sulfonyl, alkyl sulfanyl, aryl sulfanyl, heteroaryl sulfanyl, cycloalkyl sulfanyl, heterocycloalkyl sulfanyl, alkyl sulfinyl, aryl sulfinyl, heteroaryl sulfinyl, cycloalkyl sulfinyl, heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl; $R^4$ is halogen, haloalkyl, cyano, optionally substituted amino, hydroxyl, thiol, optionally substituted alkoxy, optionally substituted acyloxy, optionally substituted alkoxycarbonyl, carboxy, ureido, alkyl sulfonyl, aryl sulfonyl, heteroaryl sulfonyl, cycloalkyl sulfonyl, heterocycloalkyl sulfonyl, alkyl sulfanyl, aryl sulfanyl, heteroaryl sulfanyl, cycloalkyl sulfanyl, heterocycloalkyl sulfanyl, alkyl sulfinyl, aryl sulfinyl, heteroaryl sulfinyl, cycloalkyl sulfinyl, heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

i is an integer from 0-3; and x is an integer from 0-5, or a pharmaceutically acceptable salt thereof.

In some embodiments, the compound is represented by formula (VII)

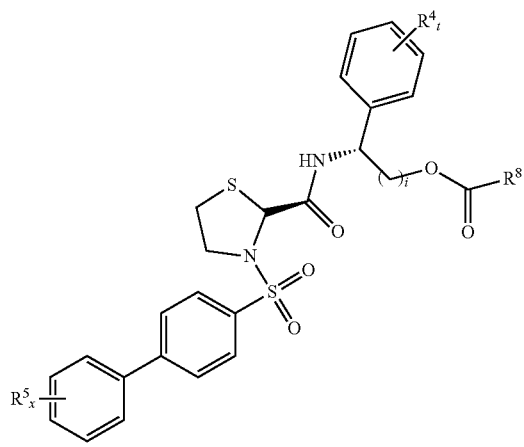

(VIII)

wherein $R^8$ is optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl, preferably wherein $R^8$ is amino-substituted alkyl, such as 1-amino $C_1$-$C_6$ alkyl (e.g., (S)-1-amino $C_1$-$C_6$ alkyl or (R)-1-amino $C_1$-$C_6$ alkyl, for example, (S)-1-amino-2-methylpropyl, (S)-1-amino-2-methylbutyl, (S)-1-amino-3-methylbutyl, (R)-1-amino-2-methylpropyl, (R)-1-amino-2-methylbutyl, or (R)-1-amino-3-methylbutyl;

each $R^5$ is independently halogen, haloalkyl, cyano, optionally substituted amino, hydroxyl, thiol, optionally substituted alkoxy, optionally substituted acyloxy, optionally substituted alkoxycarbonyl, carboxy, ureido, alkyl sulfonyl, aryl sulfonyl, heteroaryl sulfonyl, cycloalkyl sulfonyl, heterocycloalkyl sulfonyl, alkyl sulfanyl, aryl sulfanyl, heteroaryl sulfanyl, cycloalkyl sulfanyl, heterocycloalkyl sulfanyl, alkyl sulfinyl, aryl sulfinyl, heteroaryl sulfinyl, cycloalkyl sulfinyl, heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl; $R^4$ is halogen, haloalkyl, cyano, optionally substituted amino, hydroxyl, thiol, optionally substituted alkoxy, optionally substituted acyloxy, optionally substituted alkoxycarbonyl, carboxy, ureido, alkyl sulfonyl, aryl sulfonyl, heteroaryl sulfonyl, cycloalkyl sulfonyl, heterocycloalkyl sulfonyl, alkyl sulfanyl, aryl sulfanyl, heteroaryl sulfanyl, cycloalkyl sulfanyl, heterocycloalkyl sulfanyl, alkyl sulfinyl, aryl sulfinyl, heteroaryl sulfinyl, cycloalkyl sulfinyl, heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

i is an integer from 0-3;

t is an integer from 0-5; and x is an integer from 0-5, or a pharmaceutically acceptable salt thereof.

In some embodiments of any of the above aspects, the method includes providing to the subject compound (1). This can be achieved, for example, by administering to the subject compound (2), a pharmaceutically acceptable salt thereof, or another compound that is metabolized to compound (1) in vivo.

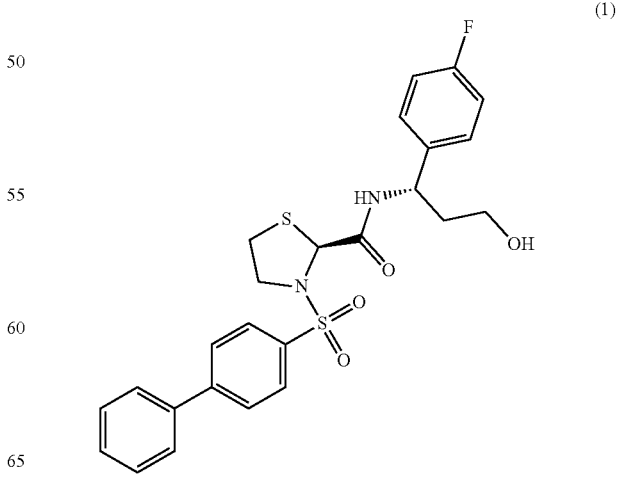

(1)

In some embodiments of any of the above aspects, the method includes administering to the subject compound (2)

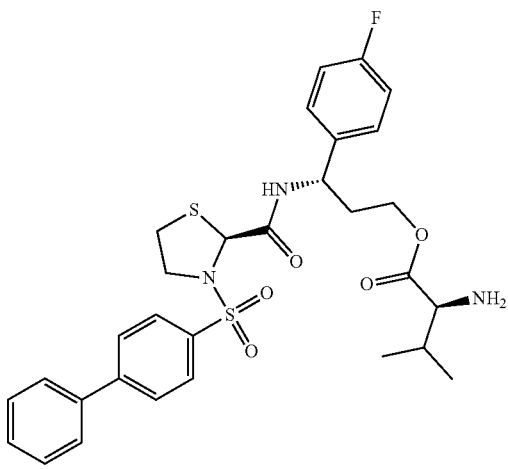

(2)

or a pharmaceutically acceptable salt thereof, such as the chloride salt thereof, represented by formula (3).

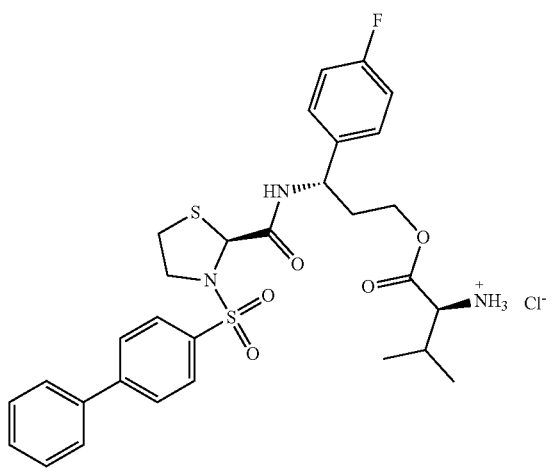

(3)

In some embodiments of any of the above aspects, the compound is in a crystalline state. For example, the compound may be crystalline compound (3), and exhibit:
(a) characteristic X-ray powder diffraction peaks at about 7.0° 2θ, about 8.1° 2θ, about 10.0° 2θ, about 12.0° 2θ, about 13.1° 2θ, about 14.1° 2θ, about 16.4° 2θ, about 18.4° 2θ, about 20.1° 2θ, about 21.0° 2θ, about 23.5° 2θ, and about 29.5° 2θ;
(b) $^1$H nuclear magnetic resonance (NMR) peaks centered at about 1.1 ppm, about 3.3 ppm, about 4.9 ppm, about 5.4 ppm, about 7.1 ppm, about 7.7 ppm, about 7.9 ppm, and about 8.0 ppm;
(c) an endotherm at from about 145° C. to about 147° C. as measured by differential scanning calorimetry;
(d) a weight loss of from about 0.2% to about 0.6% when heated from 25° C. to 100° C. as measured by thermogravimetric analysis; and/or
(e) a weight loss of from about 2.5% to about 3.5% when heated from 100° C. to 160° C. as measured by thermogravimetric analysis.

In some embodiments of any of the above aspects, the nifedipine is administered to the subject in one or more doses per 12 hours, 24 hours, 48 hours, or one week. For instance, the nifedipine may be administered to the subject in from one to ten doses (e.g., 1, 2, 3, 4, 5, 6, 7, 8, 9, or 10 doses) every 12 hours, one to ten doses (e.g., 1, 2, 3, 4, 5, 6, 7, 8, 9, or 10 doses) every 14 hours, one to ten doses (e.g., 1, 2, 3, 4, 5, 6, 7, 8, 9, or 10 doses) every 16 hours, one to ten doses (e.g., 1, 2, 3, 4, 5, 6, 7, 8, 9, or 10 doses) every 18 hours, one to ten doses (e.g., 1, 2, 3, 4, 5, 6, 7, 8, 9, or 10 doses) every 20 hours, one to ten doses (e.g., 1, 2, 3, 4, 5, 6, 7, 8, 9, or 10 doses) every 22 hours, one to ten doses (e.g., 1, 2, 3, 4, 5, 6, 7, 8, 9, or 10 doses) every 24 hours, one to ten doses (e.g., 1, 2, 3, 4, 5, 6, 7, 8, 9, or 10 doses) every 26 hours, one to ten doses (e.g., 1, 2, 3, 4, 5, 6, 7, 8, 9, or 10 doses) every 28 hours, one to ten doses (e.g., 1, 2, 3, 4, 5, 6, 7, 8, 9, or 10 doses) every 30 hours, one to ten doses (e.g., 1, 2, 3, 4, 5, 6, 7, 8, 9, or 10 doses) every 32 hours, one to ten doses (e.g., 1, 2, 3, 4, 5, 6, 7, 8, 9, or 10 doses) every 34 hours, one to ten doses (e.g., 1, 2, 3, 4, 5, 6, 7, 8, 9, or 10 doses) every 36 hours, one to ten doses (e.g., 1, 2, 3, 4, 5, 6, 7, 8, 9, or 10 doses) every 38 hours, one to ten doses (e.g., 1, 2, 3, 4, 5, 6, 7, 8, 9, or 10 doses) every 40 hours, one to ten doses (e.g., 1, 2, 3, 4, 5, 6, 7, 8, 9, or 10 doses) every 42 hours, one to ten doses (e.g., 1, 2, 3, 4, 5, 6, 7, 8, 9, or 10 doses) every 44 hours, one to ten doses (e.g., 1, 2, 3, 4, 5, 6, 7, 8, 9, or 10 doses) every 46 hours, one to ten doses (e.g., 1, 2, 3, 4, 5, 6, 7, 8, 9, or 10 doses) every 48 hours, one to ten doses (e.g., 1, 2, 3, 4, 5, 6, 7, 8, 9, or 10 doses) every 60 hours, one to ten doses (e.g., 1, 2, 3, 4, 5, 6, 7, 8, 9, or 10 doses) every 72 hours, one to ten doses (e.g., 1, 2, 3, 4, 5, 6, 7, 8, 9, or 10 doses) every 84 hours, one to ten doses (e.g., 1, 2, 3, 4, 5, 6, 7, 8, 9, or 10 doses) every 96 hours, one to ten doses (e.g., 1, 2, 3, 4, 5, 6, 7, 8, 9, or 10 doses) every 108 hours, one to ten doses (e.g., 1, 2, 3, 4, 5, 6, 7, 8, 9, or 10 doses) every 120 hours, one to ten doses (e.g., 1, 2, 3, 4, 5, 6, 7, 8, 9, or 10 doses) every 132 hours, one to ten doses (e.g., 1, 2, 3, 4, 5, 6, 7, 8, 9, or 10 doses) every 144 hours, one to ten doses (e.g., 1, 2, 3, 4, 5, 6, 7, 8, 9, or 10 doses) every 156 hours, or one to ten doses (e.g., 1, 2, 3, 4, 5, 6, 7, 8, 9, or 10 doses) every week.

In some embodiments of any of the above aspects, the nifedipine is administered to the subject once every 4 two 12 hours, such as once every 4 hours, once every 5 hours, once every 6 hours, once every 7 hours, once every 8 hours, once every 9 hours, once every 10 hours, once every 11 hours, or once every 12 hours.

In some embodiments of any of the above aspects, the nifedipine is administered to the subject in an amount of from about 5 mg to about 40 mg per dose. For instance, the nifedipine may be administered to the subject in an amount of 5 mg per dose, 6 mg per dose, 7 mg per dose, 8 mg per dose, 9 mg per dose, 10 mg per dose, 11 mg per dose, 12 mg per dose, 13 mg per dose, 14 mg per dose, 15 mg per dose, 16 mg per dose, 17 mg per dose, 18 mg per dose, 19 mg per dose, 20 mg per dose, 21 mg per dose, 22 mg per dose, 23 mg per dose, 24 mg per dose, 25 mg per dose, 26 mg per dose, 27 mg per dose, 28 mg per dose, 29 mg per dose, 30 mg per dose, 31 mg per dose, 32 mg per dose, 33 mg per dose, 34 mg per dose, 35 mg per dose, 36 mg per dose, 37 mg per dose, 38 mg per dose, 39 mg per dose, or 40 mg per dose. In some embodiments, the nifedipine is administered to the subject in an amount of from about 10 mg to about 30 mg per dose, such as in an amount of 10 mg per dose, 11 mg per dose, 12 mg per dose, 13 mg per dose, 14 mg per dose, 15 mg per dose, 16 mg per dose, 17 mg per dose, 18 mg per dose, 19 mg per dose, 20 mg per dose, 21 mg per dose, 22 mg per dose, 23 mg per dose, 24 mg per dose, 25 mg per dose, 26 mg per dose, 27 mg per dose, 28 mg per dose, 29 mg per dose, or 30 mg per dose. In some embodiments, the nifedipine is administered to the subject in an amount of about 20 mg per dose, such as an amount of 20 mg per dose given one or more times per 12 hours, 24 hours, 48 hours, or week.

In some embodiments of any of the above aspects, the nifedipine is administered to the subject in an amount of from about 60 mg to about 180 mg per day. For instance, the nifedipine may be administered to the subject in an amount of 60 mg per day, 65 mg per day, 70 mg per day, 75 mg per day, 80 mg per day, 85 mg per day, 90 mg per day, 95 mg per day, 100 mg per day, 105 mg per day, 110 mg per day, 115 mg per day, 120 mg per day, 125 mg per day, 130 mg per day, 135 mg per day, 140 mg per day, 145 mg per day, 150 mg per day, 155 mg per day, 160 mg per day, 165 mg per day, 170 mg per day, 175 mg per day, or 180 mg per day. In some embodiments, the nifedipine is administered to the subject in an amount of about 120 mg per day.

In some embodiments of any of the above aspects, the nifedipine is administered to the subject in an amount of from about 40 mg to about 120 mg per day. For instance, the nifedipine may be administered to the subject in an amount of 40 mg per day, 45 mg per day, 50 mg per day, 55 mg per day, 60 mg per day, 65 mg per day, 70 mg per day, 75 mg per day, 80 mg per day, 85 mg per day, 90 mg per day, 95 mg per day, 100 mg per day, 105 mg per day, 110 mg per day, 115 mg per day, or 120 mg per day. In some embodiments, the nifedipine is administered to the subject in an amount of about 80 mg per day.

In some embodiments of any of the above aspects, the nifedipine is administered to the subject in an amount of from about 30 mg to about 90 mg per day. For instance, the nifedipine may be administered to the subject in an amount of 30 mg per day, 35 mg per day, 40 mg per day, 45 mg per day, 50 mg per day, 55 mg per day, 60 mg per day, 65 mg per day, 70 mg per day, 75 mg per day, 80 mg per day, 85 mg per day, or 90 mg per day. In some embodiments, the nifedipine is administered to the subject in an amount of about 60 mg per day.

In some embodiments of any of the above aspects, the nifedipine is administered to the subject in an amount of from about 20 mg to about 60 mg per day. For instance, the nifedipine may be administered to the subject in an amount of 20 mg per day, 25 mg per day, 30 mg per day, 35 mg per day, 40 mg per day, 45 mg per day, 50 mg per day, 55 mg per day, or 60 mg per day. In some embodiments, the nifedipine is administered to the subject in an amount of about 40 mg per day.

In some embodiments of any of the above aspects, the nifedipine is administered to the subject in an amount of from about 420 mg to about 1,260 mg per week. For instance, the nifedipine may be administered to the subject in an amount of 420 mg per week, 425 mg per week, 430 mg per week, 435 mg per week, 440 mg per week, 445 mg per week, 450 mg per week, 455 mg per week, 460 mg per week, 465 mg per week, 470 mg per week, 475 mg per week, 480 mg per week, 485 mg per week, 490 mg per week, 495 mg per week, 500 mg per week, 505 mg per week, 510 mg per week, 515 mg per week, 520 mg per week, 525 mg per week, 530 mg per week, 535 mg per week, 540 mg per week, 545 mg per week, 550 mg per week, 555 mg per week, 560 mg per week, 565 mg per week, 570 mg per week, 575 mg per week, 580 mg per week, 585 mg per week, 590 mg per week, 595 mg per week, 600 mg per week, 605 mg per week, 610 mg per week, 615 mg per week, 620 mg per week, 625 mg per week, 630 mg per week, 635 mg per week, 640 mg per week, 645 mg per week, 650 mg per week, 655 mg per week, 660 mg per week, 665 mg per week, 670 mg per week, 675 mg per week, 680 mg per week, 685 mg per week, 690 mg per week, 695 mg per week, 700 mg per week, 705 mg per week, 710 mg per week, 715 mg per week, 720 mg per week, 725 mg per week, 730 mg per week, 735 mg per week, 740 mg per week, 745 mg per week, 750 mg per week, 755 mg per week, 760 mg per week, 765 mg per week, 770 mg per week, 775 mg per week, 780 mg per week, 785 mg per week, 790 mg per week, 795 mg per week, 800 mg per week, 805 mg per week, 810 mg per week, 815 mg per week, 820 mg per week, 825 mg per week, 830 mg per week, 835 mg per week, 840 mg per week, 845 mg per week, 850 mg per week, 855 mg per week, 860 mg per week, 865 mg per week, 870 mg per week, 875 mg per week, 880 mg per week, 885 mg per week, 890 mg per week, 895 mg per week, 900 mg per week, 905 mg per week, 910 mg per week, 915 mg per week, 920 mg per week, 925 mg per week, 930 mg per week, 935 mg per week, 940 mg per week, 945 mg per week, 950 mg per week, 955 mg per week, 960 mg per week, 965 mg per week, 970 mg per week, 975 mg per week, 980 mg per week, 985 mg per week, 990 mg per week, 995 mg per week, 1,000 mg per week, 1,005 mg per week, 1,010 mg per week, 1,015 mg per week, 1,020 mg per week, 1,025 mg per week, 1,030 mg per week, 1,035 mg per week, 1,040 mg per week, 1,045 mg per week, 1,050 mg per week, 1,055 mg per week, 1,060 mg per week, 1,065 mg per week, 1,070 mg per week, 1,075 mg per week, 1,080 mg per week, 1,085 mg per week, 1,090 mg per week, 1,095 mg per week, 1,100 mg per week, 1,105 mg per week, 1,110 mg per week, 1,115 mg per week, 1,120 mg per week, 1,125 mg per week, 1,130 mg per week, 1,135 mg per week, 1,140 mg per week, 1,145 mg per week, 1,150 mg per week, 1,155 mg per week, 1,160 mg per week, 1,165 mg per week, 1,170 mg per week, 1,175 mg per week, 1,180 mg per week, 1,185 mg per week, 1,190 mg per week, 1,195 mg per week, 1,200 mg per week, 1,205 mg per week, 1,210 mg per week, 1,215 mg per week, 1,220 mg per week, 1,225 mg per week, 1,230 mg per week, 1,235 mg per week, 1,240 mg per week, 1,245 mg per week, 1,250 mg per week, 1,255 mg per week, or 1,260 mg per week. In some embodiments, the nifedipine is administered to the subject in an amount of about 840 mg per week.

In some embodiments of any of the above aspects, the nifedipine is administered to the subject in an amount of from about 280 mg to about 840 mg per week. For instance, the nifedipine may be administered to the subject in an amount of 280 mg per week, 285 mg per week, 290 mg per week, 295 mg per week, 300 mg per week, 305 mg per week, 310 mg per week, 315 mg per week, 320 mg per week, 325 mg per week, 330 mg per week, 335 mg per week, 340 mg per week, 345 mg per week, 350 mg per week, 355 mg per week, 360 mg per week, 365 mg per week, 370 mg per week, 375 mg per week, 380 mg per week, 385 mg per week, 390 mg per week, 395 mg per week, 400 mg per week, 405 mg per week, 410 mg per week, 415 mg per week, 420 mg per week, 425 mg per week, 430 mg per week, 435 mg per week, 440 mg per week, 445 mg per week, 450 mg per week, 455 mg per week, 460 mg per week, 465 mg per week, 470 mg per week, 475 mg per week, 480 mg per week, 485 mg per week, 490 mg per week, 495 mg per week, 500 mg per week, 505 mg per week, 510 mg per week, 515 mg per week, 520 mg per week, 525 mg per week, 530 mg per week, 535 mg per week, 540 mg per week, 545 mg per week, 550 mg per week, 555 mg per week, 560 mg per week, 565 mg per week, 570 mg per week, 575 mg per week, 580 mg per week, 585 mg per week, 590 mg per week, 595 mg per week, 600 mg per week, 605 mg per week, 610 mg per week, 615 mg per week, 620 mg per week, 625 mg per week, 630 mg per week, 635 mg per week, 640 mg per week, 645 mg per week, 650 mg per week, 655 mg per week, 660 mg per week, 665 mg per week, 670 mg per week, 675 mg per week, 680 mg per week, 685 mg per week, 690 mg per week, 695 mg per week, 700 mg per week, 705 mg per week, 710 mg per week, 715 mg per week, 720 mg per week, 725 mg per week, 730 mg per week, 735 mg per week, 740 mg per week, 745 mg per week, 750 mg per week, 755 mg per week, 760 mg per week, 765 mg per week, 770 mg per week, 775 mg per week, 780 mg per week, 785 mg per week, 790 mg per week, 795 mg per week, 800 mg per week, 805 mg per week, 810 mg per week, 815 mg per week, 820 mg per week, 825 mg per week, 830 mg per week, 835 mg per week, or 840 mg per week. In some embodiments, the nifedipine is administered to the subject in an amount of about 560 mg per week.

In some embodiments of any of the above aspects, the nifedipine is administered to the subject in an amount of from about 210 mg to about 630 mg per week. For instance, the nifedipine may be administered to the subject in an amount of 210 mg per week, 215 mg per week, 220 mg per week, 225 mg per week, 230 mg per week, 235 mg per week, 240 mg per week, 245 mg per week, 250 mg per week, 255 mg per week, 260 mg per week, 265 mg per week, 270 mg per week, 275 mg per week, 280 mg per week, 285 mg per week, 290 mg per week, 295 mg per week, 300 mg per week, 305 mg per week, 310 mg per week, 315 mg per week, 320 mg per week, 325 mg per week, 330 mg per week, 335 mg per week, 340 mg per week, 345 mg per week, 350 mg per week, 355 mg per week, 360 mg per week, 365 mg per week, 370 mg per week, 375 mg per week, 380 mg per week, 385 mg per week, 390 mg per week, 395 mg per week, 400 mg per week, 405 mg per week, 410 mg per week, 415 mg per week, 420 mg per week, 425 mg per week, 430 mg per week, 435 mg per week, 440 mg per week, 445 mg per week, 450 mg per week, 455 mg per week, 460 mg per week, 465 mg per week, 470 mg per week, 475 mg per week, 480 mg per week, 485 mg per week, 490 mg per week, 495 mg per week, 500 mg per week, 505 mg per week, 510 mg per week, 515 mg per week, 520 mg per week, 525 mg per week, 530 mg per week, 535 mg per week, 540 mg per week, 545 mg per week, 550 mg per week, 555 mg per week, 560 mg per week, 565 mg per week, 570 mg per week, 575 mg per week, 580 mg per week, 585 mg per week, 590 mg per week, 595 mg per week, 600 mg per week, 605 mg per week, 610 mg per week, 615 mg per week, 620 mg per week, 625 mg per week, or 630 mg per week. In some embodiments, the nifedipine is administered to the subject in an amount of about 420 mg per week.

In some embodiments of any of the above aspects, the nifedipine is administered to the subject in an amount of from about 140 mg to about 420 mg per week. For instance, the nifedipine may be administered to the subject in an amount of 140 mg per week, 145 mg per week, 150 mg per week, 155 mg per week, 160 mg per week, 165 mg per week, 170 mg per week, 175 mg per week, 180 mg per week, 185 mg per week, 190 mg per week, 195 mg per week, 200 mg per week, 205 mg per week, 210 mg per week, 215 mg per week, 220 mg per week, 225 mg per week, 230 mg per week, 235 mg per week, 240 mg per week, 245 mg per week, 250 mg per week, 255 mg per week, 260 mg per week, 265 mg per week, 270 mg per week, 275 mg per week, 280 mg per week, 285 mg per week, 290 mg per week, 295 mg per week, 300 mg per week, 305 mg per week, 310 mg per week, 315 mg per week, 320 mg per week, 325 mg per week, 330 mg per week, 335 mg per week, 340 mg per week, 345 mg per week, 350 mg per week, 355 mg per week, 360 mg per week, 365 mg per week, 370 mg per week, 375 mg per week, 380 mg per week, 385 mg per week, 390 mg per week, 395 mg per week, 400 mg per week, 405 mg per week, 410 mg per week, 415 mg per week, or 420 mg per week. In some embodiments, the nifedipine is administered to the subject in an amount of about 280 mg per week.

In some embodiments of any of the above aspects, the nifedipine is administered to the subject until the subject reaches a gestational age of at least about 34 weeks (e.g., a gestational age of from about 34 weeks to about 40 weeks, such as a gestational age of 34 weeks, 35 weeks, 36 weeks, 37 weeks, 38 weeks, 39 weeks, or 40 weeks), or until the subject undergoes delivery. In some embodiments, the nifedipine is administered to the subject until the subject reaches a gestational age of about 37 weeks (e.g., a gestational age of from about 37 weeks to about 40 weeks, such as a gestational age of 37 weeks, 38 weeks, 39 weeks, or 40 weeks), or until the subject undergoes delivery. In some embodiments, the nifedipine is periodically administered to the subject over a treatment period of from about 1 day to about 20 weeks, for example, using a dosing regimen described above or herein (e.g., over a treatment period of from about 2 days to about 20 weeks, from about 2 days to about 19 weeks, from about 2 days to about 18 weeks, from about 2 days to about 17 weeks, from about 2 days to about 16 weeks, from about 2 days to about 15 weeks, from about 2 days to about 14 weeks, from about 2 days to about 13 weeks, from about 2 days to about 12 weeks, from about 2 days to about 11 weeks, from about 2 days to about 10 weeks, from about 2 days to about 9 weeks, from about 2 days to about 8 weeks, from about 2 days to about 7 weeks, from about 2 days to about 6 weeks, from about 2 days to about 5 weeks, from about 2 days to about 4 weeks, from about 2 days to about 3 weeks, from about 2 days to about 2 weeks, from about 2 days to about 1 week, from about 2 days to about 6 days, from about 2 days to about 5 days, from about 2 days to about 4 days, from about 1 week to about 20 weeks, from about 1 week to about 19 weeks, from about 1 week to about 18 weeks, from about 1 week to about 17 weeks, from about 1 week to about 16 weeks, from about 1 week to about 15 weeks, from about 1 week to about 14 weeks, from about 1 week to about 13 weeks, from about 1 week to about 12 weeks, from about 1 week to about 11 weeks, from about 1 week to about 10 weeks, from about 1 week to about 9 weeks, from about 1 week to about 8 weeks, from about 1 week to about 7 weeks, from about 1 week to about 6 weeks, from about 1 week to about 5 weeks, from about 1 week to about 4 weeks, from about 1 week to about 3 weeks, or from about 1 week to about 2 weeks, such as over a treatment period of 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days, 100 days, 101 days, 102 days, 103 days, 104 days, 105 days, 106 days, 107 days, 108 days, 109 days, 110 days, 111 days, 112 days, 113 days, 114 days, 115 days, 116 days, 117 days, 118 days, 119 days, 120 days, 121 days, 122 days, 123 days, 124 days, 125 days, 126 days, 127 days, 128 days, 129 days, 130 days, 131 days, 132 days, 133 days, 134 days, 135 days, 136 days, 137 days, 138 days, 139 days, or 140 days).

In some embodiments of any of the above aspects, the nifedipine is administered to the subject orally. The nifedipine may be, for example, formulated a tablet, gel cap, powder, liquid solution, or liquid suspension.

The nifedipine may be, for example, administered in a dosage form of from about 10 mg to about 30 mg, and may optionally be formulated as an extended release composition. Extended release nifedipine formulations may include one or more, or all, of the excipients selected from cellulose acetate, hydroxypropyl cellulose, hypromellose, magnesium stearate, polyethylene glycol, polyethylene oxide, red ferric oxide, sodium chloride, and titanium dioxide.

In some embodiments of any of the above aspects, the nifedipine is administered to the subject sublingually.

In some embodiments of any of the above aspects, the PGF2α receptor antagonist, such as the compound of any one of formulas (I) through (VIII), for example, compound (1), compound (2), or compound (3), among other PGF2α receptor antagonists described herein, is administered to the subject in one or more doses per 12 hours, 24 hours, 48 hours, or one week. For instance, the PGF2α receptor antagonist may be administered to the subject in from one to ten doses (e.g., 1, 2, 3, 4, 5, 6, 7, 8, 9, or 10 doses) every 12 hours, one to ten doses (e.g., 1, 2, 3, 4, 5, 6, 7, 8, 9, or 10 doses) every 14 hours, one to ten doses (e.g., 1, 2, 3, 4, 5, 6, 7, 8, 9, or 10 doses) every 16 hours, one to ten doses (e.g., 1, 2, 3, 4, 5, 6, 7, 8, 9, or 10 doses) every 18 hours, one to ten doses (e.g., 1, 2, 3, 4, 5, 6, 7, 8, 9, or 10 doses) every 20 hours, one to ten doses (e.g., 1, 2, 3, 4, 5, 6, 7, 8, 9, or 10 doses) every 22 hours, one to ten doses (e.g., 1, 2, 3, 4, 5, 6, 7, 8, 9, or 10 doses) every 24 hours, one to ten doses (e.g., 1, 2, 3, 4, 5, 6, 7, 8, 9, or 10 doses) every 26 hours, one to ten doses (e.g., 1, 2, 3, 4, 5, 6, 7, 8, 9, or 10 doses) every 28 hours, one to ten doses (e.g., 1, 2, 3, 4, 5, 6, 7, 8, 9, or 10 doses) every 30 hours, one to ten doses (e.g., 1, 2, 3, 4, 5, 6, 7, 8, 9, or 10 doses) every 32 hours, one to ten doses (e.g., 1, 2, 3, 4, 5, 6, 7, 8, 9, or 10 doses) every 34 hours, one to ten doses (e.g., 1, 2, 3, 4, 5, 6, 7, 8, 9, or 10 doses) every 36 hours, one to ten doses (e.g., 1, 2, 3, 4, 5, 6, 7, 8, 9, or 10 doses) every 38 hours, one to ten doses (e.g., 1, 2, 3, 4, 5, 6, 7, 8, 9, or 10 doses) every 40 hours, one to ten doses (e.g., 1, 2, 3, 4, 5, 6, 7, 8, 9, or 10 doses) every 42 hours, one to ten doses (e.g., 1, 2, 3, 4, 5, 6, 7, 8, 9, or 10 doses) every 44 hours, one to ten doses (e.g., 1, 2, 3, 4, 5, 6, 7, 8, 9, or 10 doses) every 46 hours, one to ten doses (e.g., 1, 2, 3, 4, 5, 6, 7, 8, 9, or 10 doses) every 48 hours, one to ten doses (e.g., 1, 2, 3, 4, 5, 6, 7, 8, 9, or 10 doses) every 60 hours, one to ten doses (e.g., 1, 2, 3, 4, 5, 6, 7, 8, 9, or 10 doses) every 72 hours, one to ten doses (e.g., 1, 2, 3, 4, 5, 6, 7, 8, 9, or 10 doses) every 84 hours, one to ten doses (e.g., 1, 2, 3, 4, 5, 6, 7, 8, 9, or 10 doses) every 96 hours, one to ten doses (e.g., 1, 2, 3, 4, 5, 6, 7, 8, 9, or 10 doses) every 108 hours, one to ten doses (e.g., 1, 2, 3, 4, 5, 6, 7, 8, 9, or 10 doses) every 120 hours, one to ten doses (e.g., 1, 2, 3, 4, 5, 6, 7, 8, 9, or 10 doses) every 132 hours, one to ten doses (e.g., 1, 2, 3, 4, 5, 6, 7, 8, 9, or 10 doses) every 144 hours, one to ten doses (e.g., 1, 2, 3, 4, 5, 6, 7, 8, 9, or 10 doses) every 156 hours, or one to ten doses (e.g., 1, 2, 3, 4, 5, 6, 7, 8, 9, or 10 doses) every week.

In some embodiments of any of the above aspects, the PGF2α receptor antagonist, such as the compound of any one of formulas (I) through (VIII), for example, compound (1), compound (2), or compound (3), among other PGF2α receptor antagonists described herein, is administered to the subject in from one to six doses per day. For example, PGF2α receptor antagonist, such as the compound of any one of formulas (I) through (VIII), for example, compound (1), compound (2), or compound (3), may be administered to the subject once daily. In some embodiments, the PGF2α receptor antagonist is administered to the subject twice daily.

In some embodiments of any of the above aspects, the PGF2α receptor antagonist is administered to the subject once every 4 two 12 hours, such as once every 4 hours, once every 5 hours, once every 6 hours, once every 7 hours, once every 8 hours, once every 9 hours, once every 10 hours, once every 11 hours, or once every 12 hours.

In some embodiments of any of the above aspects, the PGF2α receptor antagonist is administered to the subject in an amount of from about 100 mg to about 3,000 mg per dose, such as in an amount of 100 mg per dose, 150 mg per dose, 200 mg per dose, 250 mg per dose, 300 mg per dose, 350 mg per dose, 400 mg per dose, 450 mg per dose, 500 mg per dose, 550 mg per dose, 600 mg per dose, 650 mg per dose, 700 mg per dose, 750 mg per dose, 800 mg per dose, 850 mg per dose, 900 mg per dose, 950 mg per dose, 1,000 mg per dose, 1,050 mg per dose, 1,100 mg per dose, 1,150 mg per dose, 1,200 mg per dose, 1,250 mg per dose, 1,300 mg per dose, 1,350 mg per dose, 1,400 mg per dose, 1,450 mg per dose, 1,500 mg per dose, 1,550 mg per dose, 1,600 mg per dose, 1,650 mg per dose, 1,700 mg per dose, 1,750 mg per dose, 1,800 mg per dose, 1,850 mg per dose, 1,900 mg per dose, 1,950 mg per dose, 2,000 mg per dose, 2,050 mg per dose, 2,100 mg per dose, 2,150 mg per dose, 2,200 mg per dose, 2,250 mg per dose, 2,300 mg per dose, 2,350 mg per dose, 2,400 mg per dose, 2,450 mg per dose, 2,500 mg per dose, 2,550 mg per dose, 2,600 mg per dose, 2,650 mg per dose, 2,700 mg per dose, 2,750 mg per dose, 2,800 mg per dose, 2,850 mg per dose, 2,900 mg per dose, 2,950 mg per dose, or 3,000 mg per dose. The PGF2α receptor antagonist may be administered to the subject in an amount of from about 500 mg to about 2,500 mg per dose, such as in an amount of 500 mg per dose, 550 mg per dose, 600 mg per dose, 650 mg per dose, 700 mg per dose, 750 mg per dose, 800 mg per dose, 850 mg per dose, 900 mg per dose, 950 mg per dose, 1,000 mg per dose, 1,050 mg per dose, 1,100 mg per dose, 1,150 mg per dose, 1,200 mg per dose, 1,250 mg per dose, 1,300 mg per dose, 1,350 mg per dose, 1,400 mg per dose, 1,450 mg per dose, 1,500 mg per dose, 1,550 mg per dose, 1,600 mg per dose, 1,650 mg per dose, 1,700 mg per dose, 1,750 mg per dose, 1,800 mg per dose, 1,850 mg per dose, 1,900 mg per dose, 1,950 mg per dose, 2,000 mg per dose, 2,050 mg per dose, 2,100 mg per dose, 2,150 mg per dose, 2,200 mg per dose, 2,250 mg per dose, 2,300 mg per dose, 2,350 mg per dose, 2,400 mg per dose, 2,450 mg per dose, or 2,500 mg per dose. In some embodiments, the PGF2α receptor antagonist is administered to the subject in an amount of from about 750 mg to about 2,250 mg per dose, such as in an amount of 750 mg per dose, 800 mg per dose, 850 mg per dose, 900 mg per dose, 950 mg per dose, 1,000 mg per dose, 1,050 mg per dose, 1,100 mg per dose, 1,150 mg per dose, 1,200 mg per dose, 1,250 mg per dose, 1,300 mg per dose, 1,350 mg per dose, 1,400 mg per dose, 1,450 mg per dose, 1,500 mg per dose, 1,550 mg per dose, 1,600 mg per dose, 1,650 mg per dose, 1,700 mg per dose, 1,750 mg per dose, 1,800 mg per dose, 1,850 mg per dose, 1,900 mg per dose, 1,950 mg per dose, 2,000 mg per dose, 2,050 mg per dose, 2,100 mg per dose, 2,150 mg per dose, 2,200 mg per dose, or 2,250 mg per dose. For example, the PGF2α receptor antagonist may be administered to the subject in an amount of from about 1,000 mg to about 2,000 mg per dose, such as in an amount of 1,000 mg per dose, 1,050 mg per dose, 1,100 mg per dose, 1,150 mg per dose, 1,200 mg per dose, 1,250 mg per dose, 1,300 mg per dose, 1,350 mg per dose, 1,400 mg per dose, 1,450 mg per dose, 1,500 mg per dose, 1,550 mg per dose, 1,600 mg per dose, 1,650 mg per dose, 1,700 mg per dose, 1,750 mg per dose, 1,800 mg per dose, 1,850 mg per dose, 1,900 mg per dose, 1,950 mg per dose, or 2,000 mg per dose.

In some embodiments of any of the above aspects, the PGF2α receptor antagonist is administered to the subject until the subject reaches a gestational age of at least about 34 weeks (e.g., a gestational age of from about 34 weeks to about 40 weeks, such as a gestational age of 34 weeks, 35 weeks, 36 weeks, 37 weeks, 38 weeks, 39 weeks, or 40 weeks), or until the subject undergoes delivery. In some embodiments, the PGF2α receptor antagonist is administered to the subject until the subject reaches a gestational age of about 37 weeks (e.g., a gestational age of from about 37 weeks to about 40 weeks, such as a gestational age of 37 weeks, 38 weeks, 39 weeks, or 40 weeks), or until the subject undergoes delivery. In some embodiments, the PGF2α receptor antagonist is periodically administered to the subject over a treatment period of from about 1 day to about 20 weeks, for example, using a dosing regimen described above or herein (e.g., over a treatment period of from about 2 days to about 20 weeks, from about 2 days to about 19 weeks, from about 2 days to about 18 weeks, from about 2 days to about 17 weeks, from about 2 days to about 16 weeks, from about 2 days to about 15 weeks, from about 2 days to about 14 weeks, from about 2 days to about 13 weeks, from about 2 days to about 12 weeks, from about 2 days to about 11 weeks, from about 2 days to about 10 weeks, from about 2 days to about 9 weeks, from about 2 days to about 8 weeks, from about 2 days to about 7 weeks, from about 2 days to about 6 weeks, from about 2 days to about 5 weeks, from about 2 days to about 4 weeks, from about 2 days to about 3 weeks, from about 2 days to about 2 weeks, from about 2 days to about 1 week, from about 2 days to about 6 days, from about 2 days to about 5 days, from about 2 days to about 4 days, from about 1 week to about 20 weeks, from about 1 week to about 19 weeks, from about 1 week to about 18 weeks, from about 1 week to about 17 weeks, from about 1 week to about 16 weeks, from about 1 week to about 15 weeks, from about 1 week to about 14 weeks, from about 1 week to about 13 weeks, from about 1 week to about 12 weeks, from about 1 week to about 11 weeks, from about 1 week to about 10 weeks, from about 1 week to about 9 weeks, from about 1 week to about 8 weeks, from about 1 week to about 7 weeks, from about 1 week to about 6 weeks, from about 1 week to about 5 weeks, from about 1 week to about 4 weeks, from about 1 week to about 3 weeks, or from about 1 week to about 2 weeks, such as over a treatment period of 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days, 100 days, 101 days, 102 days, 103 days, 104 days, 105 days, 106 days, 107 days, 108 days, 109 days, 110 days, 111 days, 112 days, 113 days, 114 days, 115 days, 116 days, 117 days, 118 days, 119 days, 120 days, 121 days, 122 days, 123 days, 124 days, 125 days, 126 days, 127 days, 128 days, 129 days, 130 days, 131 days, 132 days, 133 days, 134 days, 135 days, 136 days, 137 days, 138 days, 139 days, or 140 days).

In some embodiments of any of the above aspects, the PGF2α receptor antagonist is administered to the subject orally. The PGF2α receptor antagonist may be, for example, formulated a tablet, gel cap, powder, liquid solution, or liquid suspension.

In some embodiments of any of the above aspects, the PGF2α antagonist and the nifedipine are administered to the subject at the same time (e.g., for the initial dose of each agent when these agents are administered to the subject periodically over the course of a treatment period). In some embodiments of any of the above aspects, the PGFα antagonist and the nifedipine are administered to the subject at different times.

In some embodiments of any of the above aspects,

In some embodiments of any of the above aspects, the subject has a singleton or twin pregnancy.

In some embodiments of any of the above aspects, the subject is undergoing or at risk of undergoing preterm labor. Conditions that may identify the subject as at risk of undergoing preterm labor include (i) the subject having a gestational age of from about 24 weeks to about 36 weeks prior to administration of the nifedipine and the PGF2α receptor antagonist (e.g., a gestational age of from about 24 weeks to about 34 weeks, such as a gestational age of from about 28 weeks to about 33 and 6/7 weeks, prior to administration of the nifedipine and the PGF2α receptor antagonist), (ii) the subject exhibiting four or more uterine contractions per 30 minutes prior to administration of the nifedipine and the PGF2α receptor antagonist, (iii) the subject exhibiting a cervical dilation of from about 1 cm to about 4 cm prior to administration of the nifedipine and the PGF2α receptor antagonist, (iv) the subject testing positive for the presence of fetal fibronectin and/or insulin-like growth factor-binding protein-1 (IGFBP-1) in a sample of cervical secretion obtained from the subject prior to administration of the nifedipine and the PGF2α receptor antagonist, (v) the subject exhibiting a cervical length of about 25 mm or less prior to administration of the nifedipine and the PGF2α receptor antagonist, (vi) the subject exhibiting a progressive cervical dilation prior to administration of the nifedipine and the PGF2α receptor antagonist (e.g., a cervical dilation rate of from about 0.5 cm per hour to about 0.7 cm per hour prior to administration of the nifedipine and the PGF2α receptor antagonist), and (vii) the subject exhibiting an effacement of at least 50% prior to administration of the nifedipine and the PGF2α receptor antagonist. The subject may be one, for example, that exhibits one or more, or all, of these characteristics prior to the first administration of nifedipine and the PGF2α receptor antagonist to the subject. In some embodiments, the subject exhibits one or more, or all, of these characteristics up to three hours prior to administration of the nifedipine and the PGF2α receptor antagonist.

In some embodiments of any of the above aspects, the delivery by the subject is delayed by from about four hours to about six weeks following the first administration of the nifedipine and the PGF2α receptor antagonist to the subject. For instance, the delivery may be delayed by from about 12 hours to about 28 days, by about 18 hours to about 21 days, by about 24 hours to about 14 days, by about 24 hours to about 14 days, by about 48 hours, or by about 7 days following the first administration of the nifedipine and the PGF2α receptor antagonist to the subject. In some embodiments, following administration of the nifedipine and the PGF2α receptor antagonist to the subject, the subject undergoes delivery at a gestational stage of at least about 34 weeks, such as a gestational age of about 34 weeks, 35 weeks, 36 weeks, 37 weeks, 38 weeks, 39 weeks, or 40 weeks (e.g., a gestational age of about 34 weeks to about 40 weeks). In some embodiments, following administration of the nifedipine and the PGF2α receptor antagonist to the subject, the subject undergoes delivery at a gestational stage of from about 36 weeks to about 40 weeks. In some embodiments, following administration of the nifedipine and the PGF2α receptor antagonist to the subject, the subject undergoes delivery at a gestational stage of at least about 37 weeks (e.g., a gestational age of from about 37 weeks to about 40 weeks, such as a gestational age of about 37 weeks, 38 weeks, 39 weeks, or 40 weeks).

In an additional aspect, the invention features a kit containing a PGF2α receptor antagonist, such as the compound of any one of formulas (I) through (VIII), for example, compound (1), compound (2), or compound (3), among other PGF2α receptor antagonists described herein, and a package insert instructing a user of the kit to administer the PGF2α receptor antagonist to a pregnant human subject in accordance with the method of any of the above-described aspects or embodiments of the invention. In some embodiments, the PGF2α receptor antagonist is a compound represented by formula (1).

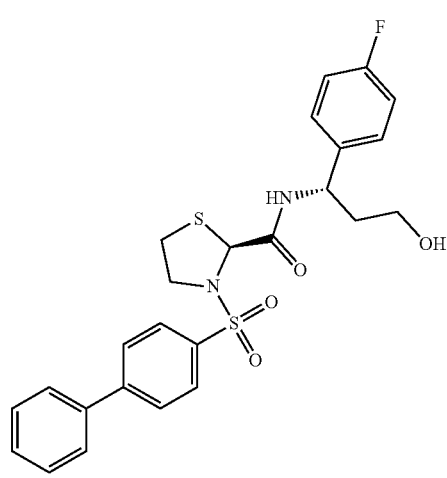

The PGF2α receptor antagonist may be a compound represented by formula (2)

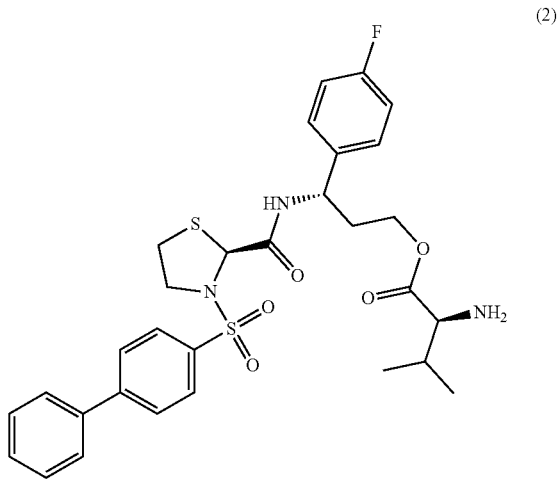

or a pharmaceutically acceptable salt thereof. For example, in some embodiments, the PGF2α receptor antagonist is the chloride salt of compound (2), represented by formula (3), below.

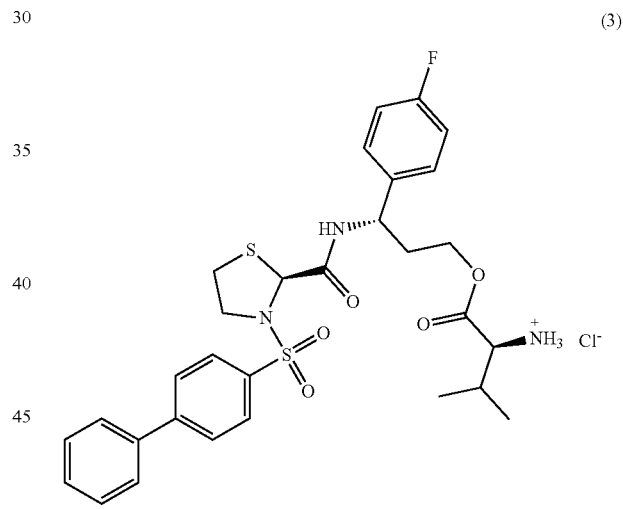

In some embodiments, the kit further contains nifedipine, such as in a dosage form of from about 10 mg to about 30 mg. The nifedipine within the kit may be formulated as an extended release composition, such as a nifedipine formulation containing one or more, or all, of the excipients selected from cellulose acetate, hydroxypropyl cellulose, hypromellose, magnesium stearate, polyethylene glycol, polyethylene oxide, red ferric oxide, sodium chloride, and titanium dioxide.

Definitions

As used herein, the term "about" refers to a value that is within 10% above or below the value being described. For instance, a value of "about 5 mg" refers to a quantity that is from 4.5 mg to 5.5 mg.

As used herein, the term "affinity" refers to the strength of a binding interaction between two molecules, such as a ligand and a receptor. The term "Ki", as used herein, is intended to refer to the inhibition constant of an antagonist for a particular molecule of interest, and is expressed as a molar concentration (M). Ki values for antagonist-target interactions can be determined, e.g., using methods established in the art. Methods that can be used to determine the Ki of an antagonist for a molecular target include competitive binding experiments, such as competitive radioligand binding assays, e.g., as described in U.S. Pat. Nos. 8,415,480; 9,447,055; and 9,834,528, the disclosures of each of which are incorporated herein by reference in their entirety. The term "$K_d$", as used herein, is intended to refer to the dissociation constant, which can be obtained, e.g., from the ratio of the rate constant for the dissociation of the two molecules ($k_d$) to the rate constant for the association of the two molecules ($k_a$) and is expressed as a molar concentration (M). $K_d$ values for receptor-ligand interactions can be determined, e.g., using methods established in the art. Methods that can be used to determine the $K_d$ of a receptor-ligand interaction include surface plasmon resonance, e.g., through the use of a biosensor system such as a BIACORE® system.

As used herein, the terms "benefit" and "response" are used interchangeably in the context of a subject, such as a pregnant human subject undergoing therapy for the treatment or prevention of preterm labor. These terms refers to any clinical improvement in the subject's condition. Exemplary benefits in the context of a subject undergoing, or at risk of undergoing, preterm labor and receiving treatment with nifedipine and a prostaglandin receptor F2α (PGF2α) antagonist as described herein (e.g., a 1,3-thiazolidine-2-carboxamide compound described herein, such as (3S)-3-({[(2S)-3-(biphenyl-4-ylsulfonyl)-1,3-thiazolidin-2-yl]carbonyl}-amino)-3-(4-fluorophenyl)propyl L-valinate or a pharmaceutically acceptable salt thereof, such as (3S)-3-({[(2S)-3-(biphenyl-4-ylsulfonyl)-1,3-thiazolidin-2-yl]carbonyl}-amino)-3-(4-fluorophenyl)propyl L-valinate hydrochloride) include, without limitation, (i) a delay in the onset of delivery by the subject, such as a delay of one or more hours, days, or weeks (e.g., a delay of from about 1 hour to about 16 weeks, such as a delay of 1 hour, 6 hours, 12 hours, 18 hours, 24 hours, 48 hours, 72 hours, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, or 16 weeks, among others) following the first administration of nifedipine and the PGF2α receptor antagonist to the subject, (ii) a delay in the onset of delivery by the subject such that the subject undergoes delivery at a gestational age of at least about 34 weeks, such as at a gestational age of from about 34 weeks to about 40 weeks (e.g., at a gestational age of about 34 weeks, 35 weeks, 36 weeks, 37 weeks, 38 weeks, 39 weeks, or 40 weeks) following administration of nifedipine and the PGF2α receptor antagonist to the subject, (iii) a reduction in vaginal bleeding by the subject following administration of nifedipine and the PGF2α receptor antagonist to the subject, (iv) a delay in the onset of amniorrhexis by the subject (e.g., a delay of from about 1 hour to about 16 weeks, such as a delay of 1 hour, 6 hours, 12 hours, 18 hours, 24 hours, 48 hours, 72 hours, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, or 16 weeks, among others, following the first administration of nifedipine and the PGF2α receptor antagonist to the subject), (v) a reduction in the expression of one or more proinflammatory genes, such as cyclooxygenase-2 (Cox2) by the subject (as assessed, e.g., by observing a decrease in myometrial Cox2 expression) following administration of nifedipine and the PGF2α receptor antagonist to the subject, and (vi) a reduction in the frequency of, peak amplitude of, duration of, and/or work done by, uterine contractions in the subject following administration of nifedipine and the PGF2α receptor antagonist to the subject.

As used herein, the term "crystalline" or "crystalline form" means having a physical state that is a regular three-dimensional array of atoms, ions, molecules or molecular assemblies. Crystalline forms have lattice arrays of building blocks called asymmetric units that are arranged according to well-defined symmetries into unit cells that are repeated in three-dimensions. In contrast, the term "amorphous" or "amorphous form" refers to an unorganized (no orderly) structure. The physical state of a therapeutic compound may be determined by exemplary techniques such as x-ray diffraction, polarized light microscopy and/or differential scanning calorimetry.

As used herein, the term "dose" refers to the quantity of a therapeutic agent, such as nifedipine and/or PGF2α receptor antagonist described herein, that is administered to a subject for the treatment of a disorder or condition, such as to treat or prevent preterm labor in a pregnant subject (e.g., a pregnant human subject). A therapeutic agent as described herein may be administered in a single dose or in multiple doses. In each case, the therapeutic agent may be administered using one or more unit dosage forms of the therapeutic agent. For instance, a single dose of 200 mg of a therapeutic agent may be administered using, e.g., two 100 mg unit dosage forms of the therapeutic agent.

As used herein, the terms "effacement" and "effaced" refer to the preparation of the cervix for delivery, a process that manifests in a progressive thinning of the cervix. Effacement may be expressed as a percentage, such as 10%, 20%, 30%, 40%, 50%, 60%, 70%, 80%, 90%, or 100%. As effacement occurs, the cervix shortens, eventually becoming part of the lower uterine wall. Methods for measuring cervical effacement on the basis of the thickness and dilation of the cervix are known in the art and are described, for example, in U.S. Pat. No. 5,876,357, the disclosure of which is incorporated herein by reference as it pertains to the measurement of cervical effacement.

As used herein, the term "endogenous" describes a molecule (e.g., a polypeptide, nucleic acid, or cofactor) that is found naturally in a particular organism (e.g., a human) or in a particular location within an organism (e.g., an organ, a tissue, or a cell, such as a human cell).

As used herein, the term "exogenous" describes a molecule (e.g., a polypeptide, nucleic acid, or cofactor) that is not found naturally in a particular organism (e.g., a human) or in a particular location within an organism (e.g., an organ, a tissue, or a cell, such as a human cell). Exogenous materials include those that are provided from an external source to an organism or to cultured matter extracted therefrom.

As used herein, the term "gestational age" describes how far along a particular pregnancy is, and is measured from the first day of a pregnant female subject's last menstrual cycle to the current date. As used herein, the term "labor" (which may also be termed birth) relates to the expulsion of the fetus and placenta from the uterus of a pregnant female subject. For a normal human pregnancy, labor generally occurs at a gestational age of approximately 40 weeks. "Preterm labor" as used herein refers to a condition in which labor commences more than three weeks before the full gestation period, which is typically about 40 weeks in human subjects. That is, preterm labor may occur at any stage prior to, e.g., 38 weeks of gestation. Preterm labor typically leads to the occurrence of labor, or physiological changes associated with labor in a pregnant female subject, if not treated. Preterm labor may or may not be associated with vaginal bleeding or rupture of uterine membranes. Preterm labor may also be referred to as premature labor.

As used herein, the term "$IC_{50}$" refers to the concentration of a substance (antagonist) that reduces the efficacy of a reference agonist or the constitutive activity of a biological target by 50%, e.g., as measured in a competitive ligand binding assay. Exemplary competitive ligand binding assays include competitive radioligand binding assays, competitive enzyme-linked immunosorbent assays (ELISA), and fluorescence anisotropy-based assays, among others known in the art.

As used herein in the context of providing or administering two or more therapeutic agents to a subject, the phrase "in combination with" refers to the delivery of two or more therapeutic agents to a subject (e.g., a mammalian subject, such as a pregnant human subject) either (i) concurrently or (ii) at different times such that the later-administered agent is provided to the subject while there is still a detectable concentration of the earlier-administered agent, or a metabolite thereof, in the plasma and/or one or more tissue(s) (e.g., myometrial tissue) of the subject. For example, one therapeutic agent may be administered to a subject in combination with another by administering both agents to the subject concurrently, such as in a single pharmaceutical composition or in separate compositions that are administered to the subject simultaneously (e.g., by different routes of administration). In another example, one therapeutic agent may be administered to a subject in combination with another by first administering to the subject one therapeutic agent and subsequently administering the other therapeutic agent, either by the same or different route of administration, while there is still a detectable quantity of the first agent in the plasma and/or tissue(s) of the subject. After the first administration of each agent (e.g., concurrently or at different times), it is not necessary that the subject receive the remaining agent(s) each and every time the subject receives a dose of the first agent. For instance, two or more agents are said to be administered "in combination with" one another if the subject receives a daily dosage of a first agent and a weekly dosage of the remaining agent(s). The timing of administration of the two or more agents need not coincide.

As used herein, the term "menstrual cycle" refers to a recurring cycle of physiological changes in females, such as human females, that is associated with reproductive fertility. While the cycle length may vary from woman to woman, 28 days is generally taken as representative of the average ovulatory cycle in human females.

As used herein, the term "once daily" refers to administration of a therapeutic agent to a subject in a single dose each day. The time of day at which the therapeutic agent is administered to the subject may be constant or may vary. Similarly, the terms "twice daily," "three times daily," and the like refer to administration of a therapeutic agent to a subject in two doses or three doses each day, respectively.

As used herein, the term "pharmaceutical composition" means a mixture containing a therapeutic compound to be administered to a patient, such as a mammal, e.g., a human, in order to prevent, treat or control a particular disease or condition affecting the mammal, such as preterm labor or dysmenorrhea.

As used herein, the term "pharmaceutically acceptable" refers to those compounds, materials, compositions and/or dosage forms, which are suitable for contact with the tissues of a patient, such as a mammal (e.g., a human) without excessive toxicity, irritation, allergic response and other problem complications commensurate with a reasonable benefit/risk ratio.

As used herein in the context of administration of a therapeutic agent, the term "periodically" refers to administration of the agent two or more times over the course of a treatment period (e.g., two or more times daily, weekly, monthly, or yearly).

As used herein, the term "progressive cervical dilation" refers to a steady opening of the cervix in a subject, such as a pregnant human subject undergoing or at risk of undergoing preterm labor. A subject is considered to exhibit progressive cervical dilation if the subject's cervix is opening (i.e., dilating) at a constant linear rate, such as a rate of from about 0.5 cm per hour to about 0.7 cm per hour.

As used herein, the term "prostaglandin F2α receptor antagonist" or "PGF2α receptor antagonist" refers to a compound that specifically and/or selectively binds the PGF2α receptor and is capable of inhibiting receptor signalling, for instance, in uterine myocytes. Inhibition of PGF2α receptor signal transduction may manifest, for example, in suppression of phospholipase C activity, which may be observed as a reduction in: (i) phosphatidylinositol-4,5-bisphosphate ($PIP_2$) cleavage, (ii) diacylglycerol (DAG) production, (iii) inositol-1,4,5-trisphosphate ($IP_3$) production, and/or (iv) intracellular calcium ($Ca^{2+}$) release by sarcoplasmic reticula. Inhibition of PGF2α receptor signaling may also manifest as a reduction in one or more downstream physiological events associated with calcium mobilization, such as a reduction in uterine muscle contractions and/or reduction in endothelial cell necrosis within the corpus *luteum*, a progesterone-secreting structure that supports a developing fetus. PGF2α receptor antagonists that may be used in conjunction with the compositions and methods described herein include 1,3-thiazolidine-2-carboxamides, such as (3S)-3-({[(2S)-3-(biphenyl-4-ylsulfonyl)-1,3-thiazolidin-2-yl]carbonyl}-amino)-3-(4-fluorophenyl) propyl L-valinate or a pharmaceutically acceptable salt thereof (e.g., (3S)-3-({[(2S)-3-(biphenyl-4-ylsulfonyl)-1,3-thiazolidin-2-yl]carbonyl}-amino)-3-(4-fluorophenyl)propyl L-valinate hydrochloride), or another 1,3-thiazolidine-2-carboxamide that gives rise to 3-([1,1'-biphenyl]-4-ylsulfonyl)-N-[1-(4-fluorophenyl)-3-hydroxypropyl]-1,3-thiazolidine-2-carboxamide in vivo, e.g., as described in U.S. Pat. Nos. 8,415,480; 9,447,055; and 9,834,528, the disclosures of each of which are incorporated herein by reference in their entirety.

As used herein in the context of therapeutic treatment, the terms "provide" and "providing" refer to the delivery of a therapeutic agent to a subject (e.g., a mammalian subject, such as a human) in need of treatment, such as a subject experiencing or at risk of undergoing preterm labor. A therapeutic agent may be provided to a subject in need thereof, for instance, by direct administration of the therapeutic agent to the subject, or by administration of a prodrug that is converted in vivo to the therapeutic agent upon administration of the prodrug to the subject. Exemplary prodrugs include, without limitation, esters, phosphates, and other chemical functionalities susceptible to hydrolysis upon administration to a subject. Prodrugs include those known in the art, such as those described, for instance, in Vig et al., Adv. Drug Deliv. Rev. 65:1370-1385 (2013), and Huttunen et al., Pharmacol. Rev. 63:750-771 (2011), the disclosures of each of which are incorporated herein by reference.

As used herein, the term "sample" refers to a specimen (e.g., blood, blood component (e.g., serum or plasma), urine, saliva, amniotic fluid, cerebrospinal fluid, tissue (e.g., placental or myometrial), pancreatic fluid, chorionic villus sample, and cells) isolated from a patient.

As used herein, the phrases "specifically binds" and "binds" refer to a binding reaction which is determinative of the presence of a particular protein in a heterogeneous population of proteins and other biological molecules that is recognized, e.g., by a ligand with particularity. A ligand (e.g., a protein, proteoglycan, or glycosaminoglycan) that specifically binds to a protein will bind to the protein, e.g., with a $K_D$ of less than 100 nM. For example, a ligand that specifically binds to a protein may bind to the protein with a $K_D$ of up to 100 nM (e.g., between 1 pM and 100 nM). A ligand that does not exhibit specific binding to a protein or a domain thereof will exhibit a $K_D$ of greater than 100 nM (e.g., greater than 200 nM, 300 nM, 400 nM, 500 nM, 600 nm, 700 nM, 800 nM, 900 nM, 1 pM, 100 pM, 500 pM, or 1 mM) for that particular protein or domain thereof. A variety of assay formats may be used to determine the affinity of a ligand for a specific protein. For example, solid-phase ELISA assays are routinely used to identify ligands that specifically bind a target protein. See, e.g., Harlow & Lane, Antibodies, A Laboratory Manual, Cold Spring Harbor Press, New York (1988) and Harlow & Lane, Using Antibodies, A Laboratory Manual, Cold Spring Harbor Press, New York (1999), for a description of assay formats and conditions that can be used to determine specific protein binding.

As used herein, the terms "subject' and "patient" are used interchangeably and refer to an organism, such as a mammal (e.g., a human) that receives therapy for the treatment or prevention of preterm labor as described herein. Patients that may receive therapy, or that are considered to be in need of therapy, for the treatment or prevention of preterm labor include subjects (e.g., pregnant human subjects) that are actively undergoing preterm labor, as well as those at risk of undergoing preterm labor. A variety of clinical indicators can be used to identify a patient as "at risk" of undergoing preterm labor. Examples of patients (e.g., human patients) that are "at risk" of undergoing preterm labor include (i) the subject having a gestational age of from about 24 weeks to about 36 weeks prior to administration of a tocolytic agent, such as nifedipine and/or a PGF2α receptor antagonist described herein (e.g., a gestational age of from about 24 weeks to about 34 weeks, such as a gestational age of from about 28 weeks to about 33 and 6/7 weeks, e.g., prior to administration of the nifedipine and the PGF2α receptor antagonist), (ii) the subject exhibiting four or more uterine contractions per 30 minutes, e.g., prior to administration of the tocolytic agent(s), (iii) the subject exhibiting a cervical dilation of from about 1 cm to about 4 cm, e.g., prior to administration of the tocolytic agent(s), (iv) the subject testing positive for the presence of fetal fibronectin and/or insulin-like growth factor-binding protein-1 (IGFBP-1) in a sample of cervical secretion obtained from the subject, e.g., prior to administration of the tocolytic agent(s), and (v) the subject exhibiting a cervical length of about 25 mm or less, e.g., prior to administration of the tocolytic agent(s). Pregnant subjects that are "at risk" of undergoing preterm labor may exhibit one or more, or all, of these characteristics, for example, prior to the first administration of nifedipine and a PGF2α receptor antagonist in accordance with the compositions and methods described herein.

As used herein in the context of a calcium channel inhibitor, such as nifedipine, and a PGF2α receptor antagonist, such as a compound of any one of formulas (I) through (VIII) herein, the term "therapeutically effective amounts" refers to quantities of each agent that, when administered in combination with one another, are capable of achieving a beneficial treatment outcome for a subject undergoing or at risk of undergoing preterm labor. For example, "therapeutically effective amounts" of a calcium channel inhibitor and a PGF2α receptor antagonist described herein are amounts of each agent that, when administered in combination with one another, are capable of achieving (i) a delay in the onset of delivery by a pregnant human subject, such as a delay of one or more hours, days, or weeks (e.g., a delay of from about 1 hour to about 16 weeks, such as a delay of 1 hour, 6 hours, 12 hours, 18 hours, 24 hours, 48 hours, 72 hours, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, or 16 weeks, among others) following the first administration of each agent to the subject, (ii) a delay in the onset of delivery by the subject such that the subject undergoes delivery at a gestational age of at least about 34 weeks, such as at a gestational age of from about 34 weeks to about 40 weeks (e.g., at a gestational age of about 34 weeks, 35 weeks, 36 weeks, 37 weeks, 38 weeks, 39 weeks, or 40 weeks) following administration of each agent to the subject, (iii) a reduction in vaginal bleeding by the subject following administration of each agent to the subject, (iv) a delay in the onset of amniorrhexis by the subject (e.g., a delay of from about 1 hour to about 16 weeks, such as a delay of 1 hour, 6 hours, 12 hours, 18 hours, 24 hours, 48 hours, 72 hours, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, or 16 weeks, among others, following the first administration of each agent to the subject, (v) a reduction in the expression of one or more proinflammatory genes, such as cyclooxygenase-2 (Cox2) by the subject (as assessed, e.g., by observing a decrease in myometrial Cox2 expression) following administration of each agent to the subject, and (vi) a reduction in the frequency of, peak amplitude of, duration of, and/or work done by, uterine contractions in the subject following administration of each agent to the subject. The two or more agents are said to be administered "in combination with" one another if they are administered at the same time to the subject (e.g., in a single or in separate compositions) or at different times, such that the later-administered agent is provided to the subject while there is still a detectable concentration of the earlier-administered agent, or a metabolite thereof, in the plasma and/or one or more tissue(s) (e.g., myometrial tissue) of the subject. For example, one therapeutic agent may be administered to a subject in combination with another by administering both agents to the subject concurrently, such as in a single pharmaceutical composition or in separate compositions that are administered to the subject simultaneously (e.g., by different routes of administration). In another example, one therapeutic agent may be administered to a subject in combination with another by first administering to the subject one therapeutic agent and subsequently administering the other therapeutic agent, either by the same or different route of administration. After the first administration of each agent (e.g., concurrently or at different times), it is not necessary that the subject receive the remaining agent each and every time the subject receives a dose of the first agent. For instance, the agents are said to be administered "in combination with" one another if the subject receives a daily dosage of a first agent and a weekly dosage of the remaining agent. The timing of administration of the agents need not coincide.

As used herein, the term "tocolytic agent" refers to a substance capable of delaying the onset of labor in a subject (e.g., a mammalian subject, such as a human subject). Tocolytic agents may function to suppress uterine contractility, for instance, by increasing cytoplasmic cAMP levels and inhibiting the mobilization of intracellular $Ca^{2+}$. Exemplary tocolytic agents are described, for instance, in Haas et al. Int. J. Women's Health. 6:343-349 (2014), the disclosure of which is incorporated herein by reference. Tocolytic agents for use in conjunction with the compositions and methods described herein include, without limitation, calcium channel inhibitors, such as nifedipine, as well as PGF2α receptor antagonists, such as a PGF2α receptor antagonist described herein (e.g., a 1,3-thiazolidine-2-carboxamide compound described herein, such as (3S)-3-({[(2S)-3-(biphenyl-4-ylsulfonyl)-1,3-thiazolidin-2-yl]carbonyl}-amino)-3-(4-fluorophenyl)propyl L-valinate or a pharmaceutically acceptable salt thereof, such as (3S)-3-({[(2S)-3-(biphenyl-4-ylsulfonyl)-1,3-thiazolidin-2-yl]carbonyl}-amino)-3-(4-fluorophenyl)propyl L-valinate hydrochloride).

As used herein in the context of preterm labor, the terms "treat" or "treatment" refer to therapeutic treatment, in which the object is to delay the onset of labor by a pregnant subject (e.g., a pregnant human subject). Successful treatment of a pregnant subject with nifedipine and a PGF2α receptor antagonist described herein (e.g., a 1,3-thiazolidine-2-carboxamide compound described herein, such as (3S)-3-({[(2S)-3-(biphenyl-4-ylsulfonyl)-1,3-thiazolidin-2-yl]carbonyl}-amino)-3-(4-fluorophenyl)propyl L-valinate or a pharmaceutically acceptable salt thereof, such as (3S)-3-({[(2S)-3-(biphenyl-4-ylsulfonyl)-1,3-thiazolidin-2-yl]carbonyl}-amino)-3-(4-fluorophenyl)propyl L-valinate hydrochloride) may manifest in a variety of ways. Desired treatment outcomes that may be achieved using the compositions and methods described herein include, without limitation, a delay in the onset of delivery by the subject, such as a delay of one or more hours, days, or weeks (e.g., a delay of from about 1 hour to about 16 weeks, such as a delay of 1 hour, 6 hours, 12 hours, 18 hours, 24 hours, 48 hours, 72 hours, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, or 16 weeks, among others) following the first administration of nifedipine and the PGF2α receptor antagonist to the subject. Another clinical indicator of successful treatment is the observation of a delay in the onset of delivery by the subject such that the subject undergoes delivery at a gestational age of at least about 34 weeks, such as at a gestational age of from about 34 weeks to about 40 weeks (e.g., at a gestational age of about 34 weeks, 35 weeks, 36 weeks, 37 weeks, 38 weeks, 39 weeks, or 40 weeks) following administration of nifedipine and the PGF2α receptor antagonist to the subject. Successful treatment may also be signaled by a reduction in vaginal bleeding by the subject following administration of nifedipine and the PGF2α receptor antagonist to the subject, as well as by a delay in the onset of amniorrhexis by the subject (e.g., a delay of from about 1 hour to about 16 weeks, such as a delay of 1 hour, 6 hours, 12 hours, 18 hours, 24 hours, 48 hours, 72 hours, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, or 16 weeks, among others, following the first administration of nifedipine and the PGF2α receptor antagonist to the subject. In another example, a subject (e.g., a pregnant human subject) may be considered to have undergone successful treatment upon observing a reduction in the expression of one or more proinflammatory genes, such as cyclooxygenase-2 (Cox2) by the subject (as assessed, e.g., by observing a decrease in myometrial Cox2 expression) following administration of nifedipine and the PGF2α receptor antagonist to the subject. Additional clinical indicators of successful treatment of preterm labor include a reduction in the frequency of, peak amplitude of, duration of, and/or work done by, uterine contractions in the subject following administration of nifedipine and the PGF2α receptor antagonist to the subject.

As used herein, the term "treatment period" refers to a duration of time over which a patient may be administered a therapeutic agent, such as nifedipine and a PGF2α receptor antagonist described herein, so as to treat or prevent preterm labor. Treatment periods as described herein may have a duration of several hours, days, or weeks. For instance, a treatment period for administration of a 1,3-thiazolidine-2-carboxamide compound described herein, such as (3S)-3-({[(2S)-3-(biphenyl-4-ylsulfonyl)-1,3-thiazolidin-2-yl]carbonyl}-amino)-3-(4-fluorophenyl)propyl L-valinate or a pharmaceutically acceptable salt thereof (for example, (3S)-3-({[(2S)-3-(biphenyl-4-ylsulfonyl)-1,3-thiazolidin-2-yl]carbonyl}-amino)-3-(4-fluorophenyl)propyl L-valinate hydrochloride) may last for from about 1 hour weeks to about 16 weeks, or until the subject undergoes delivery. In some embodiments, for example, the nifedipine is administered to the subject one or more times every hour, every 2 hours, every 4 hours, every 6 hours, every 8 hours, every 10 hours, every 12 hours, every 24 hours, or every 48 hours, and the PGF2α receptor antagonist is administered to the subject one or more times (e.g., once or twice) daily.

As used herein, the term "$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

As used herein, the term "aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenantrenyl and the like.

As used herein, the term "$C_1$-$C_6$-alkyl aryl" refers to $C_1$-$C_6$-alkyl groups having an aryl substituent, including benzyl, phenethyl and the like.

As used herein, the term "heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

As used herein, the term "$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl) ethyl and the like. "$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl, —$CH_2$CH=$CH_2$) and the like.

As used herein, the term "$C_2$-$C_6$-alkenyl aryl" refers to $C_2$-$C_6$-alkenyl groups having an aryl substituent, including 2-phenylvinyl and the like.

As used herein, the term "$C_2$-$C_6$-alkenyl heteroaryl" refers to $C_2$-$C_6$-alkenyl groups having a heteroaryl substituent, including 2-(3-pyridinyl)vinyl and the like.

As used herein, the term "$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—CH$_2$C≡CH), and the like.

As used herein, the term "$C_2$-$C_6$-alkynyl aryl" refers to $C_2$-$C_6$-alkynyl groups having an aryl substituent, including phenylethynyl and the like.

As used herein, the term "$C_2$-$C_6$-alkynyl heteroaryl" refers to $C_2$-$C_6$-alkynyl groups having a heteroaryl substituent, including 2-thienylethynyl and the like.

As used herein, the term "$C_3$-$C_8$-cycloalkyl" refers to a saturated carbocyclic group of from 3 to 8 carbon atoms having a single ring (e.g., cyclohexyl) or multiple condensed rings (e.g., norbornyl).

Preferred cycloalkyl include cyclopentyl, cyclohexyl, norbornyl and the like.

As used herein, the term "heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Preferred heterocycloalkyl include pyrrolidine, piperidine, piperazine, 1-methylpiperazine, morpholine, and the like.

As used herein, the term "$C_1$-$C_6$-alkyl cycloalkyl" refers to $C_1$-$C_6$-alkyl groups having a cycloalkyl substituent, including cyclohexylmethyl, cyclopentylpropyl, and the like. "$C_1$-$C_6$-alkyl heterocycloalkyl" refers to $C_1$-$C_6$-alkyl groups having a heterocycloalkyl substituent, including 2-(1-pyrrolidinyl)ethyl, 4-morpholinylmethyl, (1-methyl-4-piperidinyl)methyl and the like.

As used herein, the term "carboxy" refers to the group —C(O)OH.

As used herein, the term "$C_1$-$C_5$-alkyl carboxy" refers to $C_1$-$C_5$-alkyl groups having a carboxy substituent, including 2-carboxyethyl and the like.

As used herein, the term "acyl" refers to the group —C(O)R where R includes "$C_1$-$C_6$-alkyl", "aryl", "heteroaryl", "$C_1$-$C_6$-alkyl aryl" or "$C_1$-$C_6$-alkyl heteroaryl".

As used herein, the term "$C_1$-$C_5$-alkyl acyl" refers to $C_1$-$C_5$ alkyl groups having an acyl substituent, including 2-acetylethyl and the like.

As used herein, the term "acyloxy" refers to the group —OC(O)R where R includes "$C_1$-$C_6$-alkyl", "aryl", "heteroaryl", "$C_1$-$C_6$-alkyl aryl" or "$C_1$-$C_6$-alkyl heteroaryl".

As used herein, the term "$C_1$-$C_5$-alkyl acyloxy" refers to $C_1$-$C_5$-alkyl groups having an acyloxy substituent, including 2-(acetyloxy)ethyl and the like.

As used herein, the term "alkoxy" refers to the group —O—R where R includes "$C_1$-$C_6$-alkyl" or "aryl" or "heteroaryl" or "$C_1$-$C_6$-alkyl aryl" or "$C_1$-$C_6$-alkyl heteroaryl". Preferred alkoxy groups include by way of example, methoxy, ethoxy, phenoxy and the like.

As used herein, the term "$C_1$-$C_5$-alkyl alkoxy" refers to $C_1$-$C_5$-alkyl groups having an alkoxy substituent, including 2-ethoxyethyl and the like.

As used herein, the term "alkoxycarbonyl" refers to the group —C(O)OR where R includes H, "$C_1$-$C_6$-alkyl" or "aryl" or "heteroaryl" or "$C_1$-$C_6$-alkyl aryl" or "$C_1$-$C_6$-alkyl heteroaryl".

As used herein, the term "$C_1$-$C_5$-alkyl alkoxycarbonyl" refers to $C_1$-$C_5$-alkyl groups having an alkoxycarbonyl substituent, including 2-(benzyloxycarbonyl)ethyl and the like.

As used herein, the term "aminocarbonyl" refers to the group —C(O)NRR' where each R, R' includes independently hydrogen or $C_1$-$C_6$-alkyl or aryl or heteroaryl or "$C_1$-$C_6$-alkyl aryl" or "$C_1$-$C_6$-alkyl heteroaryl".

As used herein, the term "$C_1$-$C_5$-alkyl aminocarbonyl" refers to $C_1$-$C_5$-alkyl groups having an aminocarbonyl substituent, including 2-(dimethylaminocarbonyl)ethyl and the like.

As used herein, the term "acylamino" refers to the group —NRC(O)R' where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl".

As used herein, the term "$C_1$-$C_5$-alkyl acylamino" refers to $C_1$-$C_5$-alkyl groups having an acylamino substituent, including 2-(propionylamino)ethyl and the like.

As used herein, the term "ureido" refers to the group —NRC(O)NR'R" where each R, R', R" is independently hydrogen or "$C_1$-$C_6$-alkyl" or "aryl" or "heteroaryl" or "$C_1$-$C_6$-alkyl aryl" or "$C_1$-$C_6$-alkyl heteroaryl" "cycloalkyl" or "heterocycloalkyl", and where R' and R", together with the nitrogen atom to which they are attached, can optionally form a 3-8-membered heterocycloalkyl ring.

As used herein, the term "$C_1$-$C_5$-alkyl ureido" refers to $C_1$-$C_5$-alkyl groups having an ureido substituent, including 2-(N'-methylureido)ethyl and the like.

As used herein, the term "amino" refers to the group —NRR' where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl" or "cycloalkyl" or "heterocycloalkyl" and where R and R', together with the nitrogen atom to which they are attached, can optionally form a 3-8-membered heterocycloalkyl ring.

As used herein, the term "$C_1$-$C_5$-alkyl amino" refers to $C_1$-$C_5$-alkyl groups having an amino substituent, including 2-(1-pyrrolidinyl)ethyl and the like.

As used herein, the term "ammonium" refers to a positively charged group —N$^+$RR'R", where each R, R', R" is independently "$C_1$-$C_6$-alkyl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

As used herein, the term "halogen" refers to fluoro, chloro, bromo and iodo atoms.

As used herein, the term "sulfonyloxy" refers to a group —OSO$_2$—R wherein R is selected from H, "$C_1$-$C_6$-alkyl", "$C_1$-$C_6$-alkyl" substituted with halogens, e.g., an —OSO$_2$—CF$_3$ group, "aryl", "heteroaryl", "$C_1$-$C_6$-alkyl aryl" or "$C_1$-$C_6$-alkyl heteroaryl".

As used herein, the term "$C_1$-$C_5$-alkyl sulfonyloxy" refers to $C_1$-$C_5$-alkyl groups having a sulfonyloxy substituent, including 2-(methylsulfonyloxy)ethyl and the like.

As used herein, the term "sulfonyl" refers to group "—SO$_2$—R" wherein R is selected from H, "aryl", "heteroaryl", "$C_1$-$C_6$-alkyl", "$C_1$-$C_6$-alkyl" substituted with halogens, e.g., an —SO$_2$—CF$_3$ group, "$C_1$-$C_6$-alkyl aryl" or "$C_1$-$C_6$-alkyl heteroaryl".

As used herein, the term "$C_1$-$C_5$-alkyl sulfonyl" refers to $C_1$-$C_5$-alkyl groups having a sulfonyl substituent, including 2-(methylsulfonyl)ethyl and the like.

As used herein, the term "sulfinyl" refers to a group "—S(O)—R" wherein R is selected from H, "$C_1$-$C_6$-alkyl", "C₁-C₆-alkyl" substituted with halogens, e.g., a —SO—CF₃ group, "aryl", "heteroaryl", "C₁-C₆-alkyl aryl" or "C₁-C₆-alkyl heteroaryl".

As used herein, the term "C₁-C₅-alkyl sulfinyl" refers to C₁-C₅-alkyl groups having a sulfinyl substituent, including 2-(methylsulfinyl)ethyl and the like.

As used herein, the term "sulfanyl" refers to groups —S—R where R includes "C₁-C₆-alkyl" or "aryl" or "hetero-aryl" or "C₁-C₆-alkyl aryl" or "C₁-C₆-alkyl heteroaryl". Preferred sulfanyl groups include methylsulfanyl, ethylsulfanyl, and the like.

As used herein, the term "C₁-C₅-alkyl sulfanyl" refers to C₁-C₅-alkyl groups having a sulfanyl substituent, including 2-(ethylsulfanyl)ethyl and the like. "Sulfonylamino" refers to a group —NRSO₂—R' where each R, R' is independently hydrogen or "C₁-C₆-alkyl" or "aryl" or "heteroaryl" or "C₁-C₆-alkyl aryl" or "C₁-C₆-alkyl heteroaryl".

As used herein, the term "C₁-C₅-alkyl sulfonylamino" refers to C₁-C₅-alkyl groups having a sulfonylamino substituent, including 2-(ethylsulfonylamino)ethyl and the like.

Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "C₁-C₆-alkyl", "C₂-C₆-alkenyl", "C₂-C₆-alkynyl", "cycloalkyl", "heterocycloalkyl", "C₁-C₆-alkyl aryl", "C₁-C₆-alkyl heteroaryl", "C₁-C₆-alkyl cycloalkyl", "C₁-C₆-alkyl heterocycloalkyl", "amino", "ammonium", "acyl", "acyloxy", "acylamino", "aminocarbonyl", "alkoxycarbonyl", "ureido", "aryl", "heteroaryl", "sulfinyl", "sulfonyl", "alkoxy", "sulfanyl", "halogen", "carboxy", trihalomethyl, cyano, hydroxy, mercapto, nitro, and the like. Alternatively said substitution could also comprise situations where neighboring substituents have undergone ring closure, notably when vicinal functional substituents are involved, thus forming, e.g., lactams, lactones, cyclic anhydrides, but also acetals, thioacetals, aminals formed by ring closure for instance in an effort to obtain a protective group.

As used herein, the term "pharmaceutically acceptable salts or complexes" refers to salts or complexes of the below-identified compounds of formulae (I) and (II) that retain the desired biological activity. Examples of such salts include, but are not restricted to acid addition salts formed with inorganic acids (e.g., hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. Said compounds can also be administered as pharmaceutically acceptable quaternary salts known by a person skilled in the art, which specifically include the quaternary ammonium salt of the formula —NR,R',R"⁺Z⁻, wherein R, R', R" is independently hydrogen, alkyl, or benzyl, C₁-C₆-alkyl, C₂-C₆-alkenyl, C₂-C₆-alkynyl, C₁-C₆-alkyl aryl, C₁-C₆-alkyl heteroaryl, cycloalkyl, heterocycloalkyl, and Z is a counterion, including chloride, bromide, iodide, —O-alkyl, toluenesulfonate, methyl sulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

As used herein, the term "derivative" refers to structural variants of a reference compound, such as variants that differ from the reference compound by the inclusion and/or location of one or more substituents, as well as variants that are isomers of a reference compound, such as structural isomers (e.g., regioisomers) or stereoisomers (e.g., enantiomers or diastereomers).

The structural compositions described herein also include tautomers, its geometrical isomers, enantiomers, diastereomers, and racemic forms, as well as pharmaceutically acceptable salts thereof. Such salts include, e.g., acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

DETAILED DESCRIPTION

Figure 1:
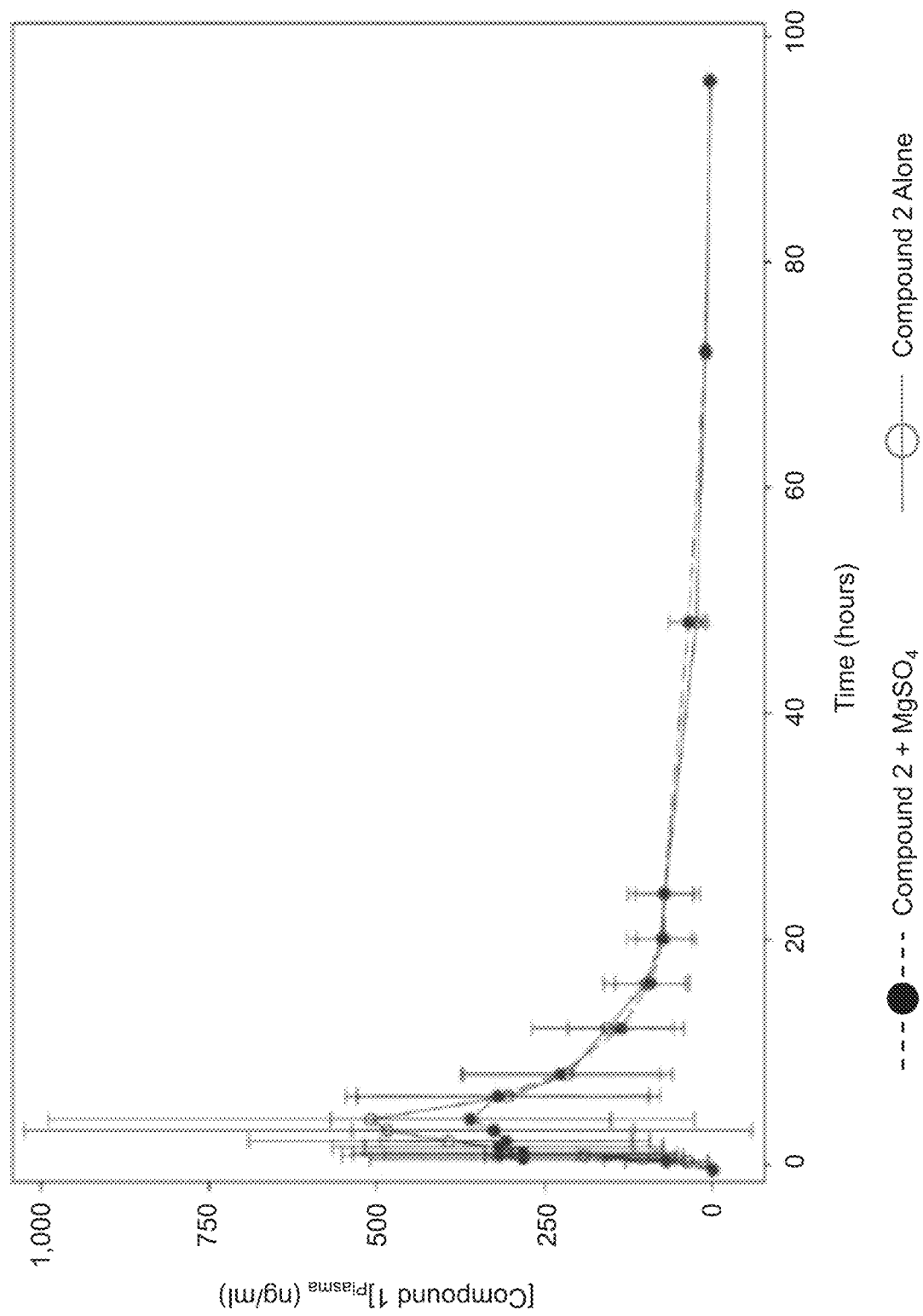
FIG. 1 is a graph showing the mean plasma concentration of compound (1) resulting from administration of compound (2) alone (solid line, open circles) or from administration of compound (2) in combination with magnesium sulfate (dashed line, closed circles) as a function of time following administration to human female subjects.

Provided herein are compositions and methods for the treatment and/or prevention of preterm labor in a patient, such as a mammalian patient (e.g., a human female patient). Using the compositions and methods described herein, a prostaglandin F2α (PGF2α) receptor antagonist may be administered to a patient undergoing or at risk of undergoing premature parturition, so as to slow the onset of delivery, for instance, by a matter of hours, days, or weeks. The PGF2α receptor antagonist may be administered to the patient in combination with nifedipine. The PGF2α receptor antagonist may be, for example, a 1,3-thiazolidine-2-carboxamide compound described herein, such as (3S)-3-({[(2S)-3-(biphenyl-4-ylsulfonyl)-1,3-thiazolidin-2-yl]carbonyl}-amino)-3-(4-fluorophenyl)propyl L-valinate or a pharmaceutically acceptable salt thereof, such as (3S)-3-({[(2S)-3-(biphenyl-4-ylsulfonyl)-1,3-thiazolidin-2-yl]carbonyl}-amino)-3-(4-fluorophenyl)propyl L-valinate hydrochloride, or another 1,3-thiazolidine-2-carboxamide that gives rise to 3-([1,1'-biphenyl]-4-ylsulfonyl)-N-[1-(4-fluorophenyl)-3-hydroxypropyl]-1,3-thiazolidine-2-carboxamide in vivo.

The compositions and methods described herein are based, in part, on the surprising discovery of a beneficial drug-drug interaction between nifedipine and PGF2α receptor antagonists, such as (3S)-3-({[(2S)-3-(biphenyl-4-ylsulfonyl)-1,3-thiazolidin-2-yl]carbonyl}-amino)-3-(4-fluorophenyl)propyl L-valinate or a pharmaceutically acceptable salt thereof (e.g., (3S)-3-({[(2S)-3-(biphenyl-4-ylsulfonyl)-1,3-thiazolidin-2-yl]carbonyl}-amino)-3-(4-fluorophenyl)propyl L-valinate hydrochloride) and other 1,3-thiazolidine-2-carboxamides that give rise to 3-([1,1'-biphenyl]-4-ylsulfonyl)-N-[1-(4-fluorophenyl)-3-hydroxy-propyl]-1,3-thiazolidine-2-carboxamide in vivo. It has presently been discovered that administration of nifedipine and such PGF2α receptor antagonists leads to an unexpected increase in nifedipine exposure. This discovery provides the clinical benefit of being able to administer nifedipine to a pregnant patient in a reduced amount and/or frequency when given in combination with a PGF2α receptor antagonist relative to the amount or frequency would be used if nifedipine were administered alone, while still achieving beneficial treatment effects, such as a prolonged pregnancy and delayed onset of labor. The reduced nifedipine dosing that can be achieved using the compositions and methods descried herein is advantageous, as patients receiving low doses of nifedipine in combination with a PGF2α receptor antagonist described herein have a reduced likelihood of experiencing nifedipine-induced side effects while still being able to experience successful treatment outcomes.

To obtain these advantageous pharmacological benefits, the patient may be administered therapeutically effective amounts of the PGF2α receptor antagonist and nifedipine, for example, either concurrently or at different times. The patient may receive multiple, continuous doses of the PGF2α antagonist and/or the nifedipine. The same or different dosing schedules may be used for administration of the PGF2α antagonist and the nifedipine. For instance, each time the patient receives a dose of one of these agents, the patient may or may not receive a dose of the second agent. The patient may receive the PGF2α antagonist, for example, one or more times per day (such as once or twice daily) and the nifedipine may be administered to the subject, for example, one or more times every 4, 6, 8, 10, 12, 14, 16, 18, 20, 22, 24, 36, or 48 hours, or more. The combined administration of nifedipine and the PGF2α receptor antagonist may occur one or more times per day, week, or month, as described herein, and may continue, for example, up until the patient undergoes delivery or until a full gestational term has been reached.

The sections that follow provide a description of the nifedipine formulations and PGF2α receptor antagonists that may be used in conjunction with the compositions and methods described herein, as well as the dosing amounts and schedules that may be employed for administering these tocolytic agents.

PGF2α Receptor Antagonists

PGF2α receptor antagonists that may be used in conjunction with the compositions and methods described herein include 1,3-thiazolidine-2-carboxamide compounds, such as those PGF2α receptor antagonists described, for example, in U.S. Pat. Nos. 8,415,480; 9,447,055; and 9,834,528, the disclosures of each of which are incorporated herein by reference in their entirety. Exemplary PGF2α receptor antagonists include, for instance, compounds represented by formula (I)

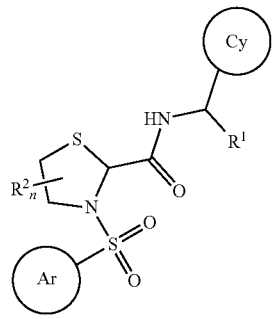

(I)

wherein ring Ar is an optionally fused, optionally substituted aryl group or an optionally fused, optionally substituted heteroaryl group;

ring Cy is an optionally fused, optionally substituted aryl group, optionally fused, optionally substituted heteroaryl group, optionally fused, optionally substituted cycloalkyl group, or an optionally fused, optionally substituted heterocycloalkyl group;

$R^1$ is H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_1$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_1$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, or substituted $C_2$-$C_6$-alkynyl heteroaryl;

each $R^2$ is independently $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, or substituted $C_2$-$C_6$-alkyny; and n is an integer from 0 to 2, or a pharmaceutically acceptable salt thereof.

In some embodiments, the ring Ar is selected from substituents (Ia) to (Iy):

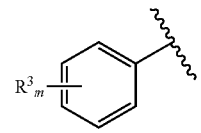

(Ia)

-continued
(Ib) 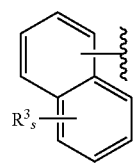
(Ic) 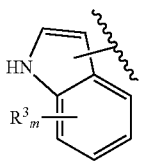
(Id) 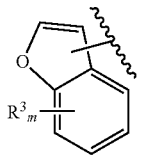
(Ie) 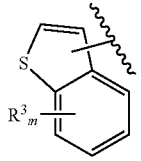
(If) 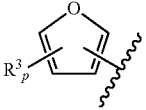
(Ig) 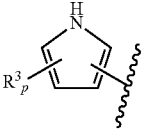
(Ih) 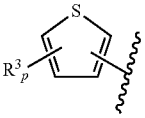
(Ii) 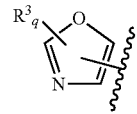
(Ij) 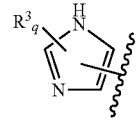
(Ik) 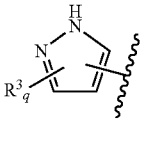
(Im) 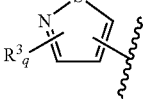
-continued
(In) 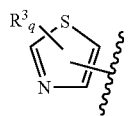
(Io) 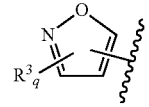
(Ip) 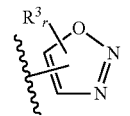
(Iq) 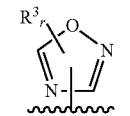
(Ir) 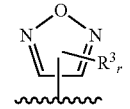
(Is) 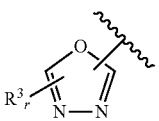
(It) 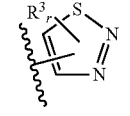
(Iu) 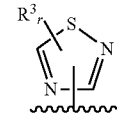
(Iv) 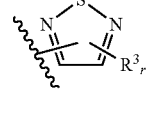
(Iw) 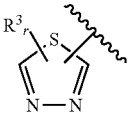
(Ix) 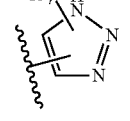
(Iy) 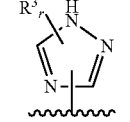
wherein each $R^3$ is independently halogen, haloalkyl, cyano, optionally substituted amino, hydroxyl, thiol, optionally substituted alkoxy, optionally substituted acyloxy, optionally substituted alkoxycarbonyl, carboxy, ureido, alkyl sulfonyl, aryl sulfonyl, heteroaryl sulfonyl, cycloalkyl sulfonyl, heterocycloalkyl sulfonyl, alkyl sulfanyl, aryl sulfanyl, heteroaryl sulfanyl, cycloalkyl sulfanyl, heterocycloalkyl sulfanyl, alkyl sulfinyl, aryl sulfinyl, heteroaryl sulfinyl, cycloalkyl sulfinyl, heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

each m is independently an integer from 0-5;
each p is independently an integer from 0-3;
each q is independently an integer from 0-2;
each r is independently an integer from 0-1; and
each s is independently an integer from 0-7.

In some embodiments, each $R^3$ is independently selected from substituents (IIa) to (IIy).

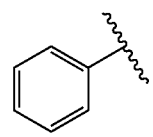  (IIa)

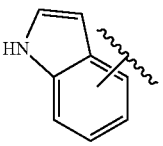  (IIb)

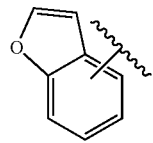  (IIc)

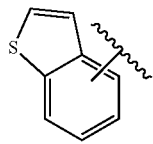  (IId)

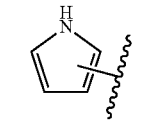  (IIe)

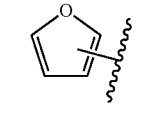  (IIf)

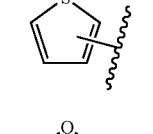  (IIg)

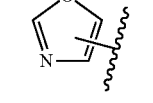  (IIh)

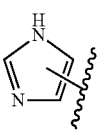  (IIi)

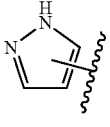  (IIj)

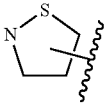  (IIk)

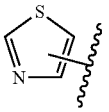  (IIm)

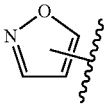  (IIn)

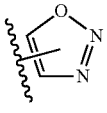  (IIp)

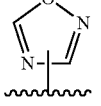  (IIq)

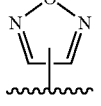  (IIr)

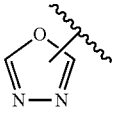  (IIs)

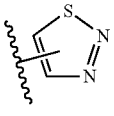  (IIt)

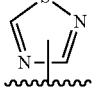  (IIu)

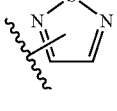  (IIv)

-continued (IIw) 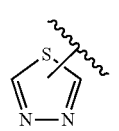

(IIx) 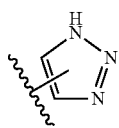

(IIy) 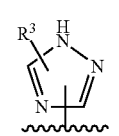

In some embodiments, the ring Ar is a substituent represented by formula (Ia)

(Ia) 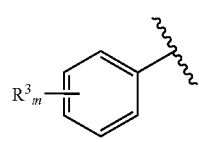

and each $R^3$ is, independently, optionally substituted and optionally fused aryl, optionally substituted and optionally fused heteroaryl, optionally substituted and optionally fused cycloalkyl, or optionally substituted and optionally fused heterocycloalkyl.

In some embodiments, the ring Cy is selected from substituents (IIIa) to (IIIaa):

(Ia) 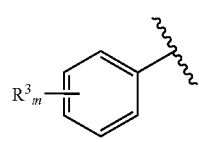

(Ib) 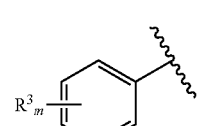

(Ic) 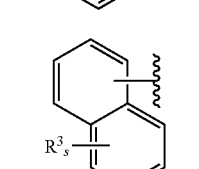

(Id) 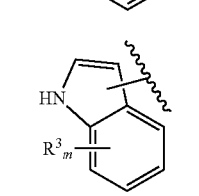

(Ie) 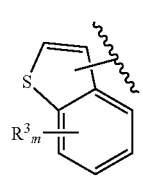

(If) 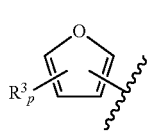

(Ig) 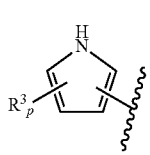

(Ih) 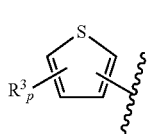

(Ii) 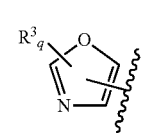

(Ij) 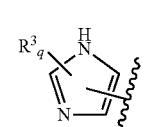

(IIIk) 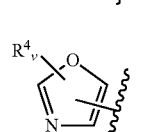

(IIIm) 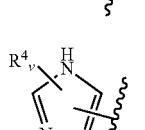

(IIIn) 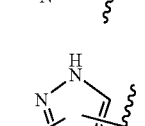

(IIIo) 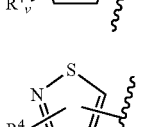

(IIIp) 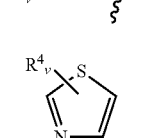

(IIIq) 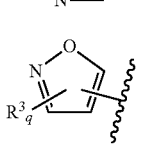

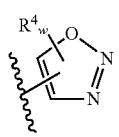 (IIIr)

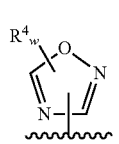 (IIIs)

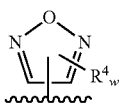 (IIIt)

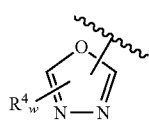 (IIIu)

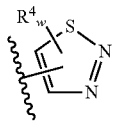 (IIIv)

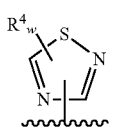 (IIIw)

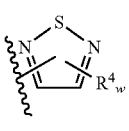 (IIIx)

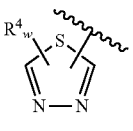 (IIIy)

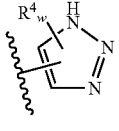 (IIIz)

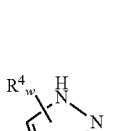 (IIIaa)

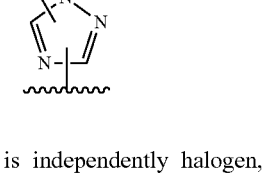

wherein each $R^4$ is independently halogen, haloalkyl, cyano, optionally substituted amino, hydroxyl, thiol, optionally substituted alkoxy, optionally substituted acyloxy, optionally substituted alkoxycarbonyl, carboxy, ureido, alkyl sulfonyl, aryl sulfonyl, heteroaryl sulfonyl, cycloalkyl sulfonyl, heterocycloalkyl sulfonyl, alkyl sulfanyl, aryl sulfanyl, heteroaryl sulfanyl, cycloalkyl sulfanyl, heterocycloalkyl sulfanyl, alkyl sulfinyl, aryl sulfinyl, heteroaryl sulfinyl, cycloalkyl sulfinyl, heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

each G is independently —CH$_2$—, —CR$^4$H—, —NH—, —NR$^4$—, —O—, or —S—;

each t is independently an integer from 0-5;
each u is independently an integer from 0-3;
each v is independently an integer from 0-2;
each w is independently an integer from 0-1;
each x is independently an integer from 0-7; and
each y is independently an integer from 0-4.

In some embodiments, the ring Cy is an optionally substituted aryl group represented by formula (IVa).

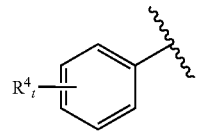 (IVa)

In some embodiments, the ring Cy is a substituted aryl group represented by formula (IVb).

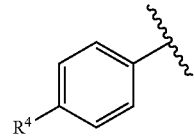 (IVb)

In some embodiments, $R^1$ is $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, substituted $C_1$-$C_5$-alkyl carboxy, substituted $C_1$-$C_5$-alkyl acyl, substituted $C_1$-$C_5$-alkyl alkoxycarbonyl, or substituted $C_1$-$C_5$-alkyl acyloxy. In some embodiments, $R^1$ is optionally substituted $C_1$-$C_5$-alkyl acyloxy.

In some embodiments, the compound is represented by formula (V)

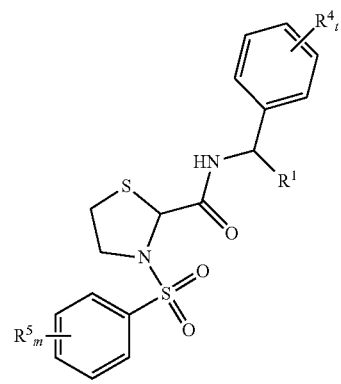 (V)

wherein $R^1$ is $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, substituted $C_1$-$C_5$-alkyl carboxy, substituted $C_1$-$C_5$-alkyl acyl, substituted $C_1$-$C_5$-alkyl alkoxycarbonyl, or substituted $C_1$-$C_5$-alkyl acyloxy;

each $R^3$ is independently halogen, haloalkyl, cyano, optionally substituted amino, hydroxyl, thiol, optionally substituted alkoxy, optionally substituted acyloxy, optionally substituted alkoxycarbonyl, carboxy, ureido, alkyl sulfonyl, aryl sulfonyl, heteroaryl sulfonyl, cycloalkyl sulfonyl, heterocycloalkyl sulfonyl, alkyl sulfanyl, aryl sulfanyl, heteroaryl sulfanyl, cycloalkyl sulfanyl, heterocycloalkyl sulfanyl, alkyl sulfinyl, aryl sulfinyl, heteroaryl sulfinyl, cycloalkyl sulfinyl, heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

each $R^4$ is independently halogen, haloalkyl, cyano, optionally substituted amino, hydroxyl, thiol, optionally substituted alkoxy, optionally substituted acyloxy, optionally substituted alkoxycarbonyl, carboxy, ureido, alkyl sulfonyl, aryl sulfonyl, heteroaryl sulfonyl, cycloalkyl sulfonyl, heterocycloalkyl sulfonyl, alkyl sulfanyl, aryl sulfanyl, heteroaryl sulfanyl, cycloalkyl sulfanyl, heterocycloalkyl sulfanyl, alkyl sulfinyl, aryl sulfinyl, heteroaryl sulfinyl, cycloalkyl sulfinyl, heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

m is an integer from 0-5; and t is an integer from 0-5, or a pharmaceutically acceptable salt thereof.

In some embodiments, the compound is represented by formula (Va)

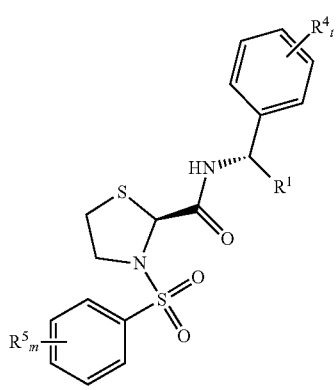

(Va)

or a pharmaceutically acceptable salt thereof.

In some embodiments, the compound is represented by formula (VI)

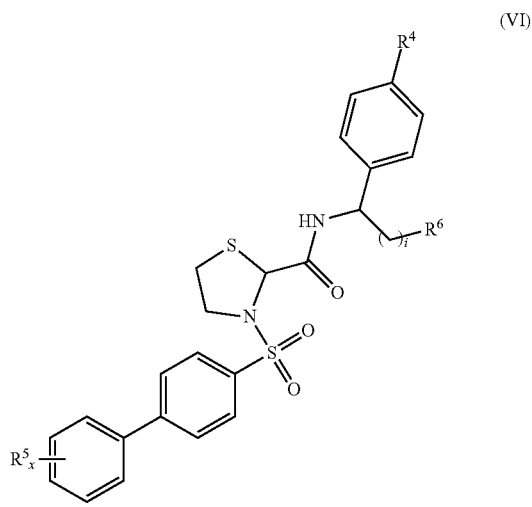

(VI)

wherein $R^6$ is hydroxyl, acyl, alkoxycarbonyl, or acyloxy;

each $R^5$ is independently halogen, haloalkyl, cyano, optionally substituted amino, hydroxyl, thiol, optionally substituted alkoxy, optionally substituted acyloxy, optionally substituted alkoxycarbonyl, carboxy, ureido, alkyl sulfonyl, aryl sulfonyl, heteroaryl sulfonyl, cycloalkyl sulfonyl, heterocycloalkyl sulfonyl, alkyl sulfanyl, aryl sulfanyl, heteroaryl sulfanyl, cycloalkyl sulfanyl, heterocycloalkyl sulfanyl, alkyl sulfinyl, aryl sulfinyl, heteroaryl sulfinyl, cycloalkyl sulfinyl, heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

$R^4$ is halogen, haloalkyl, cyano, optionally substituted amino, hydroxyl, thiol, optionally substituted alkoxy, optionally substituted acyloxy, optionally substituted alkoxycarbonyl, carboxy, ureido, alkyl sulfonyl, aryl sulfonyl, heteroaryl sulfonyl, cycloalkyl sulfonyl, heterocycloalkyl sulfonyl, alkyl sulfanyl, aryl sulfanyl, heteroaryl sulfanyl, cycloalkyl sulfanyl, heterocycloalkyl sulfanyl, alkyl sulfinyl, aryl sulfinyl, heteroaryl sulfinyl, cycloalkyl sulfinyl, heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

i is an integer from 0-3; and x is an integer from 0-5, or a pharmaceutically acceptable salt thereof.

In some embodiments, the compound is represented by formula (VII)

(VII)

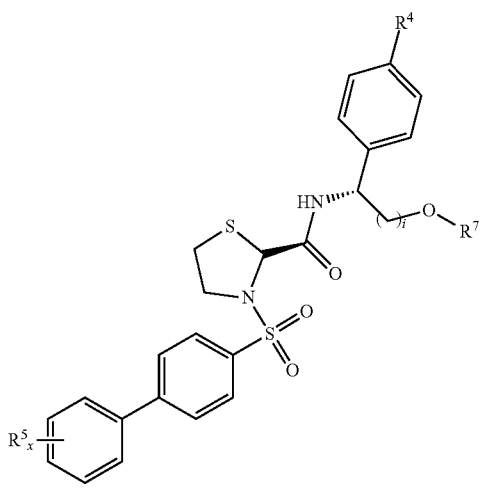

wherein $R^7$ is H or optionally substituted aminoacyl;

each $R^5$ is independently halogen, haloalkyl, cyano, optionally substituted amino, hydroxyl, thiol, optionally substituted alkoxy, optionally substituted acyloxy, optionally substituted alkoxycarbonyl, carboxy, ureido, alkyl sulfonyl, aryl sulfonyl, heteroaryl sulfonyl, cycloalkyl sulfonyl, heterocycloalkyl sulfonyl, alkyl sulfanyl, aryl sulfanyl, heteroaryl sulfanyl, cycloalkyl sulfanyl, heterocycloalkyl sulfanyl, alkyl sulfinyl, aryl sulfinyl, heteroaryl sulfinyl, cycloalkyl sulfinyl, heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

$R^4$ is halogen, haloalkyl, cyano, optionally substituted amino, hydroxyl, thiol, optionally substituted alkoxy, optionally substituted acyloxy, optionally substituted alkoxycarbonyl, carboxy, ureido, alkyl sulfonyl, aryl sulfonyl, heteroaryl sulfonyl, cycloalkyl sulfonyl, heterocycloalkyl sulfonyl, alkyl sulfanyl, aryl sulfanyl, heteroaryl sulfanyl, cycloalkyl sulfanyl, heterocycloalkyl sulfanyl, alkyl sulfinyl, aryl sulfinyl, heteroaryl sulfinyl, cycloalkyl sulfinyl, heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

i is an integer from 0-3; and x is an integer from 0-5, or a pharmaceutically acceptable salt thereof.

In some embodiments, the compound is represented by formula (VII)

(VIII)

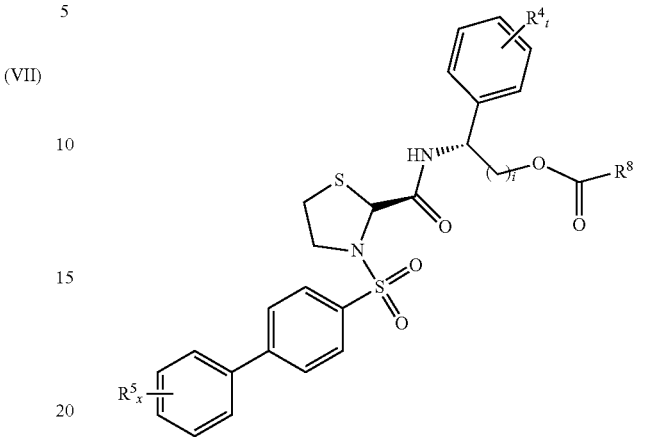

wherein $R^8$ is optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl, preferably wherein $R^8$ is amino-substituted alkyl, such as 1-amino $C_1$-$C_6$ alkyl (e.g., (S)-1-amino $C_1$-$C_6$ alkyl or (R)-1-amino $C_1$-$C_6$ alkyl, for example, (S)-1-amino-2-methylpropyl, (S)-1-amino-2-methylbutyl, (S)-1-amino-3-methylbutyl, (R)-1-amino-2-methylpropyl, (R)-1-amino-2-methylbutyl, or (R)-1-amino-3-methylbutyl;

each $R^5$ is independently halogen, haloalkyl, cyano, optionally substituted amino, hydroxyl, thiol, optionally substituted alkoxy, optionally substituted acyloxy, optionally substituted alkoxycarbonyl, carboxy, ureido, alkyl sulfonyl, aryl sulfonyl, heteroaryl sulfonyl, cycloalkyl sulfonyl, heterocycloalkyl sulfonyl, alkyl sulfanyl, aryl sulfanyl, heteroaryl sulfanyl, cycloalkyl sulfanyl, heterocycloalkyl sulfanyl, alkyl sulfinyl, aryl sulfinyl, heteroaryl sulfinyl, cycloalkyl sulfinyl, heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

$R^4$ is halogen, haloalkyl, cyano, optionally substituted amino, hydroxyl, thiol, optionally substituted alkoxy, optionally substituted acyloxy, optionally substituted alkoxycarbonyl, carboxy, ureido, alkyl sulfonyl, aryl sulfonyl, heteroaryl sulfonyl, cycloalkyl sulfonyl, heterocycloalkyl sulfonyl, alkyl sulfanyl, aryl sulfanyl, heteroaryl sulfanyl, cycloalkyl sulfanyl, heterocycloalkyl sulfanyl, alkyl sulfinyl, aryl sulfinyl, heteroaryl sulfinyl, cycloalkyl sulfinyl, heterocycloalkyl sulfinyl, optionally substituted alkyl, optionally substituted alkenyl, optionally substituted alkynyl, optionally substituted and optionally fused aryl, optionally substituted and optionally fused heteroaryl, optionally substituted and optionally fused cycloalkyl, or optionally substituted and optionally fused heterocycloalkyl;

i is an integer from 0-3;

t is an integer from 0-5; and x is an integer from 0-5, or a pharmaceutically acceptable salt thereof.

(3S)-3-({[(2S)-3-(biphenyl-4-ylsulfonyl)-1,3-thiazo-
lidin-2-yl]carbonyl}-amino)-3-(4-fluorophenyl)pro-
pyl L-valinate (Compound 2)

Particular PGF2α receptor antagonists that may be administered to a patient (e.g., a pregnant human patient) to treat or prevent preterm labor include (3S)-3-({[(2S)-3-(biphenyl-4-ylsulfonyl)-1,3-thiazolidin-2-yl]carbonyl}-amino)-3-(4-fluorophenyl)propyl L-valinate, represented by formula (2), below) and pharmaceutically acceptable salts thereof. This compound is converted in vivo to 3-([1,1'-biphenyl]-4-ylsulfonyl)-N-[1-(4-fluorophenyl)-3-hydroxy-propyl]-1,3-thiazolidine-2-carboxamide (represented by formula (1), below). Compound 1, previously described in U.S. Pat. No. 8,415,480, is an antagonist of the prostaglandin F receptor, as this compound exhibits an inhibition constant (Ki) of 6 nM for human PGF2α receptor as determined by competitive radioligand binding assays (experimental details of competitive radioligand binding assays useful for the determination of Ki values are described, e.g., in U.S. Pat. No. 8,415,480, Example 51). Following administration to a subject, compound 2 is de-esterified in vivo so as to form compound 1 due to the activity of endogenous esterases, such as those present in the gastrointestinal tract.

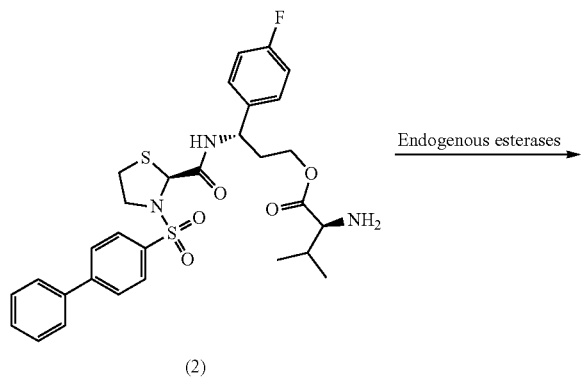

(2)

It has been discovered that compound 2 is an inhibitor of the prostaglandin F2α receptor, as compound 2 inhibits the receptor with a Ki of 1 nM. Compound 2 exhibits improvements in several physicochemical characteristics relative to compound 1, including solubility in water as well as in media that simulate the small intestinal contents in the fed (FeSSIF) and fasted (FaSSIF) states. These data are described, e.g., in U.S. Pat. No. 9,447,055.

In addition to exhibiting enhanced aqueous solubility, compound 2 and salts thereof feature a particularly beneficial absorption mechanism. Compound 2 is de-esterified by ambient esterases in the small intestine and subsequently penetrates the small intestinal epithelium passively. Compound 2 and salts thereof are not substrates for the Pept1 transporter protein, a proton-coupled co-transporter that mediates the absorption of peptidic nutrients. Pept1 is known to mediate the absorption of a variety of valinate esters, as described, for example, in Vig et al., Adv. Drug Deliv. Rev. 65:1370-1385 (2013), and in Yang et al., Drug Metab. Dispos. 41:608-614 (2013). Pept1 exhibits broad substrate specificity, as evidenced by the structural diversity of compounds that are transported across the intestinal epithelium by this protein. Surprisingly, despite the presence the valinate ester functionality, compound 2 and salts thereof are not dependent upon this transporter for absorption across the small intestinal epithelium. This is an advantageous property, as compound 2 and salts thereof (for instance, the chloride salt thereof, represented by formula (3)) thus do not compete with natural substrates of Pept1, such as peptidic nutrients, for binding to, and transport by, this protein. Rather, compound 2 and salts thereof are converted in vivo to a form that is readily absorbed in a manner independent of energy and local proton gradient. This beneficial property, coupled with the high aqueous solubility of compound I and salts thereof, fosters a pharmacokinetic profile in which compound 2 and salts thereof readily dissolve in an aqueous environment and are in turn converted into a form capable of transported-independent absorption.

(3S)-3-({[(2S)-3-(biphenyl-4-ylsulfonyl)-1,3-thiazo-
lidin-2-yl]carbonyl}-amino)-3-(4-fluorophenyl)pro-
pyl L-valinate hydrochloride (Compound 3)

The chloride salt of compound 2, (3S)-3-({[(2S)-3-(biphenyl-4-ylsulfonyl)-1,3-thiazolidin-2-yl]carbonyl}-amino)-3-(4-fluorophenyl)propyl L-valinate hydrochloride, designated as compound 3 herein) exhibits additional advantageous characteristics. For example, this compound is readily crystallized using a several distinct experimental procedures. Compound 3 assumes a single, reproducible crystal form upon crystallization from a variety of media and under different ambient conditions. Moreover, this crystal form of compound 3 exhibits extended stability under ambient conditions and in the presence of elevated relative humidity. Compound 3 exhibits a low hygroscopicity and thus does not demonstrate a propensity to absorb moisture from the local atmosphere. Compound 3 therefore exhibits a resistance to chemical changes, such as hydrolysis, as well as a resistance to the incorporation of impurities. For instance, impurities associated with atmospheric water are not readily integrated into the crystalline form of compound 3.

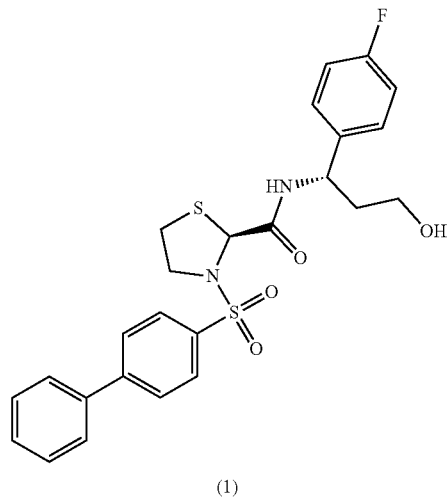

(1)

(3) Additional PGF2α Receptor Antagonists

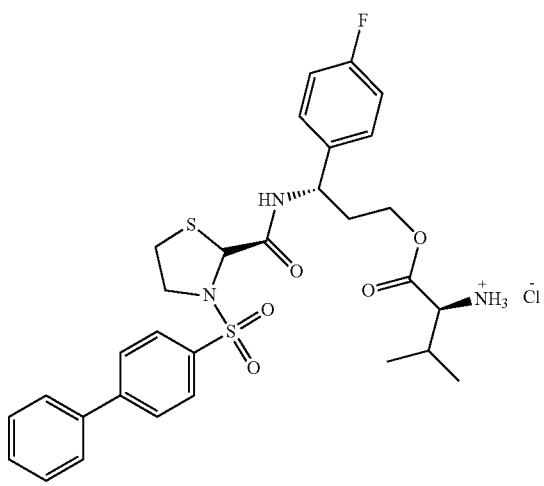

PGF2α receptor antagonists that may be used in conjunction with the compositions and methods described herein include additional 1,3-thiazolidine-2-carboxamides, such as additional 1,3-thiazolidine-2-carboxamides that give rise to compound (1) in vivo (e.g., by way of de-esterification of a compound of formula (VIII) due to the activity of endogenous esterases in vivo). Examples of additional PGF2α receptor antagonists that may be used in conjunction with the compositions and methods described herein include those compounds set forth in Table 1, below, the syntheses of which are reported in U.S. Pat. No. 8,415,480, the disclosure of which is incorporated herein by reference in its entirety.

TABLE 1

Exemplary PGF2α Receptor Antagonists Useful in Combination with Nifedipine for the Treatment or Prevention of Preterm Labor

| Ex. | Compound | Reported $^1$H NMR and/or ESI Spectral Properties |
|---|---|---|
| 1 | | $^1$H NMR (300 MHz, CDCl$_3$); 1.85-2.3 (m, 2H), 2.55-3.15 (m, CH$_2$S, 2H), 3.65-3.9 (m, CH$_2$N, CH$_2$O, 4H), 5.2-5.3 (m, CH, 1H), 5.37 (s, CH, 1H), 7.25-8.0 (m, CH(Ar), 14H); M$^+$(ESI$^+$): 483.0; M–(ESI–) 481.0 |
| 2 | | $^1$H NMR (300 MHz, CDCl$_3$); 2.4-2.9 (m, CH$_2$S, 2H), 3.5-3.7 (m, CH$_2$N, 2H), 3.7-3.9 (m, CH$_2$O, 2H), 4.9 (m, CH, 1H), 5.2 (s, CH, 1H), 7.1-7.9 (m, CH(Ar), 14H); M$^+$(ESI$^+$): 469.2; M–(ESI–) 467.1 |
| 3 | | $^1$H NMR (300 MHz, CDCl$_3$); 2.5-3.0 (m, CH$_2$S, 2H), 3.6-4.0 (m, CH$_2$N, 2H), 5.41 (s, CH, 0.5H), 5.42 (s, CH, 0.5H), 6.07 (m, CH, 1H), 5.2 (s, CH, 1H), 7.1-7.8 (m, CH(Ar), 16H), 7.8-7.9 (m, CH, 1H), 8.5-8.6 (m, CH, 1H); M$^+$(ESI$^+$): 516.3; M–(ESI–) 514.1. |

TABLE 1-continued

Exemplary PGF2α Receptor Antagonists Useful in Combination with Nifedipine for the Treatment or Prevention of Preterm Labor

| Ex. | Compound | Reported $^1$H NMR and/or ESI Spectral Properties |
|---|---|---|
| 4 | 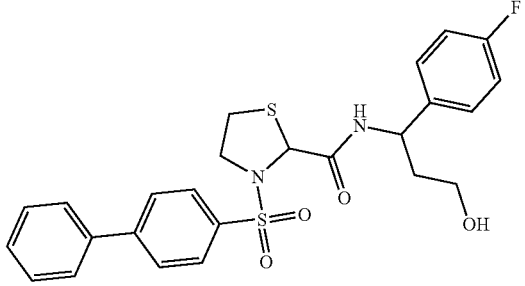 [SMILES: O=C(NC(CCO)c1ccc(F)cc1)C1SCCN1S(=O)(=O)c1ccc(-c2ccccc2)cc1] | $^1$H NMR (400 MHz, CDCl$_3$); 1.8-2.15 (m, CH$_2$, 2H), 2.5-2.9 (m, CH$_2$S, 2H), 3.5-3.8 (m, CH$_2$N, CH$_2$O, 4H), 5.15 (m, CH, 1H), 5.25 (s, CH, 1H), 7.1-7.9 (m, CH(Ar), 13H); M$^+$(ESI$^+$): 501.3. |
| 5 | 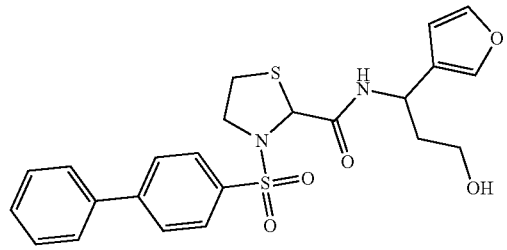 [SMILES: O=C(NC(CCO)c1ccoc1)C1SCCN1S(=O)(=O)c1ccc(-c2ccccc2)cc1] | $^1$H NMR (400 MHz, CDCl$_3$); 1.7-2.2 (m, CH$_2$, 2H), 2.5-2.9 (m, CH$_2$S, 2H), 3.6-3.8 (m, CH$_2$N, CH$_2$O, 4H), 5.12 (m, CH, 1H), 5.21 (s, CH, 1H), 6.25-6.35 (d, CH(furyl), 1H), 6.9-7.1 (m, CH(furyl), 1H), 7.3-7.9 (m, CH(Ar), 10H); M$^+$(ESI$^+$): 473.1; M−(ESI−): 471.1. |
| 6 | 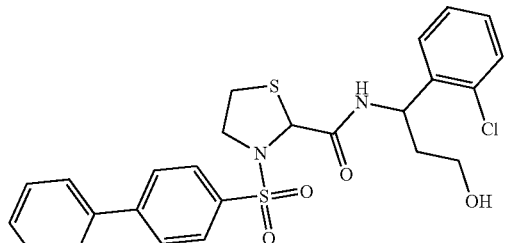 | $^1$H NMR (400 MHz, CDCl$_3$); 1.95-2.15 (m, CH$_2$, 2H), 2.5-2.9 (m, CH$_2$S, 2H), 3.6-3.8 (m, CH$_2$N, CH$_2$O, 4H), 5.28 (s, CH, 0.5H), 5.29 (s, CH, 0.5H), 5.4-5.5 (m, CH, 1H), 7.1-7.9 (m, CH(Ar), 13H); M$^+$(ESI$^+$): 517.3. |
| 7 | 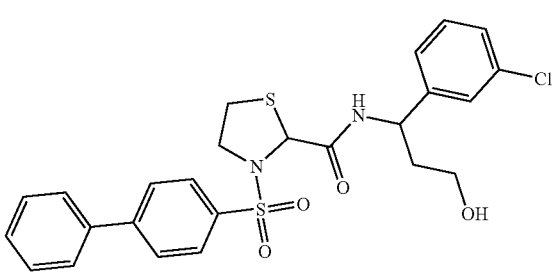 [SMILES: O=C(NC(CCO)c1cccc(Cl)c1)C1SCCN1S(=O)(=O)c1ccc(-c2ccccc2)cc1] | $^1$H NMR (400 MHz, CDCl$_3$); 1.8-2.2 (m, CH$_2$, 2H), 2.55-3.0 (m, CH$_2$S, 2H), 3.6-3.8 (m, CH$_2$N, CH$_2$O, 4H), 5.1-5.2 (m, CH, 1H), 5.24 (s, CH, 0.5H), 5.28 (s, CH, 0.5H), 7.2-7.9 (m, CH(Ar), 13H); M$^+$(ESI$^+$): 517.1; M−(ESI−): 514.8. |
| 8 | 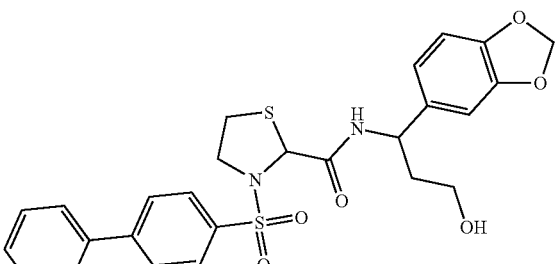 | $^1$H NMR (400 MHz, CDCl$_3$); 1.7-2.2 (m, CH$_2$, 2H), 2.45-3.0 (m, CH$_2$S, 2H), 3.6-3.95 (m, CH$_2$N, CH$_2$O, 4H), 5.0-5.1 (m, CH, 1H), 5.26 (s, CH, 0.5H), 5.28 (s, CH, 0.5H), 5.87 (s, CH, 1H), 5.89 (s, CH, 1H), 6.8-7.9 (m, CH(Ar), 12H); M$^+$(ESI$^+$): 527.1; M−(ESI−): 525.0. |

TABLE 1-continued

Exemplary PGF2α Receptor Antagonists Useful in Combination with Nifedipine for the Treatment or Prevention of Preterm Labor

| Ex. | Compound | Reported ¹H NMR and/or ESI Spectral Properties |
|---|---|---|
| 9 | | ¹H NMR (400 MHz, CDCl$_3$); 1.27 (s, CH$_3$, 9H), 1.65-2.15 (m, CH$_2$, 2H), 2.45-2.95 (m, CH$_2$S, 2H), 3.6-3.95 (m, CH$_2$N, CH$_2$O, 4H), 5.1-5.2 (m, CH, 1H), 5.26 (s, CH, 1H), 7.3-7.7 (m, CH(Ar), 9H); M⁺(ESI⁺): 463.1; M−(ESI−): 461.6. |
| 10 | | ¹H NMR (400 MHz, CDCl$_3$); 0.63 (t, J = 7.3 Hz, 3H), 1.29 (s, CH$_3$, 6H), 1.65 (q, J = 7.4 Hz, 2H), 1.88 (m, CH$_2$, 1H), 2.19 (m, CH$_2$, 1H), 2.5 (m, CH$_2$S, 1H), 2.94 (dt, J = 12 Hz and 5.6 Hz, CH$_2$S, 1H), 3.65-3.87 (m, CH$_2$N, CH$_2$O, 4H), 5.2 (td, J = 6.6 Hz and 3.8 Hz, CH, 1H), 5.32 (s, CH, 1H), 7.25-7.8 (m, CH(Ar), 9H); M⁺(ESI⁺): 477.2; M−(ESI−): 475.0. |
| 11 | | ¹H NMR (400 MHz, CDCl$_3$); 2.24 (m, 3H), 2.25 (m, 1H), 2.95 (m, 1H), 3.63-3.90 (m, 4H), 5.31 (m, 2H), 6.99-7.86 (m, 13H).; M⁺(ESI⁺): 501; M−(ESI−): 499. |
| 12 | | ¹H NMR (300 MHz, CDCl$_3$); 1.86 (m, 1H), 2.09 (m, 1H), 2.36 (s, 3H), 2.57 (m, 1H), 2.99 (m, 1H), 3.72-3.92 (m, 4H), 5.31-5.40 (m, 2H), 7.19-7.88 (m, 13H); M⁺(ESI⁺): 497; M−(ESI−): 495. |
| 13 | | ¹H NMR (300 MHz, CDCl$_3$); 2.00 (m, 2H), 2.57 (m, 1H), 2.87-2.98 (m, 2H), 3.62-3.70 (m, 3H), 3.92 (m, 0.4H), 3.92 (s, 1.8H), 3.98 (s, 1.2H), 4.04 (m, 0.6H), 5.23 (m, 1H), 5.43 (m, 1H), 6.92 (m, 2H), 7.22-7.45 (m, 2H), 7.46 (m, 3H), 7.60 (m, 2H), 7.77 (m, 2H), 7.90 (m, 2H), 8.26 (d, J = 11.7 Hz, 0.6H), 8.47 (d, J = 9.8 Hz, 0.4H); M⁺(ESI⁺): 513; M−(ESI−): 511. |

TABLE 1-continued

Exemplary PGF2α Receptor Antagonists Useful in Combination with Nifedipine for the Treatment or Prevention of Preterm Labor

| Ex. | Compound | Reported $^1$H NMR and/or ESI Spectral Properties |
|---|---|---|
| 14 | | $^1$H NMR (300 MHz, CDCl$_3$); 2.01 (m, 2H), 2.69 (m, 1H), 3.00 (m, 1H), 3.69-3.96 (m, 4H), 4.32 (m, 0.5H), 5.36 (m, 1H), 5.62 (m, 1H), 6.91-7.91 (m, 13H).; M$^+$(ESI$^+$): 519; M–(ESI–): 517. |
| 15 | | $^1$H NMR (300 MHz, CDCl$_3$); 1.94 (m, 1H), 2.09 (m, 1H), 2.30 (m, 6H), 2.56 (m, 1H), 2.87 (m, 0.5H), 2.99 (m, 0.5H), 3.70 (m, 3H), 391 (m, 1H), 5.31-5.37 (m, 2H), 6.76 (m, 2H), 6.99 (m, 2H), 7.45-7.93 (m, 9H).; M–(ESI–): 511. M–(ESI–): 509. |
| 16 | | $^1$H NMR (300 MHz, CDCl$_3$); $^1$H NMR (300 MHz, CDCl$_3$); 1.85-2.2 (m, 2H), 2.5 (s, CH$_3$N, 3H), 2.45-3.00 (m, CH$_2$S, 2H), 2.7-3.0 (m, CH$_2$N, 2H), 3.6 (m, CH$_2$N, 2H), 4.2 (m, CH$_2$N, 2H), 4.7 (m, CH, 1H), 5.3 (s, CH, 1H), 6.37 (m, CH(furyl), 1H), 6.56 (m, CH(furyl), 1H), 7.05-8.0 (m, CH(Ar), 15H), 8.7 (m, NH, 1H); M$^+$(ESI$^+$): 576.1; M–(ESI–): 573.8. |
| 17 | | $^1$H NMR (400 MHz, DMSO); 1.05 (t, J = 7.3 Hz, 6H), 1.88 (m, CH$_2$, 2H), 2.79-2.81 (m, CH$_2$N, 6H), 3.05 (m, CH$_2$S, 1H), 3.05-3.50 (broad, H$_2$O), 3.81 (m, CH$_2$N, 2H), 4.86 (td, J = 6.6 Hz and 3.8 Hz, CH, 1H), 5.44 (s, CH, 1H), 6.58 (s, CH$_2$, 2H), 7.24-7.33 (m, CH(Ar), 5H); 7.53 (m, CH(Ar), 3H), 7.76 (m, CH(Ar), 2H), 7.95 (m, CH(Ar), 4H), 8.68 (m, 1H, NH); M$^+$(ESI$^+$): 538.0; M–(ESI–): 536.0. |

TABLE 1-continued

Exemplary PGF2α Receptor Antagonists Useful in Combination with Nifedipine for the Treatment or Prevention of Preterm Labor

| Ex. | Compound | Reported $^1$H NMR and/or ESI Spectral Properties |
|---|---|---|
| 18 | | $^1$H NMR (300 MHz, CDCl$_3$); 1.75-2.1 (m, 2H), 2.2 (s, CH$_3$N, 3H), 2.3-2.9 (m, CH$_2$S, 2H), 3.3-3.5 (m, CH$_2$N, 2H), 3.6 (s, CH$_2$N, 2H), 3.9 (m, CH$_2$N, 2H), 5.0 (m, CH, 1H), 5.3 (s, CH, 1H), 7.0-8.0 (m, CH(Ar), 19H), 8.6 (m, NH, 1H); M$^+$(ESI$^+$): 586.2; M−(ESI−): 583.8. |
| 19 | | $^1$H NMR (400 MHz, DMSO); 1.75 (m, CH$_2$, 6H), 2.18 (s, CH$_3$, 3H), 2.36 (m, CH, 1H), 2.50 (m, CHS, 1H), 2.55-2.85 (m, CH, 3H), 2.95 (m, CHS, 1H), 2.37 (m, CH$_2$, 2H), 3.67-3.74 (m, 2H, CH$_2$N), 4.70 (s, CH, 1H), 5.34 (s, CH, 1H), 6.47 (s, 2H, Hvinyl), 7.14-7.25 (m, CH(Ar), 7H); 7.40-7.49 (m, CH(Ar), 3H), 7.50-7.70 (m, CH(Ar), 3H), 7.83 (m, CH(Ar), 4H), 8.33 (m, CH(Ar), 1H), 8.58 (m, 1H, NH); M$^+$(ESI$^+$): 601; M(ESF): 599 |
| 20 | | $^1$H NMR (300 MHz, CDCl$_3$); 1.8-2.2 (m, 2H), 2.36 (s, CH$_3$N, 3H), 2.45-3.05 (m, CH$_2$S, 2H), 2.6-2.7 (m, CH$_2$N, 4H), 3.7 (m, CH$_2$O, 2H), 3.7-4.1 (m, CH$_2$N, 2H), 5.1-5.25 (m, CH, 1H), 5.48 (s, CH, 1H), 7.25-8.0 (m, CH(Ar), 14H), 8.55 (m, NH, 1H); M$^+$(ES0: 540.2; M−(ESF): 537.99. |
| 21 | | $^1$H NMR (300 MHz, CDCl$_3$); 1.8-2.2 (m, 2H), 2.4 (s, CH$_3$N, 3H), 2.5-3.0 (m, CH$_2$S, 2H), 2.6-2.7 (m, CH$_2$N, 2H), 3.4 (s, CH$_2$N, 2H), 3.69 (s, CH$_3$O, 3H), 3.7-4.0 (m, CH$_2$N, 2H), 5.1 (m, CH, 1H), 5.49 (s, CH, 1H), 7.2-8.0 (m, CH(Ar), 14H), 8.6 (m, NH, 1H); M$^+$(ESI$^+$): 568.2; M−(ESI−): 565.8. |

TABLE 1-continued

Exemplary PGF2α Receptor Antagonists Useful in Combination with Nifedipine for the Treatment or Prevention of Preterm Labor

| Ex. | Compound | Reported $^1$H NMR and/or ESI Spectral Properties |
|---|---|---|
| 22 | | $^1$H NMR (300 MHz, CDCl$_3$); 2.15-2.4 (m, CH$_2$, 6H), 2.45-3.05 (m, CH$_2$S, 2H), 2.5-3.5 (m, CH$_2$N, 6H), 3.9-4.25 (m, CH$_2$N, 2H), 5.2 (m, CH, 1H), 5.5 (s, CH, 1H), 7.2-8.0 (m, CH(Ar), 14H), 8.5 (m, NH, 1H); M$^+$(ESI$^+$): 536.3; M–(ESI–): 534.2. |
| 23 | | $^1$H NMR (300 MHz, CDCl$_3$); 2.2-2.7 (m, CH$_2$, 2H), 2.45-3.00 (m, CH$_2$S, 2H), 2.7 (s, CH$_3$N, 3H), 2.9 (s, CH$_3$N, 3H), 3.5-3.9 (m, CH$_2$N, 2H), 4.0-4.25 (m, CH$_2$N, 2H), 5.0 (m, CH, 1H), 5.3 (s, CH, 1 H), 7.2-8.0 (m, CH (Ar), 14H), 8.5 (m, NH, 1H); M$^+$(ESI$^+$): 510.2; M–(ESI–): 508.1. |
| 24 | | M$^+$(ESI$^+$): 564.3; M–(ESI–): 562.3. |
| 25 | | M$^+$(ESI$^+$): 550.3; M–(ESI–): 548.2. |
| 26 | | M$^+$(ESI$^+$): 552.3; M–(ESI–): 550.2. |

TABLE 1-continued

Exemplary PGF2α Receptor Antagonists Useful in Combination with Nifedipine for the Treatment or Prevention of Preterm Labor

| Ex. | Compound | Reported $^1$H NMR and/or ESI Spectral Properties |
|---|---|---|
| 27 | | M$^+$(ESI$^+$): 616.3; M−(ESI−): 614.9. |
| 28 | | M$^+$(ESI$^+$): 630.4; M−(ESI−): 628.2. |
| 29 | | M$^+$(ESI$^+$): 580.6; M−(ESI−): 578.8. |
| 30 | | M$^+$(ESI$^+$): 571.8; M−(ESI−): 569.99. |

TABLE 1-continued

Exemplary PGF2α Receptor Antagonists Useful in Combination with Nifedipine for the Treatment or Prevention of Preterm Labor

| Ex. | Compound | Reported $^1$H NMR and/or ESI Spectral Properties |
|---|---|---|
| 31 | | M+(ESI+): 586.9; M−(ESI−): 585.3. |
| 32 | | $^1$H NMR (400 MHz, CDCl$_3$); 2.6-3.1 (m, CH$_2$S, 2H), 3.7-4.1 (m, CH$_2$N, 2H), 4.6-4.7 (m, NCH$_2$Ar, 2H), 5.6 (s, CH, 1H), 7.3-8.15 (m, CH(Ar), 14H); M+(ESI+): 439.1; M−(ESI−): 437.0. |
| 33 | | $^1$H NMR (300 MHz, CDCl$_3$); 1.1 (s, CH$_3$, 3H), 2.3-2.8 (m, CH$_2$S, 2H), 3.5-3.8 (m, CH2N, 2H), 4.2-4.4 (m, NCH$_2$Ar, 2H), 5.2 (s, CH, 1H), 7.0-7.65 (m, CH(Ar), 9H) 9H); M+(ESI+): 419.8; M−(ESI−): 417.4. |
| 34 | | $^1$H NMR (400 MHz, CDCl$_3$); 2.6-3.1 (m, CH$_2$S, 2H), 3.7-4.1 (m, CH$_2$N, 2H), 3.8 (s, CH$_3$O, 3H), 4.6-4.7 (m, NCH$_2$Ar, 2H), 5.6 (s, CH, 1H), 7.3-8.1 (m, CH(Ar), 13H); M+(ESI+): 469.1; M−(ESI−): 467.4. |
| 35 | | $^1$H NMR (400 MHz, CDCl$_3$); 2.55-3.1 (m, CH$_2$S, 2H), 3.65-4.05 (m, CH$_2$N, 2H), 4.6-4.85 (m, NCH$_2$Ar, 2H), 5.5 (s, CH, 2H), 6.95-8.05 (m, CH(Ar), 12H); M+(ESI+): 445.1; M−(ESI−): 443.1. |

TABLE 1-continued

Exemplary PGF2α Receptor Antagonists Useful in Combination with Nifedipine for the Treatment or Prevention of Preterm Labor

| Ex. | Compound | Reported ¹H NMR and/or ESI Spectral Properties |
|---|---|---|
| 36 | | ¹H NMR (300 MHz, CDCl₃); 2.6-3.1 (m, CH₂S, 2H), 3.8-4.3 (m, CH₂N, 2H), 4.6-4.75 (m, NCH₂Ar, 2H), 5.7 (s, CH, 2H), 6.6 (m, CH(furyl), 2H), 7.45-8.3 (m, CH(Ar), 10H); M⁺(ESI⁺): 429.5; M−(ESI−): 427.5. |
| 37 | | ¹H NMR (400 MHz, CDCl₃); 2.65-3.1 (m, CH₂S, 2H), 3.7-4.1 (m, CH₂N, 2H), 4.6-4.7 (m, NCH₂Ar, 2H), 5.6 (s, CH, 1H), 6.9-7.9 (m, CH(Ar), 13H); M⁺(ESI⁺): 457.4; M−(ESI−): 455.2. |
| 38 | | ¹H NMR (400 MHz, CDCl₃); 2.3-2.9 (m, CH₂S, 2H), 3.5-3.9 (m, CH₂N, 2H), 5.3 (s, CH, 1H), 6.2 (s × 2, NCHAr, 1H), 7.3-8.15 (m, CH(Ar), 19H); M⁺(ESI⁺): 515.3; M−(ESI−): 513.7. |
| 39 | | M⁺(ESI⁺): 471.2; M−(ESI−): 469.0. |

TABLE 1-continued

Exemplary PGF2α Receptor Antagonists Useful in Combination with Nifedipine for the Treatment or Prevention of Preterm Labor

| Ex. | Compound | Reported ¹H NMR and/or ESI Spectral Properties |
|---|---|---|
| 40 | | M⁺(ESI⁺): 453.2; M−(ESI−): 451.0. |
| 41 | | M⁺(ESI⁺): 475.2; M−(ESI−): 473.0. |
| 42 | | M⁺(ESI⁺): 475.4; M−(ESI−): 472.6. |
| 43 | | $^1$H NMR (400 MHz, CDCl$_3$); 2.6-3.1 (m, CH$_2$S, 2H), 3.7-4.1 (m, CH$_2$N, 2H), 3.8 (s, CH$_3$O 3H), 4.6-4.7 (m, NCH$_2$Ar, 2H), 5.6 (s, CH, 1H), 7.3-8.1 (m, CH(Ar), 13H); M⁺(ESI⁺): 469.2; M−(ESI−): 467.6. |
| 44 | | M⁺(ESI⁺): 473.3; M−(ESI−): 470.2. |

TABLE 1-continued

Exemplary PGF2α Receptor Antagonists Useful in Combination with Nifedipine for the
Treatment or Prevention of Preterm Labor

| Ex. | Compound | Reported $^1$H NMR and/or ESI Spectral Properties |
|---|---|---|
| 45 | | M$^+$(ESI$^+$): 457.03; M−(ESI−): 455.4. |
| 46 | | $^1$H NMR (400 MHz, CDCl$_3$); 1.80-2.10 (m, 6H, CH$_3$, CH$_2$S, CH$_2$), 2.54 (m, 1H, CH$_2$S), 2.97-3.10 (m, 2H, CH$_2$), 3.50-3.90 (m, 3H, NH, CH$_2$N), 5.0-5.10 (m, 1H, CH), 5.24 (s, 1H, CH), 5.98-6.11 (m, 1H, NH), 7.25-7.89 (m, 14H, CH(Ar)); M$^+$(ESI$^+$): 523.71; M−(ESI−): 522.05. |
| 47 | | $^1$H NMR (400 MHz, CDCl$_3$); 1.80-2.10 (m, 3H, CH$_2$S, CH$_2$), 2.88 (s, 3H, CH$_3$), 3.0-3.50 (m, 3H, CH$_2$S, CH$_2$), 3.70-3.85 (m, 2H, CH$_2$N), 4.45 (m, 1H, NH), 5.13-5.21 (m, 1H, CH), 5.35 (s, 1H, CH), 6.86-6.94 (m, 1H, NH), 7.35-8.10 (m, 14H, CH(Ar)); M$^+$(ESI$^+$): 560.21; M−(ESI−): 558.47. |
| 48 | | $^1$H NMR (400 MHz, CDCl$_3$); 2.22-2.40 (m, 2H, CH$_2$), 2.41-2.50 (m, 1H, CH$_2$S), 2.78-2.81 (m, 1H, CH$_2$S), 3.56-3.93 (m, 4H, CH$_2$N, CH$_2$O), 5.21 (m, 1H, CH), 5.31 (s, 1H, CH), 6.79-6.92 (m, 4H, CH(Ar) and NH), 7.20-7.85 (m, 16H, CH(Ar)); M$^+$(ESI$^+$): 559.39; M−(ESI−): 557.61. |
| 49 | | $^1$H NMR (300 MHz, CDCl$_3$); 2.58 (m, 1H), 2.93 (m, 1H), 3.77 (m, 2H), 5.28 (s, 0.5H), 5.31 (s, 0.5H), 6.07 (m, 1H), 7.13 (m, 4H), 7.37 (m, 7H), 7.55 (m, 2H), 7.71 (m, 2H), 7.87 (m, 2H), 8.30 (m, 1H). M$^+$(ESI$^+$): 550; M−(ESI−): 548. |

TABLE 1-continued

Exemplary PGF2α Receptor Antagonists Useful in Combination with Nifedipine for the Treatment or Prevention of Preterm Labor

| Ex. | Compound | Reported $^1$H NMR and/or ESI Spectral Properties |
|---|---|---|
| 50 | | $^1$H NMR (300 MHz, CDCl$_3$); 2.60 (m, 1H), 2.94 (m, 1H), 3.72 (m, 1H), 3.86 (m, 1H), 5.31 (s, 0.5H), 5.36 (s, 0.5H), 6.21 (m, 1H), 7.36 (m, 11H), 7.60 (m, 2H), 7.76 (m, 2H), 7.90 (m, 2H), 8.34 (m, 1H). M$^+$(ESI$^+$): 550; M−(ESI−): 548. |
| 51 | | $^1$H NMR (300 MHz, DMSO-d$_6$); 2.58 (m, 1H), 2.97 (m, 1H), 3.69 (m, 2H), 5.41 (m, 1H), 5.65 (m, 1H), 6.18 (m, 1H), 7.20 (m, 10H), 7.60 (m, 2H), 7.77 (m, 4H), 8.73 (m, 1H), 11.37 (br s, 1 H). M$^+$(ESI$^+$): 532; M−(ESI−): 530. |
| 52 | | $^1$H NMR (300 MHz, CDCl$_3$); 2.61 (m, 1H), 2.99 (m, 1H), 3.15 (s, 6H), 3.72 (m, 1H), 3.90 (s, 1H), 5.36 (s, 0.5H), 5.39 (s, 0.5H), 6.10 (m, 1H), 6.56 (m, 1H), 7.13 (m, 1H), 7.28 (m, 6H), 7.46 (m, 3H), 7.60 (m, 2H), 7.73 (m, 2H), 7.91 (m, 2H), 8.02 (m, 0.5H), 8.09 (m, 0.5H). M$^+$(ESI$^+$): 559; M−(ESI−): 558. |
| 53 | | $^1$H NMR (300 MHz, CDCl$_3$); 2.63 (m, 7H), 2.99 (m, 3H), 3.71 (m, 1H), 4.02 (m, 1H), 4.26 (br s, 2H), 5.48 (s, 0.5H), 5.49 (s, 0.5H), 6.02 (s, 0.5H), 6.05 (s, 0.5H), 7.25 (m, 6H), 7.44 (m, 4FI), 7.58 (m, 2FI), 7.70 (m, 2H), 7.93 (m, 2H), 8.33 (m, 2H). M$^+$(ESI$^+$): 603; M−(ESI−): 601. |

TABLE 1-continued

Exemplary PGF2α Receptor Antagonists Useful in Combination with Nifedipine for the Treatment or Prevention of Preterm Labor

| Ex. | Compound | Reported ¹H NMR and/or ESI Spectral Properties |
|---|---|---|
| 54 | 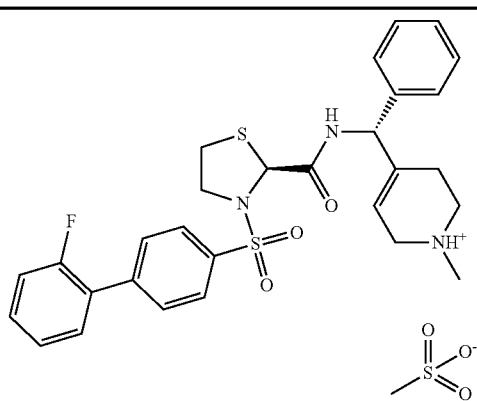 | ¹H NMR (300 MHz, DMSO-c/6); 1.40 (m, 2H), 1.92 (m, 2H), 2.29 (s, 3H), 2.70 (m, 3H), 3.06 (m, 1H), 3.31 (m, 4H), 3.82 (m, 2H), 4.58 (m, 1H), 5.50 (s, 1H), 7.34 (m, 7H), 7.56 (m, 2H), 7.90 (m, 4H), 8.57 (m, 1H), 9.10 (m, 1H). M⁺(ESI⁺): 554; M−(ESI−): 552. |
| 55 | 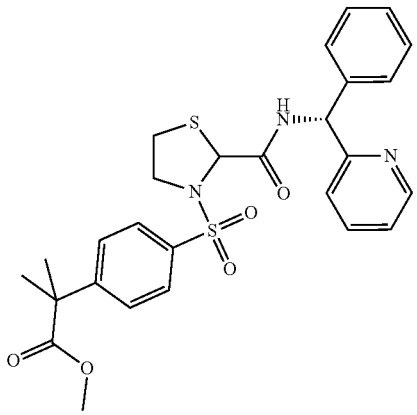 [SMILES: COC(=O)C(C)(C)c1ccc(S(=O)(=O)N2CCSC2C(=O)N[C@H](c2ccccc2)c2ccccn2)cc1] | ¹H NMR (300 MHz, CDCl₃); δ 8.63 (s, 1H); 7.82-7.91 (m, 3H); 7.33-7.51 (m, 9H); 6.2 (s, 1H); 5.65 (s, 1H); 3.88 (m, 2H); 3.66 (s, 3H); 3.10 (m, 1H); 2.65 (m, 1H); 1.6 (s, 6H). M⁺(ESI⁺): 540.1; M−(ES$^{I-}$): 538.0. |
| 56 | 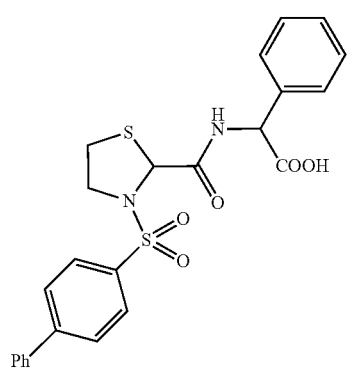 [SMILES: O=C(O)C(NC(=O)C1SCCN1S(=O)(=O)c1ccc(-c2ccccc2)cc1)c1ccccc1] | ¹H NMR (300 MHz, DMSO-d6); 2.68 (m, 1H), 3.08 (m, 1H), 3.84 (m, 2H), 5.30 (m, 1H), 5.76 (s, 0.5H), 5.82 (s, 0.5H), 7.44 (m, 8H), 7.78 (m, 2H), 7.93 (m, 4H), 8.91 (m, 1H), 13.10 (br s, 1H). M⁺(ESI⁺): 483; M−(ESI−): 481. |
| 57 | 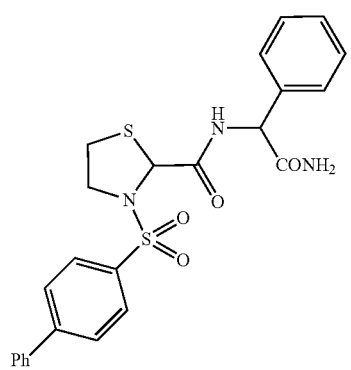 | ¹H NMR (300 MHz, DMSO-d6); 2.64 (m, 1H), 3.04 (m, 1H), 3.78 (m, 2H), 5.34 (m, 1H), 5.84 (m, 1H), 7.29 (m, 4H), 7.47 (m, 4H), 7.76 (m, 2H), 7.90 (m, 4H), 8.77 (m, 1H). M⁺(ESI⁺): 482; M−(ESI−): 480. |

TABLE 1-continued

Exemplary PGF2α Receptor Antagonists Useful in Combination with Nifedipine for the Treatment or Prevention of Preterm Labor

| Ex. | Compound | Reported $^1$H NMR and/or ESI Spectral Properties |
|---|---|---|
| 58 | | $^1$H NMR (300 MHz, CDCl$_3$); 2.61 (m, 1H), 2.99 (m, 1H), 3.72 (m, 2H), 5.35 (s, 0.5H), 5.41 (s, 0.5H), 6.06 (m, 0.5H), 6.17 (m, 0.5H), 7.17 (m, 1H), 7.47 (m, 8H), 7.61 (m, 2H), 7.77 (m, 2H), 7.91 (m, 2H). M$^+$(ESI$^+$): 464; M–(ESI–): 462. |
| 59 | | $^1$H NMR (300 MHz, CDCl$_3$); 2.35 (br s, 2H), 2.55 (m, 2H), 3.00 (m, 1H), 3.60-3.93 (m, 2H), 5.30 (s, 0.5H), 5.40 (s, 0.5H), ), 5.64 (m, 1H) 7.05-8.17 (m, 14H, H arom.). M$^+$(ESI$^+$): 497. M–(ESI–): 495. |
| 60 | | $^1$H NMR (300 MHz, CDCl$_3$); δ 8.07 (m, 2H); 7.82-7.97 (m, 3H); 7.28-7.58 (m, 9H); 6.26 (s, 1H); 3.86 (m, 2H); 3.36 (d, 2H); 3.635 (m, 1H); 2.71 (m, 1H); 1.36 (s, 1H) M$^+$(ESI$^+$): 512.4. M–(ESI–): 510.3.<br>$^1$H-RMN (CH$_2$Cl2) δ 8.58 (m, 2H); 7.83 (t, Jt = 8.29, 2H); 7.65 (m, 1H); 7.19-7.40 (m, 9H); 6.10 (s, 1H); 5.46 (s, 1H); 3.95-4.06 (m, 1H); 3.65-3.78 (m, 1H); 2.92-2.99 (m, 3H); 2.55-2.64 (m, 1H); 1.25-1.37 (m, 6H). $^{19}$F-RMN (CH$_2$Cl$_2$) δ -138.6. M$^+$(ESI$^+$): 514.2; M–(ESF): 512.2 |
| 61 | | M$^+$(ESI$^+$): 516; M–(ESI–): 514. |

TABLE 1-continued

Exemplary PGF2α Receptor Antagonists Useful in Combination with Nifedipine for the
Treatment or Prevention of Preterm Labor

| Ex. | Compound | Reported $^1$H NMR and/or ESI Spectral Properties |
|---|---|---|
| 62 | | M$^+$(ESI$^+$): 501.6; M−(ESI−): 499.2. |
| 63 | | M$^+$(ESI$^+$): 519.9; M−(ESI−): 517.8 |
| 64 | | M$^+$(ESI$^+$): 537.9; M−(ESI−): 535.9. |
| 65 | | M$^+$(ESI$^+$): 501.9; M−(ESI−): 499.5. |
| 66 | | M$^+$(ESI$^+$): 636.7; M−(ESI−): 634.3. |

TABLE 1-continued

Exemplary PGF2α Receptor Antagonists Useful in Combination with Nifedipine for the Treatment or Prevention of Preterm Labor

| Ex. | Compound | Reported ¹H NMR and/or ESI Spectral Properties |
|---|---|---|
| 67 | | M⁺(ESI⁺): 618.9; M−(ESI−): 616.5. |
| 68 | | M⁺(ESI⁺): 582.9; M−(ESI−): 581.3. |
| 69 | | M⁺(ESI⁺): 600.8; M−(ESI−): 598.6. |
| 70 | | M⁺(ESI⁺): 519.6; M−(ESI−): 517.6. |

Nifedipine

Nifedipine, sold under the names PROCARDIA® and ADALAT®, among others, is a calcium ion influx inhibitor that inhibits the release of calcium ions from the sarcoplasmic reticulum into the cytoplasm of uterine myocytes. Uterine contractility is dependent, in part, upon this mobilization of divalent calcium ions. Nifedipine inhibits calcium ion influx in uterine myocytes without altering serum calcium concentrations. Nifedipine is represented structurally as compound (4), below.

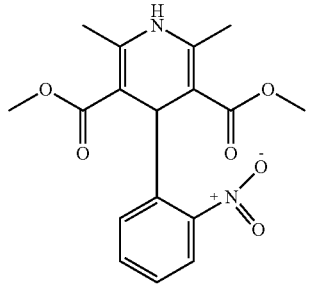

(4)

In some embodiments, nifedipine is orally administered to a patient undergoing or at risk of undergoing preterm labor. The nifedipine may be, for example, formulated a tablet, gel cap, powder, liquid solution, or liquid suspension. The nifedipine may be administered in a dosage form of from about 10 mg to about 30 mg, and may optionally be formulated as an extended release composition. Extended release nifedipine formulations may include one or more, or all, of the excipients selected from cellulose acetate, hydroxypropyl cellulose, hypromellose, magnesium stearate, polyethylene glycol, polyethylene oxide, red ferric oxide, sodium chloride, and titanium dioxide.

Methods of Treatment
Combination Therapy

A PGF2α receptor antagonist, such as a 1,3-thiazolidine-2-carboxamide compound described herein, may be administered to a subject (e.g., a pregnant human subject) in combination with nifedipine so as to treat or prevent preterm parturition. Endogenous PGF2α is synthesized in, and released by, uterine epithelial cells in response to the signal transduction cascades initiated by oxytocin. Upon binding of PGF2α to PGF2α receptor on the extracellular surface of a uterine myocyte, phospholipase C cleaves phosphatidylinositol-4,5-bisphosphate ($PIP_2$) to yield diacylglycerol (DAG) and inositol-1,4,5-trisphosphate ($IP_3$). $IP_3$ in turn potentiates the release of intracellular calcium ($Ca^{2+}$) sarcoplasmic reticula. The sudden increase in calcium stores ultimately leads to uterine muscle contractions and a necrosis of endothelial cells of the corpus *luteum*, a progesterone-secreting structure that supports a developing fetus. The aberrant initiation of uterine contractions and degradation of the corpus *luteum* caused by PGF2α secretion can lead to preterm labor. Recent reports also indicate that oxytocin induces production of prostaglandins in human myometrial cells via potentiation of cyclooxygenase-2 (Cox2). Such a mechanism may explain the sustained release of prostaglandins in uterine tissue that promotes labor.

PGF2α receptor antagonists, such as those described herein, may be administered to a subject to attenuate the phospholipase C-mediated formation of $IP_3$, and the subsequent mobilization of intracellular calcium stores, by inhibiting the association of PGF2α with PGF2α receptor. Without being limited by mechanism, this represents one way in which PGF2α receptor antagonists (e.g., compounds represented by formulas (I) through (VIII), such as compounds (1), (2), and (3)) delay the onset of labor in subject, e.g., by one or more hours, days, or weeks, such as from about 1 hour to about 16 weeks (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or about 1, 2, 3, 4, 5, 6, 7, 8, 9, 10, 11, 12, 13, 14, 15, or 16 weeks). The PGF2α receptor antagonists described herein may additionally be used to alleviate one or more symptoms associated with preterm labor, such as vaginal bleeding and rupture of uterine membranes.

The PGF2α receptor antagonists described herein can be administered to a patient (such as a patient undergoing or at risk of undergoing preterm labor) in combination with a calcium channel inhibitor, such as nifedipine. Calcium channel inhibitors may function by suppressing the release of $Ca^{2+}$ from sarcoplasmic reticula, thereby preventing the mobilization of $Ca^{2+}$ that stimulates uterine muscle contractions. In this way, calcium channel inhibitors, such as nifedipine, may be used to delay the onset of labor in subject, e.g., by one or more hours, days, or weeks, such as from about 1 hour to about 16 weeks (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or about 1, 2, 3, 4, 5, 6, 7, 8, 9, 10, 11, 12, 13, 14, 15, or 16 weeks). Calcium channel inhibitors, such as nifedipine, may additionally be used to alleviate one or more symptoms associated with preterm labor, such as vaginal bleeding and rupture of uterine membranes.

The compositions and methods described herein provide important clinical benefits. Particularly, the compositions and methods described herein enable the administration of reduced amounts of nifedipine when administered in combination with a PGF2α receptor antagonist to the subject while, surprisingly, still achieving a therapeutic effect. It has been discovered that, when administered in combination with a PGF2α receptor antagonist (e.g., a 1,3-thiazolidine-2-carboxamide compound represented by any one of formulas (I) through (VIII) described herein, such as compound (1), compound (2), or compound (3)), nifedipine may be administered to the subject in a reduced dosage and/or in a reduced frequency relative to the dosage or frequency with which the nifedipine would otherwise be administered if given in the absence of the PGF2α receptor antagonist, while still retaining the therapeutic benefit of treating or preventing preterm labor. This property is due to an unexpected drug-drug interaction between nifedipine and PGF2α receptor antagonists (e.g., the 1,3-thiazolidine-2-carboxamide PGF2α receptor antagonists described herein). This interaction manifests as an increase in the plasma concentration of nifedipine in a subject (e.g., a pregnant human subject) when administered in combination with a PGF2α receptor antagonist relative to the concentration of nifedipine in plasma that is achieved when nifedipine is administered alone. Thus, using the compositions and methods described herein, subjects undergoing or at risk of undergoing preterm labor may receive reduced quantities of nifedipine, and are therefore less likely to experience nifedipine-induced side effects, while still receiving the therapeutic benefit, e.g., of a delayed onset of labor.

Antenatal Corticosteroids

Additionally, nifedipine and a PGF2α receptor antagonist, such as a PGF2α antagonist described herein, may be administered to a patient (e.g., a patient undergoing or at risk of undergoing preterm labor) in conjunction with a corticosteroid. Antenatal corticosteroids, such as betamethasone, dexamethasone, and hydrocortisone, represent a class of therapeutic agents that can be administered to a subject in order to accelerate fetal lung maturation prior to birth. Treatment with antenatal corticosteroids is associated with an overall reduction in neonatal death, respiratory distress syndrome, intraventricular hemorrhage, necrotizing enterocolitis, respiratory support, intensive care admissions, and systemic infections in the first 48 hours of life. Additionally, antenatal corticosteroid therapy is effective in women with premature rupture of membranes (PROM) and pregnancy-related hypertension syndromes.

There is evidence to suggest benefit across a wide range of gestational ages, such as from about 26 to about 34 weeks, among others (Miracle et al. J. Perinat. Med. 36:191-196 (2008), the disclosure of which is incorporated herein by reference). Thus, using the compositions and methods described herein, a patient may be administered nifedipine and a PGF2α receptor antagonist (such as a compound represented by any one of formulas (I) through (VIII), e.g., compound (1), (2), or (3)) so as to delay the onset of delivery, thereby providing additional time to administer an antenatal corticosteroid in order to accelerate fetal lung development before birth.

Assessing Patient Response

A variety of methods known in the art and described herein can be used to determine whether a patient (e.g., a patient undergoing or at risk of undergoing preterm labor) is responding favorably to tocolytic treatment. For example, successful treatment with nifedipine and a PGF2α receptor antagonist, such as a 1,3-thiazolidine-2-carboxamide compound described herein, may be signaled by:

(a) a delay in the onset of delivery by the subject, such as a delay of one or more hours, days, or weeks (e.g., a delay of from about 1 hour to about 16 weeks, such as a delay of 1 hour, 6 hours, 12 hours, 18 hours, 24 hours, 48 hours, 72 hours, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, or 16 weeks, among others) following the first administration of nifedipine and the PGF2α receptor antagonist to the subject;

(b) a delay in the onset of delivery by the subject such that the subject undergoes delivery at a gestational age of at least about 34 weeks, such as at a gestational age of from about 34 weeks to about 40 weeks (e.g., at a gestational age of about 34 weeks, 35 weeks, 36 weeks, 37 weeks, 38 weeks, 39 weeks, or 40 weeks) following administration of nifedipine and the PGF2α receptor antagonist to the subject;

(c) a reduction in vaginal bleeding by the subject following administration of nifedipine and the PGF2α receptor antagonist to the subject;

(d) a delay in the onset of amniorrhexis by the subject (e.g., a delay of from about 1 hour to about 16 weeks, such as a delay of 1 hour, 6 hours, 12 hours, 18 hours, 24 hours, 48 hours, 72 hours, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, or 16 weeks, among others, following the first administration of nifedipine and the PGF2α receptor antagonist to the subject);

(e) a reduction in the expression of one or more proinflammatory genes, such as cyclooxygenase-2 (Cox2) by the subject (as assessed, e.g., by observing a decrease in myometrial Cox2 expression) following administration of nifedipine and the PGF2α receptor antagonist to the subject; and/or (f) a reduction in the frequency of, peak amplitude of, duration of, and/or work done by, uterine contractions in the subject following administration of nifedipine and the PGF2α receptor antagonist to the subject.

Routes of Administration and Dosing

Using the compositions and methods described herein, nifedipine and a PGF2α receptor antagonist may be administered to a subject (e.g., a pregnant human subject) so as to treat or prevent preterm labor. Particularly, when administered in combination with a PGF2α receptor antagonist (e.g., a 1,3-thiazolidine-2-carboxamide compound represented by any one of formulas (I) through (VIII) described herein, such as compound (1), compound (2), or compound (3)), the nifedipine may be administered to the subject in a reduced dosage and/or in a reduced frequency relative to the dosage or frequency with which the nifedipine would otherwise be administered if given in the absence of the PGF2α receptor antagonist, while still retaining the therapeutic effect of treating or preventing preterm labor. Exemplary dosage amounts and schedules that may be used for administration of nifedipine and the PGF2α receptor antagonists described herein are described in the sections that follow.

Nifedipine

Exemplary doses of nifedipine that may be used in conjunction with the compositions and methods described herein include doses of about 40 mg or less. For instance, the nifedipine may be administered to the subject in an amount of from about 1 mg to about 40 mg per dose, about 2 mg to about 39 mg per dose, about 3 mg to about 38 mg per dose, about 4 mg to about 37 mg per dose, about 5 mg to about 36 mg per dose, about 6 mg to about 35 mg per dose, about 7 mg to about 34 mg per dose, about 8 mg to about 33 mg per dose, about 9 mg to about 32 mg per dose, about 10 mg to about 30 mg per dose, about 11 mg to about 29 mg per dose, about 12 mg to about 28 mg per dose, about 13 mg to about 27 mg per dose, about 14 mg to about 26 mg per dose, about 15 mg to about 25 mg per dose, about 16 mg to about 24 mg per dose, about 17 mg to about 23 mg per dose, about 18 mg to about 22 mg per dose, or about 19 mg to about 21 mg per dose, among others. Exemplary doses of nifedipine that may be administered to the subject include doses of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as a dose of about 20 mg, among others.

As an example, the nifedipine may be administered to the subject in an amount of about 40 mg or less in the first hour of treatment. For instance, the nifedipine may be administered to the subject in an amount of from about 1 mg to about 40 mg in the first hour of treatment, about 2 mg to about 39 mg in the first hour of treatment, about 3 mg to about 38 mg in the first hour of treatment, about 4 mg to about 37 mg in the first hour of treatment, about 5 mg to about 36 mg in the first hour of treatment, about 6 mg to about 35 mg in the first hour of treatment, about 7 mg to about 34 mg in the first hour of treatment, about 8 mg to about 33 mg in the first hour of treatment, about 9 mg to about 32 mg in the first hour of treatment, about 10 mg to about 30 mg in the first hour of treatment, about 11 mg to about 29 mg in the first hour of treatment, about 12 mg to about 28 mg in the first hour of treatment, about 13 mg to about 27 mg in the first hour of treatment, about 14 mg to about 26 mg in the first hour of treatment, about 15 mg to about 25 mg in the first hour of treatment, about 16 mg to about 24 mg in the first hour of treatment, about 17 mg to about 23 mg in the first hour of treatment, about 18 mg to about 22 mg in the first hour of treatment, or about 19 mg to about 21 mg in the first hour of treatment, among others. Exemplary amounts of nifedipine that may be administered to the subject in the first hour of treatment include amounts of nifedipine of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, and 40 mg, such as an amount of about 20 mg, among others.

Using the compositions and methods described herein, nifedipine may be administered to the subject in an amount of about 200 mg or less per day. For example, the nifedipine may be administered to the subject in an amount of from about 1 mg to about 200 mg per day, about 2 mg to about 199 mg per day, about 3 mg to about 198 mg per day, about 4 mg to about 197 mg per day, about 5 mg to about 196 mg per day, about 6 mg to about 195 mg per day, about 7 mg to about 194 mg per day, about 8 mg to about 193 per day, about 9 mg to about 192 per day, about 10 mg to about 191 per day, about 11 mg to about 190 per day, about 12 mg to about 189 per day, about 13 mg to about 188 per day, about 14 mg to about 187 per day, about 15 mg to about 186 per day, about 16 mg to about 185 mg per day, about 17 mg to about 184 per day, about 18 mg to about 183 per day, about 19 mg to about 182 per day, about 20 mg to about 181 mg per day, about 21 mg to about 180 per day, about 22 mg to about 179 mg per day, about 23 mg to about 178 mg per day, about 24 mg to about 177 mg per day, about 25 mg to about 176 mg per day, about 26 mg to about 175 mg per day, about 27 mg to about 174 mg per day, about 28 mg to about 173 mg per day, about 29 mg to about 172 mg per day, about 30 mg to about 171 mg per day, about 31 mg to about 170 mg per day, about 32 mg to about 169 mg per day, about 33 mg to about 168 mg per day, about 34 mg to about 167 mg per day, about 35 mg to about 166 mg per day, about 36 mg to about 165 mg per day, about 37 mg to about 164 mg per day, about 38 mg to about 163 mg per day, about 39 mg to about 162 per day, about 40 mg to about 161 mg per day, about 41 to about 160 mg per day, about 42 to about 159 mg per day, about 43 mg to about 158 mg per day, about 44 mg to about 157 mg per day, about 45 mg to about 156 mg per day, about 46 mg to about 155 mg per day, about 47 mg to about 154 mg per day, about 48 mg to about 153 mg per day, about 49 mg to about 152 mg per day, about 50 mg to about 151 mg per day, about 51 mg to about 150 mg per day, about 52 mg to about 149 mg per day, about 53 mg to about 148 mg per day, about 54 mg to about 147 mg per day, about 55 mg to about 146 mg per day, about 56 mg to about 145 mg per day, about 57 mg to about 144 mg per day, about 58 mg to about 143 mg per day, about 59 mg to about 142 mg per day, about 60 mg to about 141 mg per day, about 61 mg to about 140 mg per day, about 62 mg to about 139 mg per day, about 63 mg to about 138 mg per day, about 64 mg to about 137 mg per day, about 65 mg to about 136 mg per day, about 66 mg to about 135 mg per day, about 67 mg to about 134 mg per day, about 68 mg to about 133 mg per day, about 69 mg to about 132 mg per day, about 70 mg to about 131 mg per day, about 71 mg to about 130 mg per day, about 72 mg to about 129 per day, about 73 mg to about 128 mg per day, about 74 mg to about 127 mg per day, about 75 mg to about 126 mg per day, about 76 mg to about 125 mg per day, about 77 mg to about 124 mg per day, about 78 mg to about 123 mg per day, about 79 mg to about 122 mg per day, about 80 mg to about 121 mg per day, about 81 mg to about 120 mg per day, about 82 mg to about 119 mg per day, about 83 mg to about 118 mg per day, about 84 mg to about 117 mg per day, about 85 mg to about 116 mg per day, about 86 mg to about 115 mg per day, about 87 mg to about 114 mg per day, about 88 mg to about 113 mg per day, about 89 mg to about 112 mg per day, about 90 mg to about 111 mg per day, about 91 mg to about 110 mg per day, about 92 mg to about 109 mg per day, about 93 mg to about 108 mg per day, about 94 mg to about 107 mg per day, about 95 mg to about 106 mg per day, about 96 mg to about 105 mg per day, about 97 mg to about 104 mg per day, about 98 mg to about 103 mg per day, about 99 mg to about 102 mg per day, or about 100 to about 101 mg per day, among others. Exemplary total daily quantities of nifedipine that may be administered to the subject include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, and 200 mg, among others.

Using the compositions and methods described herein, nifedipine may be administered to a subject (e.g., a pregnant human subject) in an amount of about 1,500 mg or less per week. For example, the patient may be administered from about 1 mg to about 1,500 mg of nifedipine per week, such as from about 10 mg to about 1,490 mg per week, about 20 mg to about 1,480 mg per week, about 30 mg to about 1,470 mg per week, about 40 mg to about 1,460 mg per week, about 50 mg to about 1,450 mg per week, about 60 mg to about 1,440 mg per week, about 70 mg to about 1,430 mg per week, about 80 mg to about 1,420 mg per week, about 90 mg to about 1,410 mg per week, about 100 mg to about 1,400 mg per week, about 110 mg to about 1,390 mg per week, about 120 mg to about 1,380 mg per week, about 130 mg to about 1,370 mg per week, about 140 mg to about 1,360 mg per week, about 150 mg to about 1,350 mg per week, about 160 mg to about 1,340 mg per week, about 170 mg to about 1,330 mg per week, about 180 mg to about 1,320 mg per week, about 190 mg to about 1,310 mg per week, about 200 mg to about 1,300 mg per week, about 210 mg to about 1,290 mg per week, about 220 mg to about 1,280 mg per week, about 230 mg to about 1,270 mg per week, about 240 mg to about 1,260 mg per week, about 250 mg to about 1,250 mg per week, about 260 mg to about 1,240 mg per week, about 270 mg to about 1,230 mg per week, about 280 mg to about 1,220 mg per week, about 290 mg to about 1,210 mg per week, about 300 mg to about 1,200 mg per week, about 310 mg to about 1,190 mg per week, about 320 mg to about 1,180 mg per week, about 330 mg to about 1,170 mg per week, about 340 mg to about 1,160 mg per week, about 350 mg to about 1,150 mg per week, about 360 mg to about 1,140 mg per week, about 370 mg to about 1,130 mg per week, about 380 mg to about 1,120 mg per week, about 390 mg to about 1,110 mg per week, about 400 mg to about 1,100 mg per week, about 410 mg to about 1,090 mg per week, about 420 mg to about 1,080 mg per week, about 430 mg to about 1,070 mg per week, about 440 mg to about 1,060 mg per week, about 450 mg to about 1,050 mg per week, about 460 mg to about 1,040 mg per week, about 470 mg to about 1,030 mg per week, about 480 mg to about 1,020 mg per week, about 490 mg to about 1,010 mg per week, about 500 mg to about 1,000 mg per week, about 510 mg to about 990 mg per week, about 520 mg to about 980 mg per week, about 530 mg to about 970 mg per week, about 540 mg to about 960 mg per week, about 550 mg to about 950 mg per week, about 560 mg to about 940 mg per week, about 570 mg to about 930 mg per week, about 580 mg to about 920 mg per week, about 590 mg to about 910 mg per week, about 600 mg to about 900 mg per week, about 610 mg to about 890 mg per week, about 620 mg to about 880 mg per week, about 630 mg to about 870 mg per week, about 640 mg to about 860 mg per week, about 650 mg to about 850 mg per week, about 660 mg to about 840 mg per week, about 670 mg to about 830 mg per week, about 680 mg to about 820 mg per week, about 690 mg to about 810 mg per week, about 700 mg to about 800 mg per week, about 710 mg to about 790 mg per week, about 720 mg to about 780 mg per week, about 730 mg to about 770 mg per week, or about 740 mg to about 760 mg per week, among others.

For example, when administered to a subject in combination with a PGF2α receptor antagonist, such as a 1,3-thiazolidine-2-carboxamide compound described herein, the nifedipine that may be administered in an amount of 20 mg per week, 25 mg per week, 30 mg per week, 35 mg per week, 40 mg per week, 45 mg per week, 50 mg per week, 55 mg per week, 60 mg per week, 65 mg per week, 70 mg per week, 75 mg per week, 80 mg per week, 85 mg per week, 90 mg per week, 95 mg per week, 100 mg per week, 105 mg per week, 110 mg per week, 115 mg per week, 120 mg per week, 125 mg per week, 130 mg per week, 135 mg per week, 140 mg per week, 145 mg per week, 150 mg per week, 155 mg per week, 160 mg per week, 165 mg per week, 170 mg per week, 175 mg per week, 180 mg per week, 185 mg per week, 190 mg per week, 195 mg per week, 200 mg per week, 205 mg per week, 210 mg per week, 215 mg per week, 220 mg per week, 225 mg per week, 230 mg per week, 235 mg per week, 240 mg per week, 245 mg per week, 250 mg per week, 255 mg per week, 260 mg per week, 265 mg per week, 270 mg per week, 275 mg per week, 280 mg per week, 285 mg per week, 290 mg per week, 295 mg per week, 300 mg per week, 305 mg per week, 310 mg per week, 315 mg per week, 320 mg per week, 325 mg per week, 330 mg per week, 335 mg per week, 340 mg per week, 345 mg per week, 350 mg per week, 355 mg per week, 360 mg per week, 365 mg per week, 370 mg per week, 375 mg per week, 380 mg per week, 385 mg per week, 390 mg per week, 395 mg per week, 400 mg per week, 405 mg per week, 410 mg per week, 415 mg per week, 420 mg per week, 425 mg per week, 430 mg per week, 435 mg per week, 440 mg per week, 445 mg per week, 450 mg per week, 455 mg per week, 460 mg per week, 465 mg per week, 470 mg per week, 475 mg per week, 480 mg per week, 485 mg per week, 490 mg per week, 495 mg per week, 500 mg per week, 505 mg per week, 510 mg per week, 515 mg per week, 520 mg per week, 525 mg per week, 530 mg per week, 535 mg per week, 540 mg per week, 545 mg per week, 550 mg per week, 555 mg per week, 560 mg per week, 565 mg per week, 570 mg per week, 575 mg per week, 580 mg per week, 585 mg per week, 590 mg per week, 595 mg per week, 600 mg per week, 605 mg per week, 610 mg per week, 615 mg per week, 620 mg per week, 625 mg per week, 630 mg per week, 635 mg per week, 640 mg per week, 645 mg per week, 650 mg per week, 655 mg per week, 660 mg per week, 665 mg per week, 670 mg per week, 675 mg per week, 680 mg per week, 685 mg per week, 690 mg per week, 695 mg per week, 700 mg per week, 705 mg per week, 710 mg per week, 715 mg per week, 720 mg per week, 725 mg per week, 730 mg per week, 735 mg per week, 740 mg per week, 745 mg per week, 750 mg per week, 755 mg per week, 760 mg per week, 765 mg per week, 770 mg per week, 775 mg per week, 780 mg per week, 785 mg per week, 790 mg per week, 795 mg per week, 800 mg per week, 805 mg per week, 810 mg per week, 815 mg per week, 820 mg per week, 825 mg per week, 830 mg per week, 835 mg per week, 840 mg per week, 845 mg per week, 850 mg per week, 855 mg per week, 860 mg per week, 865 mg per week, 870 mg per week, 875 mg per week, 880 mg per week, 885 mg per week, 890 mg per week, 895 mg per week, 900 mg per week, 905 mg per week, 910 mg per week, 915 mg per week, 920 mg per week, 925 mg per week, 930 mg per week, 935 mg per week, 940 mg per week, 945 mg per week, 950 mg per week, 955 mg per week, 960 mg per week, 965 mg per week, 970 mg per week, 975 mg per week, 980 mg per week, 985 mg per week, 990 mg per week, 995 mg per week, 1,000 mg per week, 1,005 mg per week, 1,010 mg per week, 1,015 mg per week, 1,020 mg per week, 1,025 mg per week, 1,030 mg per week, 1,035 mg per week, 1,040 mg per week, 1,045 mg per week, 1,050 mg per week, 1,055 mg per week, 1,060 mg per week, 1,065 mg per week, 1,070 mg per week, 1,075 mg per week, 1,080 mg per week, 1,085 mg per week, 1,090 mg per week, 1,095 mg per week, 1,100 mg per week, 1,105 mg per week, 1,110 mg per week, 1,115 mg per week, 1,120 mg per week, 1,125 mg per week, 1,130 mg per week, 1,135 mg per week, 1,140 mg per week, 1,145 mg per week, 1,150 mg per week, 1,155 mg per week, 1,160 mg per week, 1,165 mg per week, 1,170 mg per week, 1,175 mg per week, 1,180 mg per week, 1,185 mg per week, 1,190 mg per week, 1,195 mg per week, 1,200 mg per week, 1,205 mg per week, 1,210 mg per week, 1,215 mg per week, 1,220 mg per week, 1,225 mg per week, 1,230 mg per week, 1,235 mg per week, 1,240 mg per week, 1,245 mg per week, 1,250 mg per week, 1,255 mg per week, 1,260 mg per week, 1,265 mg per week, 1,270 mg per week, 1,275 mg per week, 1,280 mg per week, 1,285 mg per week, 1,290 mg per week, 1,295 mg per week, 1,300 mg per week, 1,305 mg per week, 1,310 mg per week, 1,315 mg per week, 1,320 mg per week, 1,325 mg per week, 1,330 mg per week, 1,335 mg per week, 1,340 mg per week, 1,345 mg per week, 1,350 mg per week, 1,355 mg per week, 1,360 mg per week, 1,365 mg per week, 1,370 mg per week, 1,375 mg per week, 1,380 mg per week, 1,385 mg per week, 1,390 mg per week, 1,395 mg per week, 900 mg per week, 1,405 mg per week, 1,410 mg per week, 1,415 mg per week, 1,420 mg per week, 1,425 mg per week, 1,430 mg per week, 1,435 mg per week, 1,440 mg per week, 1,445 mg per week, 1,450 mg per week, 1,455 mg per week, 1,460 mg per week, 1,465 mg per week, 1,470 mg per week, 1,475 mg per week, 1,480 mg per week, 1,485 mg per week, 1,490 mg per week, 1,495 mg per week, or 1,500 mg per week.

Using the compositions and methods described herein, nifedipine may be administered to a subject (e.g., a pregnant human subject) in a reduced frequency when administered in combination with a PGF2α receptor antagonist (such as a 1,3-thiazolidine-2-carboxamide compound described herein) relative to the frequency with which the nifedipine would otherwise be administered to the subject if given alone. For example, nifedipine may be administered to a subject (e.g., a pregnant human subject undergoing or at risk of undergoing preterm labor) in more doses per 12 hours, 24 hours, 48 hours, or one week. For instance, the nifedipine may be administered to the subject in from one to ten doses (e.g., 1, 2, 3, 4, 5, 6, 7, 8, 9, or 10 doses) every 12 hours, one to ten doses (e.g., 1, 2, 3, 4, 5, 6, 7, 8, 9, or 10 doses) every 14 hours, one to ten doses (e.g., 1, 2, 3, 4, 5, 6, 7, 8, 9, or 10 doses) every 16 hours, one to ten doses (e.g., 1, 2, 3, 4, 5, 6, 7, 8, 9, or 10 doses) every 18 hours, one to ten doses (e.g., 1, 2, 3, 4, 5, 6, 7, 8, 9, or 10 doses) every 20 hours, one to ten doses (e.g., 1, 2, 3, 4, 5, 6, 7, 8, 9, or 10 doses) every 22 hours, one to ten doses (e.g., 1, 2, 3, 4, 5, 6, 7, 8, 9, or 10 doses) every 24 hours, one to ten doses (e.g., 1, 2, 3, 4, 5, 6, 7, 8, 9, or 10 doses) every 26 hours, one to ten doses (e.g., 1, 2, 3, 4, 5, 6, 7, 8, 9, or 10 doses) every 28 hours, one to ten doses (e.g., 1, 2, 3, 4, 5, 6, 7, 8, 9, or 10 doses) every 30 hours, one to ten doses (e.g., 1, 2, 3, 4, 5, 6, 7, 8, 9, or 10 doses) every 32 hours, one to ten doses (e.g., 1, 2, 3, 4, 5, 6, 7, 8, 9, or 10 doses) every 34 hours, one to ten doses (e.g., 1, 2, 3, 4, 5, 6, 7, 8, 9, or 10 doses) every 36 hours, one to ten doses (e.g., 1, 2, 3, 4, 5, 6, 7, 8, 9, or 10 doses) every 38 hours, one to ten doses (e.g., 1, 2, 3, 4, 5, 6, 7, 8, 9, or 10 doses) every 40 hours, one to ten doses (e.g., 1, 2, 3, 4, 5, 6, 7, 8, 9, or 10 doses) every 42 hours, one to ten doses (e.g., 1, 2, 3, 4, 5, 6, 7, 8, 9, or 10 doses) every 44 hours, one to ten doses (e.g., 1, 2, 3, 4, 5, 6, 7, 8, 9, or 10 doses) every 46 hours, one to ten doses (e.g., 1, 2, 3, 4, 5, 6, 7, 8, 9, or 10 doses) every 48 hours, one to ten doses (e.g., 1, 2, 3, 4, 5, 6, 7, 8, 9, or 10 doses) every 60 hours, one to ten doses (e.g., 1, 2, 3, 4, 5, 6, 7, 8, 9, or 10 doses) every 72 hours, one to ten doses (e.g., 1, 2, 3, 4, 5, 6, 7, 8, 9, or 10 doses) every 84 hours, one to ten doses (e.g., 1, 2, 3, 4, 5, 6, 7, 8, 9, or 10 doses) every 96 hours, one to ten doses (e.g., 1, 2, 3, 4, 5, 6, 7, 8, 9, or 10 doses) every 108 hours, one to ten doses (e.g., 1, 2, 3, 4, 5, 6, 7, 8, 9, or 10 doses) every 120 hours, one to ten doses (e.g., 1, 2, 3, 4, 5, 6, 7, 8, 9, or 10 doses) every 132 hours, one to ten doses (e.g., 1, 2, 3, 4, 5, 6, 7, 8, 9, or 10 doses) every 144 hours, one to ten doses (e.g., 1, 2, 3, 4, 5, 6, 7, 8, 9, or 10 doses) every 156 hours, or one to ten doses (e.g., 1, 2, 3, 4, 5, 6, 7, 8, 9, or 10 doses) every week.

Administration of the nifedipine may continue until the subject exhibits one or more clinical benefits associated with the treatment or prevention of preterm labor. For example, the nifedipine may be administered to the subject until the subject reaches a gestational age of at least about 34 weeks (e.g., a gestational age of from about 34 weeks to about 40 weeks, such as a gestational age of 34 weeks, 35 weeks, 36 weeks, 37 weeks, 38 weeks, 39 weeks, or 40 weeks), or until the subject undergoes delivery. In some embodiments, the nifedipine is administered to the subject until the subject reaches a gestational age of about 37 weeks.

Nifedipine may be given to a subject by way of a variety of routes of administration. In some embodiments, the nifedipine is administered to the subject orally. The nifedipine may be, for example, formulated a tablet, gel cap, powder, liquid solution, or liquid suspension.

Further examples of nifedipine dosage amounts, routes of administration, and frequencies of administration that may be used in conjunction with the compositions and methods of the disclosure are shown in Table 2, below.

TABLE 2

Exemplary nifedipine dosage amounts, routes of administration, and frequencies of administration of the present disclosure

| Quantity of Nifedipine per Dose | Route of Administration | Frequency of Administration |
|---|---|---|
| 10 mg | Oral | Once every 10-60 minutes (e.g., once every 10 minutes, once every 15 minutes, once every 20 minutes, once every 25 minutes, once every 30 minutes, once every 35 minutes, once every 40 minutes, once every 45 minutes, once every 50 minutes, once every 55 minutes, or once every 60 minutes), for example, to a maximum of 40 mg during the first hour of treatment |
| 10 mg | Oral | Once every 4-6 hours (e.g., once every 4 hours, once every 5 hours, or once every 6 hours) |
| 10 mg | Oral | Once every 6-8 hours (e.g., once every 6 hours, once every 7 hours, or once every 8 hours) |
| 10 mg | Oral | Once every 6-12 hours (e.g., once every 6 hours, once every 7 hours, once every 8 hours, once every 9 hours, once every 10 hours, once every 11 hours, or once every 12 hours) |
| 10 mg | Oral | Once every 8-12 hours (e.g., once every 8 hours, once every 9 hours, once every 10 hours, once every 11 hours, or once every 12 hours) |
| 20 mg | Oral | Once every 4-6 hours (e.g., once every 4 hours, once every 5 hours, or once every 6 hours) |
| 20 mg | Oral | Once every 6-8 hours (e.g., once every 6 hours, once every 7 hours, or once every 8 hours) |
| 20 mg | Oral | Once every 6-12 hours (e.g., once every 6 hours, once every 7 hours, once every 8 hours, once every 9 hours, once every 10 hours, once every 11 hours, or once every 12 hours) |
| 20 mg | Oral | Once every 8-12 hours (e.g., once every 8 hours, once every 9 hours, once every 10 hours, once every 11 hours, or once every 12 hours) |
| 30 mg | Oral | Once every 4-6 hours (e.g., once every 4 hours, once every 5 hours, or once every 6 hours) |
| 30 mg | Oral | Once every 6-8 hours (e.g., once every 6 hours, once every 7 hours, or once every 8 hours) |
| 30 mg | Oral | Once every 6-12 hours (e.g., once every 6 hours, once every 7 hours, once every 8 hours, once every 9 hours, once every 10 hours, once every 11 hours, or once every 12 hours) |
| 30 mg | Oral | Once every 8-12 hours (e.g., once every 8 hours, once every 9 hours, once every 10 hours, once every 11 hours, or once every 12 hours) |
| 5 mg | Sublingual | Once every 15 minutes (e.g., to a maximum of 40 mg during the first two hours of treatment) |
| 10 mg | Sublingual | Once every 15 minutes (e.g., to a maximum of 40 mg during the first hour of treatment) |
| 10 mg | Sublingual | Once every 20 minutes (e.g., to a maximum of 40 mg during the first hour of treatment) |
| 10 mg | Sublingual | Once every 30 minutes |

PGF2α Receptor Antagonists

Using the compositions and methods described herein, a PGF2α receptor antagonist (such as the compound of any one of formulas (I) through (VIII), for example, compound (1), compound (2), or compound (3), among other PGF2α receptor antagonists described herein) may be administered to a subject (e.g., a pregnant human subject) so as to treat or prevent preterm labor. The PGF2α receptor antagonist may be administered to the subject in one or more doses per 12 hours, 24 hours, 48 hours, or one week. For instance, the PGF2α receptor antagonist may be administered to the subject in from one to ten doses (e.g., 1, 2, 3, 4, 5, 6, 7, 8, 9, or 10 doses) every 12 hours, one to ten doses (e.g., 1, 2, 3, 4, 5, 6, 7, 8, 9, or 10 doses) every 14 hours, one to ten doses (e.g., 1, 2, 3, 4, 5, 6, 7, 8, 9, or 10 doses) every 16 hours, one to ten doses (e.g., 1, 2, 3, 4, 5, 6, 7, 8, 9, or 10 doses) every 18 hours, one to ten doses (e.g., 1, 2, 3, 4, 5, 6, 7, 8, 9, or 10 doses) every 20 hours, one to ten doses (e.g., 1, 2, 3, 4, 5, 6, 7, 8, 9, or 10 doses) every 22 hours, one to ten doses (e.g., 1, 2, 3, 4, 5, 6, 7, 8, 9, or 10 doses) every 24 hours, one to ten doses (e.g., 1, 2, 3, 4, 5, 6, 7, 8, 9, or 10 doses) every 26 hours, one to ten doses (e.g., 1, 2, 3, 4, 5, 6, 7, 8, 9, or 10 doses) every 28 hours, one to ten doses (e.g., 1, 2, 3, 4, 5, 6, 7, 8, 9, or 10 doses) every 30 hours, one to ten doses (e.g., 1, 2, 3, 4, 5, 6, 7, 8, 9, or 10 doses) every 32 hours, one to ten doses (e.g., 1, 2, 3, 4, 5, 6, 7, 8, 9, or 10 doses) every 34 hours, one to ten doses (e.g., 1, 2, 3, 4, 5, 6, 7, 8, 9, or 10 doses) every 36 hours, one to ten doses (e.g., 1, 2, 3, 4, 5, 6, 7, 8, 9, or 10 doses) every 38 hours, one to ten doses (e.g., 1, 2, 3, 4, 5, 6, 7, 8, 9, or 10 doses) every 40 hours, one to ten doses (e.g., 1, 2, 3, 4, 5, 6, 7, 8, 9, or 10 doses) every 42 hours, one to ten doses (e.g., 1, 2, 3, 4, 5, 6, 7, 8, 9, or 10 doses) every 44 hours, one to ten doses (e.g., 1, 2, 3, 4, 5, 6, 7, 8, 9, or 10 doses) every 46 hours, one to ten doses (e.g., 1, 2, 3, 4, 5, 6, 7, 8, 9, or 10 doses) every 48 hours, one to ten doses (e.g., 1, 2, 3, 4, 5, 6, 7, 8, 9, or 10 doses) every 60 hours, one to ten doses (e.g., 1, 2, 3, 4, 5, 6, 7, 8, 9, or 10 doses) every 72 hours, one to ten doses (e.g., 1, 2, 3, 4, 5, 6, 7, 8, 9, or 10 doses) every 84 hours, one to ten doses (e.g., 1, 2, 3, 4, 5, 6, 7, 8, 9, or 10 doses) every 96 hours, one to ten doses (e.g., 1, 2, 3, 4, 5, 6, 7, 8, 9, or 10 doses) every 108 hours, one to ten doses (e.g., 1, 2, 3, 4, 5, 6, 7, 8, 9, or 10 doses) every 120 hours, one to ten doses (e.g., 1, 2, 3, 4, 5, 6, 7, 8, 9, or 10 doses) every 132 hours, one to ten doses (e.g., 1, 2, 3, 4, 5, 6, 7, 8, 9, or 10 doses) every 144 hours, one to ten doses (e.g., 1, 2, 3, 4, 5, 6, 7, 8, 9, or 10 doses) every 156 hours, or one to ten doses (e.g., 1, 2, 3, 4, 5, 6, 7, 8, 9, or 10 doses) every week.

The PGF2α receptor antagonists described herein, such as the compound of any one of formulas (I) through (VIII) (for example, compound (1), compound (2), or compound (3), among other 1,3-thiazolidine-2-carboxamides described herein), are particularly well suited for daily dosing to a subject undergoing or at risk of undergoing preterm labor. For instance, the PGF2α receptor antagonist may be administered to the subject in from one to six doses per day. For example, the PGF2α receptor antagonists described herein may be administered to the subject once every 4 two 12 hours, such as once every 4 hours, once every 5 hours, once every 6 hours, once every 7 hours, once every 8 hours, once every 9 hours, once every 10 hours, once every 11 hours, or once every 12 hours. As a particular example, the PGF2α receptor antagonist may be administered to the subject once or twice daily.

The PGF2α receptor antagonist (for example, compound (1), compound (2), or compound (3), among other PGF2α receptor antagonists described herein) may be administered to the subject in an amount, for example, of from about 100 mg to about 3,000 mg per dose, such as in an amount of 100 mg per dose, 150 mg per dose, 200 mg per dose, 250 mg per dose, 300 mg per dose, 350 mg per dose, 400 mg per dose, 450 mg per dose, 500 mg per dose, 550 mg per dose, 600 mg per dose, 650 mg per dose, 700 mg per dose, 750 mg per dose, 800 mg per dose, 850 mg per dose, 900 mg per dose, 950 mg per dose, 1,000 mg per dose, 1,050 mg per dose, 1,100 mg per dose, 1,150 mg per dose, 1,200 mg per dose, 1,250 mg per dose, 1,300 mg per dose, 1,350 mg per dose, 1,400 mg per dose, 1,450 mg per dose, 1,500 mg per dose, 1,550 mg per dose, 1,600 mg per dose, 1,650 mg per dose, 1,700 mg per dose, 1,750 mg per dose, 1,800 mg per dose, 1,850 mg per dose, 1,900 mg per dose, 1,950 mg per dose, 2,000 mg per dose, 2,050 mg per dose, 2,100 mg per dose, 2,150 mg per dose, 2,200 mg per dose, 2,250 mg per dose, 2,300 mg per dose, 2,350 mg per dose, 2,400 mg per dose, 2,450 mg per dose, 2,500 mg per dose, 2,550 mg per dose, 2,600 mg per dose, 2,650 mg per dose, 2,700 mg per dose, 2,750 mg per dose, 2,800 mg per dose, 2,850 mg per dose, 2,900 mg per dose, 2,950 mg per dose, or 3,000 mg per dose. The PGF2α receptor antagonist may be administered to the subject in an amount of from about 500 mg to about 2,500 mg per dose, such as in an amount of 500 mg per dose, 550 mg per dose, 600 mg per dose, 650 mg per dose, 700 mg per dose, 750 mg per dose, 800 mg per dose, 850 mg per dose, 900 mg per dose, 950 mg per dose, 1,000 mg per dose, 1,050 mg per dose, 1,100 mg per dose, 1,150 mg per dose, 1,200 mg per dose, 1,250 mg per dose, 1,300 mg per dose, 1,350 mg per dose, 1,400 mg per dose, 1,450 mg per dose, 1,500 mg per dose, 1,550 mg per dose, 1,600 mg per dose, 1,650 mg per dose, 1,700 mg per dose, 1,750 mg per dose, 1,800 mg per dose, 1,850 mg per dose, 1,900 mg per dose, 1,950 mg per dose, 2,000 mg per dose, 2,050 mg per dose, 2,100 mg per dose, 2,150 mg per dose, 2,200 mg per dose, 2,250 mg per dose, 2,300 mg per dose, 2,350 mg per dose, 2,400 mg per dose, 2,450 mg per dose, or 2,500 mg per dose. In some embodiments, the PGF2α receptor antagonist is administered to the subject in an amount of from about 750 mg to about 2,250 mg per dose, such as in an amount of 750 mg per dose, 800 mg per dose, 850 mg per dose, 900 mg per dose, 950 mg per dose, 1,000 mg per dose, 1,050 mg per dose, 1,100 mg per dose, 1,150 mg per dose, 1,200 mg per dose, 1,250 mg per dose, 1,300 mg per dose, 1,350 mg per dose, 1,400 mg per dose, 1,450 mg per dose, 1,500 mg per dose, 1,550 mg per dose, 1,600 mg per dose, 1,650 mg per dose, 1,700 mg per dose, 1,750 mg per dose, 1,800 mg per dose, 1,850 mg per dose, 1,900 mg per dose, 1,950 mg per dose, 2,000 mg per dose, 2,050 mg per dose, 2,100 mg per dose, 2,150 mg per dose, 2,200 mg per dose, or 2,250 mg per dose. For example, the PGF2α receptor antagonist may be administered to the subject in an amount of from about 1,000 mg to about 2,000 mg per dose, such as in an amount of 1,000 mg per dose, 1,050 mg per dose, 1,100 mg per dose, 1,150 mg per dose, 1,200 mg per dose, 1,250 mg per dose, 1,300 mg per dose, 1,350 mg per dose, 1,400 mg per dose, 1,450 mg per dose, 1,500 mg per dose, 1,550 mg per dose, 1,600 mg per dose, 1,650 mg per dose, 1,700 mg per dose, 1,750 mg per dose, 1,800 mg per dose, 1,850 mg per dose, 1,900 mg per dose, 1,950 mg per dose, or 2,000 mg per dose.

Administration of the PGF2α receptor antagonist (for example, compound (1), compound (2), or compound (3), among other PGF2α receptor antagonists described herein) may continue until the subject exhibits one or more clinical benefits associated with the treatment or prevention of preterm labor. For example, the PGF2α receptor antagonist may be administered to the subject until the subject reaches a gestational age of at least about 34 weeks (e.g., a gestational age of from about 34 weeks to about 40 weeks, such as a gestational age of 34 weeks, 35 weeks, 36 weeks, 37 weeks, 38 weeks, 39 weeks, or 40 weeks), or until the subject undergoes delivery. In some embodiments, the PGF2α receptor antagonist is administered to the subject until the subject reaches a gestational age of about 37 weeks.

In some embodiments, the PGF2α receptor antagonist (for example, compound (1), compound (2), or compound (3), among other PGF2α receptor antagonists described herein) is administered to the subject orally. The PGF2α receptor antagonist may be, for example, formulated a tablet, gel cap, powder, liquid solution, or liquid suspension.

Pharmaceutical Compositions

The tocolytic agents (e.g., nifedipine and the PGF2α receptor antagonists) suitable for use with the compositions and methods described herein can be formulated into pharmaceutical compositions for administration to a patient, such as a pregnant human patient, in a biologically compatible form suitable for administration in vivo. A pharmaceutical composition containing, for example, nifedipine or a PGF2α receptor antagonist, such as a PGF2α receptor antagonist described herein (e.g., (3S)-3-({[(2S)-3-(biphenyl-4-ylsulfonyl)-1,3-thiazolidin-2-yl]carbonyl}-amino)-3-(4-fluorophenyl)propyl L-valinate or a pharmaceutically acceptable salt thereof, such as the chloride salt thereof), may additionally contain a suitable diluent, carrier, or excipient. PGF2α receptor antagonists can be administered to a patient, for example, orally or by intravenous injection. Under ordinary conditions of storage and use, a pharmaceutical composition may contain a preservative, e.g., to prevent the growth of microorganisms.

Procedures and ingredients for the selection and preparation of suitable formulations are described, for example, in Remington: The Science and Practice of Pharmacy (2012, $22^{nd}$ ed.) and in The United States Pharmacopeia: The National Formulary (2015, USP 38 NF 33).

Pharmaceutical compositions may include sterile aqueous solutions, dispersions, or powders, e.g., for the extemporaneous preparation of sterile solutions or dispersions. In all cases the form may be sterilized using techniques known in the art and may be fluidized to the extent that may be easily administered to a patient in need of treatment.

A pharmaceutical composition may be administered to a patient, e.g., a human patient, alone or in combination with one or more pharmaceutically acceptable carriers, e.g., as described herein, the proportion of which may be determined by the solubility of the compound, the chemical nature of the compound, and/or the chosen route of administration, among other factors.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regards as their invention.

Example One. Administration of a PGF2α Receptor Antagonist in Combination with Nifedipine Results in an Elevated Plasma Concentration of Nifedipine Objectives The objectives of this study included to investigate the safety, tolerability, and pharmacokinetic parameters of compound (2) when administered to human female subjects in combination with magnesium sulfate, betamethasone, and the tocolytic agents, atosiban and nifedipine.

Study Population

Healthy women aged between 18 and 45 years with a body mass index of 18.0 to 30.0 $kg/m^2$ were included in these investigations. Subjects were screened 55 days before the first drug administration and had to be healthy according to medical history, physical examinations, blood pressure tests, electrocardiogram results and laboratory assessment of blood and urine. Subjects with current/recurrent disease, including psychiatric illness, cardiac conditions, clinically relevant laboratory abnormalities, and history of any condition precluding administration of $MgSO_4$, atosiban, nifedipine or betamethasone, were excluded.

Study Design

An open-label, randomized, three-period crossover study was conducted, assessing co-administration of single doses of compound (2) (1,100 mg) and $MgSO_4$ (15.5 g). Additionally, an open-label, single-sequence crossover study was performed, assessing the interactions of compound (2) (1,000 mg per day) at steady-state when co-administered with single doses of atosiban (60.75 mg), nifedipine (20 mg), and betamethasone (12 mg). Both studies enrolled 12 healthy, non-pregnant women of reproductive age. All women were hospitalized throughout the clinical phase of the 14-day study with atosiban, nifedipine, and betamethasone. During the $MgSO_4$ study, women stayed in the clinic from Day −1 to Day 4 of each period. Safety and pharmacokinetics were assessed in accordance with European and United States clinical drug-interaction guidelines. Additional electrocardiogram and neurological examinations were performed assessing safety following $MgSO_4$ administration.

This study was performed at Croydon University Hospital, Croydon, UK. The study protocol (EudraCT: 2016-001958-18) was reviewed and approved by a National Health Service (NHS) Research Ethics Committee (South Central-Berkshire B, UK) and the Medicines and Healthcare products Regulatory Authority (MHRA). The study was conducted according to the ethical principles enshrined in UK law, the Declaration of Helsinki and Good Clinical Practice guidelines. All subjects were informed of the purpose of the study and signed voluntary consent forms before being enrolled. The study was performed in two parts, briefly: (A) compound (2) or $MgSO_4$ administered alone in a crossover design followed by compound (2) co-administered with $MgSO_4$; and (B) atosiban, nifedipine, and betamethasone given sequentially, followed by compound (2) alone, then sequential co-administration of compound (2) with each of the foregoing tocolytic drugs.

Part A

One cohort of 12 subjects was admitted to the study unit on day −1, period 1. On day 1, subjects were randomized to receive either a single oral dose of compound (2) (1,100 mg) or an intravenous treatment course of $MgSO_4$. Subjects were discharged on day 3, and had a minimum washout period of 7 days before returning to the unit on day −1, period 2. On day 1, subjects were crossed over and received the alternate treatment to that in period 1. Subjects were discharged on day 3, and after washout returned on day −1, period 3. On day 1, all subjects received compound (2) co-administered with $MgSO_4$. Outpatient visits occurred on days 4 and 5 followed by a final visit 7 days (±1 day) later. Venous blood samples used in pharmacokinetic analyses were taken pre-dose then 0.25, 0.5, 0.75, 1, 1.5, 2, 3, 4, 6, 8, 12, 16 and 20 hours post dose on day 1 of each treatment period. Single samples for pharmacokinetic analysis were also drawn on days 2, 3, 4 and 5 of each treatment period.

Part B

One cohort of 12 subjects received atosiban, nifedipine, betamethasone and compound (2) sequentially. Once at steady state, compound (2) was sequentially co-administered with each of the other tocolytic drugs. Subjects were admitted to the study unit on day −1. On day 1, each subject received a single intravenous treatment course of atosiban. On day 2, a single oral dose of 20 mg nifedipine was administered, followed by a single intramuscular injection of betamethasone on day 3. From days 4 to 9, oral doses of compound (2) (1,000 mg) were administered until reaching steady state. On days 1, 2 and 3, pharmacokinetic samples were taken pre-dose, and then again at 0.25, 0.5, 0.75, 1, 1.5, 2, 3, 4, 6, 8, 10, 12, 16 and 20 hours after doses of atosiban, nifedipine, and betamethasone, respectively. Two additional samples were taken at 24 and 48 hours post dose to determine betamethasone concentration, due to the longer half-life of this drug. Pharmacokinetic sampling also occurred before compound (2) administration on days 4, 5, 6, 7, 8 and 9, with an additional 0.25 hour post-dose sample taken on day 9 to determine concentration of compound (2) and its metabolite, compound (1). On days 10, 11 and 12, compound (2) was co-administered with atosiban, nifedipine, and betamethasone, respectively. Pharmacokinetic samples were obtained at the times stated above on days 10, 11 and 12, and additional betamethasone samples were obtained 24 and 48 hours post-dose. Subjects were discharged on day 14 and returned for a follow-up visit on day 21.

Pharmacokinetic Analysis

Plasma samples used to determine drug concentration were analyzed by SGS (SGS CEPHAC, France) using a validated methods. Non-compartmental analysis was used to estimate pharmacokinetic parameters and pharmacokinetic modeling was used to access time-dependent pharmacokinetics. The following pharmacokinetic parameters were estimated for all drugs: maximal and minimal plasma concentration ($C_{max}$ and $C_{min}$, respectively); time at which $C_{max}$ occurred ($t_{max}$), termination elimination rate constant ($\lambda z$); terminal elimination of half-life ($t_{1/2}$); mean residence time (MRT); area under the plasma concentration curve from administration to last measured time point ($AUC_{0-last}$); area under the plasma concentration-time curve from time 0 extrapolated to infinite time ($AUC_{0-\infty}$); area under the plasma concentration curve from administration to 24 hours ($AUC_{0-24h}$); apparent total plasma clearance (CL); volume of distribution (Vdz). Values of $AUC_{0-24h}$, $AUC_{0-last}$ and $AUC_{0-\infty}$ were calculated using the linear/log trapezoidal method, applying the linear trapezoidal rule up to $C_{max}$ and the log trapezoidal rule for the remainder of the curve. Other pharmacokinetic parameters were calculated according to standard equations.

Statistical Analysis

Study parameters were summarized using descriptive statistics and compared values obtained upon administration of compound (2) or other drugs alone against values obtained upon administration of combination regimens.

Pharmacokinetic interaction assessments were performed on logarithmically transformed $AUC_{0-24}$, $AUC_{0-\infty}$ and $C_{max}$ values using ANOVA models with fixed effects for sequence (Part A only), period, and treatment and a random term for subject within sequence. The 90% confidence intervals (90% CI) for the geometric mean ratio of $AUC_{0-24}$, $AUC_{0-\infty}$ and $C_{max}$ were constructed, comparing treatments administered alone versus combination treatments.

Absence of pharmacokinetic interaction was concluded if the 90% CI of the ratio $\mu_{combined}/\mu_{single}$ was fully contained within the acceptance range for AUC and $C_{max}$ (80%, 125%). Differences in $t_{max}$ were explored by computing the Hodges-Lehmann estimate and the corresponding 90% CI according to Tukey using the approximate method. The Wilcoxon signed rank test was used to test differences in $t_{max}$. Unrecorded values were treated as missing.

Results

Subject Disposition

In total, 25 subjects were screened and randomized. In Part A, each of 6 subjects was treated with $MgSO_4$ and compound (2) or compound (2)/$MgSO_4$ alone, followed by Period 3, which featured combined treatment. Two subjects discontinued during Period 1 and one subject was withdrawn during Period 2. In Part B, 13 subjects started sequentially administered atosiban, nifedipine, betamethasone, and compound (2) alone, and then compound (2) was co-administered with each of these drugs. One subject who had adverse events after atosiban treatment on day 1 was replaced, 12 subjects completed Part B. The mean age of all subjects in Part A was 32 years and 29 for Part B.

Pharmacokinetic Results

Compound (2) was readily transformed into its stable, pharmacologically-active metabolite, compound (1): mean compound (2) peak concentrations and $AUC_{0-\infty}$ were between 133-246 times and 771-1163 times lower than those of compound (1).

Part A: Evaluation of Pharmacokinetic Parameters of Compound (1) and Total Mg

Mean $C_{max}$ and $t_{max}$ of total Mg concentrations were similar for $MgSO_4$ alone and $MgSO_4$ plus compound (2). All AUCs were slightly lower after co-administration of compound (2) and $MgSO_4$. One subject was excluded from this analysis due to an outlying $t_{1/2}$ value that was roughly 10-fold higher than the mean $t_{1/2}$.

Mean±SD compound (1) $C_{max}$ was lower during $MgSO_4$ infusion than after compound (2) alone. This was mainly due to an outlying high compound (1) $C_{max}$ value in one subject during administration of compound (2) alone. Furthermore, compound (1) $t_{max}$ occurred slightly later when compound (2) was co-administered with $MgSO_4$ than when compound (2) and $MgSO_4$ were administered separately. Mean $t_{1/2}$ and MRT for compound (1) were nearly identical regardless of $MgSO_4$ infusion, leading to a small decrease in $AUC_{0-24}$ during co-administration compared with administration of compound (2) alone; $AUC_{0-t}$ or $AUC_{0-\infty}$ were unchanged.

Part A: Evaluation of Mutual Pharmacokinetic Interaction Between Total Mg and Compound (2)

Figure 2:
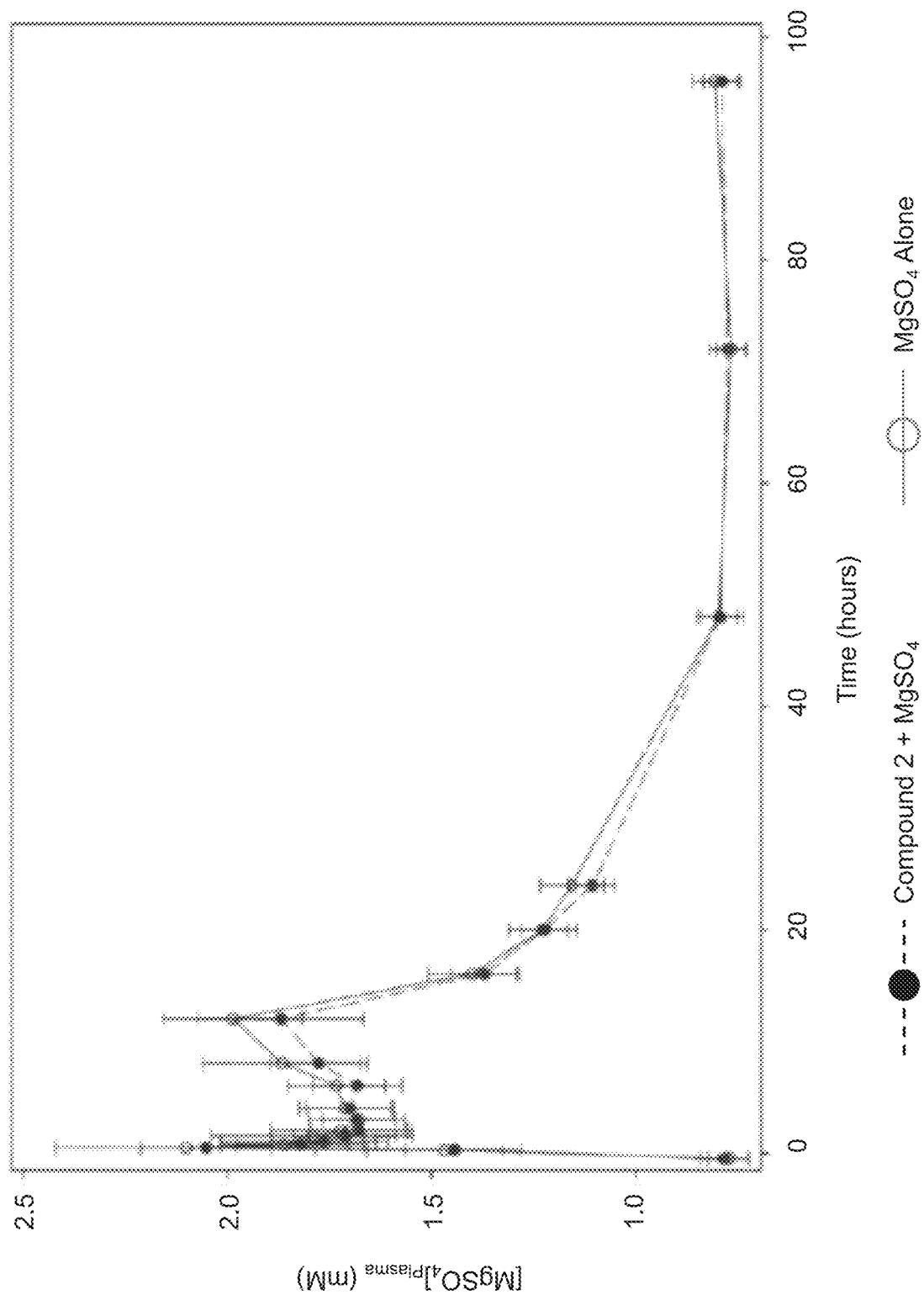
FIG. 2 is a graph showing the mean plasma concentration of magnesium sulfate, when administered alone (solid line, open circles) or in combination with compound (2) (dashed line, closed circles) as a function of time following administration to human female subjects.
Figure 3:
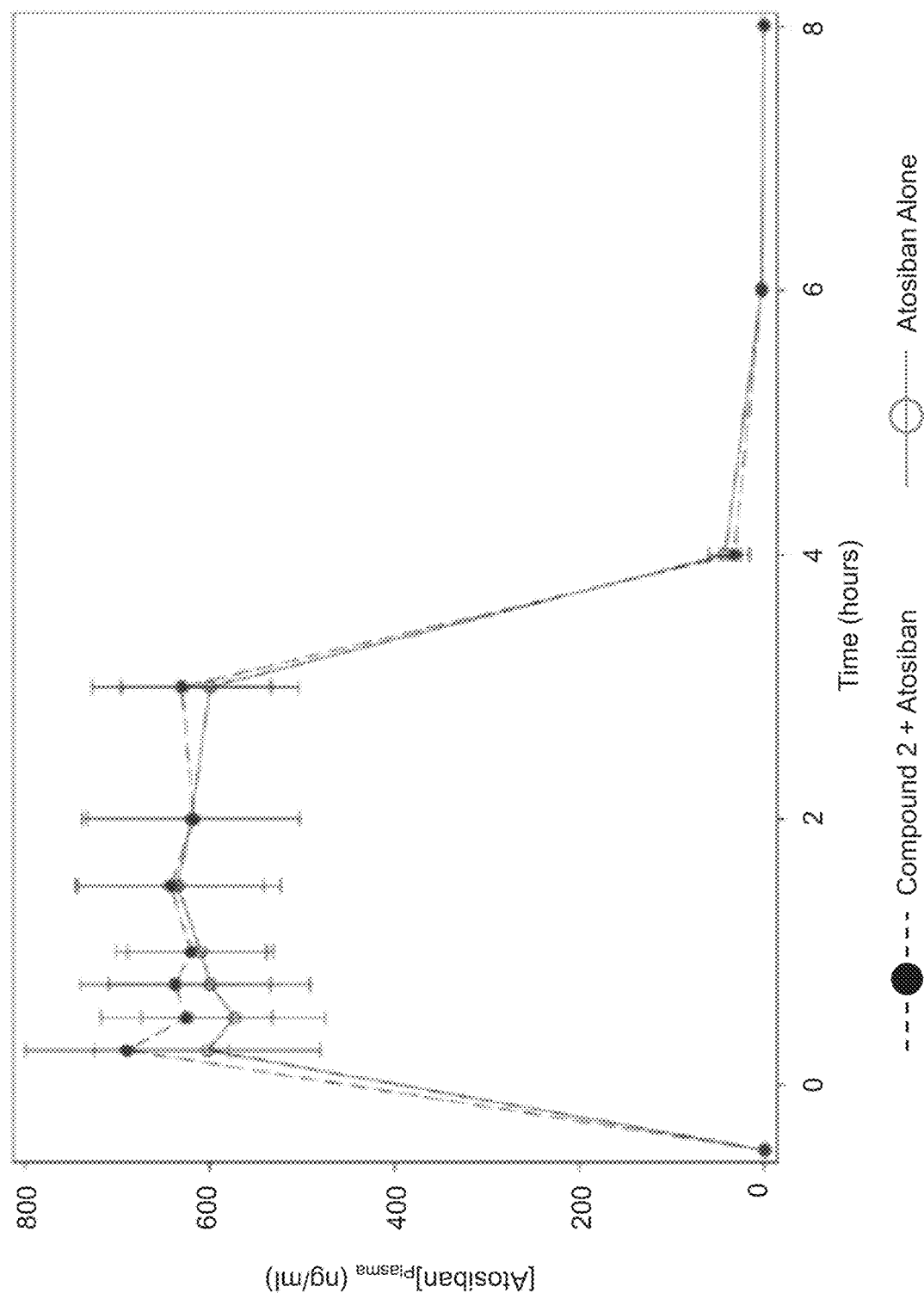
FIG. 3 is a graph showing the mean plasma concentration of atosiban, when administered alone (solid line, open circles) or in combination with compound (2) (dashed line, closed circles) as a function of time following administration to human female subjects.
Figure 4:
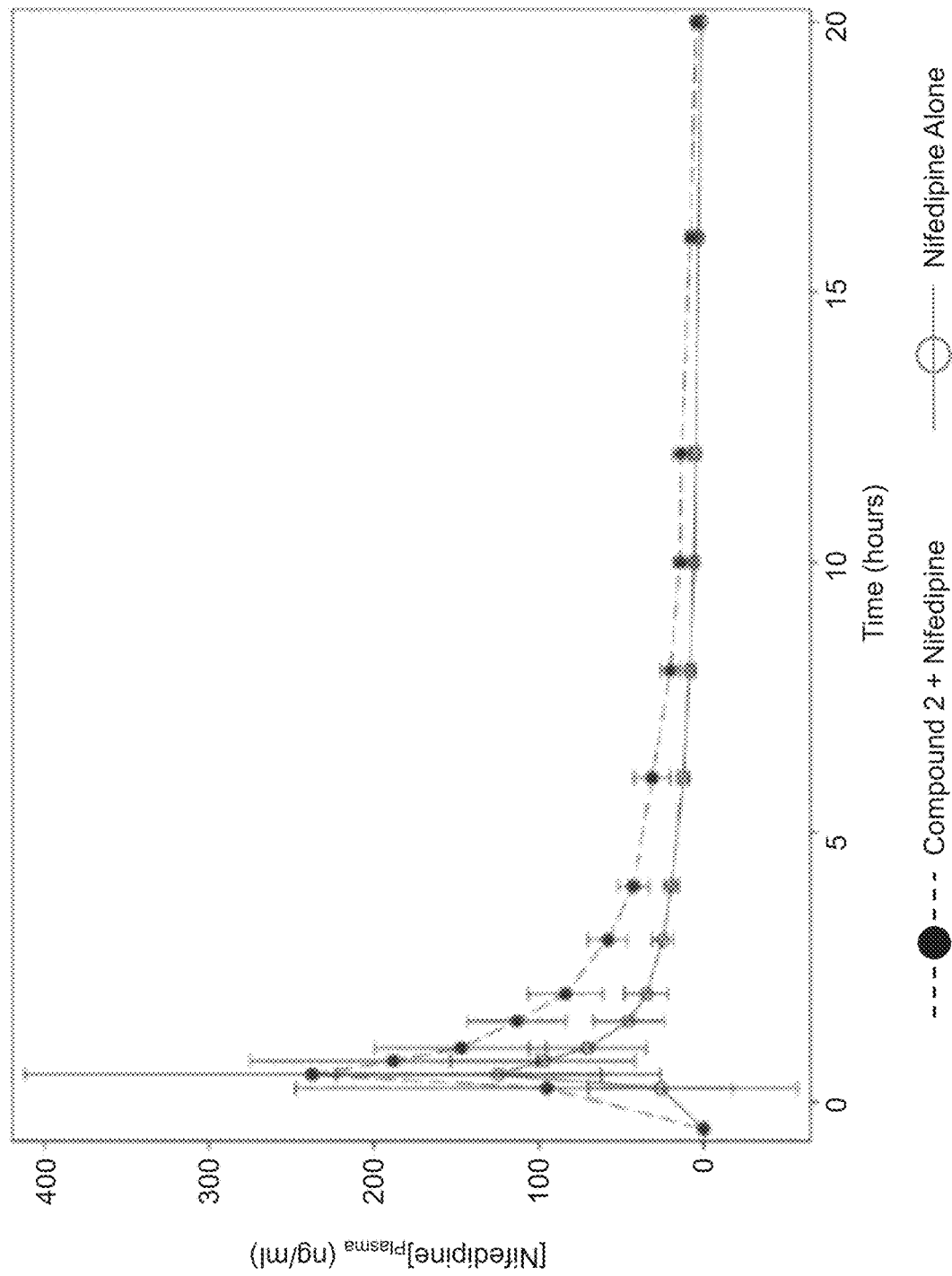
FIG. 4 is a graph showing the mean plasma concentration of nifedipine, when administered alone (solid line, open circles) or in combination with compound (2) (dashed line, closed circles) as a function of time following administration to human female subjects.
Figure 5:
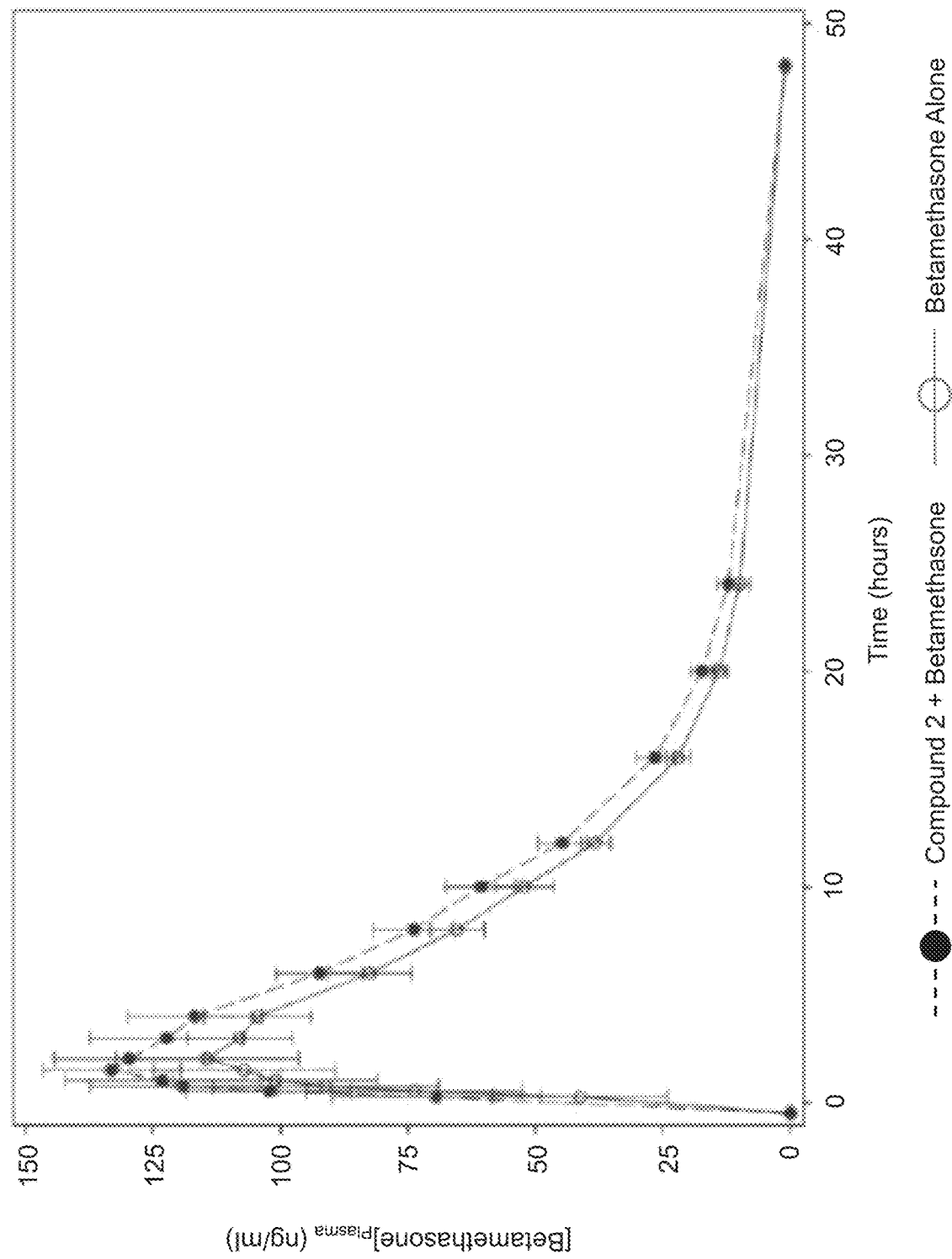
FIG. 5 is a graph showing the mean plasma concentration of betamethasone, when administered alone (solid line, open circles) or in combination with compound (2) (dashed line, closed circles) as a function of time following administration to human female subjects.
Figure 6:
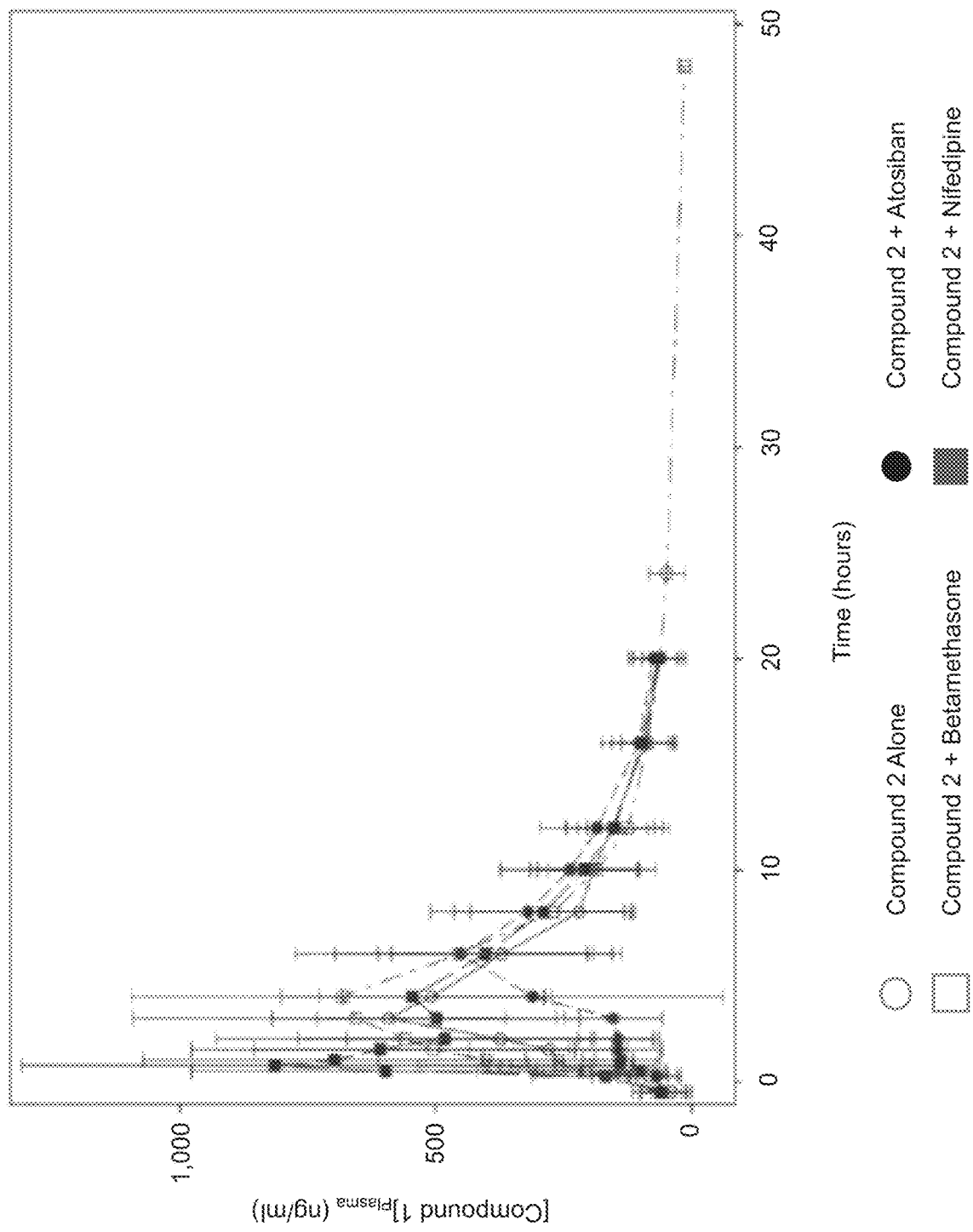
FIG. 6 is a graph showing the mean plasma concentration of compound (1) resulting from administration of compound (2) alone (open circles) or from administration of compound (2) in combination with atosiban (closed circles), nifedipine (closed squares), or betamethasone (open squares) as a function of time following administration to human female subjects.

For total Mg, administration of compound (2) induced no effects on the timing or extent of exposure (FIG. 2).

For compound (1), linear mixed model calculations showed all interaction estimates to be close to 1. Although some confidence ranges exceeded the bioequivalence limits of 0.8 to 1.25, there was no interaction of clinical significance (FIG. 1). There was no effect on $t_{max}$.

Part B: Evaluation of Pharmacokinetic Parameters of Compound (1), and Those of Atosiban, Nifedipine, and Betamethasone with and without Compound (2)

Peak atosiban plasma concentration was achieved 0.25 hours following co-administration with compound (2) compared with 1.5 hours when atosiban was administered alone. Concentration curves were otherwise similar for the two treatments. $C_{max}$ and all AUCs were similar, albeit slightly higher in the co-administration phase. All other pharmacokinetic parameters were also comparable.

Co-administration of compound (2) and nifedipine resulted in ~2-fold increases in mean nifedipine $C_{max}$ and AUC, and ~2 fold decreases in CL/F and Vz/F. Plasma elimination (t1/2, MRT) remained similar.

Betamethasone plasma concentrations increased more rapidly when co-administered with compound (2) than with betamethasone alone. Slightly increased mean $C_{max}$ and AUC values, were also observed. All other pharmacokinetic parameters remained generally comparable.

Compound (1) approached steady state by day 7, so pharmacokinetic parameters could be reliably estimated when compound (2) was co-administered with the other tocolytic drugs. Compound (2) plus atosiban induced a decrease in compound (1) $C_{max}$ and AUC, and an increase in CL/F. Compound (1) $t_{max}$ was longer than that observed upon administration of compound (2) alone, just beyond the duration of atosiban infusion. Administration of compound (2) plus nifedipine resulted in increases of 37% and 26% in compound (1) $C_{max}$ and AUC, respectively. Correspondingly, CL/F was decreased, as was $t_{max}$. Co-administration of compound (2) with betamethasone resulted in increases in compound (1) $C_{max}$ and AUC (35% and 15%, respectively), a decrease in CL/F, an increase in $t_{max}$, and 1.7 to 2-fold increases in MRT and $t_{1/2}$.

Part B: Evaluation of Mutual Pharmacokinetic Interactions Between Compound (2)/Compound (1) and Co-Administered Drugs For atosiban, the 90% CIs around the point estimates of $C_{max}$ and AUCs were fully included in the 0.8 to 1.25 bioequivalence range. Furthermore, no significant $t_{max}$ difference between atosiban alone and with compound (2) was observed in the paired analysis.

Of all the co-administered drugs, nifedipine pharmacokinetics were most strongly affected by compound (2) co-administration; mean $C_{max}$ and AUC values increased by 131-137% compared with nifedipine alone, $t_{max}$ remained unaffected.

Compound (2) co-administered with betamethasone resulted in increases in betamethasone $C_{max}$ and AUCs within or close to bioequivalence limits and significantly shorter $t_{max}$ than with betamethasone alone.

Compound (2) with atosiban led to reductions in compound (1) $C_{max}$ (−28%) and $AUC_{0-24}$ (−21%), respectively. Atosiban also significantly delayed compound (1) $t_{max}$ by an estimated 3 hours (90% CI: 2.050 to 3.000 h; p<0.0001). Co-administration of compound (2) and nifedipine or betamethasone led to somewhat increased compound (1) $C_{max}$ (+30%) and $AUC_{0-24}$ (+15 to 24%) values. Changes in compound (1) $t_{max}$ were not significant. Overall, while compound (1) values were outside of bioequivalence ranges, these modifications remained minor and were considered not to be of clinical significance.

The above pharmacokinetic results obtained from Part B of this investigation are reported graphically in FIGS. 3-6.

Conclusions

All drugs, alone or in combination, were well tolerated and did not give rise to any safety concerns. There were no relevant mutual pharmacokinetic interactions between compound (2) and $MgSO_4$. Compound (2) administration had no effect on atosiban exposure. However, atosiban slightly reduced exposure to compound (1), the pharmacologically active metabolite of the prodrug compound (2) (peak concentration ($C_{max}$) −28%, point estimate of the ratio of geometric means (PE) 0.719, 90% confidence interval (CI 90%) 0.607-0.852; Area-Under-the-Curve (AUC) −21%, PE 0.786, CI 90% 0.710-0.870). Compound (2) co-administered with betamethasone slightly increased betamethasone exposure (Cmax +18%, PE 1.179, CI 90% 1.112-1.250; AUC +27%, PE 1.266, CI 90% 1.214-1.319) and compound (1) exposure (Cmax +30%, PE 1.297, CI 90% 1.132-1.487; AUC +15%, PE 1.148, CI 90% 1.032-1.276). These changes were not considered clinically relevant.

Compound (2) co-administered with nifedipine slightly increased compound (1) exposure (Cmax +30%, PE 1.291, CI 90% 1.066-1.565; AUC +24%, PE 1.244, CI 90% 1.114-1.389). Surprisingly, co-administration of compound (2) with nifedipine resulted in a marked increase in nifedipine exposure (Cmax +133%, PE 2.333, CI 90% 1.406-3.872; AUC +131%, PE 2.314, CI 90% 2.035-2.630). In view of the unexpected drug-drug interaction with compound (2), nifedipine doses can be reduced when administered in combination with compound (2) relative to doses that would be used if nifedipine were to be administered alone.

Example Two. Use of Nifedipine and a PGF2α Receptor Antagonist for the Treatment or Prevention of Preterm Labor in a Human Patient Using the compositions and methods described herein, a patient undergoing or at risk of undergoing preterm labor may be administered nifedipine in combination with a PGF2α receptor antagonist, such as a compound of any one of formulas (I) through (VIII) described herein (e.g., compound (1), (2), or (3) described herein). A physician of skill in the art may assess the patient for risk of preterm labor, and may determine that the patient is at risk of undergoing preterm labor if the patient has a gestational age of from about 24 weeks to about 36 weeks prior to administration of a tocolytic agent, exhibits four or more uterine contractions per 30 minutes, exhibits a cervical dilation of from about 1 cm to about 4 cm, tests positive for the presence of fetal fibronectin and/or insulin-like growth factor-binding protein-1 (IGFBP-1) in a sample of cervical secretion obtained from the patient, and/or exhibits a cervical length of about 25 mm or less.

Upon determining that the patient is undergoing or at risk of undergoing preterm labor, the patient may be administered a PGF2α receptor antagonist, such as compound (2) or the chloride salt thereof, or another compound that gives rise to compound (1) in vivo, in one or more daily doses. For example, the PGF2α receptor antagonist may be administered to the subject once or twice daily, in a dose of from, e.g., 1,000 mg to 2,000 mg. The subject may be administered nifedipine in a reduced dosage and/or a reduced frequency relative to the dosage or frequency that would otherwise be used if the nifedipine were administered in the absence of a PGF2α receptor antagonist. The nifedipine may be administered to the patient, for example, in a dose of from 10 mg to 30 mg per one or more times per day, such as a single daily dose of 20 mg.

Following administration of the nifedipine and the PGF2α receptor antagonist, the patient may be assessed for successful treatment or prevention of preterm labor. Successful treatment of a pregnant subject with nifedipine and a PGF2α receptor antagonist described herein may be signaled, for instance, by observing a delay in the onset of delivery by the patient. The delay may be a matter of one or more hours, days, or weeks (e.g., a delay of from about 1 hour to about 16 weeks, such as a delay of 1 hour, 6 hours, 12 hours, 18 hours, 24 hours, 48 hours, 72 hours, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, or 16 weeks, among others) following the first administration of nifedipine and the PGF2α receptor antagonist to the subject. Additionally or alternatively, the physician may determine that the patient has been successfully treated by observing a delay in the onset of delivery such that the subject undergoes delivery at a gestational age of at least about 34 weeks, such as at a gestational age of from about 34 weeks to about 40 weeks, following administration of nifedipine and the PGF2α receptor antagonist to the subject. Successful treatment may also be signaled by a reduction in vaginal bleeding, a delay in the onset of amniorrhexis by the patient, and a reduction in the expression of one or more proinflammatory genes, such as cyclooxygenase-2 (Cox2) by the subject (as assessed, e.g., by observing a decrease in myometrial Cox2 expression) following administration of nifedipine and the PGF2α receptor antagonist. The patient may also be determined to have been successfully treated upon detecting a decrease in the frequency of, peak amplitude of, duration of, and/or work done by, uterine contractions in the patient.

Example Three. Use of Nifedipine and a PGF2α Receptor Antagonist to Delay Delivery and an Antenatal Corticosteroid to Promote Fetal Lung Maturation Prior to Birth Using the compositions and methods described herein, a patient undergoing or at risk of undergoing preterm labor may be administered nifedipine in combination with a PGF2α receptor antagonist, such as a compound of any one of formulas (I) through (VIII) described herein (e.g., compound (1), (2), or (3) described herein), in order to delay the onset of delivery, as described in Example Two, above. For example, the PGF2α receptor antagonist may be administered to the subject once or twice daily, in a dose of from, e.g., 1,000 mg to 2,000 mg. The subject may be administered nifedipine in a reduced dosage and/or a reduced frequency relative to the dosage or frequency that would otherwise be used if the nifedipine were administered in the absence of a PGF2α receptor antagonist. The nifedipine may be administered to the patient, for example, in a dose of from 10 mg to 30 mg per one or more times per day, such as a single daily dose of 20 mg.

In some instances, in addition to administering nifedipine and a PGF2α receptor antagonist to the patient, a physician may additionally prescribe and administer an antenatal corticosteroid. Antenatal corticosteroids, such as betamethasone, dexamethasone, and hydrocortisone, can be used to accelerate fetal lung maturation prior to birth. In this way, a patient may be administered nifedipine and a PGF2α receptor antagonist (such as a compound represented by any one of formulas (I) through (VIII), e.g., compound (1), (2), or (3)) so as to delay the onset of delivery and provide additional time for administration of an antenatal corticosteroid to promote fetal lung development. Administration of the corticosteroid may reduce the likelihood of neonatal death, respiratory distress syndrome, intraventricular hemorrhage, necrotizing enterocolitis, respiratory support, intensive care admissions, and systemic infections following birth.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. A method of delaying the onset of delivery in a pregnant human subject, the method comprising administering to the subject a therapeutically effective amount of a compound represented by formula (2)

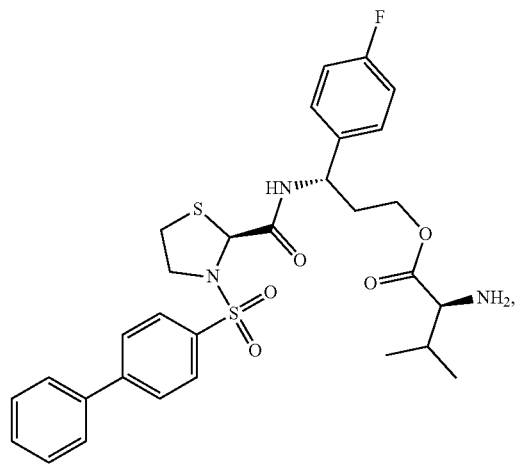

or a pharmaceutically acceptable salt thereof,
and wherein the subject is further administered nifedipine in an amount of about 20 mg per dose.

2. A method of delaying the onset of delivery in a pregnant human subject, the method comprising administering to the subject a therapeutically effective amount of a compound represented by formula (2)

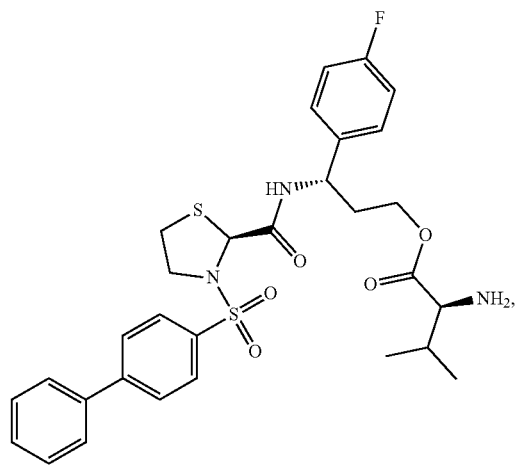

or a pharmaceutically acceptable salt thereof,
and wherein the subject is further administered nifedipine in an amount of about 20 mg in the first hour of treatment.

3. The method of claim 1, wherein the compound is represented by formula (3)

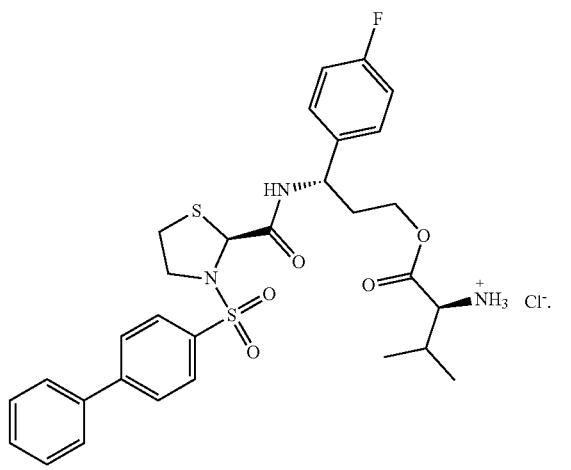

(3)

4. The method of claim 1, wherein the nifedipine is administered to the subject in one or more doses per 12 hours, 24 hours, 48 hours, or week.

5. The method of claim 4, wherein a dose of the nifedipine is administered to the subject once every 4 to 12 hours.

6. The method of claim 1, wherein the nifedipine is periodically administered to the subject until the subject reaches a gestational age of at least about 34 weeks.

7. The method of claim 6, wherein the nifedipine is periodically administered to the subject until the subject reaches a gestational age of from about 34 weeks to about 40 weeks.

8. The method of claim 1, wherein the nifedipine is administered to the subject orally.

9. The method of claim 1, wherein the subject has a gestational age of from about 24 weeks to about 36 weeks prior to administration of the nifedipine and the compound to the subject.

10. The method of claim 1, wherein the subject exhibits four or more uterine contractions per 30 minutes prior to administration of the nifedipine and the compound to the subject.

11. The method of claim 2, wherein the compound is represented by formula (3)

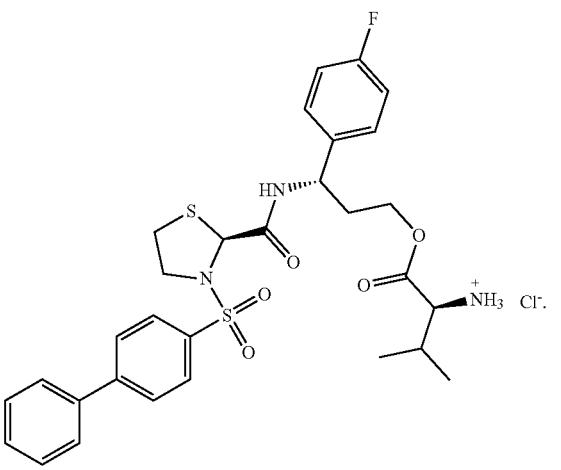

(3)

* * * * *